(12) United States Patent
Choong et al.

(10) Patent No.: US 6,878,743 B2
(45) Date of Patent: Apr. 12, 2005

(54) SMALL MOLECULE INHIBITORS OF CASPASES

(75) Inventors: Ingrid Choong, Belmont, CA (US); Matthew Burdett, Belmont, CA (US); Warren DeLano, San Carlos, CA (US); Daniel Erlanson, San Francisco, CA (US); Dennis Lee, Swarthmore, PA (US); Willard Lew, San Mateo, CA (US)

(73) Assignee: Sunesis Pharmaceuticals, Inc., South San Francisco, CA (US)

( * ) Notice: Subject to any disclaimer, the term of this patent is extended or adjusted under 35 U.S.C. 154(b) by 184 days.

(21) Appl. No.: 10/245,912

(22) Filed: Sep. 17, 2002

(65) Prior Publication Data

US 2003/0114447 A1 Jun. 19, 2003

Related U.S. Application Data

(60) Provisional application No. 60/323,270, filed on Sep. 18, 2001, and provisional application No. 60/371,762, filed on Apr. 11, 2002.

(51) Int. Cl.[7] .................. A61K 31/38; C07D 333/22

(52) U.S. Cl. ................................ 514/448; 549/72

(58) Field of Search ......................... 549/72; 514/448

(56) References Cited

U.S. PATENT DOCUMENTS

| 4,246,263 A | 1/1981 | Lombardino et al. ....... 424/251 |
| 6,103,711 A | 8/2000 | Bemis et al. ............... 514/183 |

FOREIGN PATENT DOCUMENTS

| WO | WO 98/16502 | 4/1998 |
| WO | WO 00/23421 | 4/2000 |
| WO | WO 01/10383 | 2/2001 |
| WO | WO 01/21599 | 3/2001 |
| WO | WO 01/27085 A1 | 4/2001 |
| WO | WO 01/90070 A2 | 11/2001 |

OTHER PUBLICATIONS

Form PCT/ISA/206 (Invitation to Pay Additional Fees) with Annex (Communication Relating to the Results of the Partial International Search Report), issued for corresponding PCT application PCT/US02/29536.
Dyer, et al., "Researches on Pyrimidines. CXL. Pyrimidines Derived from Carbethoxymalonic Aldehyde", 56:222–225, 1934.
Garcia–Colvo, et al., "Inhibition of Human Caspases by Peptide–based and Macromolecular Inhibitors", *The Journal of Biological Chemistry*, 273(49):32608–32613, 1998.
Gray, et al., "Evidence That Inhibition of Cathepsin-B Contributes to the Neuroprotective Properties of Caspase Inhibitor Tyr-Val-Ala-Asp-Chloromethyl Ketone", *The Journal of Biological Chemistry*, 276(35):32750–32755, 2001.

Hamprecht, et al., "Optically Active 2H–Azepines: Synthesis and Rearrangement into their 3H–Isomers", *Tetrahedron*, 52(33):10883–10902, 1996.
Irako, et al., "A New Asymmetric Synthesis of (S)–Dolaphenine and Its Heteroaromatic Congeners Utilizing (+)–2–Hydroxy–3–pinanone and (−)–3–Hydroxy–2–caranone as Chiral Auxiliaries", *Tetrahedron*, 51(46):12731–12744, 1995.
Kohara, et al., "Synthesis and Angiotensin II Receptor Antagonistic Activities of Benzimidazole Derivatives Bearing Acidic Heterocycles as Novel Tetrazole Bioisosteres", *J. Med. Chem.*, 39:5228–5235, 1996.
Lee et al., "General Solid–Phase Method for the Preparation of Mechanism–Based Cysteine Protease Inhibitors," *Journal of the American Chemical Society*, 121 (43):9907–9914, 1999.
Lee, et al., "Potent and Selective Nonpeptide Inhibitors of Caspases 3 and 7 Inhibit Apoptosis and Maintain Cell Functionality", *The Journal of Biological Chemistry*, 275(21):16007–16014, 2000.
Leung et al., "Protease Inhibitors: Current Status and Future Prospects", *Journal of Medicinal Chemistry*, 43(3):305–341, 2000.
Luke, et al., "'One–Pot' Methylation of Fmoc Amino Acids," *Tetrahedron Letters*, 37(2), 263–266, 1996.
Mjalli, et al,. "Phenylalkyl Ketones as Potent Reversible Inhibitors of Interleukin–1β Converting Enzyme", *Bioorganic & Medicinal Chemistry Letters*, 3(12):2689–2692, 1993.
Mjalli, et al., "Activated Ketones as Potent Reversible Inhibitors of Interleukin–1β Converting Enzyme", *Bioorganic & Medicinal Chemistry Letters*, 4(16):1965–1968, 1994.

(Continued)

Primary Examiner—Deborah Lambkin
(74) Attorney, Agent, or Firm—Brenda Herschbach Jarrell; Nadege M. Lagneau; Choate, Hall & Stewart

(57) ABSTRACT

The present invention provides compounds having formula (I):

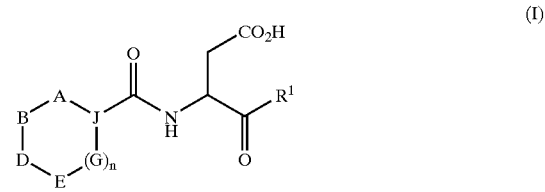

and pharmaceutically acceptable derivatives thereof, wherein A, B, D, E, G, J, n, and $R^1$ are as described generally and in classes and subclasses herein, and additionally provides pharmaceutical compositions thereof, and methods for the use thereof as caspase inhibitors and for the treatment of disorders caused by excessive apoptotic activity.

43 Claims, No Drawings

OTHER PUBLICATIONS

Mittl, et al., "Structure of Recombinant Human CPP32 in Complex with the Tetrapeptide Acetyl–Asp–Val–Ala–Asp Fluoromethyl Ketone", *The Journal of Biological Chemistry*, 272(10):6539–6547, 1997.

Moloney, et al., "Synthesis and pharmacological profile of a series of 2,5–substituted–N,N–dimethyltryptamine derivatives as novel antagonists for the vascular 5–HT$_{1B}$–like receptor", *J. Chem. Soc., Perkin Trans.* 1;2713–2723, 1999.

Murphy, et al., "Automated Synthesis of Peptide C–Terminal Aldehydes", *J. Am. Chem. Soc.*, 114:3156–3157, 1992.

Otto, et al., "Cysteine Proteases and Their Inhibitors", *Chem. Rev.*, 97:133–171, 1997.

Plouvier, et al., "Synthesis of Two New Thiazole–Containing Oligopeptides as Potential DNA Minor Groove Binding Analogs of Netropsin", *Heterocycles*, 32(4):693–701, 1991.

Talanian, et al., "Caspases as Targets for Anti–Inflammatory and Anti–Apoptotic Drug Discovery", *Journal of Medicinal Chemistry*, 43(18):3351–3371, 2000.

Thornberry, Nancy A., "Caspases: key mediators of apoptosis", *Chemistry & Biology*, 5(5):R97–R103, 1998.

Thornberry, et al., "A Combinational Approach Defines Specificities of Members of the Caspase Family and Granzyme B", *The Journal of Biological Chemistry*, 272(29):17907–17911, 1997.

Torii, et al., "A Facile Synthesis of Polyfunctionally Substituted Pyridines from Ethoxycarbonylmalonaldehyde", *Synthesis Communications*, 400–402, 1986.

Ueda, et al., "Syntheses of 2–Acylaminoacetamidine and 3–Acylaminopropionamidine Derivatives[1]", *Chem. Pharm. Bull.*, 16(12):2355–2361, 1968.

Widmer, Ulrich, "A Convenient Preparation of t–Butyl Esters", *Synthesis Communications*, 135–136, 1983.

Wright, et al., "Convenient Preparations of t–Butyl Esters and Ethers from t–Butanol", *Tetrahedron Letters*, 38(42):7345–7348, 1997.

SMALL MOLECULE INHIBITORS OF CASPASES

PRIORITY CLAIM

The present application claims priority under 35 U.S.C. §119 to U.S. Ser. No. 60/323,270, filed Sep. 18, 2001, and U.S. Ser. No. 60/371,762, filed Apr. 11, 2002, the entire contents of each of these applications are incorporated herein by reference.

BACKGROUND OF THE INVENTION

Apoptotic cell death is a fundamentally important biological process that is required to maintain the integrity and homeostasis of multicellular organisms. Inappropriate and excessive apoptosis, however, underlies the etiology of many of the most intractable of human diseases. The apoptotic pathway is predominantly executed by a series of cysteine proteases designated the "caspases" (cysteinyl aspartate-specific proteinases). Caspases are intracellular protease enzymes that play significant roles in both cytokine maturation and programmed cell death (apoptosis) (see, Thornberry et al., *Nature* 1992, 356, 768–774; Thornberry et al. *Chem. Biol.* 1998, 5, R97–103). Specifically, caspases are responsible for the proteolytic degradation of more than 100 different protein substrates, including proteins involved in DNA repair, nuclear membrane integrity, and cell structural integrity.

The first caspase to be discovered was Interleukin-1β Converting Enzyme (ICE), now also known as caspase-1 (Thornberry et al. 1992, *Nature* 356:768–774; Cerretti et al. 1992, *Science* 256:97–99). Caspase-1 was initially identified as the protease that cleaves the immature pro-IL-1β polypeptide to produce the mature IL-1β polypeptide, a critical step that precedes secretion of IL-1β from the cell. Since IL-1β is an important mediator of inflammation, it has been suggested that disruption of caspase-1 activity may reduce the inflammatory response after exposure to an appropriate stimulant. This was shown to be the case in mice containing a "knockout" of the caspase-1 gene. These mice undergo normal development but are deficient in mounting a normal inflammatory response (Kuida et al. 1995, *Science* 267:2000–2003; Li et al. 1995, *Cell* 80:401–411). Even though the predominant role of caspase-1 appears to involve the inflammatory pathway, evidence indicates that it is also important for the apoptotic pathway, since these mice also show reduced levels of apoptosis when treated with chemicals that typically induce apoptosis.

To date, approximately eleven caspases have been identified in humans. Caspases have been broadly categorized into three main functional categories. Group I caspases (e.g. caspase-1, -4 and -5) are predominantly involved in the inflammatory response pathway, Group II caspases (e.g. caspase-3, -6, and -7) are the effector caspases, and Group III caspases (e.g. caspase-8, -9 and -2) are the initiator caspases (reviewed in Thomberry 1998, *Current Biology* 5:R97–103). The initiator caspases are typically located higher in the activation pathway, with one of their main functions being the activation of the effector caspases through cleavage at conserved Asp residues located immediately upstream of both the large and small subunits. Following cleavage, the large and small subunits rearrange to form a heterotetramer, which is the catalytically active form of the enzyme. Once activated, the caspases then proceed not only to proteolytically degrade a wide range of cellular proteins, but also to amplify the apoptotic response through a positive feedback mechanism whereby downstream caspases can cleave certain members of upstream caspases.

The crystal structures of the mature active forms of caspase-1 (Wilson et al. 1994, *Nature* 370:270–275), caspase-3 (Rotunda et al. 1996, *Nature Struct. Biol.* 3:619–625; Lee et. al. 2001, *J. Med. Chem.* 44:2015–2126), caspase-7 (Wei et. al. 2000, *Chem. Biol.* 7:423–432), and caspase-8 (Watt et al. 1999, *Structure* 7:1135–1143; Blanchard et al. 1999, *Structure* 7:1125–1133) have been solved, in each case in the presence of a bound peptide or small molecule inhibitor. These structures have helped researchers understand the mechanism of peptide hydrolysis and have also aided in the design of small molecule competitive inhibitors. For example, the minimal substrate for each caspase was determined to consist of a tetrapeptide sequence (Thornberry et. al. 1997, *J. Biol. Chem.* 272:17907–17911). In addition, while the Asp residue at position P1 is conserved across all three caspases, amino acid variations are found in the P2-P4 positions. For example, caspase-3 prefers a negatively charged amino acid in the P4 position (Asp), compared to caspase-1 which prefers a bulky hydrophobic residue (Tyr). Based upon this and other information, peptide inhibitors have been designed that display both high potency and specificity. The tetrapeptide aldehyde Ac-Tyr-Val-Ala-Asp-CHO (which mimics the Tyr-Val-His-Asp caspase-1 recognition sequence within pro-IL-1β) is a potent inhibitor of caspase-1 ($K_i$=0.056 nM) but a poor inhibitor of caspase-3 ($K_i$=1960 nM). In contrast, the Ac-Asp-Glu-Val-Asp-CHO tetrapeptide aldehyde (which mimics the caspase-3 optimum recognition site) is a very potent inhibitor of caspase-3 ($K_i$=0.23 nM) but is a significantly weaker inhibitor of caspase-1 ($K_i$=18 nM) (Garcia-Calvo et. al. 1998, *J. Biol. Chem.* 273(49):32608–2613). Caspase inhibitors can be either reversible or irreversible, depending upon the nature of the "warhead" that attacks the active site cysteine. Peptide aldehydes, nitrites and ketones are potent reversible inhibitors, while compounds that form thiomethylketone adducts with the active site cysteine (e.g. peptide (acyloxy)methylketones) are potent irreversible inhibitors.

Excessive apoptosis is associated with a wide range of human diseases, and the importance of caspases in the progression of many of these disorders has been demonstrated with both small molecule and peptide-based inhibitors as well as by genetic approaches. Caspase inhibitors have been suggested to offer therapeutic benefit in numerous acute disorders, such as cardiac and cerebral ischemia/reperfusion injury (e.g. stroke), spinal cord injury, traumatic brain injury, organ damage during transplantation, liver degeneration (as caused, for example, by hepatitis), sepsis, bacterial meningitis and a number of dermatological conditions. There are also a wide range of chronic disorders in which excessive apoptosis is implicated, such as neurodegenerative diseases (e.g. Alzheimer's disease, polyglutamine-repeat disorders such as Huntington's Disease, Down's Syndrome, spinal muscular atrophy, multiple sclerosis, Parkinson's disease), immunodeficiency diseases (e. g. HIV), arthritis, atherosclerosis, diabetes, alopecia, and aging. Caspase inhibitors could also be used to extend the lifespan of purified blood products to be used for transfusions, or to enhance the lifespan of donated organs before transplantation. Thus, small molecule inhibitors of either Group I, II, or III caspases are likely to have tremendous therapeutic benefit (McBride et al. 1999, *Emerging Ther. Targets* 3(3):391–411; Talanian et al. 2000, *J. Med. Chem.* 43(18):3351–3371).

SUMMARY OF THE INVENTION

As discussed above, there remains a need for the development of novel therapeutic agents and agents useful for treating disorders mediated by caspases. The present invention provides novel compounds of general formula (I),

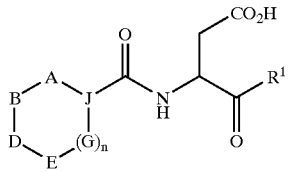

and pharmaceutical compositions thereof, as described generally and in subclasses herein, which compounds are useful as inhibitors of caspases (e.g., apoptotic caspases), and thus are useful, for example, for the treatment of disorders resulting from excessive apoptotic activity.

DESCRIPTION OF CERTAIN PREFERRED EMBODIMENTS OF THE INVENTION

In one aspect, the present invention provides inhibitors of caspases. In certain embodiments, the inventive compounds are inhibitors of apoptotic caspases and are useful for the treatment of disorders resulting from excessive apoptotic activity. In certain other embodiments, the inventive compounds are selective inhibitors of caspase-3 and are useful for the treatment of disorders mediated by caspase-3. In certain other embodiments, the inventive compounds are selective inhibitors of caspase-7 and are useful for the treatment of disorders mediated by caspase-7.

1) General Description of Compounds of the Invention

In certain embodiments, the compounds of the invention include compounds of the general formula (I) as further defined below:

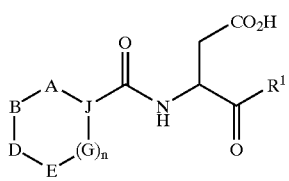

and pharmaceutically acceptable derivatives thereof, wherein $R^1$ is H, an aliphatic, heteroaliphatic, aryl, heteroaryl, alkylaryl, alkylheteroaryl, heteroalkylaryl, or heteroalkylheteroaryl moiety;

n is 0 or 1;

A is $CR^A$, $C(R^A)_2$, C=O, S, $NR^A$, $N(R^A)_2$, or O;
B is $CR^B$, $C(R^B)_2$, C=O, S, $NR^B$, $N(R^B)_2$, or O;
D is $CR^D$, $C(R^D)_2$, C=O, S, $NR^D$, $N(R^D)_2$, or O;
E is $CR^E$, $C(R^E)_2$, C=O, S, $NR^E$, $N(R^E)_2$, or O;
G is $CR^G$, $C(R^G)_2$, C=O, S, $NR^G$, $N(R^G)_2$, or O;
J is $CR^J$;

each of A—B, B—D, D—E, E—G, G—J and A—J are connected by a single or double bond as valency and stability permits;

each occurrence of $R^A$, $R^B$, $R^D$, $R^E$, $R^G$ and $R^J$ is independently hydrogen, halogen, $-OR^2$, $-N(R^2)_2$, $-SR^2$, $-CN$, $-COOR^2$, $-COR^2$, $-CON(R^2)_2$, $-SOR^2$, $-SO_2R^2$, $-SO_2N(R^2)_2$, $-NR^2SO_2R^2$, $-O(C=O)N(R^2)_2$, $-NR^2(C=O)N(R^2)_2$, $-NR^2(C=S)N(R^2)_2$, $-NR^2SO_2N(R^2)_2$, or and aliphatic, heteroaliphatic, aryl, heteroaryl, alkylaryl, alkylheteroaryl, heteroalkylaryl, or heteroalkylheteroaryl moiety optionally independently substituted with one or more occurrences of $R^2$, wherein each occurrence of $R^2$ is independently hydrogen, halogen, $-OR^3$, $-N(R^3)_2$, $-SR^3$, $-CN$, $-COOR^3$, $-COR^3$, $-CON(R^3)_2$, $-SOR^3$, $-SO_2R^3$, $-SO_2N(R^3)_2$, $-NR^3SO_2R^3$, $-O(C=O)N(R^3)_2$, $-NR^3(C=O)N(R^3)_2$, $-NR^3(C=S)N(R^3)_2$, $-NR^3SO_2N(R^3)_2$, or an aliphatic, heteroaliphatic, aryl, heteroaryl, alkylaryl, alkylheteroaryl, heteroalkylaryl, or heteroalkylheteroaryl moiety;

wherein each occurrence of $R^3$ is independently hydrogen, or an aliphatic, heteroaliphatic, aryl, heteroaryl, alkylaryl, alkylheteroaryl, heteroalkylaryl, or heteroalkylheteroaryl moiety, and wherein at least one of $R^B$ or $R^D$ comprises $-SR^2$, $-SOR^2$, $-SO_2R^2$, $-SO_2N(R^2)_2$, $-NR^2SO_2R^2$, $-N(R^2)_2$, $-(C=O)N(R^2)_2$, $-NR^2(C=O)R^2$, $-O(C=O)N(R^2)_2$, $-NR^2(C=O)N(R^2)_2$, $-NR^2(C=S)N(R^2)_2$, $-NR^2SO_2N(R^2)_2$, or is an alkyl or heteroalkyl group substituted with one or more occurrences of $R^2$, wherein $R^2$ is $-SR^3$, $-SOR^3$, $-SO_2R^3$, $-SO_2N(R^3)_2$, $-NR^3SO_2R^3$, $-N(R^3)_2$, $-(C=O)N(R^3)_2$, $-NR^3(C=O)R^3$, $-O(C=O)N(R^3)_2$, $-NR^3(C=O)N(R^3)_2$, $-NR^3(C=S)N(R^3)_2$, $-NR^3SO_2N(R^3)_2$, wherein $R^3$ is an aliphatic, heteroaliphatic, aryl, heteroaryl, alkylaryl, alkylheteroaryl, heteroalkylaryl, or heteroalkylheteroaryl moiety, whereby each of the foregoing aliphatic, heteroaliphatic, alkyl and heteroalkyl moieties may be independently substituted or unsubstituted, cyclic or acyclic, linear or branched, and each of the foregoing aryl, heteroaryl, alkylaryl, alkylheteroaryl, heteroalkylaryl and heteroalkylheteroaryl moieties may be independently substituted or unsubstituted.

In certain embodiments, compounds of the invention have the structure

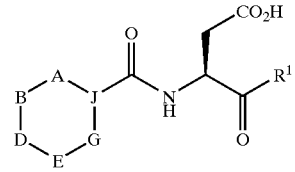

and pharmaceutically acceptable derivatives thereof, wherein n, $R^1$, A, B, D, E, G and J are as defined generally above and in classes and subclasses herein.

In certain embodiments, the present invention defines certain classes of compounds which are of special interest.

For example, one class of compounds of special interest includes those compounds as described generally above and herein, in which

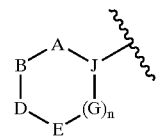

represents pyridyl and the compound has the structure:

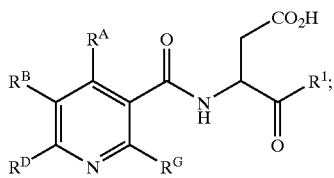

wherein $R^1$, $R^A$, $R^B$, $R^D$ and $R^G$ are each defined generally above and in subclasses herein.

Another class of compounds of special interest includes those compounds as described generally above and herein, in which

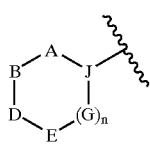

represents phenyl and the compound has the structure:

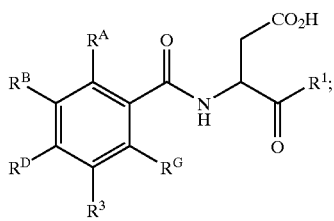

wherein $R^1$ and $R^A$—$R^E$ are each defined generally above and in subclasses herein.

Still another class of compounds of special interest includes those compounds as described generally above and herein, in which

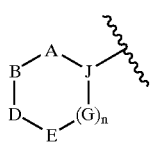

represents pyrimidine and the compound has the structure:

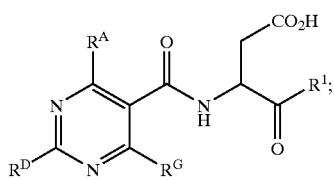

wherein $R^1$, $R^A$, $R^D$ and $R^G$ are each defined generally above and in subclasses herein.

Another class of compounds of special interest includes those compounds as described generally above and herein, in which

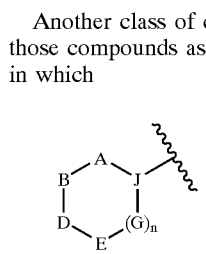

represents thiophene and the compound has the structure:

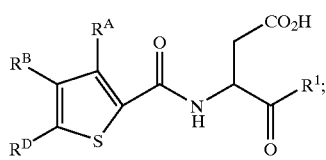

wherein $R^1$, $R^A$, $R^B$ and $R^D$ are each defined generally above and in subclasses herein.

Yet another class of compounds of special interest includes those compounds as described generally above and herein, in which

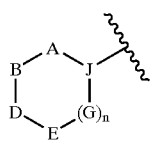

represents furyl and the compound has the structure:

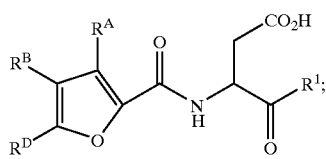

wherein $R^1$, $R^A$, $R^B$ and $R^D$ are each defined generally above and in subclasses herein.

Still another class of compounds of special interest includes those compounds as described generally above and herein, in which

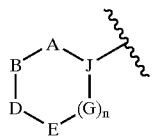

represents thiazole and the compound has the structure:

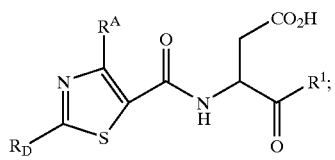

wherein $R^1$, $R^A$ and $R^D$ are each defined generally above and in subclasses herein.

Yet another class of compounds of special interest includes those compounds as described generally above and herein, in which

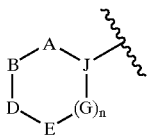

represents pyrazine and the compound has the structure:

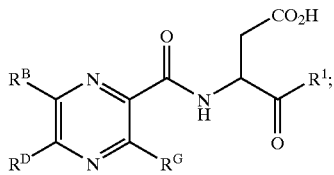

wherein $R^1$, $R^B$, $R^D$ and $R^G$ are each defined generally above and in subclasses herein.

Still another class of compounds of special interest includes those compounds as described generally above and herein, in which

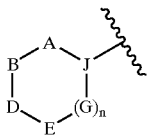

represents pyridone and the compound has the structure (and tautomers thereof):

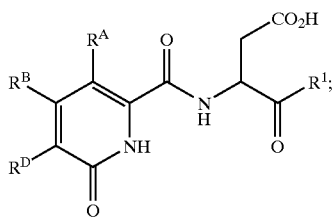

wherein $R^1$, $R^A$, $R^B$ and $R^D$ are each defined generally above and in subclasses herein.

A number of important subclasses of each of the foregoing classes deserve separate mention; these subclasses include subclasses of the foregoing classes in which:

i) compounds as described directly above with the proviso that compounds disclosed in PCT Publication Nos. WO01/10383, WO01/27085, WO01/21599, WO01/21600 and WO00/55114, each of which is incorporated herein by reference, are excluded.

ii) compounds as described directly above having one or more of the following limitations:

a) $R^1$ is not $CH_2X$, if X is F or Cl;

b) if

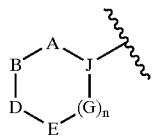

represents pyridyl, then $R^D$ is $-SR^2$, $-SOR^2$, $-SO_2R^2$, $-SO_2N(R^2)_2$, $-NR^2SO_2R^2$, $-NR^2SO_2N(R^2)_2$; or $R^D$ is an alkyl or heteroalkyl group substituted with one or more occurrences of $R^2$, wherein $R^2$ is $-SR^3$, $-SOR^3$, $-SO_2R^3$, $-SO_2N(R^3)_2$, $-NR^3SO_2R^3$, $-N(^3)_2$, $-(C=O)N(R^3)_2$, $-NR^3(C=O)R^3$, $-O(C=O)N(R^3)_2$, $-NR^3(C=O)N(R^3)_2$, $-NR^3(C=S)N(R^3)_2$, $-NR^3SO_2N(R^3)_2$, wherein $R^3$ is an aliphatic, heteroaliphatic, aryl, heteroaryl, alkylaryl, alkylheteroaryl, heteroalkylaryl, or heteroalkylheteroaryl moiety; or c)

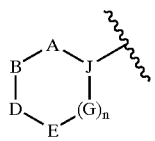

represents isoxazole, then $R^B$ or $R^D$ is not a group $-CR^XR^YNHR^3$, wherein at least one of $R^X$ or $R^Y$ is a group other than hydrogen;

iii)

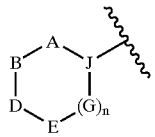

is an aryl or heteroaryl moiety;

iv)

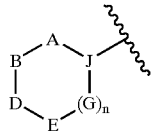

is an aryl or heteroaryl moiety having the structure:

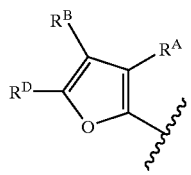 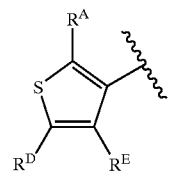

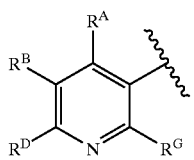 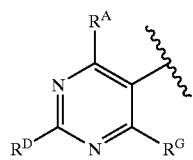

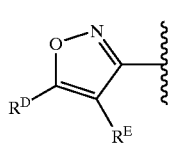 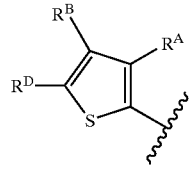

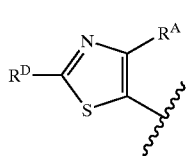 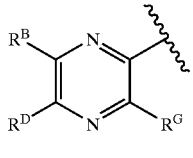

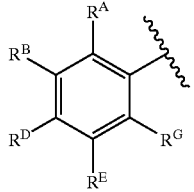 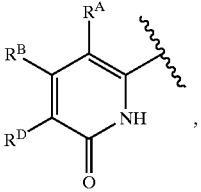

wherein $R^A$—$R^E$ are each defined generally and in subclasses herein;

v)

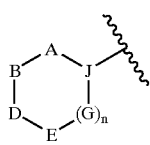

is one of the structures:

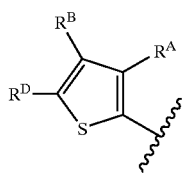 or 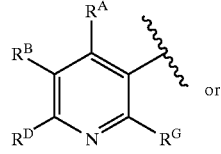 or

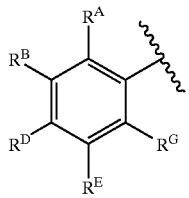

wherein $R^A$—$R^E$ are each defined generally and in subclasses herein;

vi) 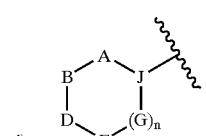 is 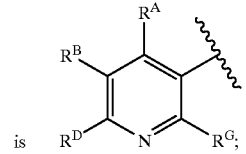;

vii) 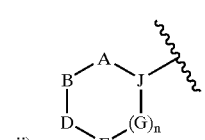 is 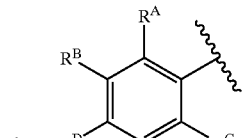;

viii) 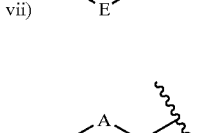 is 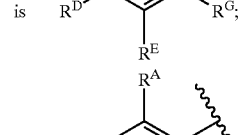;

ix) 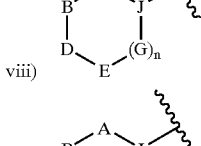 is 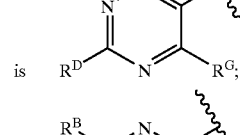;

x) [structure] is [structure];

xi) [structure] is [structure];

xii) [structure] is [structure];

xiii) [structure] is [structure];

xiv) one of $R^B$ or $R^D$ is
- —($C_{0-3}$alkyl)$NR^3$—$SO_2$—($C_{0-3}$alkyl)$R^4$;
- —($C_{0-3}$alkyl)$SO_2$—$NR^3$—($C_{0-3}$alkyl)$R^4$;
- —($C_{0-3}$alkyl)$NR^3$($C_{0-3}$alkyl)$R^4$;
- —($C_{0-3}$alkyl)$CONR^3$($C_{0-3}$alkyl)$R^4$;
- —($C_{0-3}$alkyl)$OCONR^3$($C_{0-3}$alkyl)$R^4$;
- —($C_{0-3}$alkyl) $NR^3CONR^3$($C_{0-3}$alkyl)$R^4$;
- —($C_{0-3}$alkyl)$NR^3$(C=S)$NR^3$($C_{0-3}$alkyl)$R^4$;
- —($C_{0-3}$alkyl)$NR^3SO_2NR^3$($C_{0-3}$alkyl)$R^4$, wherein each of the alkyl groups is independently substituted or unsubstituted, cyclic or acyclic, linear or branched, and wherein each occurrence of $R^3$ and $R^4$ is independently hydrogen, a substituted or unsubstituted alkyl, heteroalkyl, aryl, heteroaryl, alkylaryl, alkylheteroaryl, heteroalkylaryl, or heteroalkylheteroaryl moiety;

xv) one of $R^B$ or $R^D$ is one of

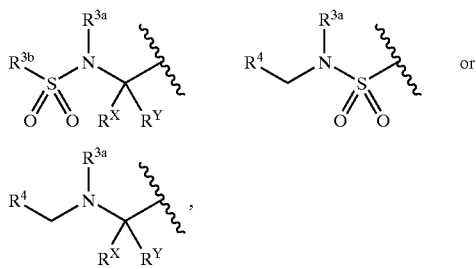

wherein each occurrence of $R^X$ and $R^Y$ is independently hydrogen or lower alkyl; each occurrence of $R^{3a}$ is independently hydrogen, lower alkyl or lower acyl; and each occurrence of $R^{3b}$ and $R^4$ is independently a substituted or unsubstituted aryl, heteroaryl, alkylaryl, alkylheteroaryl, heteroalkylaryl, or heteroalkylheteroaryl moiety;

xvi) one of $R^B$ or $R^D$ is one of

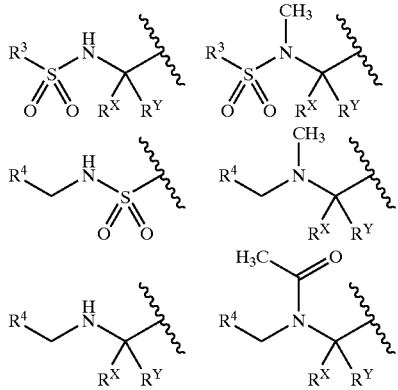

wherein each occurrence of $R^X$ and $R^Y$ is independently hydrogen or lower alkyl; and each occurrence of $R^3$ and $R^4$ is independently a substituted or unsubstituted aryl, heteroaryl, alkylaryl, alkylheteroaryl, heteroalkylaryl, or heteroalkylheteroaryl moiety;

xvii) $R^1$ is hydrogen or a substituted or unsubstituted aryl, heteroaryl, alkylaryl, heteroalkylaryl, alkylheteroaryl, or heteroalkylheteroaryl moiety;

xviii) $R^1$ is hydrogen or

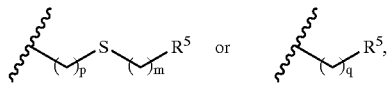

wherein $R^5$ is substituted or unsubstituted aryl, heteroaryl, alkyl or heteroalkyl; and m, p and q are each independently an integer from 0–6;

xix) $R^1$ is hydrogen, alkyl, aryl or

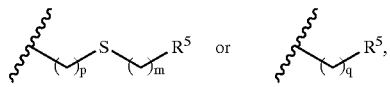

wherein $R^5$ is substituted or unsubstituted aryl, heteroaryl, alkyl or heteroalkyl; wherein the aryl, heteroaryl, alkyl or heteroalkyl group may be substituted with one or more occurrences of hydrogen, halogen, hydroxyl, lower alkoxy and/or lower alkyl; and m, p and q are each independently an integer from 0–6;

xx) $R^1$ is hydrogen or

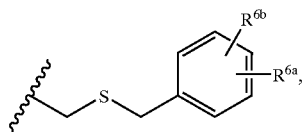

wherein $R^{6a}$ and $R^{6b}$ are each independently hydrogen, halogen, hydroxyl, lower alkoxy, or lower alkyl;

xxi) $R^1$ is hydrogen or

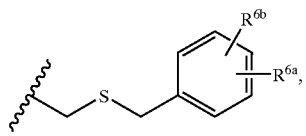

wherein $R^{6a}$ is hydrogen and $R^{6b}$ is halogen;

xxii) $R^1$ is hydrogen or

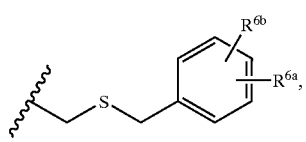

wherein $R^{6a}$ is hydrogen and $R^{6b}$ is Cl;

xxiii) $R^1$ is hydrogen or

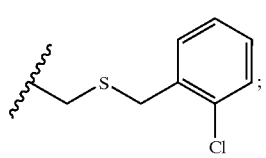

xxivi) $R^3$ and $R^4$ are independently a substituted or unsubstituted aryl, heteroaryl, alkylaryl, alkylheteroaryl, heteroalkylaryl, or heteroalkylheteroaryl moiety;

xxv) each occurrence of $R^3$ and $R^4$ independently comprises an aryl, heteroaryl, alkylaryl, alkylheteroaryl, heteroalkylaryl, or heteroalkylheteroaryl moiety substituted with at least —COOH;

xxvi) each occurrence of $R^3$ and $R^4$ is independently phenyl or —(CH$_2$)phenyl substituted with —COOH (or an ester or bioisostere thereof) and optionally further substituted with one or more occurrences of hydroxyl, alkoxy, thio, thioalkyl, —COOH, —COO(alkyl), —CONH₂, —NH(CO)alkyl, —SO₂R$^{4a}$, lower alkyl, lower heteroalkyl, aryl, heteroaryl, alkylaryl, alkylheteroaryl, heteroalkylaryl, or heteroalkylheteroaryl, or wherein two adjacent groups taken together form an aryl, heteroaryl, cycloaliphatic, or heterocycloaliphatic group, wherein R$^{4a}$ is acyl, or substituted or unsubstituted alkyl or aryl;

xxvii) each occurrence of R$^3$ and R$^4$ is independently phenyl or —(CH₂)phenyl substituted with COOH or an ester or bioisostere of COOH;

xxviii) each occurrence of R$^3$ and R$^4$ is independently phenyl or —(CH₂)phenyl substituted with any one of —COOH, acylsulfonamide, —CONH₂, tetrazole, or 5-oxo-1,2,4-oxadiazole;

xxix) one of R$^B$ or R$^D$ is —(C$_{0-3}$alkyl)NR$^3$—SO$_2$—(C$_{0-3}$alkyl)R$^4$; —(C$_{0-3}$alkyl)SO$_2$—NR$^3$—(C$_{0-3}$alkyl)R$^4$; —(C$_{0-3}$alkyl)NR$^3$(C$_{0-3}$alkyl)R$^4$; —(C$_{0-3}$alkyl)CONR$^3$(C$_{0-3}$alkyl)R$^4$; —(C$_{0-3}$alkyl)OCONR$^3$(C$_{0-3}$alkyl)R$^4$; —(C$_{0-3}$alkyl)NR$^3$CONR$^3$(C$_{0-3}$alkyl)R$^4$; —(C$_{0-3}$alkyl)NR$^3$(C=S)NR$^3$(C$_{0-3}$alkyl)R$^4$; —(C$_{0-3}$alkyl)NR$^3$SO$_2$NR$^3$(C$_{0-3}$alkyl)R$^4$, or subgroups defined generally above and herein, and the remaining groups R$^A$, R$^E$, R$^G$, and one of R$^B$ or R$^D$ are each independently hydrogen, alkyl, alkoxy, halogen, hydroxyl, thio or thioalkyl;

xxx) R$^{3a}$ is hydrogen, lower alkyl or lower acyl;

xxxi) R$^{3a}$ is hydrogen, methyl or Ac;

xxxii) R$^A$, R$^B$, R$^D$, R$^E$ and R$^G$ are independently hydrogen, alkyl, alkenyl, alkynyl, heteroalkyl, heteroalkenyl, heteroalkynyl, aryl, heteroaryl, alkylaryl, heteroalkylaryl, alkylheteroaryl, heteroalkylheteroaryl or a substituent as defined herein in the section entitled "compounds and definitions"; and xxxiii) R$^A$, R$^B$, R$^D$, R$^E$ and R$^G$ are independently hydrogen, lower alkyl, hydroxyl, lower alkoxy or halogen.

As the reader will appreciate, compounds of particular interest include, among others, those which share the attributes of one or more of the foregoing subclasses. Some of those subclasses are illustrated by the following sorts of compounds:

I) Compounds of the Formula (and Pharmaceutically Acceptable Derivatives thereof)

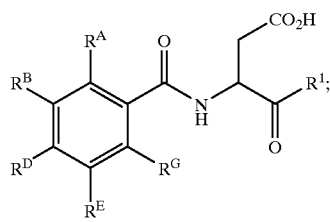

wherein R$^D$ is

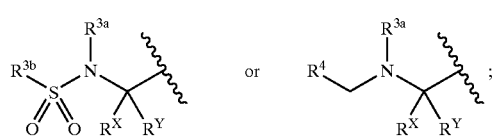

and each occurrence of R$^X$ and R$^Y$ is independently hydrogen or lower alkyl; each occurrence of R$^{3a}$ is independently hydrogen, lower alkyl or lower acyl; each occurrence of R$^{3b}$ and R$^4$ is independently a substituted or unsubstituted aryl, heteroaryl, alkylaryl, alkylheteroaryl, heteroalkylaryl, or heteroalkylheteroaryl moiety; R$^A$, R$^B$ and R$^E$ are each independently hydrogen, lower alkyl, hydroxyl, lower alkoxy, or halogen; and R$^1$ is hydrogen or

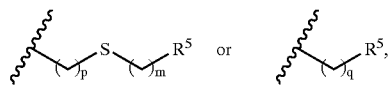

wherein R$^5$ is substituted or unsubstituted aryl, heteroaryl, alkyl or heteroalkyl; wherein the aryl, heteroaryl, alkyl or heteroalkyl group may be substituted with one or more occurrences of hydrogen, halogen, hydroxyl, lower alkoxy and/or lower alkyl; and m, p and q are each independently an integer from 0–6.

In certain embodiments of special interest R$^{3b}$ and R$^4$ are independently phenyl or —(CH₂)phenyl substituted with —COOH (or an ester or bioisostere thereof) and optionally further substituted with one or more of hydroxyl, alkoxy, thio, thioalkyl, —COOH, —COO(alkyl), —CONH₂, —NH(CO)alkyl, —SO₂R$^{4a}$, lower alkyl, lower heteroalkyl, aryl, heteroaryl, alkylaryl, alkylheteroaryl, heteroalkylaryl, or heteroalkylheteroaryl, or wherein two adjacent groups taken together form an aryl, heteroaryl, cycloaliphatic, or heterocycloaliphatic group, wherein R$^{4a}$ is acyl, or substituted or unsubstituted alkyl or aryl.

II) Compounds of the Formula (and Pharmaceutically Acceptable Derivatives thereof)

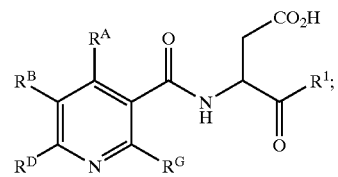

wherein R$^D$ is

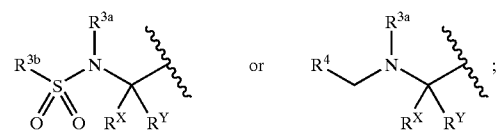

each occurrence of R$^X$ and R$^Y$ is independently hydrogen or lower alkyl; R$^{3a}$ is hydrogen, lower alkyl or lower acyl; each occurrence of R$^{3b}$ and R$^4$ is independently a substituted or unsubstituted aryl, heteroaryl, alkylaryl, alkylheteroaryl, heteroalkylaryl, or heteroalkylheteroaryl moiety; R$^A$, R$^D$ and R$^G$ are each independently hydrogen, lower alkyl, hydroxyl, lower alkoxy, or halogen; and R$^1$ is hydrogen or

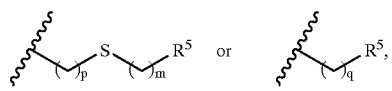

wherein R$^5$ is substituted or unsubstituted aryl, heteroaryl, alkyl or heteroalkyl; wherein the aryl, heteroaryl, alkyl or heteroalkyl group may be substituted with one or more occurrences of hydrogen, halogen, hydroxyl, lower alkoxy and/or lower alkyl; and m, p and q are each independently an integer from 0–6.

In certain embodiments of special interest, each occurrence of $R^{3b}$ and $R^4$ is independently phenyl or —($CH_2$) phenyl substituted with —COOH (or an ester or bioisostere thereof) and optionally further substituted with one or more of hydroxyl, alkoxy, thio, thioalkyl, —COOH, —COO (alkyl), —$CONH_2$, —NH(CO)alkyl, —$SO_2R^{4a}$, lower alkyl, lower heteroalkyl, aryl, heteroaryl, alkylaryl, alkylheteroaryl, heteroalkylaryl, or heteroalkylheteroaryl, or wherein two adjacent groups taken together form an aryl, heteroaryl, cycloaliphatic, or heterocycloaliphatic group, wherein $R^{4a}$ is acyl, or substituted or unsubstituted alkyl or aryl.

III) Compounds of the Formula (and Pharmaceutically Acceptable Derivatives thereof)

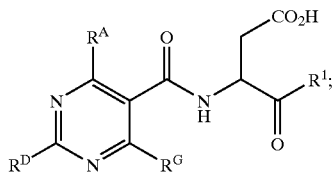

wherein $R^D$ is

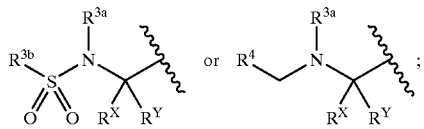

each occurrence of $R^X$ and $R^Y$ is independently hydrogen or lower alkyl; $R^{3a}$ is hydrogen, lower alkyl or lower acyl; each occurrence of $R^{3b}$ and $R^4$ is independently a substituted or unsubstituted aryl, heteroaryl, alkylaryl, alkylheteroaryl, heteroalkylaryl, or heteroalkylheteroaryl moiety; $R^A$, $R^D$ and $R^G$ are each independently hydrogen, lower alkyl, hydroxyl, lower alkoxy, or halogen; and $R^1$ is hydrogen or

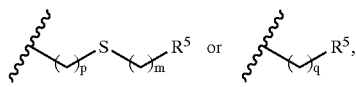

wherein $R^5$ is substituted or unsubstituted aryl, heteroaryl, alkyl or heteroalkyl; wherein the aryl, heteroaryl, alkyl or heteroalkyl group may be substituted with one or more occurrences of hydrogen, halogen, hydroxyl, lower alkoxy and/or lower alkyl; and m, p and q are each independently an integer from 0–6.

In certain embodiments of special interest each occurrence of $R^{3b}$ and $R^4$ is independently phenyl or —($CH_2$) phenyl substituted with —COOH (or an ester or bioisostere thereof) and optionally further substituted with one or more of hydroxyl, alkoxy, thio, thioalkyl, —COOH, —COO (alkyl), —$CONH_2$, —NH(CO)alkyl, —$SO_2R^{4a}$, lower alkyl, lower heteroalkyl, aryl, heteroaryl, alkylaryl, alkylheteroaryl, heteroalkylaryl, or heteroalkylheteroaryl, or wherein two adjacent groups taken together form an aryl, heteroaryl, cycloaliphatic, or heterocycloaliphatic group, wherein $R^{4a}$ is acyl, or substituted or unsubstituted alkyl or aryl.

IV) Compounds of the Formula (and Pharmaceutically Acceptable Derivatives thereof)

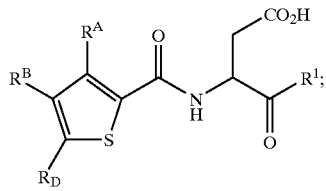

wherein $R^D$ is

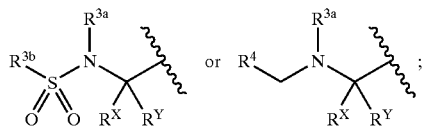

each occurrence of $R^X$ and $R^Y$ is independently hydrogen or lower alkyl; each occurrence of $R^{3a}$ is independently hydrogen, lower alkyl or lower acyl; each occurrence of $R^{3b}$ and $R^4$ is independently a substituted or unsubstituted aryl, heteroaryl, alkylaryl, alkylheteroaryl, heteroalkylaryl, or heteroalkylheteroaryl moiety; $R^A$ and $R^B$ are each independently hydrogen, lower alkyl, hydroxyl, lower alkoxy, or halogen; and $R^1$ is hydrogen or

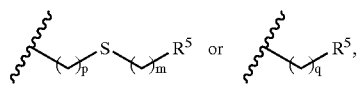

wherein $R^5$ is substituted or unsubstituted aryl, heteroaryl, alkyl or heteroalkyl; wherein the aryl, heteroaryl, alkyl or heteroalkyl group may be substituted with one or more occurrences of hydrogen, halogen, hydroxyl, lower alkoxy and/or lower alkyl; and m, p and q are each independently an integer from 0–6.

In certain embodiments of special interest, each occurrence of $R^{3b}$ and $R^4$ is independently phenyl or —($CH_2$) phenyl substituted with —COOH (or an ester or bioisostere thereof) and optionally further substituted with one or more of hydroxyl, alkoxy, thio, thioalkyl, —COOH, —COO (alkyl), —$CONH_2$, —NH(CO)alkyl, —$SO_2R^{4a}$, lower alkyl, lower heteroalkyl, aryl, heteroaryl, alkylaryl, alkylheteroaryl, heteroalkylaryl, or heteroalkylheteroaryl, or wherein two adjacent groups taken together form an aryl, heteroaryl, cycloaliphatic, or heterocycloaliphatic group, wherein $R^{4a}$ is acyl, or substituted or unsubstituted alkyl or aryl.

V) Compounds of the Formula (and Pharmaceutically Acceptable Derivatives thereof)

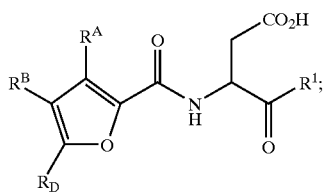

wherein $R^D$ is

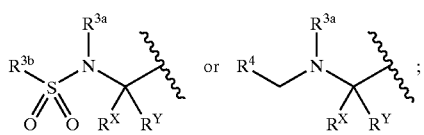

each occurrence of $R^X$ and $R^Y$ is independently hydrogen or lower alkyl; each occurrence of $R^{3a}$ is independently hydrogen, lower alkyl or lower acyl; each occurrence of $R^{3b}$ and $R^4$ is independently a substituted or unsubstituted aryl, heteroaryl, alkylaryl, alkylheteroaryl, heteroalkylaryl, or heteroalkylheteroaryl moiety; $R^A$ and $R^B$ are each independently hydrogen, lower alkyl, hydroxyl, lower alkoxy, or halogen; and $R^1$ is hydrogen or

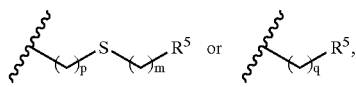

wherein $R^5$ is substituted or unsubstituted aryl, heteroaryl, alkyl or heteroalkyl; wherein the aryl, heteroaryl, alkyl or heteroalkyl group may be substituted with one or more occurrences of hydrogen, halogen, hydroxyl, lower alkoxy and/or lower alkyl; and m, p and q are each independently an integer from 0–6.

In certain embodiments of special interest, each occurrence of $R^{3b}$ and $R^4$ is independently phenyl or —(CH$_2$) phenyl substituted with —COOH (or an ester or bioisostere thereof) and optionally further substituted with one or more of hydroxyl, alkoxy, thio, thioalkyl, —COOH, —COO (alkyl), —CONH$_2$, —NH(CO)alkyl, —SO$_2$R$^{4a}$, lower alkyl, lower heteroalkyl, aryl, heteroaryl, alkylaryl, alkylheteroaryl, heteroalkylaryl, or heteroalkylheteroaryl, or wherein two adjacent groups taken together form an aryl, heteroaryl, cycloaliphatic, or heterocycloaliphatic group, wherein $R^{4a}$ is acyl, or substituted or unsubstituted alkyl or aryl.

VI) Compounds of the Formula (and Pharmaceutically Acceptable Derivatives thereof)

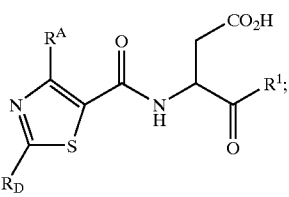

wherein $R^D$ is

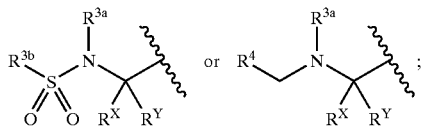

each occurrence of $R^X$ and $R^Y$ is independently hydrogen or lower alkyl; each occurrence of $R^{3a}$ is independently hydrogen, lower alkyl or lower acyl; each occurrence of $R^{3b}$ and $R^4$ is independently a substituted or unsubstituted aryl, heteroaryl, alkylaryl, alkylheteroaryl, heteroalkylaryl, or heteroalkylheteroaryl moiety; $R^A$ is hydrogen, lower alkyl, hydroxyl, lower alkoxy, or halogen; and $R^1$ is hydrogen or

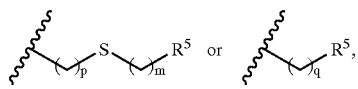

wherein $R^5$ is substituted or unsubstituted aryl, heteroaryl, alkyl or heteroalkyl; wherein the aryl, heteroaryl, alkyl or heteroalkyl group may be substituted with one or more occurrences of hydrogen, halogen, hydroxyl, lower alkoxy and/or lower alkyl; and m, p and q are each independently an integer from 0–6.

In certain embodiments of special interest, each occurrence of $R^{3b}$ and $R^4$ is independently phenyl or —(CH$_2$) phenyl substituted with —COOH (or an ester or bioisostere thereof) and optionally further substituted with one or more of hydroxyl, alkoxy, thio, thioalkyl, —COOH, —COO (alkyl), —CONH$_2$, —NH(CO)alkyl, —SO$_2$R$^{4a}$, lower alkyl, lower heteroalkyl, aryl, heteroaryl, alkylaryl, alkylheteroaryl, heteroalkylaryl, or heteroalkylheteroaryl, or wherein two adjacent groups taken together form an aryl, heteroaryl, cycloaliphatic, or heterocycloaliphatic group, wherein $R^{4a}$ is acyl, or substituted or unsubstituted alkyl or aryl.

VII) Compounds of the Formula (and Pharmaceutically Acceptable Derivatives thereof)

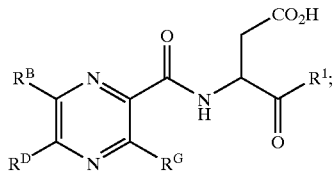

wherein $R^D$ is

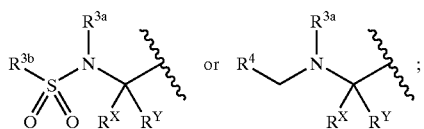

each occurrence of $R^X$ and $R^Y$ is independently hydrogen or lower alkyl; each occurrence of $R^{3a}$ is independently hydrogen, lower alkyl or lower acyl; each occurrence of $R^{3b}$ and $R^4$ is independently a substituted or unsubstituted aryl, heteroaryl, alkylaryl, alkylheteroaryl, heteroalkylaryl, or heteroalkylheteroaryl moiety; $R^A$ is hydrogen, lower alkyl, hydroxyl, lower alkoxy, or halogen; and $R^1$ is hydrogen or

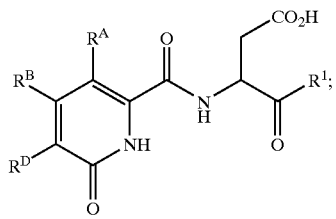

wherein $R^5$ is substituted or unsubstituted aryl, heteroaryl, alkyl or heteroalkyl; wherein the aryl, heteroaryl, alkyl or heteroalkyl group may be substituted with one or more occurrences of hydrogen, halogen, hydroxyl, lower alkoxy and/or lower alkyl; and m, p and q are each independently an integer from 0–6.

In certain embodiments of special interest, each occurrence of $R^{3b}$ and $R^4$ is independently phenyl or —(CH$_2$)phenyl substituted with —COOH (or an ester or bioisostere thereof) and optionally further substituted with one or more of hydroxyl, alkoxy, thio, thioalkyl, —COOH, —COO(alkyl), —CONH$_2$, —NH(CO)alkyl, —SO$_2$R$^{4a}$, lower alkyl, lower heteroalkyl, aryl, heteroaryl, alkylaryl, alkylheteroaryl, heteroalkylaryl, or heteroalkylheteroaryl, or wherein two adjacent groups taken together form an aryl, heteroaryl, cycloaliphatic, or heterocycloaliphatic group, wherein $R^{4a}$ is acyl, or substituted or unsubstituted alkyl or aryl.

VIII) Compounds of the Formula (and Pharmaceutically Acceptable Derivatives thereof)

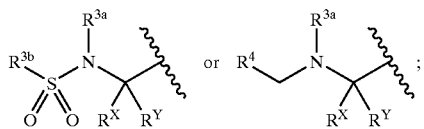

wherein $R^D$ is

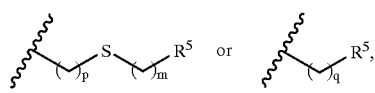

each occurrence of $R^X$ and $R^Y$ is independently hydrogen or lower alkyl; each occurrence of $R^{3a}$ is independently hydrogen, lower alkyl or lower acyl; each occurrence of $R^{3b}$ and $R^4$ is independently a substituted or unsubstituted aryl, heteroaryl, alkylaryl, alkylheteroaryl, heteroalkylaryl, or heteroalkylheteroaryl moiety; $R^A$ is hydrogen, lower alkyl, hydroxyl, lower alkoxy, or halogen; and $R^1$ is hydrogen or

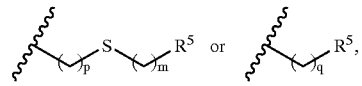

wherein $R^5$ is substituted or unsubstituted aryl, heteroaryl, alkyl or heteroalkyl; wherein the aryl, heteroaryl, alkyl or heteroalkyl group may be substituted with one or more occurrences of hydrogen, halogen, hydroxyl, lower alkoxy and/or lower alkyl; and m, p and q are each independently an integer from 0–6.

In certain embodiments of special interest each occurrence of $R^{3b}$ and $R^4$ is independently phenyl or —(CH$_2$)phenyl substituted with —COOH (or an ester or bioisostere thereof) and optionally further substituted with one or more of hydroxyl, alkoxy, thio, thioalkyl, —COOH, —COO(alkyl), —CONH$_2$, —NH(CO)alkyl, —SO$_2$R$^{4a}$, lower alkyl, lower heteroalkyl, aryl, heteroaryl, alkylaryl, alkylheteroaryl, heteroalkylaryl, or heteroalkylheteroaryl, or wherein two adjacent groups taken together form an aryl, heteroaryl, cycloaliphatic, or heterocycloaliphatic group, wherein $R^{4a}$ is acyl, or substituted or unsubstituted alkyl or aryl.

IX) Compounds of the Formula (and Pharmaceutically Acceptable Derivatives thereof)

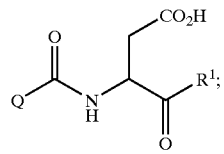

wherein Q is an aryl or heteroaryl moiety substituted with

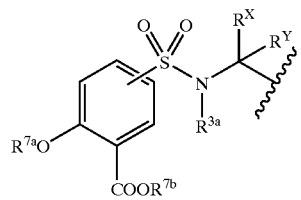

or

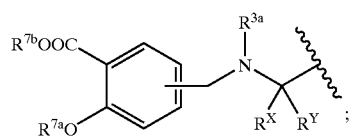

wherein $R^X$ and $R^Y$ are independently hydrogen or lower alkyl; $R^{3a}$ is hydrogen, a nitrogen protecting group, lower alkyl or lower acyl; $R^{7a}$ is hydrogen, a protecting group, lower alkyl or lower acyl; $R^{7b}$ is hydrogen, a protecting group or lower alkyl; and $R^1$ is as defined generally above and in subclasses herein. It is to be understood that Q may be additionally substituted by one or more occurrences of a variety of substitutents as defined herein in the section entitled "Compounds and Definitions".

In certain embodiments of special interest, the compound has the structure:

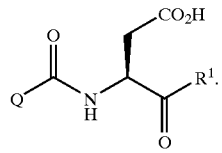

In certain embodiments, R¹ is hydrogen, alkyl, aryl or

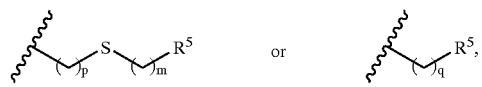

wherein R⁵ is substituted or unsubstituted aryl, heteroaryl, alkyl or heteroalkyl; wherein the aryl, heteroaryl, alkyl or heteroalkyl group may be substituted with one or more occurrences of hydrogen, halogen, hydroxyl, lower alkoxy and/or lower alkyl; and m, p and q are each independently an integer from 0–6. In certain other embodiments, $R^X$, $R^Y$, $R^{3a}$, $R^{7a}$ and $R^{7b}$ are each hydrogen. In certain exemplary embodiments, Q is a substituted or unsubstituted heteroaryl moiety. In certain embodiments, Q is a 5-6 membered aryl or heteroaryl moiety. In yet other embodiments, Q is an aryl or heteroaryl moiety having one of the structures:

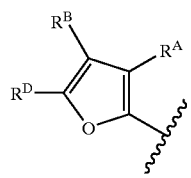 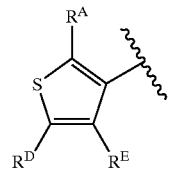

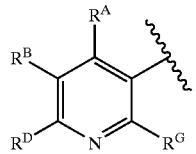 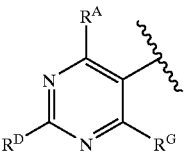

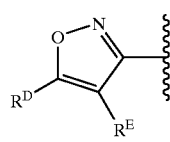 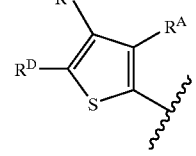

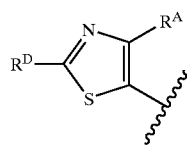 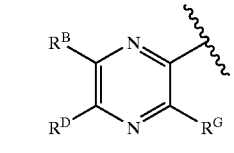

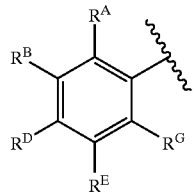 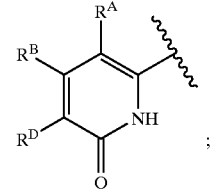 ;

wherein $R^A$—$R^G$ are as defined generally above and in classes and subclasses herein, and one of $R^A$—$R^G$ is

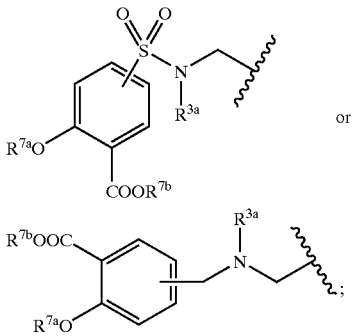

wherein $R^{3a}$ is hydrogen, a nitrogen protecting group, lower alkyl or lower acyl; $R^{7a}$ is hydrogen, a protecting group, lower alkyl or lower acyl; $R^{7b}$ is hydrogen, a protecting group or lower alkyl.

X) Compounds of the Formula (and Pharmaceutically Acceptable Derivatives thereof)

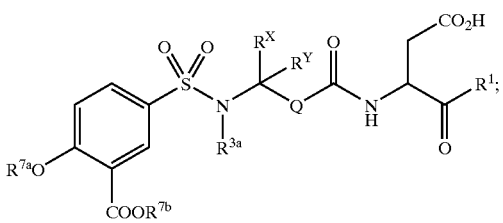

wherein R¹ is as defined generally above and in subclasses herein; Q is a substituted or unsubstituted aryl or heteroaryl moiety; $R^X$ and $R^Y$ are independently hydrogen or lower alkyl; $R^{3a}$ is hydrogen, a nitrogen protecting group, lower alkyl or lower acyl; $R^{7a}$ is hydrogen, a protecting group, lower alkyl or lower acyl; and $R^{7b}$ is hydrogen, a protecting group or lower alkyl.

In certain embodiments of special interest, $R^X$ and $R^Y$ are each hydrogen and the compound has the structure:

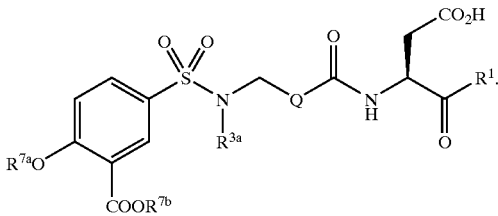

In certain other embodiments, $R^X$, $R^Y$, $R^{3a}$, $R^{7a}$ and $R^{7b}$ are each hydrogen. In certain exemplary embodiments, Q is a substituted or unsubstituted heteroaryl moiety. In certain embodiments, Q is a 5–6 membered aryl or heteroaryl moiety. In certain other embodiments, R¹ is hydrogen, alkyl, aryl or

wherein R⁵ is substituted or unsubstituted aryl, heteroaryl, alkyl or heteroalkyl; wherein the aryl, heteroaryl, alkyl or heteroalkyl group may be substituted with one or more occurrences of hydrogen, halogen, hydroxyl, lower alkoxy and/or lower alkyl; and m, p and q are each independently an integer from 0–6. In yet other embodiments, $R^X$, $R^Y$, $R^{3a}$, $R^{7a}$ and $R^{7b}$ are each hydrogen, Q is a substituted or unsubstituted heteroaryl moiety and the compound has the structure:

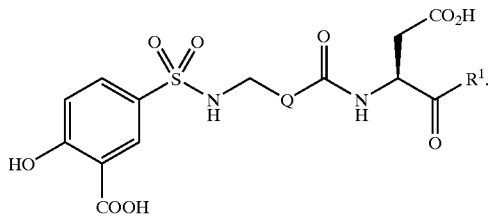

In yet other embodiments, Q is an aryl or heteroaryl moiety having one of the structures:

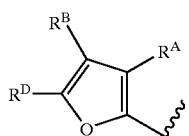 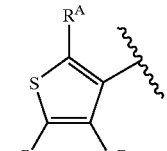

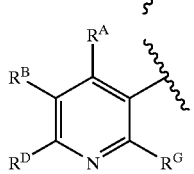 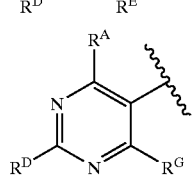

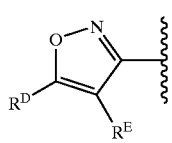 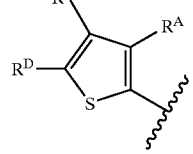

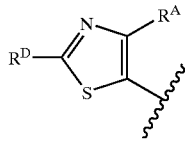 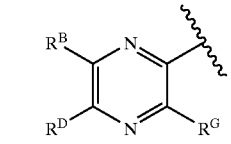

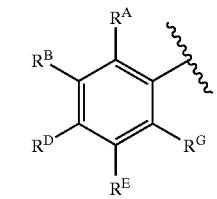 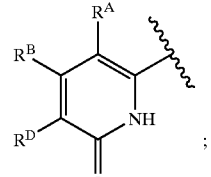

wherein $R^A$—$R^G$ are as defined generally above and in classes and subclasses herein, and one of $R^A$—$R^G$ is

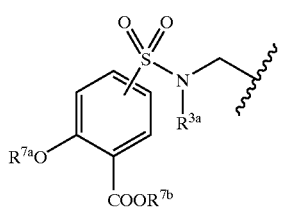 or

wherein $R^{3a}$ is hydrogen, a nitrogen protecting group, lower alkyl or lower acyl; $R^{7a}$ is hydrogen, a protecting group, lower alkyl or lower acyl; $R^{7b}$ is hydrogen, a protecting group or lower alkyl.

XI) Compounds of the Formula (and Pharmaceutically Acceptable Derivatives thereof)

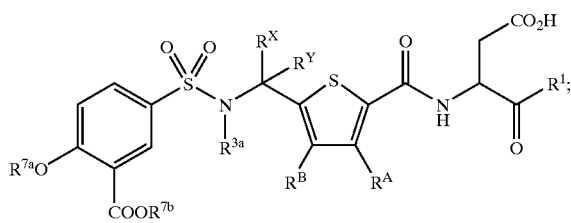

wherein $R^1$, $R^A$ and $R^B$ are as defined generally above and in subclasses herein; $R^X$ and $R^Y$ are independently hydrogen or lower alkyl; $R^{3a}$ is hydrogen, a nitrogen protecting group, lower alkyl or lower acyl; and $R^{7a}$ is hydrogen, a protecting group, lower alkyl or lower acyl; $R^{7b}$ is hydrogen, a protecting group or lower alkyl.

In certain embodiments of special interest, $R^X$ and $R^Y$ are each hydrogen and the compound has the structure:

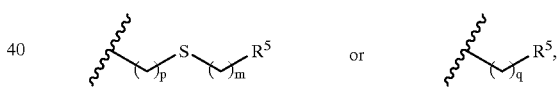

In certain other embodiments, $R^X$, $R^Y$, $R^{3a}$, $R^{7a}$ and $R^{7b}$ are each hydrogen. In certain exemplary embodiments, $R^1$ is hydrogen, alkyl, aryl or

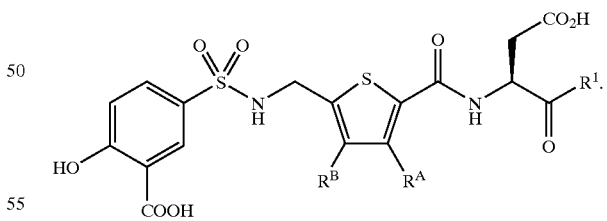

wherein $R^5$ is substituted or unsubstituted aryl, heteroaryl, alkyl or heteroalkyl; wherein the aryl, heteroaryl, alkyl or heteroalkyl group may be substituted with one or more occurrences of hydrogen, halogen, hydroxyl, lower alkoxy and/or lower alkyl; and m, p and q are each independently an integer from 0–6. In certain other embodiments, $R^A$ and $R^B$ are independently hydrogen, lower alkyl, hydroxyl, lower alkoxy or halogen. In yet other embodiments, $R^X$, $R^Y$, $R^{3a}$, $R^{7a}$ and $R^{7b}$ are each hydrogen, and the compound has the structure:

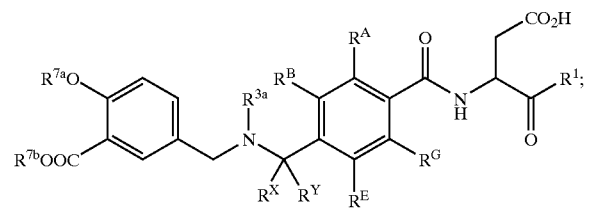

XII) Compounds of the Formula (and Pharmaceutically Acceptable Derivatives thereof)

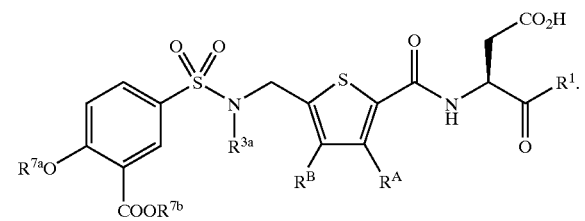

wherein $R^1$, $R^A$, $R^B$, $R^E$ and $R^G$ are as defined generally above and in subclasses herein; $R^X$ and $R^Y$ are independently hydrogen or lower alkyl; $R^{3a}$ is hydrogen, a nitrogen protecting group, lower alkyl or lower acyl; $R^{7a}$ is hydrogen, a protecting group, lower alkyl or lower acyl; and $R^{7b}$ is hydrogen, a protecting group or lower alkyl.

In certain embodiments of special interest, $R^X$ and $R^Y$ are each hydrogen and the compound has the structure:

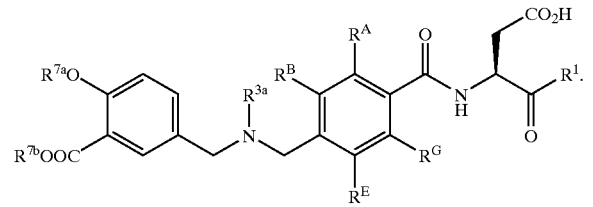

In certain embodiments, $R^A$, $R^B$, $R^E$ and $R^G$ are independently hydrogen, lower alkyl, hydroxyl, lower alkoxy or halogen. In certain other embodiments, $R^A$, $R^B$, $R^E$ and $R^G$ are each hydrogen. In certain other embodiments, $R^X$, $R^Y$, $R^{7a}$ and $R^{7b}$ are each hydrogen. In certain exemplary embodiments, $R^1$ is hydrogen, alkyl, aryl or

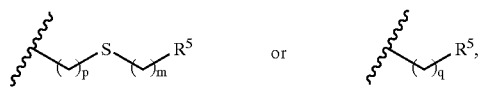

wherein $R^5$ is substituted or unsubstituted aryl, heteroaryl, alkyl or heteroalkyl; wherein the aryl, heteroaryl, alkyl or heteroalkyl group may be substituted with one or more occurrences of hydrogen, halogen, hydroxyl, lower alkoxy and/or lower alkyl; and m, p and q are each independently an integer from 0–6. In yet other embodiments, $R^X$, $R^Y$, $R^A$, $R^B$, $R^E$, $R^G$, $R^{7a}$ and $R^{7b}$ are each hydrogen, and the compound has the structure:

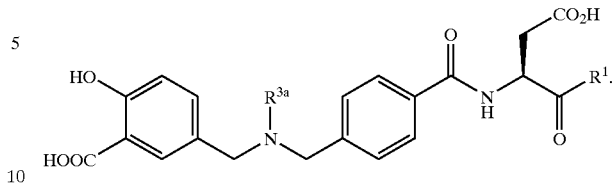

It will also be appreciated that for each of the subgroups I–XII described above, a variety of other subclasses are of special interest, including, but not limited to those classes described above i)–xxxiii) and classes, subclasses and species of compounds described above and in the examples herein.

Some of the foregoing compounds can exist in various isomeric forms, e.g., stereoisomers and/or diastereomers. Furthermore, certain compounds, as described herein may have one or more double bonds that can exist as either the Z or E isomer, unless otherwise indicated. The invention additionally encompasses the compounds as individual isomers (e.g., as either the R or S enantiomer) substantially free of other isomers and alternatively, as mixtures of various isomers, e.g., racemic mixtures of stereoisomers. In addition to the above-mentioned compounds per se, this invention also encompasses pharmaceutically acceptable derivatives of these compounds and compositions comprising one or more compounds of the invention and one or more pharmaceutically acceptable excipients or additives, as well as compositions comprising one or more inventice compounds in combination with one or more additional therapeutic agents.

Compounds of the invention may be prepared by crystallization of compound of formula (I) under different conditions and may exist as various polymorphs of compound of general formula (I) forming part of this invention. For example, using different solvents commonly used or their mixtures for recrystallization; crystallizations at different temperatures; various modes of cooling, ranging from very fast to very slow cooling during crystallizations. Polymorphs may also be obtained by heating or melting the compound followed by gradual or fast cooling. The presence of polymorphs may be determined by solid probe nmr spectroscopy, ir spectroscopy, differential scanning calorimetry, powder X-ray diffractogram or such other techniques. Thus, the present invention encompasses inventive compounds, their derivatives, their tautomeric forms, their stereoisomers, their polymorphs, their pharmaceutically acceptable salts their pharmaceutically acceptable solvates and pharmaceutically acceptable compositions containing them.

2) Compounds and Definitions

As discussed generally above and herein, in one aspect, this invention provides novel compounds with a range of biological properties. In particular, in certain embodiments, compounds of this invention have biological activities relevant for the treatment of caspase-mediated diseases, and in certain embodiments those diseases mediated by caspase-3 or -7.

Compounds of this invention include those specifically set forth above and described herein, and are illustrated in part by the various classes, subgenera and species disclosed elsewhere herein.

It will be appreciated by one of ordinary skill in the art that asymmetric centers may exist in the compounds of the present invention. Thus, inventive compounds and pharmaceutical compositions thereof may be in the form of an individual enantiomer, diastereomer or geometric isomer, or may be in the form of a mixture of stereoisomers. Furthermore, it will be appreciated that certain of the compounds disclosed herein contain one or more double bonds and these double bonds can be either Z or E, unless otherwise indicated. In certain embodiments, the compounds of the invention are enantiopure compounds. In certain other embodiments, a mixture of stereoisomers or diastereomers are provided.

Additionally, the present invention provides pharmaceutically acceptable derivatives of the inventive compounds, and methods of treating a subject using these compounds, pharmaceutical compositions thereof, or either of these in combination with one or more additional therapeutic agents. The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include among others pro-drugs. A pro-drug is a derivative of a compound, usually with significantly reduced pharmacological activity, which contains an additional moiety that is susceptible to removal in vivo yielding the parent molecule as the pharmacologically active species. An example of a pro-drug is an ester which is cleaved in vivo to yield a compound of interest. Pro-drugs of a variety of compounds, and materials and methods for derivatizing the parent compounds to create the pro-drugs, are known and may be adapted to the present invention. Certain exemplary pharmaceutical compositions and pharmaceutically acceptable derivatives will be discussed in more detail herein below.

Certain compounds of the present invention, and definitions of specific functional groups are also described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference. Furthermore, it will be appreciated by one of ordinary skill in the art that the synthetic methods, as described herein, utilize a variety of protecting groups. By the term "protecting group", has used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group must be selectively removed in good yield by readily available, preferably nontoxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen and carbon protecting groups may be utilized. For example, in certain embodiments, as detailed herein, certain exemplary oxygen protecting groups are utilized. These oxygen protecting groups include, but are not limited to methyl ethers, substituted methyl ethers (e.g., MOM (methoxymethyl ether), MTM (methylthiomethyl ether), BOM (benzyloxymethyl ether), PMBM (p-methoxybenzyloxymethyl ether), to name a few), substituted ethyl ethers, substituted benzyl ethers, silyl ethers (e.g., TMS (trimethylsilyl ether), TES (triethylsilylether), TIPS (triisopropylsilyl ether), TBDMS (t-butyldimethylsilyl ether), tribenzyl silyl ether, TBDPS (t-butyldiphenyl silyl ether), to name a few), esters (e.g., formate, acetate, benzoate (Bz), trifluoroacetate, dichloroacetate, to name a few), carbonates, cyclic acetals and ketals. In certain other exemplary embodiments, nitrogen protecting groups are utilized. These nitrogen protecting groups include, but are not limited to, carbamates (including methyl, ethyl and substituted ethyl carbarates (e.g., Troc), to name a few) amides, cyclic imide derivatives, N-Alkyl and N-Aryl amines, imine derivatives, and enamine derivatives, to name a few. Certain other exemplary protecting groups are detailed herein, however, it will be appreciated that the present invention is not intended to be limited to these protecting groups; rather, a variety of additional equivalent protecting groups can be readily identified using the above criteria and utilized in the present invention. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example of caspase-mediated disorders, as described generally above. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "aliphatic", as used herein, includes both saturated and unsaturated, straight chain (i.e., unbranched), branched, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (cyclic, acyclic, substituted, unsubstituted, branched or unbranched) having 1–6 carbon atoms.

In certain embodiments, the alkyl, alkenyl and alkynyl groups employed in the invention contain 1–20 aliphatic carbon atoms. In certain other embodiments, the alkyl, alkenyl, and alkynyl groups employed in the invention contain 1–10 aliphatic carbon atoms. In yet other embodiments, the alkyl, alkenyl, and alkynyl groups employed in the invention contain 1–8 aliphatic carbon atoms. In still other embodiments, the alkyl, alkenyl, and alkynyl groups employed in the invention contain 1–6 aliphatic carbon atoms. In yet other embodiments, the alkyl, alkenyl, and alkynyl groups employed in the invention contain 1–4 carbon atoms. Illustrative aliphatic groups thus include, but are not limited to, for example, methyl, ethyl, n-propyl, isopropyl, cyclopropyl, —$CH_2$-Cyclopropyl, allyl, n-butyl, sec-butyl, isobutyl, tert-butyl, cyclobutyl, —$CH_2$-cyclobutyl, n-pentyl, sec-pentyl, isopentyl, tert-pentyl, cyclopentyl, —$CH_2$-cyclopentyl-n, hexyl, sec-hexyl, cyclohexyl, —$CH_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "alkoxy" (or "alkyloxy"), or "thioalkyl" as used herein refers to an alkyl group, as previously defined, attached to the parent molecular moiety through an oxygen atom or through a sulfur atom. In certain embodiments, the alkyl group contains 1–20 aliphatic carbon atoms. In certain other embodiments, the alkyl group contains 1–10 aliphatic carbon atoms. In yet other embodiments, the alkyl, alkenyl, and alkynyl groups employed in the invention contain 1–8 aliphatic carbon atoms. In still other embodiments, the alkyl group contains 1–6 aliphatic carbon atoms. In yet other embodiments, the alkyl group contains 1–4 aliphatic carbon atoms. Examples of alkoxy, include but are not limited to, methoxy, ethoxy, propoxy, isopropoxy, n-butoxy, tert-butoxy, neopentoxy and n-hexoxy. Examples of thioalkyl include, but are not limited to, methylthio, ethylthio, propylthio, isopropylthio, n-butylthio, and the like.

The term "alkylamino" refers to a group having the structure —NHR' wherein R' is alkyl, as defined herein. The term "dialkylamino" refers to a group having the structure —N(R')$_2$, wherein R' is alkyl, as defined herein. The term "aminoalkyl" refers to a group having the structure $NH_2$R'—, wherein R' is alkyl, as defined herein. In certain embodiments, the alkyl group contains 1–20 aliphatic carbon atoms. In certain other embodiments, the alkyl group contains 1–10 aliphatic carbon atoms. In yet other embodiments, the alkyl, alkenyl, and alkynyl groups employed in the invention contain 1–8 aliphatic carbon atoms. In still other embodiments, the alkyl group contains 1–6 aliphatic carbon atoms. In yet other embodiments, the alkyl group contains 1–4 aliphatic carbon atoms. Examples of alkylamino include, but are not limited to, methylamino, ethylamino, iso-propylamino and the like.

Some examples of substituents of the above-described aliphatic (and other) moieties of compounds of the invention include, but are not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_X$; —$CO_2(R_X)$; —$CON(R_X)_2$; —$OC(O)R_X$; —$OCO_2R_X$; —$OCON(R_X)_2$; —$N(R_X)_2$; —$S(O)_2R_X$; —$NR_X(CO)R_X$ wherein each occurrence of $R_X$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

In general, the terms "aryl" and "heteroaryl", as used herein, refer to stable mono- or polycyclic, heterocyclic, polycyclic, and polyheterocyclic unsaturated moieties having preferably 3–14 carbon atoms, each of which may be substituted or unsubstituted. Substituents include, but are not limited to, any of the previously mentioned substitutents, i.e., the substituents recited for aliphatic moieties, or for other moieties as disclosed herein, resulting in the formation of a stable compound. In certain embodiments of the present invention, "aryl" refers to a mono- or bicyclic carbocyclic ring system having one or two aromatic rings including, but not limited to, phenyl, naphthyl, tetrahydronaphthyl, indanyl, indenyl and the like. In certain embodiements of the present invention, the term "heteroaryl", as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups (including bicyclic aryl groups) can be unsubstituted or substituted, wherein substitution includes replacement of one or more of the hydrogen atoms thereon independently with any one or more of the following moieties including, but not limited to: aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_X$; —$CO_2(R_X)$; —$CON(R_X)_2$; —$OC(O)R_X$; —$OCO_2R_X$; —$OCON(R_X)_2$; —$N(R_X)_2$; —$S(O)_2R_X$; —$NR_X(CO)R_X$ wherein each occurrence of $R_X$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additionally, it will be appreciated, that any two adjacent groups taken together may represent a 4, 5, 6, or 7-membered cyclic, substituted or unsubstituted aliphatic or heteroaliphatic moiety. Additional examples of generally applicable substituents are illustrated by the specific embodiments shown in the Examples that are described herein.

The term "cycloalkyl", as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of other aliphatic, heteroaliphatic or hetercyclic moieties, may optionally be substituted with substituents including, but not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_X$; —CO$_2$(R$_X$); —CON(R$_X$)$_2$; —OC(O)R$_X$; —OCO$_2$R$_X$; —OCON(R$_X$)$_2$; —N(R$_X$)$_2$; —S(O)$_2$R$_X$; —NR$_X$(CO)R$_X$ wherein each occurrence of R$_X$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additionally, it will be appreciated that any of the cycloaliphatic or heterocycloaliphatic moieties described above and herein may comprise an aryl or heteroaryl moiety fused thereto. Additional examples of generally applicable substituents are illustrated by the specific embodiments shown in the Examples that are described herein.

The term "heteroaliphatic", as used herein, refers to aliphatic moieties which contain one or more oxygen sulfur, nitrogen, phosphorus or silicon atoms, e.g., in place of carbon atoms. Heteroaliphatic moieties may be branched, unbranched, cyclic or acyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_X$; —CO$_2$(R$_X$); —CON(R$_X$)$_2$; —OC(O)R$_X$; —OCO$_2$R$_X$; —OCON(R$_X$)$_2$; —N(R$_X$)$_2$; —S(O)$_2$R$_X$; —NR$_X$(CO)R$_X$ wherein each occurrence of R$_X$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additionally, it will be appreciated that any of the cycloaliphatic or heterocycloaliphatic moieties described above and herein may comprise an aryl or heteroaryl moiety fused thereto. Additional examples of generally applicable substituents are illustrated by the specific embodiments shown in the Examples that are described herein.

The terms "halo" and "halogen" as used herein refer to an atom selected from fluorine, chlorine, bromine and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "heterocycloalkyl" or "heterocycle", as used herein, refers to a non-aromatic 5-, 6- or 7-membered ring or a polycyclic group, including, but not limited to a bi- or tr-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may be optionally be oxidized, (iii) the nitrogen heteroatom may optionally be quaternized, and (iv) any of the above heterocyclic rings may be fused to a substituted or unsubstituted aryl or heteroaryl ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. In certain embodiments, a "substituted heterocycloalkyl or heterocycle" group is utilized and as used herein, refers to a heterocycloalkyl or heterocycle group, as defined above, substituted by the independent replacement of one or more of the hydrogen atoms thereon with but are not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_X$; —CO$_2$(R$_X$); —CON(R$_X$)$_2$; —OC(O)R$_X$; —OCO$_2$R$_X$; —OCON(R$_X$)$_2$; —N(R$_X$)$_2$; —S(O)$_2$R$_X$; —NR$_X$(CO)R$_X$ wherein each occurrence of R$_X$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substitutents described above and herein may be substituted or unsubstituted. Additional examples or generally applicable substituents are illustrated by the specific embodiments shown in the Examples which are described herein.

3) Research Uses, Formulation and Administration

According to the present invention, the inventive compounds may be assayed in any of the available assays known in the art for identifying compounds having caspase inhibitory activity. For example, the assay may be cellular or non-cellular, in vivo or in vitro, high- or low-throughput format, etc.

In certain exemplary embodiments, compounds of this invention were assayed for their ability to inhibit caspases 3 and 7.

Thus, in one aspect, compounds of this invention which are of particular interest include those which:

exhibit the ability to act as inhibitors of caspases;

exhibit the ability to act as inhibitors of apoptotic caspases;

exhibit the ability to act as inhibitors of caspases 3;

exhibit the ability to act as inhibitors of caspases 7;

exhibit the ability to act as inhibitors of caspases 3 and/or caspases 7;

are useful in therapeutic applications related to caspase-mediated diseases.

In certain embodiments, compounds of the invention are selective Caspase 3 inhibitors. In certain exemplary embodiments, inventive compounds have K$_i$ values ($\mu$M) for caspase 1, caspase 2, caspase 4, caspase 5, caspase 6 and/or caspase 8 that are $\geq$2 fold greater than K$_i^{casp-3}$ ($\mu$M). In certain other embodiments, inventive compounds have K$_i$ values ($\mu$M) for caspase 1, caspase 2, caspase 4, caspase 5, caspase 6 and/or caspase 8 that are ≧5 fold greater than $K_i^{casp-3}$ ($\mu$M). In certain other embodiments, inventive compounds have $K_i$ values ($\mu$M) for caspase 1, caspase 2, caspase 4, caspase 5, caspase 6 and/or caspase 8 that are ≧10 fold greater than $K_i^{casp-3}$ ($\mu$M). In certain other embodiments, inventive compounds have $K_i$ values ($\mu$M) for caspase 1, caspase 2, caspase 4, caspase 5, caspase 6 and/or caspase 8 that are ≧100 fold greater than $K_i^{casp-3}$ ($\mu$M). In certain other embodiments, inventive compounds have $K_i$ values ($\mu$M) for caspase 1, caspase 2, caspase 4, caspase 5, caspase 6 and/or caspase 8 that are ≧1000 fold greater than $K_i^{casp-3}$ ($\mu$M). In certain other embodiments, inventive compounds have $K_i$ values ($\mu$M) for caspase 1, caspase 2, caspase 4, caspase 5, caspase 6 and/or caspase 8 that are ≧2000 fold greater than $K_i^{casp-3}$ ($\mu$M). In certain exemplary embodiments, inventive compounds have $K_i^{casp-3}$≦2 $\mu$M. In certain other embodiments, inventive compounds have $K_i^{casp-3}$≦1 $\mu$M. In certain other embodiments, inventive compounds have $K_i^{casp-3}$≦0.050 $\mu$M. In certain exemplary embodiments, inventive compounds have $K_i^{casp-3}$≦0.50 $\mu$M. In certain other embodiments, inventive compounds have $K_i^{casp-3}$≦0.010 $\mu$M. In yet other embodiments, inventive compounds have $K_i^{casp-3}$≦0.015 $\mu$M. In certain other embodiments, inventive compounds have $K_i^{casp-3}$≦0.005 $\mu$M.

In certain embodiments, compounds of the invention are selective Caspase 7 inhibitors. In certain exemplary embodiments, inventive compounds have $K_i$ values ($\mu$M) for caspase 1, caspase 2, caspase 4, caspase 5, caspase 6 and/or caspase 8 that are ≧2 fold greater than $K_i^{casp-7}$ ($\mu$M). In certain other embodiments, inventive compounds have $K_i$ values ($\mu$M) for caspase 1, caspase 2, caspase 4, caspase 5, caspase 6 and/or caspase 8 that are ≧5 fold greater than $K_i^{casp-7}$ ($\mu$M). In certain other embodiments, inventive compounds have $K_i$ values ($\mu$M) for caspase 1, caspase 2, caspase 4, caspase 5, caspase 6 and/or caspase 8 that are ≧10 fold greater than $K_i^{casp-7}$ ($\mu$M). In certain other embodiments, inventive compounds have $K_i$ values ($\mu$M) for caspase 1, caspase 2, caspase 4, caspase 5, caspase 6 and/or caspase 8 that are ≧50 fold greater than $K_i^{casp-7}$ ($\mu$M). In certain other embodiments, inventive compounds have $K_i$ values ($\mu$M) for caspase 1, caspase 2, caspase 4, caspase 5, caspase 6 and/or caspase 8 that are ≧100 fold greater than $K_i^{casp-7}$ ($\mu$M). In certain other embodiments, inventive compounds have $K_i$ values ($\mu$M) for caspase 1, caspase 2, caspase 4, caspase 5, caspase 6 and/or caspase 8 that are ≧200 fold greater than $K_i^{casp-7}$ ($\mu$M). In certain other embodiments, inventive compounds have $K_i$ values ($\mu$M) for caspase 1, caspase 2, caspase 4, caspase 5, caspase 6 and/or caspase 8 that are ≧500 fold greater than $K_i^{casp-7}$ ($\mu$M). In certain exemplary embodiments, inventive compounds have $K_i^{casp-7}$≦2 $\mu$M. In certain other embodiments, inventive compounds have $K_i^{casp-3}$≦1 $\mu$M. In certain other embodiments, inventive compounds have $K_i^{casp-7}$≦0.50 $\mu$M. In certain exemplary embodiments, inventive compounds have $K_i^{casp-7}$≦0.20 $\mu$M. In certain other embodiments, inventive compounds have $K_i^{casp-7}$≦0.10 $\mu$M. In yet other embodiments, inventive compounds have $K_i^{casp-7}$≦0.05 $\mu$M. In certain other embodiments, inventive compounds have $K_i^{casp-7}$≦0.005 $\mu$M.

As discussed above, in certain embodiments, certain of the compounds as described herein exhibit activity generally as inhibitors of caspases. More specifically, compounds of the invention demonstrate activity as inhibitors of apoptotic caspases and thus, in another aspect, the invention further provides a method for treating caspase-mediated disorders (such as those associated with abnormally high apoptosis) including, but not limited to, stroke, traumatic, brain injury, spinal cord injury, meningitis, Alzheimer's disease, Parkinson's disease, Huntington's disease, Kennedy's disease, prion disease, multiple sclerosis, spinal muscular atrophy, myocardial infarction, congestive heart failure and various other forms of acute and chronic heart disease, atherosclerosis, aging, burns, organ transplant rejection, graft versus host disease, hepatitis-B, -C, -G, various forms of liver disease including acute alcoholic hepatitis, yellow fever, dengue fever, Japanese encephalitis, glomerulonephritis, renal disease, *H. pylori*-associated gastric and duodenal ulcer disease, HIV infection, tuberculosis, alopecia, diabetes, sepsis, Shigellosis, uveitis, inflammatory peritonitis, pancreatitis, erythematosus, scleroderma, chronic thyroiditis, Graves' disease, autoimmune gastritis, autoimmune hemolytic anemia, autoimmune neutropenia, thrombocytopenia, HIV-related encephalitis, myasthenia gravis, small bowel ischemia in disease or post-surgery, psoriasis, atopic dermatitis, myelodysplatic syndrome, acute and chronic myelogenous leukemia, metastatic melanoma, Kaposi's sarcoma, and Wiscott-Aldrich syndrome.

In certain embodiments, the method involves the administration of a therapeutically effective amount of the compound or a pharmaceutically acceptable derivative thereof to a subject (including, but not limited to a human or animal) in need of it. In certain embodiments, a pharmaceutical composition comprising an inventive compound (or pharmaceutically acceptable derivative thereof), a carrier or diluent and optionally an additional therapeutic agent is provided.

Pharmaceutical Compositions

As discussed above this invention provides novel compounds that have biological properties useful for the treatment of disorders mediated by caspases, and in particular those mediated by apoptotic caspases. In certain embodiments, the inventive compounds as useful for the treatment of disorders resulting from an overactive apoptotic response. In certain embodiments of special interest, the compounds of the invention are useful for the treatment of stroke, traumatic, brain injury, spinal cord injury, meningitis, Alzheimer's disease, Parkinson's disease, Huntington's disease, Kennedy's disease, prion disease, multiple sclerosis, spinal muscular atrophy, myocardial infarction, congestive heart failure and various other forms of acute and chronic heart disease, atherosclerosis, aging, burns, organ transplant rejection, graft versus host disease, hepatitis-B, -C, -G, various forms of liver disease including acute alcoholic hepatitis, yellow fever, dengue fever, Japanese encephalitis, glomerulonephritis, renal disease, *H. pylori*-associated gastric and duodenal ulcer disease, HIV infection, tuberculosis, alopecia, diabetes, sepsis, Shigellosis, uveitis, inflammatory peritonitis, pancreatitis, erythematosus, scleroderma, chronic thyroiditis, Graves' disease, autoimmune gastritis, autoimmune hemolytic anemia, autoimmune neutropenia, thrombocytopenia, HIV-related encephalitis, myasthenia gravis, small bowel ischemia in disease or post-surgery, psoriasis, atopic dermatitis, myelodysplatic syndrome, acute and chronic myelogenous leukemia, metastatic melanoma, Kaposi's sarcoma, and Wiscott-Aldrich syndrome. Accordingly, in another aspect of the present invention, pharmaceutical compositions are provided, which comprise any one of the compounds described herein (or a prodrug, pharmaceutically acceptable salt or other pharmaceutically acceptable derivative thereof), and optionally comprise a pharmaceutically acceptable carrier. In certain embodiments, these compositions optionally further comprise one or more additional therapeutic agents.

Alternatively, a compound of this invention may be administered to a patient in need thereof in combination with the administration of one or more other therapeutic agents. For example, additional therapeutic agents for conjoint administration or inclusion in a pharmaceutical composition with a compound of this invention may be an approved anti-HIV/AIDS agent (e.g., protease inhibitors, retrovirals), or an agent for the treatment of ischemia/reperfusion injury (e.g., stroke and myocardial infarction) and traumatic brain and spinal cord injuries, such as NMDA antagonists and the like, or it may be any one of a number of agents undergoing approval in the Food and Drug Administration that ultimately obtain approval for the treatment of any disorder resulting from a caspase-mediated disorder or, in certain embodiments, from an inappropriate apoptotic response. It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or a pro-drug or other adduct or derivative of a compound of this invention which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in *J. Pharmaceutical Sciences*, 66: 1–19 (1977), incorporated herein by reference. The salts can be prepared in situ during the final isolation and purification of the compounds of the invention, or separately by reacting a free base or free acid function with a suitable reagent, as described generally below. For example, a free base function can be reacted with a suitable acid. Furthermore, where the compounds of the invention carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hernisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like.

Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Additionally, as used herein, the term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

Furthermore, the term "pharmaceutically acceptable prodrugs" as used herein refers to those prodrugs of the compounds of the present invention which are, within the scope of sound medical judgment, suitable for use in contact with the issues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

As described above, the pharmaceutical compositions of the present invention additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogenfree water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses and Formulations of Compounds of the Invention

As described in more detail herein, in general, the present invention provides compounds useful for the treatment of caspase-mediated disorders, and in certain embodiments provides compounds useful for the treatment of disorders resulting from an inappropriate (e.g., excessive) apoptotic response. In certain embodiments of special interest, the compounds are useful as inhibitors of caspase-3. As detailed herein, certain compounds of special interest are selective inhibitors of caspase-3, and exhibit inhibitor selectivity ($K_i(\mu M)$) in the range of 0.001 to about 0.080 $\mu$M. Additionally, certain other compounds of special interest are also inhibitors of caspase-7, and exhibit inhibitor selectivity ($K_i(\mu M)$) in the range of 0.08 $\mu$M to about 0.95 $\mu$M.

As discussed above, compounds of the invention exhibit the ability to inhibit caspases and in certain embodiments apoptotic caspases. Thus, compounds of the invention are particularly useful for the treatment of disorders resulting from overactive apoptotic activity.

Thus, as described above, in another aspect of the invention, a method for the treatment of caspase-mediated disorders is provided comprising administering a therapeutically effective amount of a compound of formula (I), as described herein, to a subject in need thereof. In certain embodiments, the method is utilized for the treatment of disorders mediated by apoptotic caspases, and in particular, those disorders resulting from an overactive apoptotic response. It will be appreciated that the compounds and compositions, according to the method of the present invention, may be administered using any amount and any route of administration effective for the treatment of caspase-mediated disorders (and including the treatment of disorders mediated by apoptotic caspases). For example, in certain exemplary embodiments, compounds of the invention are useful as inhibitors of apoptosis and thus can be used for the treatment of disorders including, but not limited to, cancer, immune disorders, HIV infection, and Alzheimer's disease, to name a few. Thus, the expression "effective amount" as used herein, refers to a sufficient amount of agent to cause a detectable decrease in the severity of the disease or in caspase activity and/or cell apoptosis, as measured by any of the assays described in the examples herein. The exact amount required will vary from subject to subject, depending on the species, age, and general condition of the subject, the severity of the infection, the particular therapeutic agent, its mode of administration, and the like. The compounds of the invention are preferably formulated in dosage unit form for ease of administration and uniformity of dosage. The expression "dosage unit form" as used herein refers to a physically discrete unit of therapeutic agent appropriate for the patient to be treated. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts (see, for example, Goodman and Gilman's, "The Pharmacological Basis of Therapeutics", Tenth Edition, A. Gilman, J. Hardman and L. Limbird, eds., McGraw-Hill Press, 155–173, 2001, which is incorporated herein by reference in its entirety).

Furthermore, after formulation with an appropriate pharmaceutically acceptable carrier in a desired dosage, the pharmaceutical compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered at dosage levels of about 0.001 mg/kg to about 50 mg/kg, from about 0.01 mg/kg to about 25 mg/kg, or from about 0.1 mg/kg to about 10 mg/kg of subject body weight per day, one or more times a day, to obtain the desired therapeutic effect. It will also be appreciated that dosages smaller than 0.001 mg/kg or greater than 50 mg/kg (for example 50–100 mg/kg) can be administered to a subject. In certain embodiments, compounds are administered orally or parenterally.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension or crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include (poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose and starch. Such dosage forms may also comprise, as in normal practice, additional substances other than inert diluents, e.g., tableting lubricants and other tableting aids such as magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms are made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

It will also be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anti-apoptotic agent, for example), or they may achieve different effects (e.g., control of any adverse effects).

For example, other therapies or anticancer agents that may be used in combination with the inventive compounds of the present invention include surgery, radiotherapy (in but a few examples, γ-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), to name a few. For a more comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

In certain embodiments, the pharmaceutical compositions of the present invention further comprises one or more additional therapeutically active ingredients (e.g., chemotherapeutic and/or palliative). For purposes of the invention, the term "Palliative" refers to treatment that is focused on the relief of symptoms of a disease and/or side effects of a therapeutic regimen, but is not curative. For example, palliative treatment encompasses painkillers, antinausea medications and anti-sickness drugs. In addition, chemotherapy, radiotherapy and surgery can all be used palliatively (that is, to reduce symptoms without going for cure; e.g., for shrinking tumors and reducing pressure, bleeding, pain and other symptoms of cancer).

Treatment Kits

In other embodiments, the present invention relates to a kit for conveniently and effectively carrying out the methods in accordance with the present invention. In general, the pharmaceutical pack or kit comprises one or more containers filled with one or more of the ingredients of the pharmaceutical compositions of the invention. Such kits are especially suited for the delivery of solid oral forms such as tablets or capsules. Such a kit preferably includes a number of unit dosages, and may also include a card having the dosages oriented in the order of their intended use. If desired, a memory aid can be provided, for example in the form of numbers, letters, or other markings or with a calendar insert, designating the days in the treatment schedule in which the dosages can be administered. Alternatively, placebo dosages, or calcium dietary supplements, either in a form similar to or distinct from the dosages of the pharmaceutical compositions, can be included to provide a kit in which a dosage is taken every day. Optionally associated with such container(s) can be a notice in the form prescribed by a governmental agency regulating the manufacture, use or sale of pharmaceutical products, which notice reflects approval by the agency of manufacture, use or sale for human administration.

Equivalents

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art.

The following examples contain important additional information, exemplification and guidance that can be adapted to the practice of this invention in its various embodiments and the equivalents thereof.

Exemplification

The compounds of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

According to the present invention, any available techniques can be used to make or prepare the inventive compounds or compositions including them. For example, combinatorial techniques, parallel synthesis and/or solid-phase synthetic methods such as those discussed in detail below may be used. Alternatively or additionally, the inventive compounds may be prepared using any of a variety of solution-phase synthetic methods known in the art (e.g., one compound at a time).

It will be appreciated as described below, that a variety of inventive compounds can be synthesized according to the methods described herein. The starting materials and reagents used in preparing these compounds are either available from commercial suppliers such as Aldrich Chemical Company (Milwaukee, Wis.), Bachem (Torrance, Calif.), Sigma (St. Louis, Mo.), or are prepared by methods well known to a person of ordinary skill in the art following procedures described in such references as Fieser and Fieser 1991, "Reagents for Organic Synthesis", vols 1–17, John Wiley and Sons, New York, N.Y., 1991; Rodd 1989 "Chemistry of Carbon Compounds", vols. 1–5 and supps, Elsevier Science Publishers, 1989; "Organic Reactions", vols 1–40, John Wiley and Sons, New York, N.Y., 1991; March 2001, "Advanced Organic Chemistry", 5th ed. John Wiley and Sons, New York, N.Y.; and Larock 1989, "Comprehensive Organic Transformations", VCH Publishers. These schemes are merely illustrative of some methods by which the compounds of this invention can be synthesized, and various modifications to these schemes can be made and will be suggested to a person of ordinary skill in the art having regard to this disclosure.

The starting materials, intermediates, and compounds of this invention may be isolated and purified using conventional techniques, including filtration, distillation, crystallization, chromatography, and the like. They may be characterized using conventional methods, including physical constants and spectral data.

Unless specified to the contrary, the reactions described herein take place at atmospheric pressure over a temperature range between about 0° C. and 125° C.

The compounds of this invention may be prepared by procedures analogous to those described in PCT International Publication No. WO 01/27085, pages 29 to 40, using reagents appropriate for compounds of this invention (resin-based syntheses); and by the procedures given in the examples described in more detail herein.

Synthetic Strategy

Unless otherwise noted, final compounds were prepared utilizing previously reported methods to prepare aspartyl aldehyde and ketone-based inhibitors. In general, N-Fmoc-protected aspartyl aldehyde or thiomethylketone, prepared from the N-Fmoc-Asp(O$^t$Bu)-OH, is attached to support using a semicarbazide linker to provide support-bound semicarbazone (Kohara et al. *J. Med. Chem.* 1996, 39, 5228–5235; PCT publication WO00/23421 (2000)). Linking through the invariant carbonyl protects the carbonyl from nucleophilic attack as well as racemization at the α-stereocenter. Removal of the Fmoc group under basic conditions, followed by acylation with Fmoc-protected heterocycles introduces a rigid linker which links generally groups $R^1$ and $R^3$ (or $R^4$) as described with reference to the compounds herein. Removal of the newly incorporated Fmoc group followed by acylation with sulfonyl chlorides (or other appropriate reagent that can be used for alternative linkers as described generally and more specifically herein) introduces the $R^3$ (or $R^4$) element. Finally, acidic cleavage of the semicarbazone linker releases the fully functionalized aldehyde/ketone inhibitors from the support.

It will be appreciated that this general synthesis can be modified for the preparation of a variety of analogues as described in more detail herein. For example, a variety of alternative linkers and $R^1$ and ($R^3$ or $R^4$) groups can be prepared according to the general methods exemplified herein. As described above, a variety of $R^3$, $R^4$ and linker groups can be prepared as detailed herein. For example, acylation with a variety of sulfonyl chlorides introduces diversity at the $R^3$ (or $R^4$) position. Described below is the synthesis of a variety of exemplary benzenesulfonyl chlorides.

II. Experimentals

General Methods

Unless otherwise noted, all reactions were conducted under a nitrogen atmosphere. All commercially available starting materials and solvents were reagent grade or better and used without further purification. Solutions containing products were dried over anhydrous magnesium sulfate ($MgSO_4$) or sodium sulfate ($Na_2SO_4$) followed by vacuum filtration. Flash column chromatography was carried out using Merck Kieselgel 60 silica gel (230–400 mesh). Solid-phase reactions were conducted on aminomethylated polystyrene HL (100–200 mesh) from Novabiochem in Alltech 8-mL or 25-mL Extract-Clean™ reservoirs fitted with the corresponding frits and caps with agitation supplied by an orbital shaker table and a Supelco™ Vacuum Manifold used for resin washing. Preparative HPLC purification was carried out on a Gilson HPLC fitted with a Waters Nova-Pak C-18 (25×100 mm) column eluting at 25 mL/min with a gradient of 10%–100% acetonitrile in water (0.1% TFA) over 10 min and holding at 100% for 3 min. Fractions were pooled and lyophilized to provide final products as the free acid or TFA salt as indicated. $^1$H NMR spectroscopy was determined on a 400 MHz Bruker spectrometer with chemical shifts reported in units of parts per million (ppm). Elemental analysis were carried out by Robertson Microlit Laboratories Inc., Madison, N.J.

Scheme 1.
General Scheme for Analog Synthesis

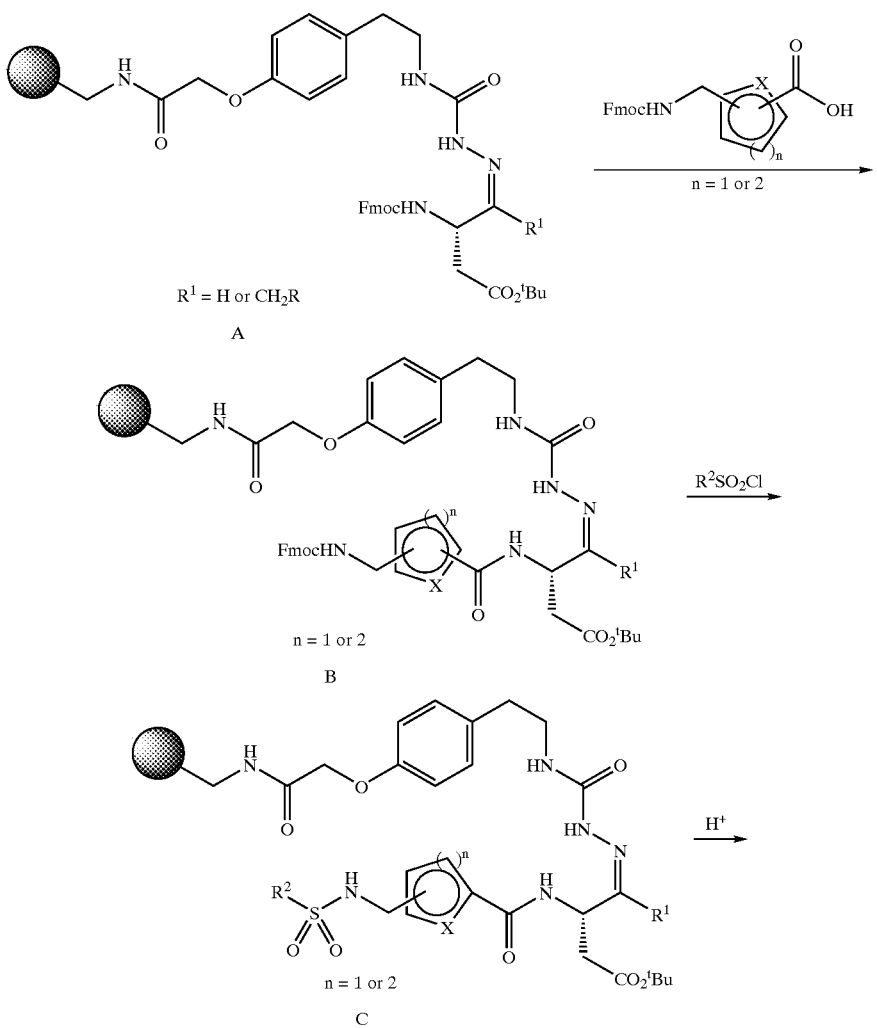

-continued

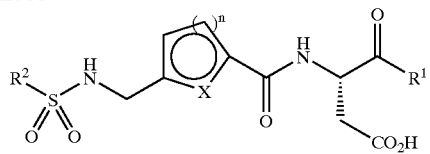

n = 1 or 2

D

General Method for Solid-Phase Synthesis of Aldehyde and Ketone Analogs

The general method is outlined above in Scheme 1. Resin A (PCT publication: WO00/23421(2000)) (300 mg, 0.06 mmol) was suspended in 20% piperidine in DMF (3 mL) followed by gentle agitation for 20 min. After filtration, the resin was washed successively with DMF (3×5 mL) and $CH_2Cl_2$ (3×5 mL). The resin was then resuspended in DMF (3 mL) followed by treatment with DIPEA (63 µL, 0.36 mmol), the desired N-Fmoc-protected heterocyclic acid (0.12 mmol) and PyBOP (93 mg, 0.18 mmol). After agitating at room temperature for 12 h, the solution was drained and the resin was washed successively with DMF (3×5 mL) and $CH_2Cl_2$ (3×5 mL) to afford resin B. This resin was then treated with 20% piperidine in DMF (3 mL) and agitated for 20 min. The resin was drained and washed successively with DMF (3×5 mL) and $CH_2Cl_2$ (3×5 mL). To the resin was then added $CH_2Cl_2$ (3 mL), the desired benzene sulfonyl chloride (0.12 mmol) and DIPEA (0.063 mL, 0.36 mmol). The suspension was agitated at room temperature for 12 h followed by filtration and washing with DMF (3×5 mL) and $CH_2Cl_2$ (3×5 mL) to afford resin C. The resin was then cleaved under the appropriate cleavage conditions to give the final product D which was purified via reverse-phase preparatory HPLC.

General Methods for Cleavage of Aldehyde Analogs from Resin

To derivatized aldehyde resin (300 mg, 0.06 mmol) was added $TFA/HOAc/CH_3CHO/THF$ (0.25:1:1:5, 3 mL). After agitation at room temperature for 3 h, the resin was filtered and washed with $CH_2Cl_2$ (2×2 mL). The filtrate and washings were combined and the solvent was removed under reduced pressure to provide a residue which was treated with $TFA/CH_2Cl_2/H_2O$ (1:1:0.1, 2 mL) at room temperature for 30 min. The solvent was removed under reduced pressure and the product purified by preparative reverse-phase HPLC.

General Methods for Cleavage of Ketone Analogs from Resin

To derivatized ketone resin (300 mg, 0.06 mmol) was added $TFA/H_2O$ (9:1, 3 mL). After agitation at room temperature for 15 min, the resin was filtered and washed with $CH_2Cl_2$ (2×2 mL). The filtrate and washings were combined and the solvent was removed under reduced pressure to provide a residue which was purified by preparative reverse-phase HPLC.

Resin chemistry (<2 g) was performed in Alltech 8-mL or 25-mL Extract-Clean™ reservoirs with the corresponding frits and caps. An orbital shaker was used for resin agitation and Supelco™ Vacuum Manifolds were used for resin washing.

III. Synthesis of Intermediates and Exemplary Compounds

EXAMPLE 1

This example describes the synthesis of the compound below

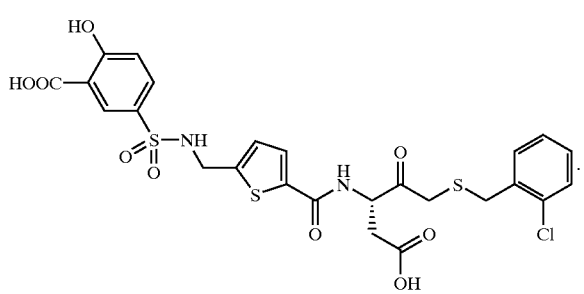

Scheme 2 illustrates the synthesis of compound 2 and resin 4

SCHEME 2

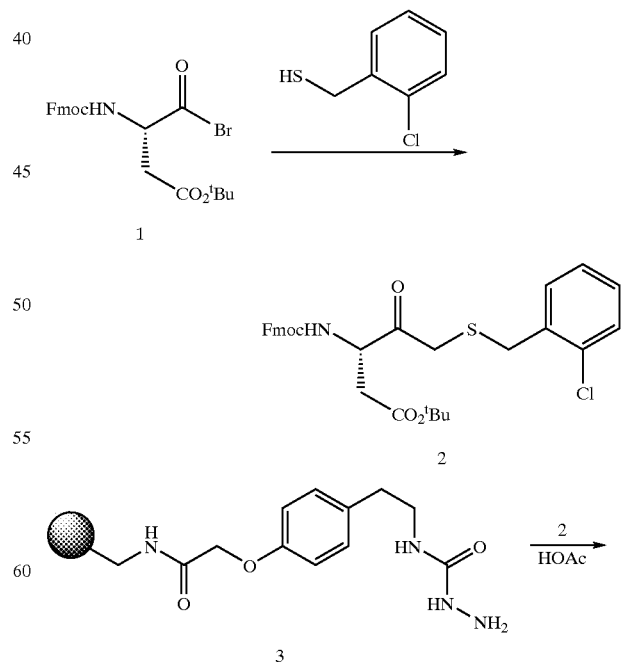

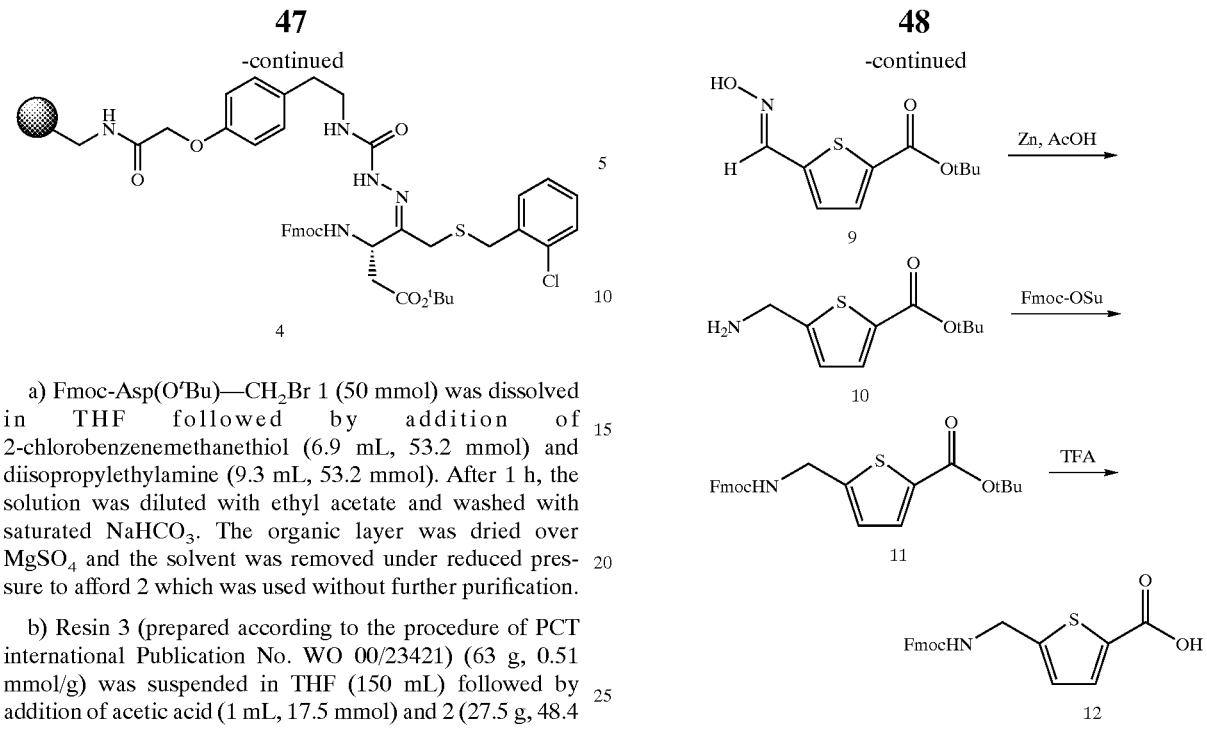

a) Fmoc-Asp(O^tBu)—CH_2Br 1 (50 mmol) was dissolved in THF followed by addition of 2-chlorobenzenemethanethiol (6.9 mL, 53.2 mmol) and diisopropylethylamine (9.3 mL, 53.2 mmol). After 1 h, the solution was diluted with ethyl acetate and washed with saturated NaHCO$_3$. The organic layer was dried over MgSO$_4$ and the solvent was removed under reduced pressure to afford 2 which was used without further purification.

b) Resin 3 (prepared according to the procedure of PCT international Publication No. WO 00/23421) (63 g, 0.51 mmol/g) was suspended in THF (150 mL) followed by addition of acetic acid (1 mL, 17.5 mmol) and 2 (27.5 g, 48.4 mmol). After stirring for 12 h, the resin was filtered and washed successively with CH$_2$Cl$_2$ (3×200 mL) and ether (3×200 mL) to afford resin 4. After drying resin 4 in vacuo, an aliquot of the resin (0.300 g) was treated with a solution of TFA/H$_2$O (9:1 v/v, 3 mL) to release 2. Based on the mass balance of the cleaved material, the resin loading was calculated to be approximately 0.2 mmol/g.

Scheme 3 describes an exemplary synthesis of compound 12.

SCHEME 3

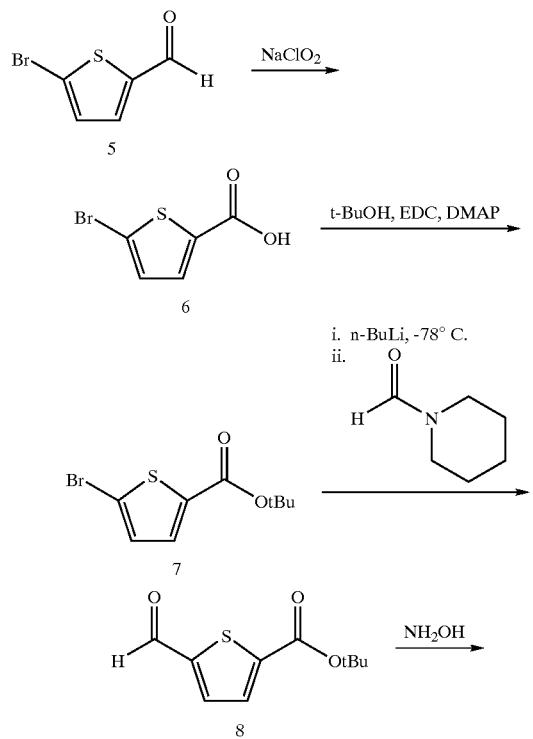

c) To a solution of 5-bromothiophene carboxaldehyde 5 (18 g, 94.3 mmol) and 2,3-dimethylbutene (22 mL, 189 mmol) in $^t$BuOH (470 mL) was added a solution of NaClO$_2$ (10.6 g, 118 mmol) and NaH$_2$PO$_4$ (14.1 g, 118 mmol) in H$_2$O (94 mL). After stirring at rt for 12 h, the organic solvent was removed under reduced pressure and the remaining slurry was basified with 1 M NaOH (200 mL). The aqueous layer was washed successively with hexanes (3×200 mL) followed by acidification with 1 M HCl (300 mL) and extraction of the desired 6 into ether (3×150 mL). The organic layer was dried over MgSO$_4$ and the solvent was removed under reduced pressure to afford 6 which was carried onto the next step without further purification. ES (+) MS: m/e=208.9 (M+H)$^+$.

d) To a solution of 6 in CH$_2$Cl$_2$ (316 mL) was added $^t$BuOH (116 mL, 1.3 mol), EDC (24.3 g, 12.7 mmol) and DMAP (7.8 g, 63.3 mmol). After stirring at rt for 3 h, the solution was diluted with CH$_2$Cl$_2$ (200 mL) and washed with 1 M HCl (3×200 mL). The organic layer was dried over MgSO$_4$ and the solvent was removed under reduced pressure. The crude residue was purified by silica gel chromatography (30:70 ethyl acetate/hexanes) to afford 12.5 g (50%) of 7 after two steps. ES (+) MS: m/e=206.9 (M-$^t$Bu)$^+$.

e) To a solution of 7 (7.5 g, 28.5 mmol) in ether (60 mL) at −78° C. was dropwise added a solution of 0.8 M n-BuLi (32.1 mL, 25.7 mmol). After stirring for 1 h at −78° C., a solution of N-formyl piperdine (4.7 mL, 42.8 mmol) in ether (10 mL) was added dropwise. After stirring for an additional 30 min at −78° C., the reaction was quenched with 1 M HCl and allowed to warm to rt. The solution was diluted with ether (200 mL) and washed with 1 M HCl (3×100 mL). The organic layer was dried over MgSO$_4$ and the solvent was removed under reduced pressure. The crude residue was purified by silica gel chromatography (30:70 ethyl acetate/hexanes) to provide 3.0 g (50%) of 8. ES (+) MS: m/e=157.1 (M+H)$^+$.

f) To a solution of 8 (3.0 g, 14.1 mmol) in MeOH (15 mL) was added a solution of 16.3 M NH$_2$OH in H$_2$O (1.3 mL, 2.1 mmol). After stirring for 1 h at rt, the solvent was removed under reduced pressure to provide 9 which was used without further purification. ES (+) MS: m/e=172.1 (M+H)$^+$.

g) To a solution of 9 (14.1 mmol) in acetic acid (28 mL) at 0° C. was added zinc dust (3.6 g, 56.4 mmol). The slurry was warmed to rt and stirred for 3 h. The slurry was filtered over Celite and the solvent was removed under reduced pressure to provide crude 10 which was used without further purification. ES (+) MS: m/e=141.1 (M−$^t$Bu−NH$_2$)$^+$.

h) To a solution of 10 (14.1 mmol) in H$_2$O/dioxane (1:1 v/v, 60 mL) was added NaHCO$_3$ (5.9 g, 70.5 mmol) and Fmoc-OSu (5.2 g, 15.5 mmol). After stirring at rt for 3 h, the suspension was diluted with ether (100 mL) and washed with 1 M HCl (3×100 mL). The organic layer was dried over MgSO$_4$ and the solvent was removed under reduced pressure. The crude residue was purified by silica gel chromatography (30:70 ethyl acetate/hexanes) to provide 4.62 g (75%) of 11. ES (+) MS: m/e=458.2 (M+Na)$^+$.

i) A solution of 11 in TFA/CH$_2$Cl$_2$/H$_2$O (1:4:0.1 v/v/v, 30 mL) was stirred for 2 h at rt. The solvent was removed under reduced pressure to afford 12 which was used without further purification. $^1$H NMR (MeOD) δ 7.78 (d, J=7.4 Hz, 2H), 7.60–7.65 (m, 3H), 7.38 (t, J=7.3 Hz, 2H), 7.29 (t, J=7.3 Hz, 2H), 6.95 (s, 1H), 4.45 (s, 2H), 4.40 (d, J=6.8 Hz, 2H), 421 (t, J=6.7 Hz, 1H). ES (+) MS: m/e=402.0 (M+Na)$^+$.

An intermediate, compound 15, was synthesized as described in Scheme 4.

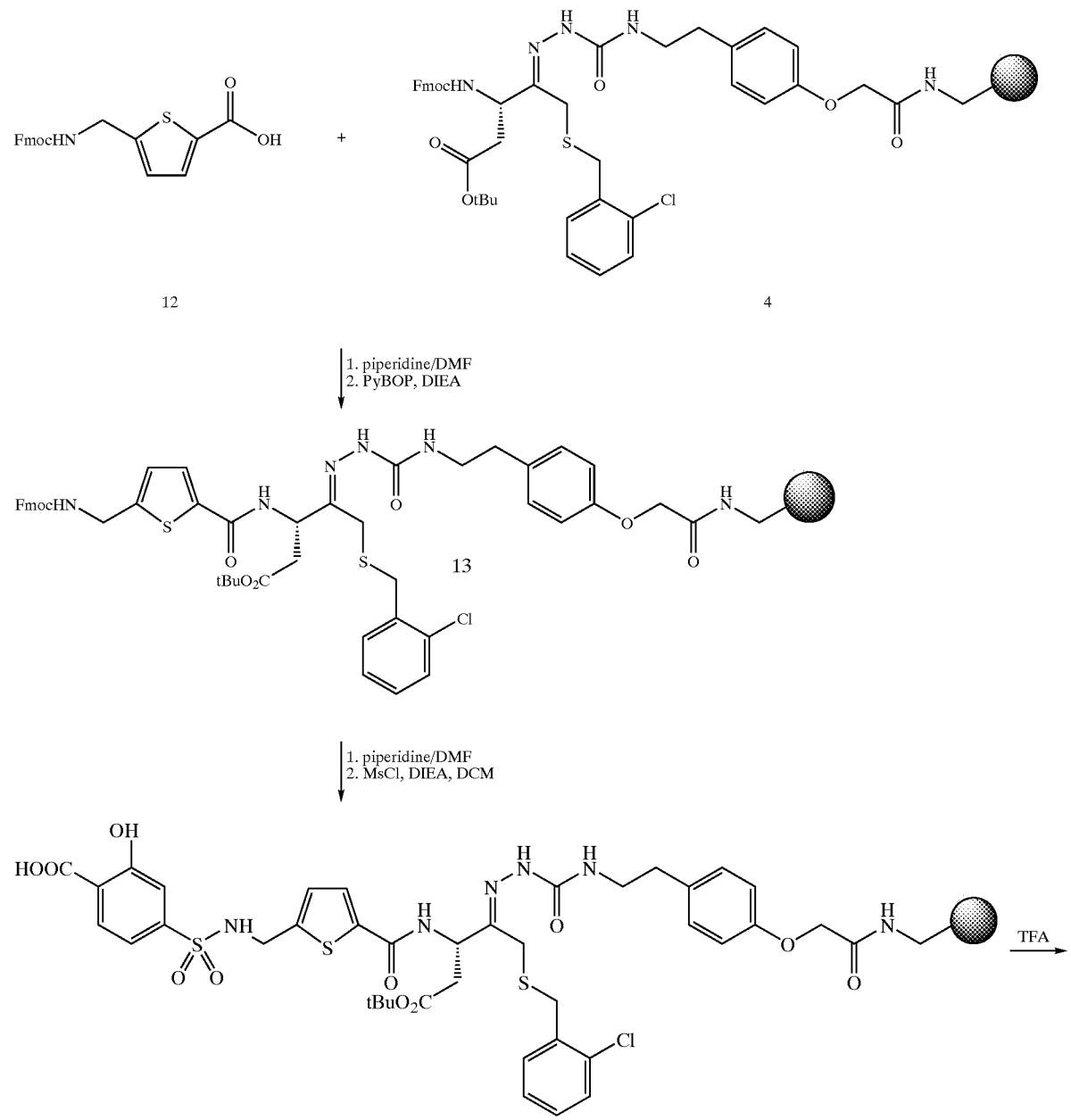

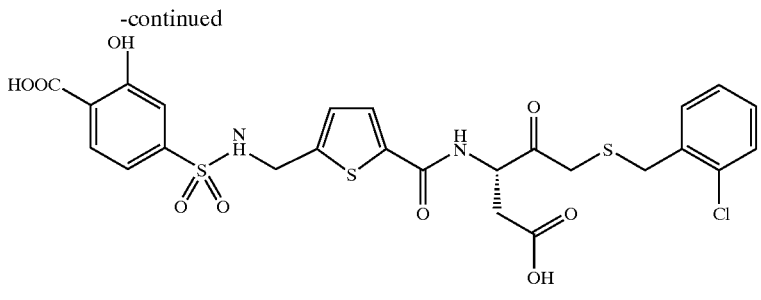

15 j) Resin 4 (2.5 g, 0.2 mmol) was suspended in DMF (20 mL) followed by addition of 12 (0.379 g, 1.0 mmol), diisoproylethylamine (0.525 mL, 3 mmol) and PyBOP (0.780 g, 1.5 mmol). After agitating for 3 h, the resin was filtered and washed successively with CH$_2$Cl$_2$ (5×15 mL) and ether (3×15 mL) and dried in vacuo to provide resin 13.

k) Resin 13 (0.300 g, 0.06 mmol) was treated with 20% piperidine in DMF (5 mL) and shaken for 30 min. The resin was washed successively with CH$_2$Cl$_2$ (3×5 mL), resuspended in CH$_2$Cl$_2$ (5 mL) and treated with diisopropylethylamine (31 uL, 0.18 mmol) and 5-chlorosulfonyl-2-hydroxybenzoic acid (9 mg, 0.12 mmoL). After agitating for 3 h, the resin was filtered and washed with CH$_2$Cl$_2$ (5×5 mL) to yield resin 14.

l) Resin 14 was treated with TFA/H$_2$O (9:1 v/v, 2 mL) and agitated for 15 min. The resin was filtered and washed with CH$_2$Cl$_2$ (2×4 mL). The combined filtrates were diluted with toluene (3 mL) and the solvent was removed under reduced pressure. The crude residue was purified by reverse-phase preparatory HPLC to afford 15. (5.1 mg, 14%). $^1$H NMR (CD$_3$OD) δ 8.26 (d, J=2.2 Hz, 1H), 7.85 (dd, J=8.8, 2.3 Hz, 1H), 7.45 (d, J=3.7 Hz, 1H), 7.33–7.37 (m, 2H), 7.16–7.22 (m, 2H), 7.00 (d, J=8.8 Hz, 1H), 6.86 (d, J=3.6 Hz, 1H), 5.09 (t, J=6.3 Hz, 1H), 4.30 (s, 2H), 3.78 (d, J=3.9 Hz, 2H), 3.44 (d, J=15.3 Hz, 1H), 3.36 (d, J=15.3, 1H), 3.00 (dd, J=16.9, 6.5 Hz, 1H), 2.75 (dd, 16.8, 6.5 Hz, 1H). ES (+) MS: m/e=627.0 (M+H)$^+$.

EXAMPLE 2

This example describes an exemplary synthesis of the compound below

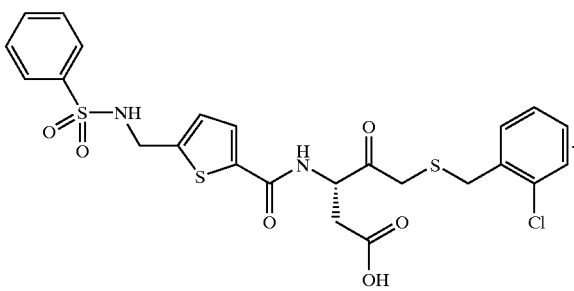

This compound was prepared according to the procedure of Example 1k–l except for using benzenesulfonyl chloride as a reagent instead of 5-chlorosulfonyl-2-hydroxybenzoic acid. (10.8 mg, 32%). $^1$H NMR (CD$_3$OD) δ 7.79 (d, J=7.4 Hz, 2H), 7.55 (d, J=7.3 Hz, 1H), 7.49 (d, J=7.7 Hz, 2H), 7.46 (m, 1H), 7.34 (m, 2H), 7.21 (m, 2H), 6.86 (d, J=3.8 Hz, 1H), 5.08 (t, J=6.5 Hz, 1H), 3.82 (d, J=13.3 Hz, 1H), 3.77 (d, J=13.3 Hz, 1H), 3.39 (m, 2H), 2.99 (dd, J=16.9, 6.3 Hz, 1H), 2.74 (dd, J=16.8, 6.8 Hz, 1H). ES (+) MS: m/e=567.0 (M+H)$^+$.

EXAMPLE 3

This example describes an exemplary synthesis of the compound below

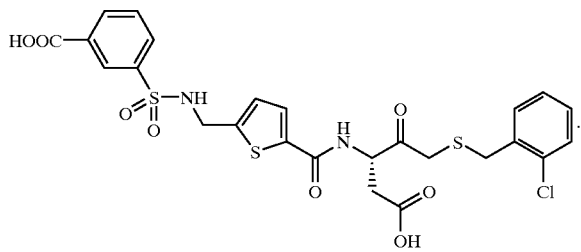

This compound was prepared according to the procedure of Example 1k–l except for 3-carboxysulfonyl chloride as a reagent instead of 5-chlorosulfonyl-2-hydroxybenzoic acid. Prepared from resin LIa, (4.3 mg, 12%). $^1$H NMR (CD$_3$OD) δ 8.37 (s, 1H), 8.16 (d, J=7.8 Hz, 1H), 7.97 (d, J=7.9 Hz, 1H), 7.59 (t, J=7.8 1H), 7.42 (d, J=3.8 Hz, 1H), 7.36 (m, 1H), 7.21 (m, 1H), 6.86 (d, 3.8 Hz, 1H), 5.08 (t, J=6.6 Hz, 1H), 4.33 (s, 2H), 3.80 (d, J=4.3 Hz, 2H), 3.44 (d, J=15.2 Hz, 1H), 3.35 (d, J=15.3 Hz, 1H), 3.00 (dd, J=16.9, 6.5 Hz, 1H), 2.74 (dd, J=16.8, 6.7 Hz, 1H). ES (+) MS: m/e=611.0 (M+H)$^+$.

EXAMPLE 4

This example describes an exemplary synthesis of the compound below

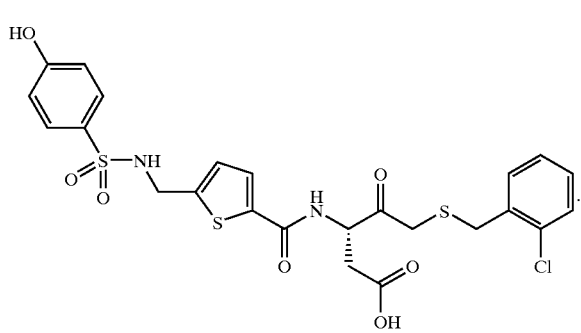

An intermediate, compound 17, was synthesized as described in Scheme 5.

SCHEME 5

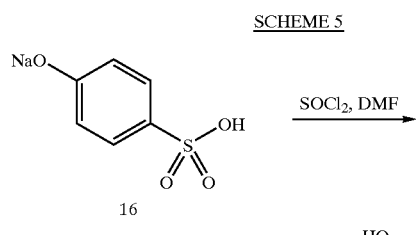

16

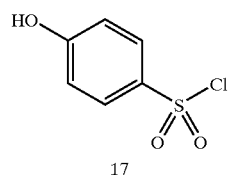

17

The sodium salt of 4-hydroxy-sulfonic acid 16 was dissolved in ethyl acetate and 1 M HCl. The layers were partitioned and separated. The organic layer dried over MgSO$_4$ and the solvent was removed under reduced pressure. To the sulfonic acid (1 g, 5.74, mmol) was added thionyl chloride (5 mL) followed by a catalytic amount of DMF. The reaction stirred at rt for several minutes then was heated to 80° C. for approximately 2 h. The reaction mixture was cooled to rt and and the solvent was removed under reduced pressure. The residue was purified by silica gel chromatography (40:60 ethyl acetate/hexanes) to give 0.650 g (59%) of 17 as a white solid.

The title compound was prepared according to the procedure of Example 1k–l except for using 17 as a reagent instead of 5-chlorosulfonyl-2-hydroxybenzoic acid. $^1$H NMR (CD$_3$OD) δ 7.62 (m, 2H), 7.45 (d, J=3.81 Hz, 1H), 7.32 (m, 2H), 7.16 (m, 2H), 6.83 (m, 3H), 5.05 (t, J=6.6 Hz, 1H), 4.19 (s, 2H), 3.76 (m, 2H), 3.37 (m, 2H), 3.26 (m, 2H), 2,96 (dd, J=16.8, 6.4 Hz, 1H), 2.70 (dd, J=16.8, 6.6 Hz, 1H).

EXAMPLE 5

This example describes an exemplary synthesis of the compound below

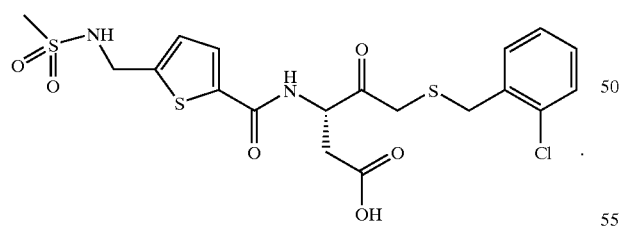

This compound was prepared according to the procedure of Example 1k–l except for using methanesulfonyl chloride as a reagent instead of 5-chlorosulfonyl-2-hydroxybenzoic acid. ES (+) MS: m/e=505.1 (M+H)$^+$.

EXAMPLE 6

This example describes an exemplary synthesis of the compound below

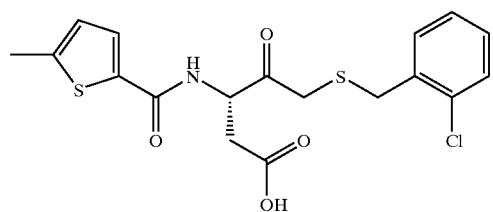

This compound was prepared according to the procedure of Example 1j,l except for using 5-methylthiophene carboxylic acid as a reagent instead 12. ES (+) MS: m/e=412.1 (M+H)$^+$.

EXAMPLE 7

This example describes an exemplary synthesis of the compound below

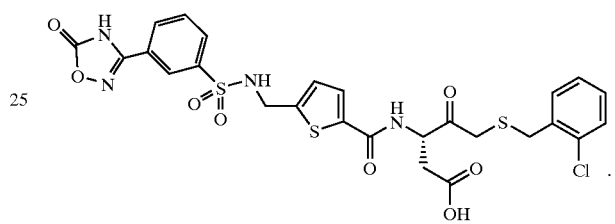

An intermediate, compound 23 was prepared as described in Scheme 6.

SCHEME 6

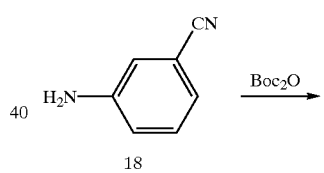

18

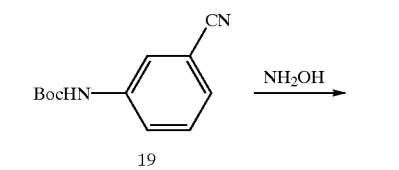

19

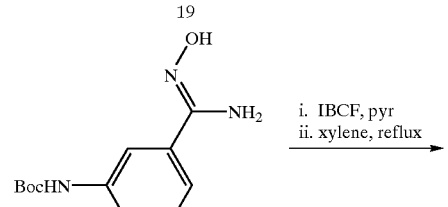

20

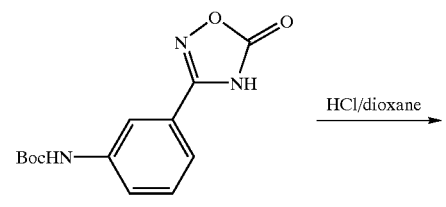

21

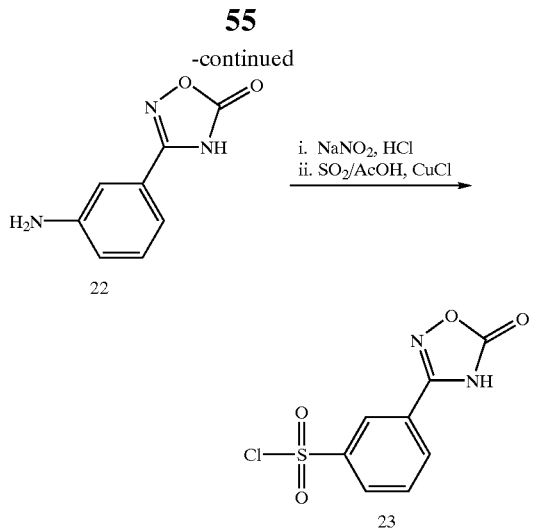

a) To a solution of 3-amino-benzonitrile 18 (4.7 g, 40 mmol) and triethylamine (5.57 mL, 40 mmol) in THF (200 mL) was added Boc$_2$O (9.6 g, 44 mmol). The resulting mixture was stirred at 60° C. for 48 h. The mixture was diluted with ether and washed with water and brine. The organic layer was dried over MgSO$_4$ and the solvent was removed under reduced pressure. The crude residue was purified by silica gel chromatography (10:90 ethyl acetate/hexanes) to give 8.13 g (93%) of 19 as white solid. ES (+) MS: m/e=163 (M−$^t$Bu)$^+$. $^1$H NMR (CDCl$_3$) δ 1.52 (s, 9H), 6.64 (s, 1H), 7.31 (d, 1H), 7.37 (t, 1H), 7.52 (d, 1H), 7.8 (s, 1H)

b) To a solution of 19 (6.54 g, 30 mol) in EtOH (60 mL), was added 16.3 M NH$_2$OH in H$_2$O (3.6 mL, 60 mmol). The resulting solution was stirred at 80° C. for 3 h. The solvent was removed under reduced pressure to yield 7.5 g (99%) of 20 which was used without further purification. ES (+) MS: m/e=252 (M+H)$^+$.

c) 2-Ethylhexyl chloroformate (2.92 mL, 15 mmol) was added dropwise to solution of 20 (2.51 g, 10 mmol) and pyridine (1.21 mL, 15 mmol) in THF (20 mL). The resulting mixture was stirred at 0° C. for 30 min. The mixture was diluted with ethyl acetate and washed with water and brine. The organic layer was dried over MgSO$_4$ and the solvent was removed under reduced pressure. The resulting residue was redissolved in xylene (50 mL) and the solution was gently heated under reflux for 2–3 h. The solvent was removed under reduced pressure and the resulting residue was diluted with ethyl acetate and washed with water and brine. The organic layer was dried over MgSO$_4$ and the solvent was removed under reduced pressure. The crude product was purified by silica gel chromatography (10:90 to 50:50 ethyl acetate/hexanes) to yield 1.95 g (70%) of 21 as off-white powder. ES (+) MS: m/e=222 (M−$^t$Bu)$^+$. $^1$H NMR (DMSO) δ 1.47 (s, 9H), 7.35 (d, 1H), 7.43 (t, 1H), 7.54 (d, 1H), 8.05 (s, 1H), 9.63 (s, 1H), 12.9 (s, 1H).

d) 21 (0.831 g, 3 mmol) was dissolved in 4 M HCl in dioxane (6 mL) and stirred at rt for 3 h. The solvent was removed under reduced pressure to provide 22. The resulting residue was added to a warm mixture of concentrated HCl (3 mL) and water (1.5 mL). Acetic acid (3 mL) was added to give a clear yellow solution which was then cooled to −10° C. A solution of NaNO$_2$ (0.248 g, 3.6 mmol) in H$_2$O (1.5 mL) was added dropwise keeping the temperature below −5° C. The resulting mixture was stirred at −5° C. for 15 min. In another flask, a solution of acetic acid (6 mL) and CuCl (0.074 g, 0.75 mmol) was saturated with SO$_2$ (g) for 45 min and then cooled to 5° C. The prepared diazonium solution was added slowly to this cuprous solution, causing vigorous evolution of N$_2$ gas. The resulting green mixture was stirred for 1 h and then allowed to warm to rt. The solvent was removed under reduced pressure and the resulting mixture was diluted with ether and washed with water, 1 M HCl and brine. The organic layer was dried over MgSO$_4$ and the solvent was removed under reduced pressure to afford 0.159 g (61%) of 23 as yellow solid. $^1$H NMR (DMSO-d$_6$) δ 13.04 (s, 1H), 8.10 (s, 1H), 7.85 (d, J=7.5 Hz, 1H), 7.75 (d, J=7.5 Hz, 1H), 7.54 (t, J=7.7 Hz, 1H). ES (+) MS: m/e=261 (M+H)$^+$.

e) The title compound was prepared according to the procedure of Example 1k–1 except for using 23 as a reagent instead of 5-chlorosulfonyl-2-hydroxybenzoic acid. (3.4 mg, 9%). $^1$H NMR (CD$_3$OD) δ 8.16 (s, 1H), 7.98 (d, J=8.2 Hz, 1H), 7.95 (d, J=7.9 Hz, 1H), 7.66 (t, J=7.9 Hz, 1H), 7.42 (d, J=3.7 Hz, 1H), 7.34–7.38 (m, 2H), 7.20–7.23 (m, 2H), 6.88 (d, J=3.6 Hz, 1H), 5.08 (t, J=6.4 Hz, 1H), 4.38 (s, 2H), 3.80 (d, J=3.7 Hz, 2H), 3.44 (d, J=15.2 Hz, 1H), 3.37 (d, J=15.3 Hz, 1H), 2.99 (dd, J=16.8, 6.4 Hz, 1H), 2.75 (dd, J=16.9, 6.6 Hz, 1H). ES (+) MS: m/e 651.0 (M+H)$^+$.

EXAMPLE 8

This example describes an exemplary synthesis of the compound below

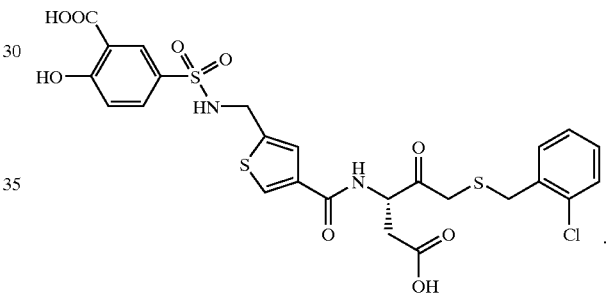

An intermediate, compound 33 was prepared as described in Scheme 7.

SCHEME 7

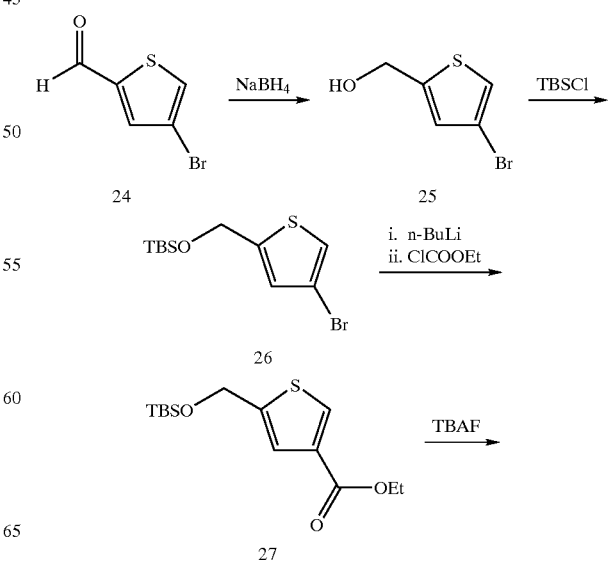

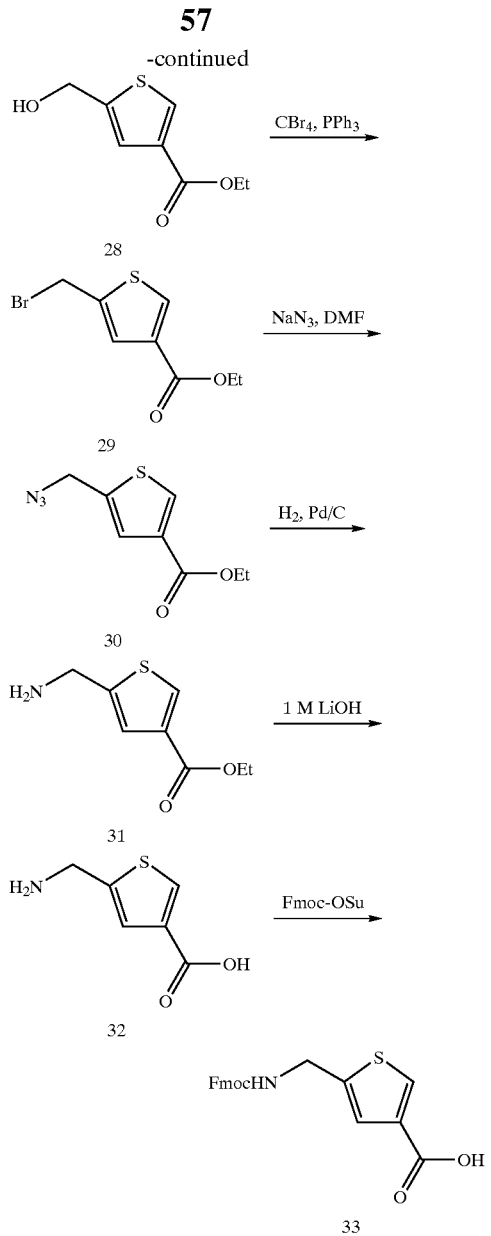

a) To a solution of 4-bromo-2-carboxaldehyde 24 (7.1 g, 37.2 mmol) in THF (80 mL) was added NaBH₄ (1.5 g, 40.9 mmol). After stirring for 30 min, saturated NaHCO₃ was slowly added to the reaction. The solution was diluted with ether (100 mL) and washed with saturated NaHCO₃ (3×50 mL). The organic layer was dried over MgSO₄ and the solvent was removed under reduced pressure to provide 25 which was used without further purification.

b) To a solution of 25 (37.1 mmol) in CH₂Cl₂ (70 mL) was added TBSCl (6.1 g, 40.8 mmol) and imidazole (2.8 g, 40.8 mmol). After stirring for 30 min at rt, the solution was diluted with CH₂Cl₂ (100 mL) and washed with 1 M HCl (3×50 mL). The organic layer was dried over MgSO₄, the solvent was removed under reduced pressure and the crude residue was purified by silica gel chromatography (0:100 to 10:90 ethyl acetate/hexanes) to provide 10.6 g (92%, 2 steps) of 26.

c) To a solution of 26 (10.6 g, 34.3 mmol) in THF (60 mL) at −78° C. was added dropwise a solution of 1.6 M n-BuLi (23.6 mL, 37.8 mmol). After stirring at −78° C. for 1 h, the reaction solution was added via cannula addition to a solution of ethyl chloroformate (4.3 mL, 44.7 mmol) in THF (80 mL) at −78° C. After stirring for 1 h, the reaction was quenched with 1 M HCl (20 mL) and warmed to rt. The organic layer was washed with 1 M HCl (3×50 mL) and dried over MgSO₄. The solvent was removed under reduced pressure and the crude residue was purified by silica gel chromatography (10:90 ethyl acetate/hexanes) to provide 10.1 g (97%) of 27.

d) To a solution of 27 (10.1 g, 33.6 mmol) in THF (70 mL) was added aeetic acid (12 mL) and 1 M TBAF in THF (36.9 mL, 36.9 mmol). After stirring for 12 h, the solution was diluted with ether (100 mL) and washed with saturated NaHCO₃. The organic layer was dried over MgSO₄ and the solvent was removed under reduced pressure. The crude residue was purified by silica gel chromatography (30:70 ethyl acetate/hexanes) to give 2.2 g (35%) of 28. ES (+) MS: m/e=187.1 (M+H)⁺.

e) To a solution of 28 (3.0 g, 16.1 mmol) in THF (80 mL) was added CBr₄ (5.9 g, 17.7 mmol) and PPh₃ (4.6 g, 17.7 mmol). After stirring for 1 h, the suspension was filtered and the solvent was removed under reduced pressure. The crude residue was purified by silica gel chromatography (20:80 ethyl acetate/hexanes) to give 4.0 g (100%) of 29. ES (+) MS: m/e=250.9 (M+H)⁺.

f) To a solution of 29 (4.0 g, 16.1 mmol) in DMF (30 mL) was added NaN₃ (1.2 g, 17.7 mmol). After stirring at 50° C. for 30 min, the solution was diluted with ether (60 mL) and washed with H₂O (3×50 mL). The organic layer was dried over MgSO₄ and the solvent was removed under reduced pressure to provide 1.9 g (56%) of 30 which was used without further purification. ES (+) MS: m/e=212.9 (M+H)⁺.

g) To a solution of 30 (1.9 g, 9.0 mmol) in EtOH (30 mL) was added palladium on carbon (10% w/w, 0.100 g). After shaking for 2 h under 30 psi of hydrogen, the suspension was filtered through Celite and the solvent was removed under reduced pressure to provide 0.900 g (52%) of 31 which was used without further purification. ES (+) MS: m/e=169.1 (M−NH₂)⁺.

h) To a solution of 31 (0.900 g, 4.9 mmol) in dioxane (10 mL) was added 1 M LiOH (10 mL). After stirring for 1 h at rt, the solution was neutralized with 1 M HCl (10 mL) and the solvent was removed under reduced pressure to provide 32 which was used without further purification.

i) To a solution of 32 (4.9 mmol) in H₂O/dioxane (1:1 v/v, 10 mL) was added NaHCO₃ (2.1 g, 24.5 mmol) and Fmoc-OSu (1.8 g, 5.4 mmol). After stirring for 3 h at rt, the solution was diluted with ether (30 mL) and washed with 1 M HCl (3×20 mL). The organic layer was dried over MgSO₄ and the solvent was removed under reduced pressure. The crude residue was purified by silica gel chromatography (95:5, ethyl acetate/MeOH) to provide 33. ¹H NMR (CDCl₃) δ 8.04 (s, 1H), 7.78 (d, J=7.4 Hz, 3H), 7.63 (d, J=7.4 Hz, 2H), 7.28–7.39 (m, 4H), 4.43 (d, J=4.8 Hz, 2H), 4.36 (J=6.9 Hz, 2H), 4.20 (t, J=6.8 Hz, 1H). ES (+) MS: m/e=402.3 (M)⁺.

j) The title compound was prepared according to the procedure of Example 1j–1 except for using 33 instead of 12. (5.2 mg, 14%). ¹H NMR (CD₃OD) δ 8.27 (d, J=2.3 Hz, 1H), 7.91 (d, J=1.2 Hz, 1H), 7.85 (dd, J=8.8, 2.4 Hz, 1H), 7.34–7.38 (m, 2H), 7.18–7.23 (m, 3H), 7.01 (d, J=8.8 Hz, 1H), 5.09 (t, J=6.4 Hz, 1H), 4.28 (s, 2H), 3.81 (d, J=3.6 Hz, 2H), 3.44 (d, J=15.2 Hz, 1H), 3.36 (d, J=15.2 Hz, 1H), 3.00 (dd, J=16.8, 6.4 Hz, 1H), 2.75 (dd, J=16.8, 6.5 Hz, 1H). ES (+) MS: m/e=627.0 (M+H)⁺.

EXAMPLE 9

This example describes an exemplary synthesis of the compound below

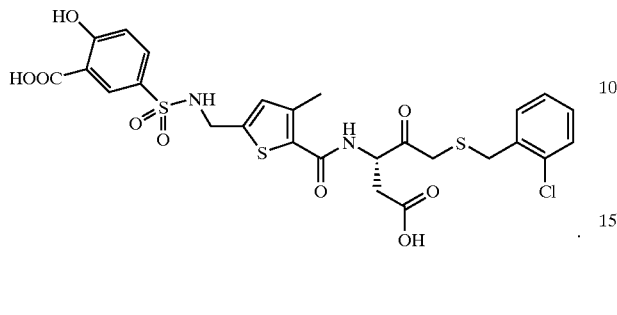

An intermediate, compound 43, was synthesized as described in Scheme 8.

SCHEME 8

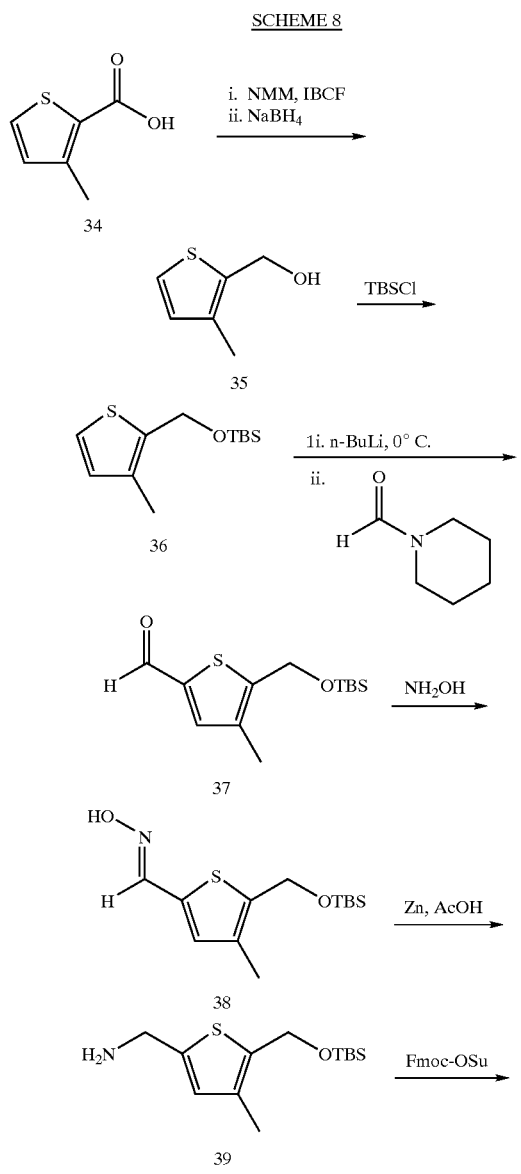

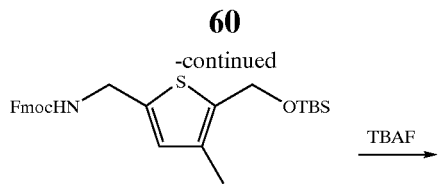

a) To a solution of 2-carboxylic acid-3-methylthiophene 34 (10.0 g, 70.3 mmol) in THF (140 mL) at 0° C. was added NMM (8.5 mL, 77.5 mmol) and isobutyl chloroformate (10.0 mL, 77.3 mmol). After stirring for 30 min, the mixture was cooled to −78° C. and a slurry of NaBH$_4$ (7.8 g, 211 mmol) in THF/EtOH (5:1 v/v, 50 mL) was added. The mixture was warmed to rt and stirred for 2 h. The solution was diluted with ether (100 mL) and washed with 1 M HCl (3×50 mL). The organic layer was dried over MgSO$_4$ and the solvent was removed under reduced pressure to provide 35 which was used without further purification. ES (+) MS: m/e=111.2 (M−OH)$^+$.

b) To a solution of 35 (70.3 mmol) in CH$_2$Cl$_2$ (150 mL) was added TBSCl (11.6 g, 77.3 mmol) and imidazole (5.2 g, 77.3 mmol). After stirring for 30 min at rt, the solution was diluted with CH$_2$Cl$_2$ (200 mL) and washed with 1 M HCl (3×100 mL). The organic layer was dried over MgSO$_4$, the solvent was removed under reduced pressure and the crude residue was purified using silica gel chromatography (20:80 ethyl acetate/hexanes) to provide 13.7 g (80%, 2 steps) of 36. ES (+) MS: m/e=237.1 (M−5H)$^+$.

c) To a solution of 36 (2.82 g, 11.6 mmol) in ether (39 mL) at −78° C. was added 1.6 M n-BuLi (6.5 mL, 10.5 mmol). After stirring at −78° C. for 30 min, the solution was added via cannula addition to a solution of N-formyl piperidine (1.42 mL, 12.8 mmoL) in ether (30 mL) at −78° C. After stirring for 30 min, the reaction was quenched with 1 M NH$_4$Cl (20 mL) and warmed to rt. The solution was diluted with ether (50 mL) and washed with 1 M NH$_4$Cl (3×50 mL). The organic layer was dried over MgSO$_4$ and the solvent was removed under reduced pressure to afford 37 which was used without further purification. ES (+) MS: m/e=272.1 (M+H)$^+$.

d) To a solution of 37 (3.0 g, 11.1 mmol) in MeOH (20 mL) was added 16.3 M NH$_2$OH in H$_2$O (1 mL, 16.6 mmol). After stirring for 1 h, the solvent was removed under reduced pressure to afford 38 which was used without further purification. ES (+) MS: m/e=286.1 (M+H)$^+$.

e) To a solution of 38 (1.66 g. 5.8 mmol) in acetic acid (58 mL) was added zinc dust (1.5 g, 22.9 mmol). After stirring for 2 h, the mixture was filtered through Celite and the solvent was removed under reduced pressure to afford 39 which was used without further purification. ES (+) MS m/e=255 (M−OH)+.

f) To a solution of 39 (5.8 mmol) in H₂O/dioxane (1:1 v/v, 20 mL) was added NaHCO₃ (2.1 g, 6.4 mmol) and Fmoc-OSu (2.4 g, 29.1 mmol). After stirring at rt for 1 h, the mixture was diluted with ether (50 mL) and washed with 1 M HCl (3×50 mL). The organic layer was dried over MgSO₄ and the solvent was removed under reduced pressure. The crude residue was purified by silica gel chromatography (0:100 to 10:90 ethyl acetate/hexanes) to afford 1.7 g (59%, 3 steps) of 40. ES (+) MS: m/e=516.3 (M+H)+.

g) To a solution of 40 (1.7 g, 3.4 mmol) in THF (10 mL) was added acetic acid (0.5 mL) and 1 M TBAF in THF (3.8 mL, 3.8 mmol). After stirring at rt for 12 h, the reaction was diluted with ether (20 mL) and washed with a saturated NaHCO₃ (3×20 mL). The organic layer was dried over MgSO₄ and the solvent was removed under reduced pressure. The crude residue was purified by silica gel chromatography (30:70 to 50:50 ethyl acetate/hexanes) to afford 0.560 g (43%) of 41. ES (+) MS: m/e=402.2 (M+H)+.

h) To a solution of 41 (0.480 g, 1.25 mmol) in acetone (10 mL) was added a solution of Jones' reagent (0.960 mL, 1.39 mmoL). After stirring at rt for 5 min, the solution was diluted with CH₂Cl₂ (20 mL) and washed with H₂O (3×10 mL). ). The organic layer was dried over MgSO₄ and the solvent was removed under reduced pressure to provide 42 which was used crude without further purification. ES (+) MS: m/e=400.1 (M+Na)+.

i) To a solution of 42 (1.25 mmol) and 2,3-dimethylbutene (0.29 mL, 2.50 mmol) in t-BuOH (6.2 mL) was added a solution of NaClO₂ (0.139 g, 1.56 mmol) and NaH₂PO₄ (0.187 g, 1.56 mmol) in H₂O (1.2 mL). After stirring at rt for 12 h, the organic solvent was removed under reduced pressure and the remaining slurry was basified with 1 M NaOH (20 mL). The aqueous layer was washed successively with hexanes (3×20 mL) followed by acidification with 1 M HCl (30 mL) and extraction of the desired product into ether (3×15 mL). The organic layer was dried over MgSO₄ and the solvent was removed under reduced pressure to afford 43 which was carried onto the next step without further purification. ES (+) MS: m/e=416.1 (M+Na)+.

j) The title compound was prepared according to the procedure of Example 1j–1 except for using 43 as a reagent instead of 12 (3.8 mg, 10%). ¹H NMR (CD₃OD) δ 6.70 (s, 1H), 6.30 (dd, J=8.8, 2.2 Hz, 1H), 5.82–5.87 (m, 2H), 5.68 (m, 2H), 5.48 (d, J=8.8 Hz, 1H), 5.13 (s, 1H), 3.51 (t, J=5.8 Hz, 1H), 2.72 (s, 2H), 2.29 (s, 2H), 1.92 (d, J=15.2 Hz, 1H), 1.86 (d, J=15.1 Hz, 1H), 1.77 (s, 3H), 1.44 (dd, J=16.9, 5.8 Hz, 1H)), 1.29 (dd, J=16.8, 5.8 Hz, 1H). ES (+) MS: m/e=641.0 (M+H)+.

EXAMPLE 10

This example describes an exemplary synthesis of the compound below

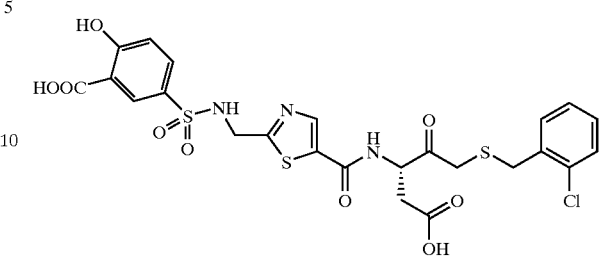

An intermediate, compound 52, was synthesized as described in Scheme 9.

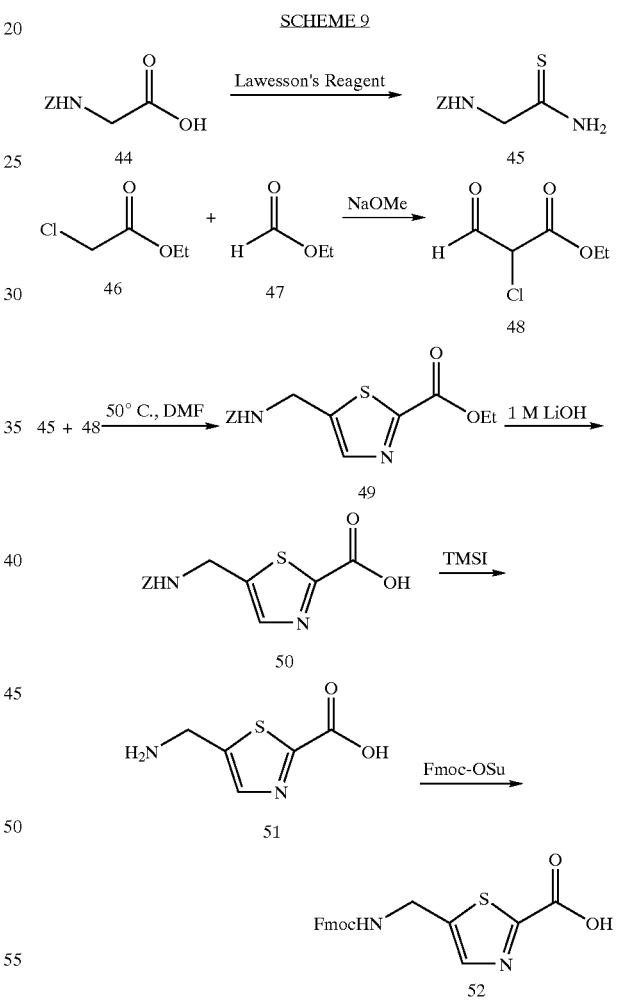

a) Z-Gly-NH₂ 44 (4 g, 20.4 mmol) and Lawesson's Reagent (4.6 g, 11.3 mmol) (Irako et al. *Tetrahedron* 1995, 51, 12731–12744) were suspended in dioxane (20 mL) and stirred at 60° C. for 30 min and then at rt for 3 h. The solvent was removed under reduced pressure. To the crude residue was added saturated NaHCO₃/H₂O (1:1 v/v, 50 mL). The resulting white precipitate was filtered and washed with saturated NaHCO₃/H₂O (1:1 v/v, 3×50 mL) to provide 4.3 g (100%) of 45. ES (+) MS: m/e=235.0 (M+Na)+.

b) To a flask containing MeOH (30 mL) was added Na metal (3.3 g, 143 mL). After stirring for 2 h, the solution was diluted with ether (60 mL) and cooled to 0° C. To this solution was added dropwise a solution of ethyl formate 46 (11.7 g, 157 mmol) and chloromethyl acetate 47 (17 g, 157 mmol) in ether (60 mL) (Plouvier et al. *Heterocycles* 1991, 32, 693–701). The mixture was warmed to rt and stirred for 12 h. The resulting mixture was acidified with 1 M HCl (100 mL) and extracted with ether (3×100 mL). The organic layer was dried over MgSO$_4$ and the solvent was removed under reduced pressure to afford 48 which was carried onto the next step without further purification.

c) To a solution of 45 (2.0 g, 9.4 mmol) in DMF (30 mL) at 60° C. was portionwise added 48 (6.8 g, 47 mmol) over 5 h. After stirring for 8 h, the solution was diluted with ether (60 mL) and washed with saturated NaHCO$_3$ (3×50 mL). The organic layer was dried over MgSO$_4$ and the solvent was removed under reduced pressure. The crude residue was purified by silica gel chromatography (50:50 ethyl acetate/hexanes) to afford 0.775 g (27%) of 49. ES (+) MS: m/e=293.1 (M−Me)$^+$.

d) To a solution of 49 (0.775 g, 2.5 mmol) in dioxane (10 mL) was added 1 M LiOH (7.6 mL). After stirring for 30 min, the solution was diluted with ethyl acetate (50 mL) and washed with 1 M HCl (3×20 mL). The organic layer was dried over MgSO$_4$ and the solvent was removed under reduced pressure to afford 50 which was used without further purification. ES (+) MS: m/e=293.1 (M+H)$^+$.

e) To a suspension of 50 (0.400 g, 1.4 mmol) in acetonitrile (5 mL) was dropwise added iodotrimethylsilane (0.350 mL, 2.4 mmol). After stirring for 2 h at rt, the solvent was removed under reduced pressure to afford 51 which was used without further purification. ES (+) MS: m/e=142.0 (M−NH$_2$)$^+$.

f) To a solution of 51 (1.4 mmol) in H$_2$O/dioxane (1:1 v/v, 10 mL) was added NaHCO$_3$ (0.588 g, 7.0 mmol) and Fmoc-OSu (0.518 g, 1.54 mmoL). After stirring for 2 h, the solution was diluted with ether (50 mL) and washed with 1 M HCl (3×20 mL). The organic layer was dried over MgSO$_4$ and the solvent was removed under reduced pressure. The crude residue was purified by silica gel chromatography (50:50 to 100:0 ethyl acetate/hexanes) to afford 0.500 g (83%) of 52. $^1$H NMR (CDCl$_3$) δ 8.23 (s, 1H), 7.79 (d, J=7.3 Hz, 1H), 7.66 (d, J=7.2 Hz, 1H), 7.31–7.49 (m, 3H), 7.10–7.23 (m, 2H), 4.56 (s, 2H), 4.46 (d, J=6.6 Hz, 1H), 4.24–4.26 (m, 1H), 2.66 (s, 1H). ES (+) MS: m/e=381.2 (M+H)$^+$.

g) The title compound was prepared according to the procedure of Example 1j–l except for using 52 as a reagent instead of 12 (1.7 mg, 5%). $^1$H NMR (CD$_3$OD) δ 8.31 (d, J=2.6 Hz, 1H), 8.14 (s, 1H), 7.90 (d, J=6.7 Hz, 1H), 7.36–7.37 (m, 2H), 7.21–7.23 (m, 2H), 7.06 (d, J=8.8 Hz, 1H), 5.12 (t, J=8.0 Hz, 1H), 4.40 (d, J=6.0 Hz, 2H), 3.92 (s, 2H), 3.41–3.49 (m, 2H), 2.72–2.99 (m, 2H). ES (+) MS: m/e=628.0 (M+H)$^+$.

EXAMPLE 11

This example describes an exemplary synthesis of the compound below

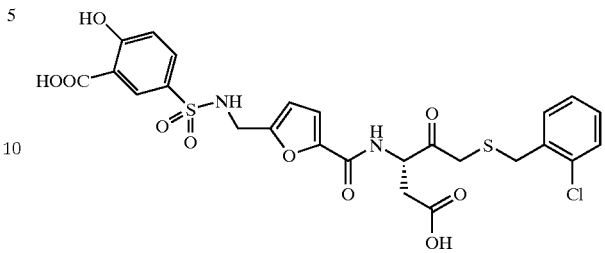

An intermediate, compound 56, was synthesized as described in Scheme 10.

SCHEME 10

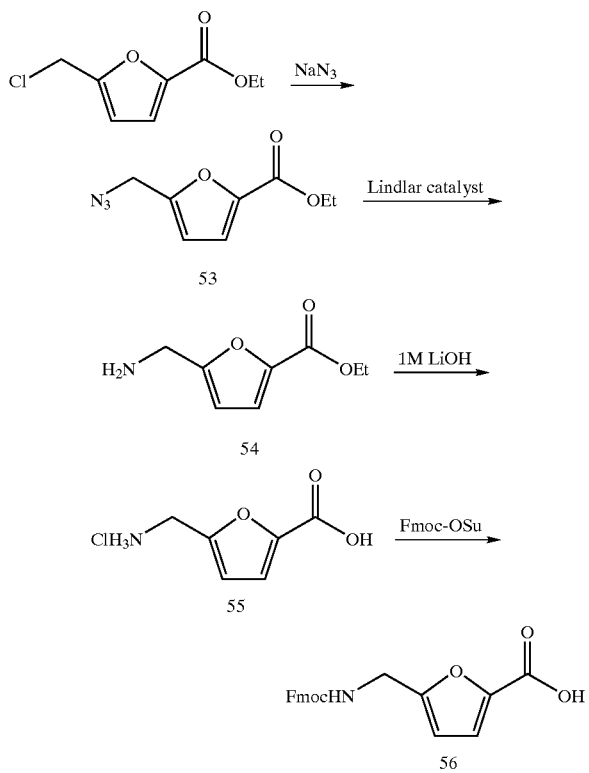

a) To a solution of ethyl-5(chloromethyl)-2-furoate (1.5 g, 8.00 mmol) in DMF (20.0 mL) was added NaN$_3$ (1.55 g, 23.8 mmol) and a catalytic amount of tetrabutylammonium iodide at rt. After stirring for 5.5 h the solvent was removed under reduced pressure and the crude residue was diluted with ether and washed with water and brine. The organic layer was dried over Na$_2$SO$_4$ and the solvent was removed under reduced pressure. The crude residue was purfied by silica gel chromatography (30:70 ether/hexanes) to provide 1.57 g (100%) of 53 as a colorless liquid.

b) The azide 53 (1.57 g, 8.00 mmol) and Lindlar catalyst (ca. 0.50 g) in EtOH (40.0 mL) was stirred for 22 h at rt under an atmosphere of hydrogen gas (1 atm via balloon). The catalyst was filtered off through a Celite and washed with hot MeOH. The filtrate was concentrated to give an oily residue which was purified by silica gel chromatography (50:50 MeOH/ethyl acetate) to give 785 mg (58%) of 54 as a pale oil. ES (+) MS m/e=153 (M−NH$_3$)$^+$.

c) Ester 54 (0.785 g, 4.64 mmol) in dioxane (15.0 mL) was stirred at rt with aqueous LiOH (12.0 mL of a 1.0 N solution) for 15 h, concentrated to dryness, acidified with excess 2.0 N HCl and concentrated to give 55 as a colorless solid which was used without further purification.

d) To a solution of amino acid 55 from the previous reaction in dioxane (20.0 mL) and $H_2O$ (20.0 mL) was added Fmoc-OSu (1.72 g) and $NaHCO_3$ (7.80 g) at rt. After stirring for 21 h, the reaction was concentrated to dryness and partitioned between 2.0 N HCl and ethyl acetate. The organic layer was separated and washed with water, brine and dried over $NaSO_4$. Concentration in vacuo and precipitation from ethyl acetate and hexanes gave 1.44 g (86%, 2 steps) of 56 as a colorless powder. ES (+) MS m/e=386 (M+Na)$^+$.

e) The title compound was prepared according to the procedure of Example 1j–1 except for using 56 as a reagent instead of 12. (5.5 mg, 14%). $^1$H NMR ($CD_3OD$) δ 8.20 (d, J=2.0 Hz, 1H), 7.82 (dd, J=8.8, 2.0 Hz, 1H), 7.33–7.38 (m, 2H), 7.19–7.21 (m, 2H), 6.99 (d, J=8.8 Hz, 1H), 6.92 (d, J=3.4 Hz, 1H), 6.27 (d, J=3.3 Hz, 1H), 5.11 (t, J=6.2 Hz, 1H), 4.18 (s, 2H), 3.80 (d, J=2.8 Hz, 2H), 3.44 (d, J=15.2 Hz, 1H), 3.36 (d, J=15.3 Hz, 1H), 2.98 (dd, J=16.9, 6.2 Hz, 1H), 2.79 (d, J=16.9, 6.2 Hz, 1H). ES (+) MS m/e=611.0 (M+H)$^+$.

EXAMPLE 12

This example describes an exemplary synthesis of the compound below

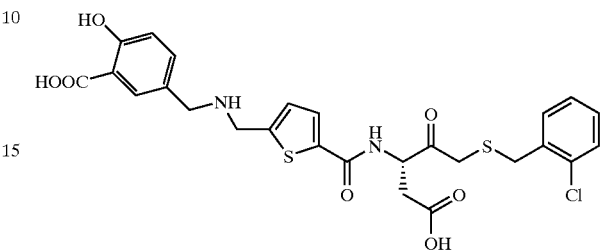

Resin 57 was synthesized as described in Scheme 11.

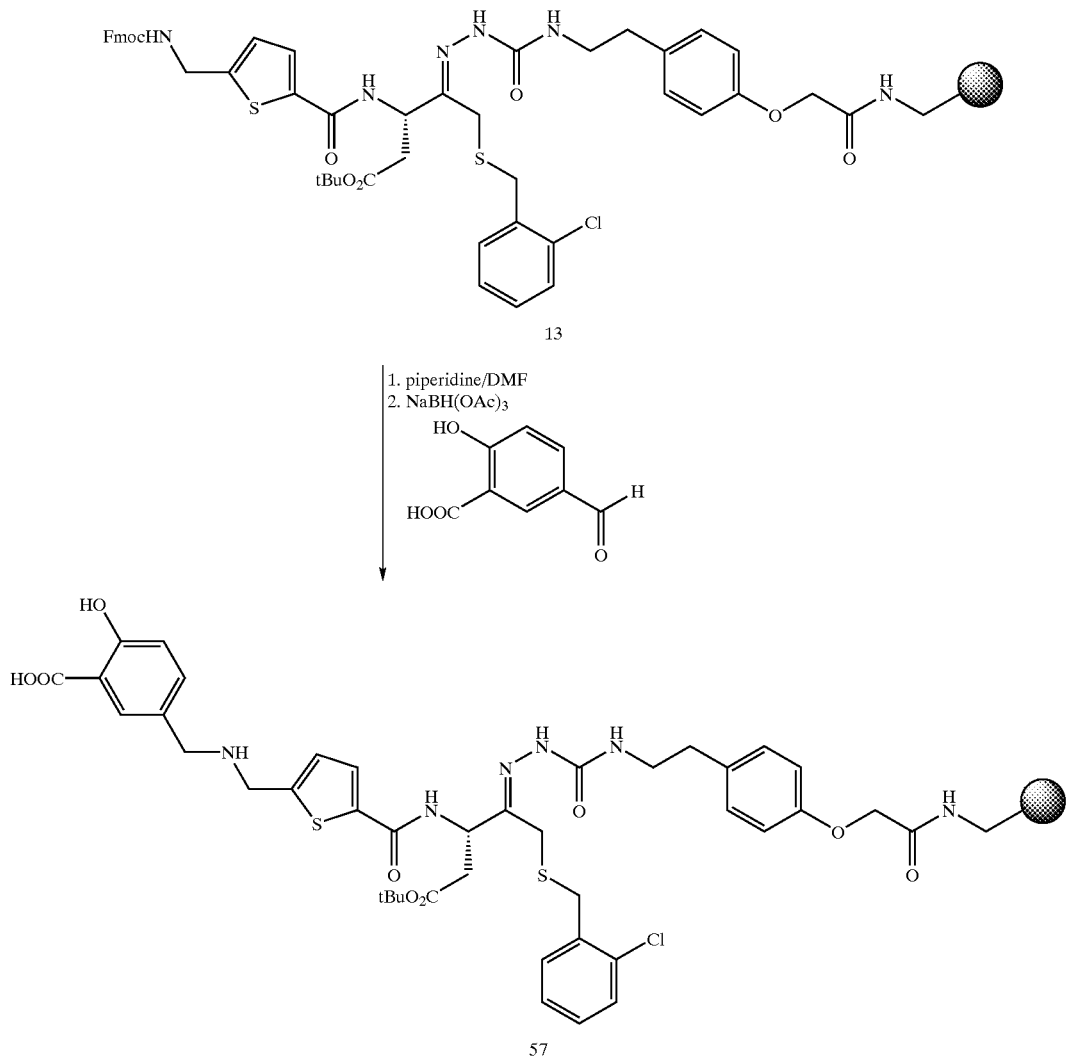

a) Resin 13 (0.650 g, 0.26 mmol) was treated with 20% piperidine in DMF (10 mL) and agitated for 30 min. The resin was washed successively with $CH_2Cl_2$ (3×10 mL) and then added 1,2-dichloroethane/acetic acid (99:1 v/v, 10 mL) followed by 5-formylsalicylic acid (0.087 g, 0.52 mmol). After gentle agitation for 8 h, $NaBH(OAc)_3$ (0.276 g, 1.3 mmol) was added and the reaction was agitated for an additional 12 h to provide 57. The resin was washed with $CH_2Cl_2$ (3×10 mL), MeOH (2×10 ml) and $CH_2Cl_2$ (2×10 mL).

b) Resin 57 was treated with $TFA/H_2O$ (9:1 v/v, 10 mL) and agitated for 15 min. The resin was filtered and washed with $CH_2Cl_2$ (2×10 mL). The combined filtrates were diluted with toluene (3 mL) and the solvent was removed under reduced pressure. The crude residue was purified by reverse-phase preparatory HPLC to afford the title compound (12.2 mg, 35%). $^1$H NMR ($CD_3OD$) δ 8.05 (m, 1H), 7.71 (m, 1H), 7.58 (m, 1H), 7.36 (m, 3H), 7.21 (m, 2H), 7.01 (m, 1H), 5.14–5.17 (m, 1H), 4.50 (s, 2H), 4.21 (s, 2H), 3.81 (s, 2H), 3.46 (d, J=15.6 Hz, 1H), 3.39 (d, J=15.1 Hz, 1H), 3.02 (dd, J=17.0, 6.3 Hz, 1H), 2.78 (J=17.0, 7.2 Hz, 1H). ES (+) MS: m/e=577.2 (M+H)$^+$.

EXAMPLE 13

This example describes an exemplary synthesis of the compound below

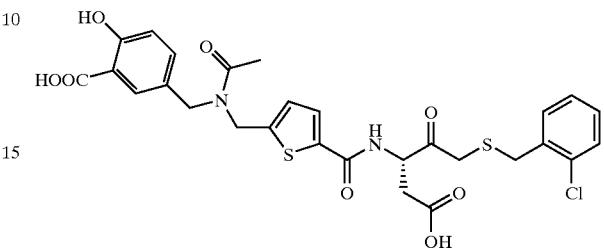

Resin 58 was synthesized as described in Scheme 12.

SCHEME 12

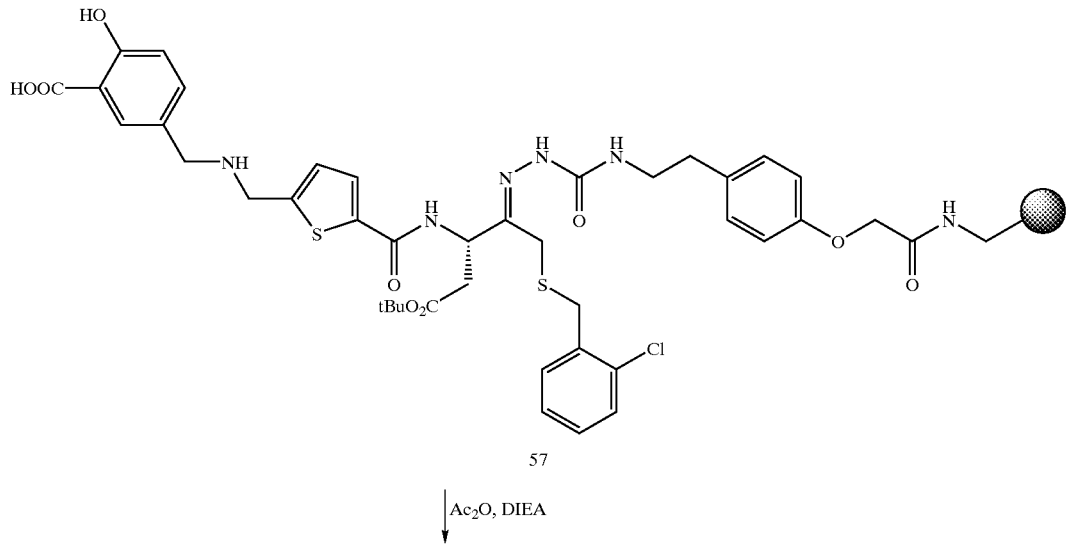

57

↓ $Ac_2O$, DIEA

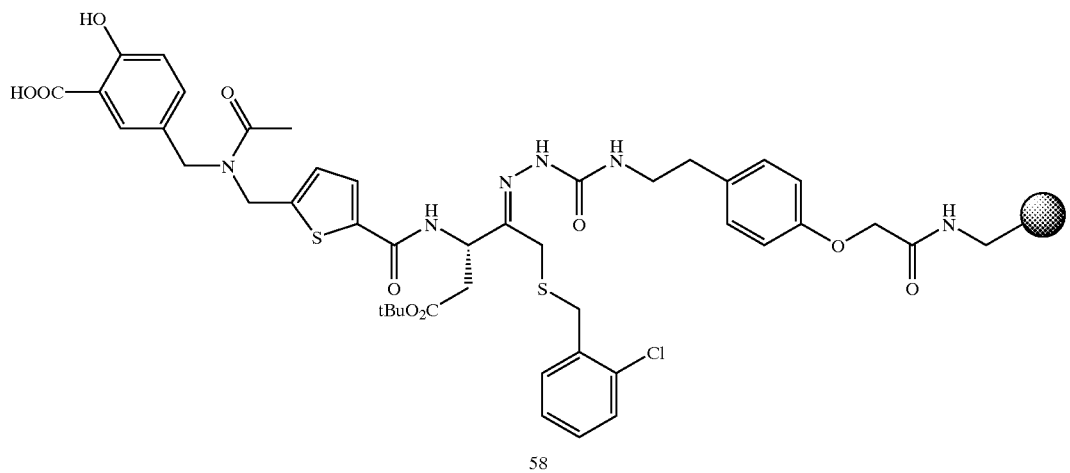

58 a) An aliquot of resin 57 (0.300 g, 0.06 mmol) was solvated in CH$_2$Cl$_2$ (5 mL) and added acetic anhydride (11 μl, 0.12 mmol). After gentle agitation for 1 h, the resin was filtered and washed with CH$_2$Cl$_2$ (3×10 mL) to afford 58.

b) Resin 58 was treated with TFA/H$_2$O (9:1 v/v, 10 mL) and agitated for 15 min. The resin was filtered and washed with CH$_2$Cl$_2$ (2×10 mL). The combined filtrates were diluted with toluene (3 mL) and the solvent was removed under reduced pressure. The crude residue was purified by reverse-phase preparatory HPLC to afford the title compound (2.4 mg, 6%). $^1$H NMR (CD$_3$OD; reported as a mixture of rotamers) δ 7.90 (s, 1H), 7.75 (s, 0.5H), 7.69 (d, 0.5H), 7.59 (d, J=3.6 Hz, 0.5H), 7.50 (d, J=3.9 Hz, 0.5H), 7.32–7.39 (m, 3H), 7.20–7.22 (m, 2H), 5.08–5.11 (m, 1H), 4.66–4.73 (m, 1H), 3.80 (d, J=4.7 Hz, 2H), 3.46 (d, J=15.3 Hz, 1H), 3.38 (d, J=15.7 Hz, 1H), 2.99–3.04 (m, 1H), 2.72–2.78 (m, 1H), 2.66 (s, 3H), 2.21 (s, 1H). ES (+) MS: m/e=619.0 (M+H)$^+$

EXAMPLE 14

This example describes an exemplary synthesis of the compound below

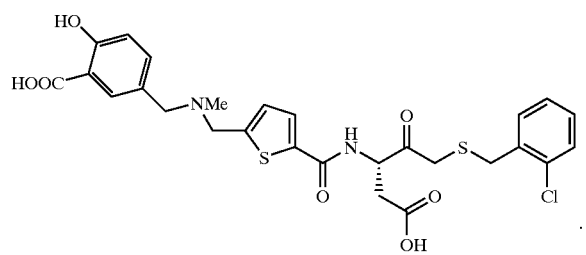

An intermediate, compound 58, was synthesized as described in Scheme 13.

SCHEME 13

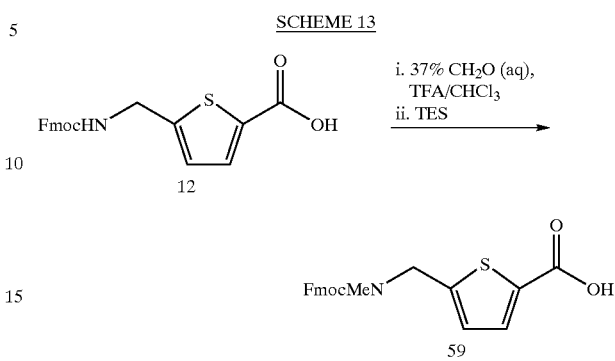

a) To a solution of 12 (6.0 g, 15.8 mmol) in TFA/CHCl$_3$ (1:1 v/v, 160 mL) was added 37% formaldehyde in H$_2$O (13 mL, 173 mmol) (Luke et al. *Tetrahedron Lett.* 1996, 37, 263–266). After stirring for 1 h, triethylsilane (28 mL, 237 mmol) was added and the reaction was stirred for an additional 1 h. The solvent was removed under reduced pressure and the crude residue was purified by silica gel chromatography (100:0 ethyl acetate/hexanes) to provide 6.2 g (100%) of 59. ES (+) MS: m/e=416.2 (M+Na)$^+$.

Resin 61 was synthesized as described in Scheme 14.

SCHEME 14

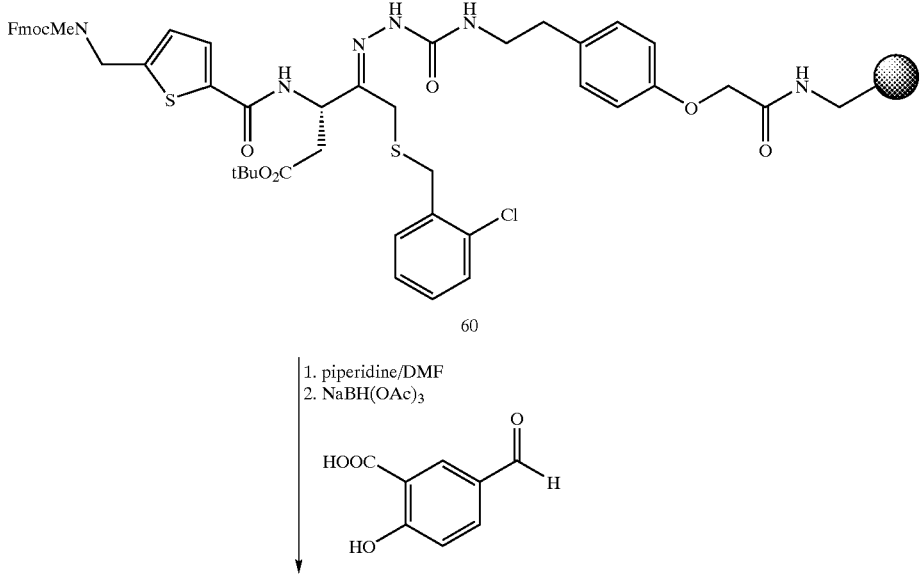

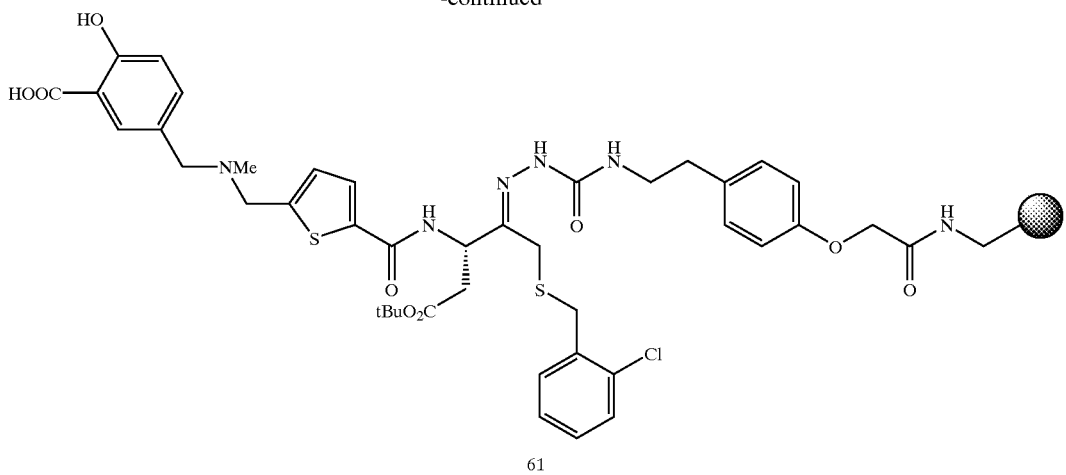

61 b) Resin 4 (0.300 g, 0.06 mmol) was treated with 20% piperidine in DMF (5 mL) and agitated for 30 min. The resin was washed successively with CH₂Cl₂ (3×5 mL) and then solvated in DMF (5 mL) followed by 59 (0.379 g, 1.0 mmol), diisoproylethylamine (0.525 mL, 3 mmol) and PyBOP (0.780 g, 1.5 mmol). After agitating for 3 h, the resin was filtered and washed with CH₂Cl₂ (5×15 mL) to provide resin 60.

c) Resin 60 (0.650 g, 0.26 mmol) was treated with 20% piperidine in DMF (5 mL) and agitated for 30 min. To the resin was added 1,2-dichloroethane/acetic acid (99:1 v/v, 6 mL) and 5-formylsalicylic acid (0.087 g, 0.52 mmol). After gentle agitation for 8 h, NaBH(OAc)₃ (0.276 g, 1.3 mmol) was added and the reaction was agitated for an additional 12 h to provide 61. The resin was washed with CH₂Cl₂ (3×10 mL), MeOH (2×10 mL) and CH₂Cl₂ (2×10 mL).

d) Resin 61 was treated with TFA/H₂O (9:1 v/v, 2 mL) and agitated for 15 min. The resin was filtered and washed with CH₂Cl₂ (2×4 mL). The combined filtrates were diluted with toluene (3 mL) and the solvent was removed under reduced pressure. The crude residue was purified by reverse-phase preparatory HPLC to afford the title compound (5.8 mg, 16%). ¹H NMR (CD₃OD) δ 8.06 (d, J=2.0 Hz, 1H), 7.74 (d, J=3.6 Hz, 1H), 7.61 (dd, J=8.3, 1.8 Hz, 1H), 7.35–7.42 (m, 3H), 7.21–7.23 (m, 2H), 7.05 (J=8.5 Hz, 1H), 5.49 (s,1H), t, J=6.4 Hz, 1H), 4.71 (1H), 4.47–4.59 (m, 2H), 4.24–4.29 (m, 1H), 3.81 (d, J=2.2 Hz, 2H), 3.47 (d, J=15.2 Hz, 1H), 3.40 (d, J=15.0 Hz, 1H), 3.03 (dd, J=16.7, 5.7 Hz, 1H), 2.75–2.83 (m, 1H). ES (+) MS: m/e=591.0 (M+H)⁺.

EXAMPLE 15

This example describes the synthesis of the compound below

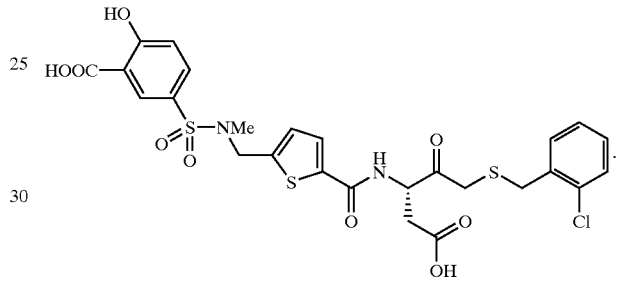

The title compound was prepared according to the procedure of Example 1k–1 except for using 59 instead of 12 (5.8 mg, 15%). ¹H NMR (CD₃OD) δ 8.28 (s, 1H), 7.89 (d, J=8.9 Hz, 1H), 7.55 (d, J=3 Hz, 1H), 7.34–7.36 (m, 2H), 7.19–7.21 (m, 2H), 7.11 (dd, J=8.8, 2.5 Hz, 1H), 7.01 (s, 1H), 5.10 (t, J=9.0 Hz, 1H), 4.44 (s, 2H), 3.80 (d, J=3.5 Hz, 2H), 3.46 (d, J=15.3 Hz, 1H), 3.38 (d, J=15.2 Hz, 1H), 2.85–3.04 (m, 1H), 2.76–2.78 (m, 1H), 2.72 (s, 3H). ES (+) MS: m/e=641.0 (M+H)⁺.

EXAMPLE 16

This example describes an exemplary synthesis of the compound below

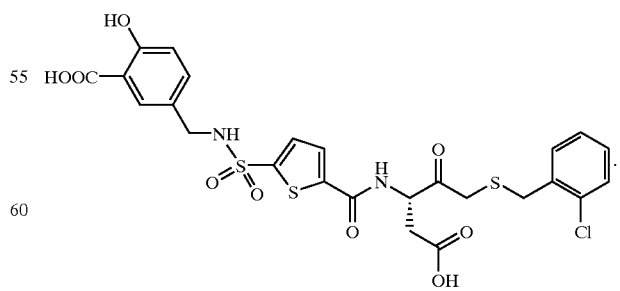

An intermediate, compound 63, is described in Scheme 15.

SCHEME 15

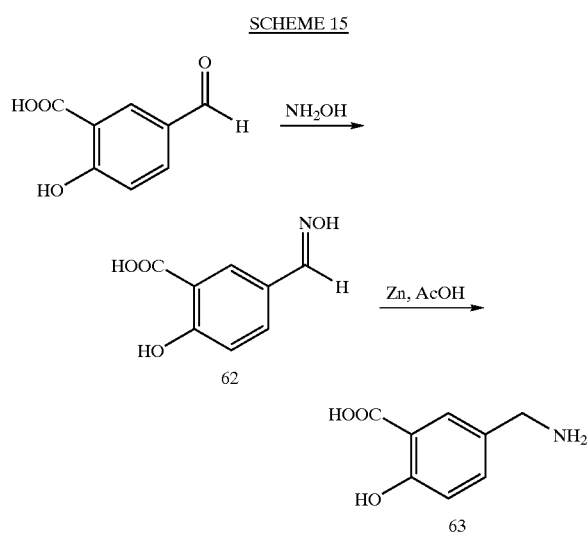

a) To a solution of 5-formylsalicylic acid (3.84 g, 23.1 mmol) in MeOH (50 mL) was added 16.3 M NH$_2$OH in H$_2$O (3 mL, 46.2 mmol). After stirring for 1 h at rt, the solvent was removed under reduced pressure to provide 62 which was used without further purification.

b) To a mixture of 62 (3.62 g, 20 mmol) in acetic acid (100 mL) was added zinc dust (7.8 g, 120 mmol). After stirring for 5 h at rt, the slurry was filtered through Celite and washed with EtOH (3×50 mL). Solvent was evaporated in vacuo and azeotroped with toluene (2×100 mL) to afford 3.1 g of 63 (93%) which was used without purification. ES (+) MS: m/e=164 (M−3H)$^+$. $^1$H NMR (CDCl$_3$) δ 8.49 (s, 1H), 7.89 (d, 1H), 7.34 (d, 1H), 4.5 (s, 2H).

Another intermediate, compound 68, was synthesized as described in Scheme 16.

SCHEME 16

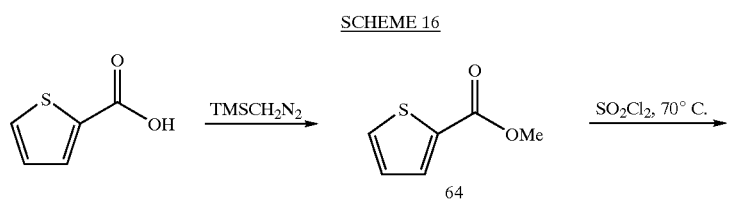

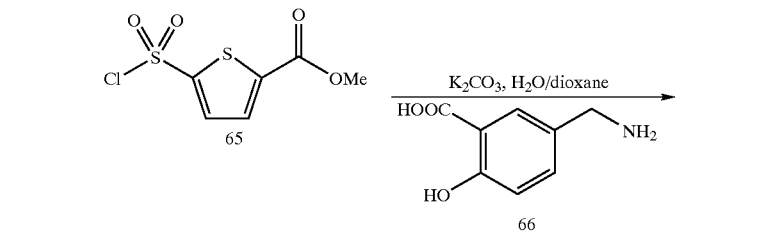

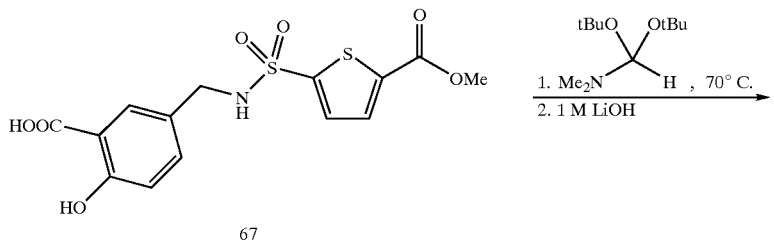

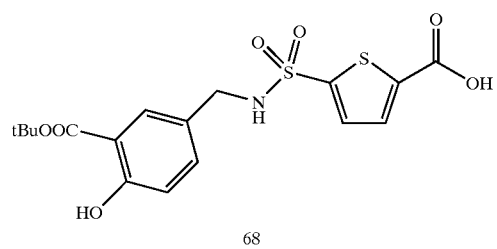

c) To a solution of 2-thiophenecarboxylic acid (5 g, 35.2 mmol) in toluene/MeOH (4:1 v/v, 70 mL) was dropwise added 2 M TMSCH$_2$N$_2$ in hexanes (19.36 mL, 38.7 mmoL). After stirring for 15 min, the solvent was removed under reduced pressure to provide 5.0 g (100%) of 64 which was used without further purification. ES (+) MS: m/e=143.05 (M+H)$^+$.

d) To a solution of 64 (2.3 g, 16.2 mmol) in CHCl$_3$ (3 mL) at 0° C. was dropwise added chlorosulfonic acid (2 mL, 32.4 mmoL). After stirring at 70° C. for 3 h, the solution was quenched with ice, diluted with CH$_2$Cl$_2$ (20 mL) and washed with 1 M HCl (3×20 mL). The organic layer was dried over MgSO$_4$ and the solvent was removed under reduced pressure to provide 65 which was used without further purification. ES (+) MS: m/e=241.0 (M+H)$^+$.

e) To a solution of 63 (0.7 g, 2.9 mmol) in H$_2$O (5 mL) was added K$_2$CO$_3$ (0.801 g, 5.8 mmol). After stirring for 5 min at rt, a solution of 65 (0.486 g, 2.9 mmol) in dioxane (5 mL) was added. After stirring for 15 min, the solution was diluted with CH$_2$Cl$_2$ and washed with 1 M HCl (3×10 mL). The organic layer was dried over MgSO$_4$ and the solvent was removed under reduced pressure to provide 66 which was used without further purification. ES (+) MS: m/e= 394.1 (M+Na)$^+$.

f) To a suspension of 66 (0.440 g, 1.2 mmol) in benzene (2 mL) at 80° C. was dropwise added N,N-dimethylformamide di-tert-butylacetal (1.1 mL, 4.7 mmol). After stirring for 4 h at 80° C., the solution was diluted with ether (10 mL) and washed with H$_2$O (3×10 mL) and brine (3×10 mL). The organic layer was dried over MgSO$_4$ and the solvent was removed under reduced pressure. The crude residue was purified by silica gel chromatography to provide 0.278 g (54%) of 67. ES (+) MS: m/e=450.1 (M+Na)$^+$.

g) To a solution of 67 (0.278 g, 0.6 mmol) in dioxane (3 mL) was added 1 M LiOH (2 mL). After stirring at rt for 2 h, the solution was diluted with ether (10 mL) and washed with 1 M HCl (3×5 mL). The organic layer was dried over MgSO$_4$ and the solvent was removed under reduced pressure to provide 68 which was used without further purification. ES (+) MS: m/e=436.1 (M+Na)$^+$.

h) The title compound was prepared according to the procedure of Example 1k–l except for using 68 as a reagent instead of 12 (1.0 mg, 3%). $^1$H NMR (CD$_3$OD) δ 7.71 (d, J=1.9 Hz, 1H), 7.60 (d, J=3.9 Hz, 1H), 7.45 (d, J=3.9 Hz, 1H), 7.36 (m, 3H), 7.21 (m, 2H), 6.82 (d, J=8.5 Hz, 1H), 5.15 (t, J=6.5 Hz, 1H), 4.12 (s, 2H), 3.82 (s, 2H), 3.48 (d, J=15.3 Hz, 1H), 3.40 (d, J=15.3 Hz, 1H), 3.16 (m, 1H), 2.86–3.01 (m, 1H), 2.75–2.85 (m, 1H). ES (+) MS: m/e= 627.0 (M+H)$^+$.

EXAMPLE 17

This example describes an exemplary synthesis of the compound below

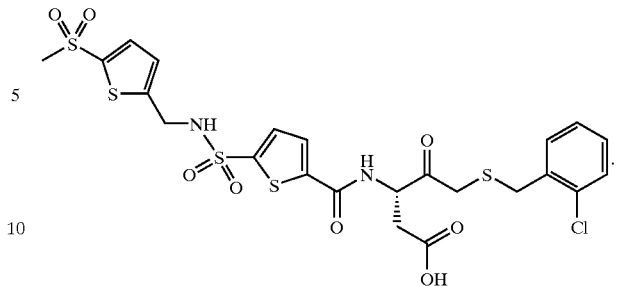

An intermediate, compound 71, was synthesized as described in Scheme 17.

SCHEME 17

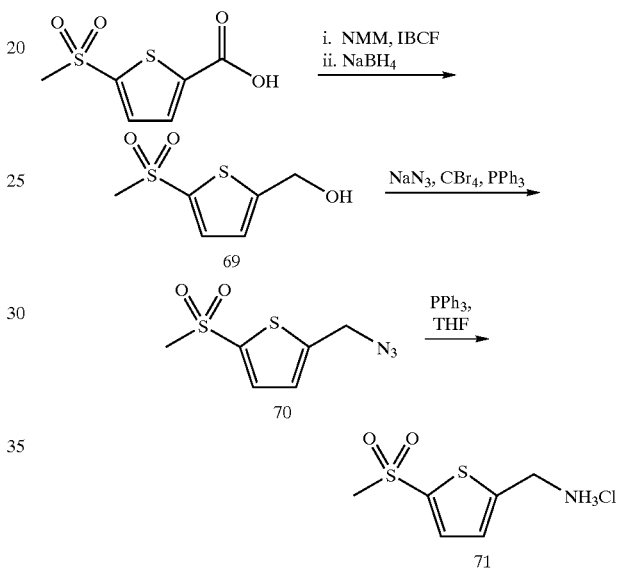

a) To a solution of 5-(methylsulfonyl)thiophene-2-carboxylic acid (2.32 g, 11.26 mmol) in dry THF (15.0 mL) cooled to 0° C. was added triethylamine (1.73 mL, 12.4 mmol) followed by dropwise addition of isobutyl chloroformate (1.61 mL, 12.4 mmol). After stirring at 0° C. for 15 min the reaction mixture was allowed to warm to rt and stirred for an additional 30 min. The reaction mixture was filtered directly into a rapidly stirred solution of NaBH$_4$ (0.90 g, 23.80 mmol) in H$_2$O (12.0 mL) cooled to 0° C. The reaction was then vigorously stirred for an additional 3.5 h at rt and acidified with 2 N HCl to pH=2. The reaction was partitioned between ethyl acetate, washed with water, saturated NaHCO$_3$, brine and dried over NaSO$_4$. Concentration in vacuo followed by purification by silica gel chromatography (70:30 ethyl acetate/hexanes) gave 1.62 g (75%) of 69 as a colorless solid.

b) To a solution of 69 (0.620 g, 3.23 mmol) in dry DMF (9.0 mL) at rt was added NaN$_3$ (315 mg, 4.85 mmol), CBr$_4$ (1.61 g, 4.85 mmol) and triphenylphosphine (1.27 g, 4.85 mmol). After stirring for 3 h, the reaction was concentrated to near dryness and partitioned between ethyl acetate and water. The organic layer was separated, washed with brine and dried over NaSO$_4$. Concentration in vacuo followed by purification by silica gel chromatography (50:50 ethyl acetate/hexanes) gave 0.632 g (90%) of 70 as a yellow oil. ES (+) MS m/e=218 (M+H)$^+$.

c) To a solution of azide 70 (0.632 g, 2.90 mmol) in THF (25.0 mL) and H$_2$O (25.0 mL) was added triphenylphosphine (913 mg, 3.48 mmol) in one portion. The reaction mixture was heated at 50° C. for 23 h, cooled, concentrated to dryness and purified by flash column chromatography on silica gel using 50% MeOH in ethyl acetate to give the amine as an oil which was treated with 1.0 N HCl in dry dioxane to give a colorless solid. The solid was collected by vacuum filtration, washed with dry ether and dried under vacuum to give 0.333 g (50%) of 71 as a fine colorless powder. ES (+) MS m/e=192 (M+H)$^+$.

Another intermediate, compound 74, was synthesized as described in Scheme 18.

SCHEME 18

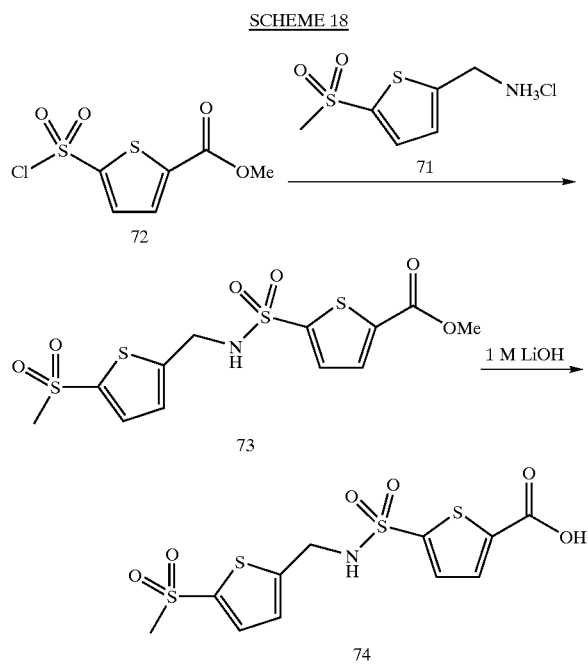

d) To a solution of 72 (0.105 g, 0.4 mmol) in CH$_2$Cl$_2$ (5 mL) was added diisopropylethylamine (0.139 mL, 0.8 mmol) and 71 (0.100 g, 0.4 mmol). After stirring for 1 h at rt, the solution was diluted with CH$_2$Cl$_2$ and washed with 1 M HCl (3×10 mL). The organic layer was dried over MgSO$_4$ and the solvent was removed under reduced pressure to provide 73 which was used without further purification.

e) To a solution of 73 (0.4 mmol) in dioxane (3 mL) was added 1 M LiOH (2 mL). After stirring at rt for 2 h, the solution was diluted with ether (10 mL) and washed with 1 M HCl (3×5 mL). The organic layer was dried over MgSO$_4$ and the solvent was removed under reduced pressure to provide 74 which was used without further purification. ES (+) m/e=363.95 (M−OH)$^+$.

f) The title compound was prepared according to the procedure of Example 1j,l except for using 74 instead of 12. ES (+) m/e=651.1 (M+H)$^+$.

EXAMPLE 18

This example describes an exemplary synthesis of the compound below

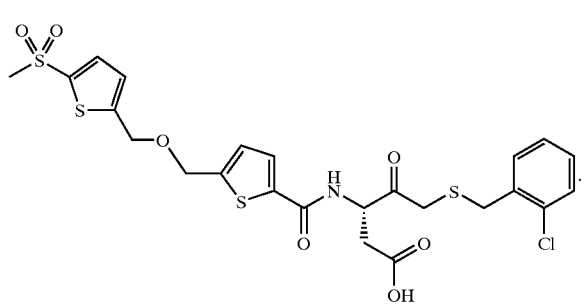

An intermediate, compound 77, was synthesized as described in Scheme 19.

SCHEME 19

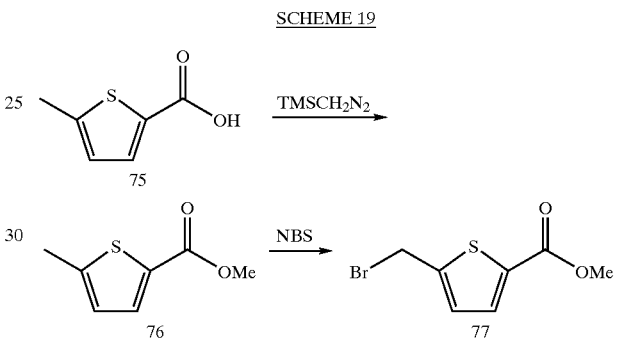

a) 5-Methylthiophene-2-carboxylic acid 75 (20.0 g, 141 mmol) was weighed into a 500 mL flask. Benzene (120 mL) was added, followed by MeOH (14 mL). The solution was stirred and cooled to 0° C. A 2.0 M solution of TMSCH$_2$N$_2$ in hexanes (80 mL, 160 mmol) was placed in an addition funnel, and added to the reaction over 20 min. The reaction was then warmed to rt, and the solvent was removed under reduced pressure. Distillation under reduced pressure BP$_{0.5}$= 88–93° C. provided 17.9 g (82%) of 76 as a colorless oil. $^1$H NMR (CDCl$_3$) δ 7.61 (d, J=3.7 Hz, 1H), 6.76 (d, J=3.6 Hz, 1H), 3.85 (s, 3H), 2.52 (s, 3H).

b) 76 (11.4 g, 72.9 mmol) was weighed into a 500 mL 3-neck flask. CCl$_4$ (200 mL) was added, followed by NBS (14.30 g, 80.3 mmol). A condenser was installed, and the apparatus was flushed with nitrogen, then left under a nitrogen atmosphere. The solution was heated to reflux for 5 min, then cooled to below reflux temperature, and AIBN (91 mg, 0.55 mmol) was added with brief removal of the septum. The solution was heated to reflux for 2 h, at which point $^1$H NMR of a filtered aliquot indicated a 1:1 ratio of starting material to product. Another portion of AIBN (81 mg, 0.49 mmol) was added, and the solution was refluxed for another 2 h. The reaction was then cooled to rt, filtered and concentrated to provide 18.8 g (110%) of 77 as an orange oil that was used without further purification. $^1$H NMR (CDCl$_3$) δ 7.63 (d, J=3.8 Hz, 1H), 7.09 (d, J=3.8 Hz, 1H), 4.67 (s, 2H), 3.88 (s, 3H).

Another intermediate, compound 80, was synthesized as described in Scheme 20.

SCHEME 20

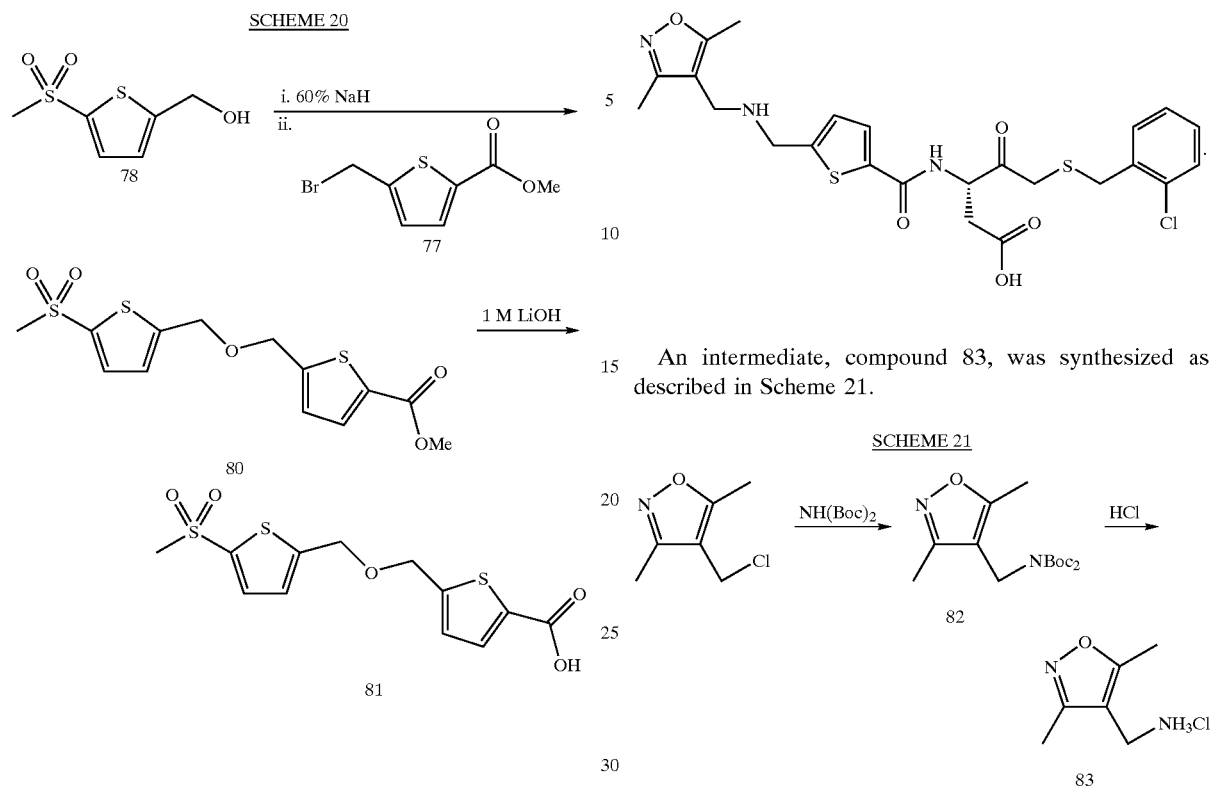

c) To a solution of 78 (0.150 g, 0.8 mmol) in THF (3 mL) at 0° C. was added 60% NaH (0.055 g, 0.89 mmol). The solution was warmed to rt for 15 min and then recooled to 0° C. To this solution was added dropwise a solution of 77 (0.184 g, 0.8 mmol) in THF (2 mL). After warming to rt, the solution was stirred for 30 min. The reaction was diluted with ethyl acetate (20 mL) and washed with saturated NaHCO$_3$ (3×10 mL). The organic layer was dried over MgSO$_4$ and the solvent was removed under reduced pressure to provide 80 which was used without further purification. ES (+) MS: m/e=315.0 (M−OMe)$^+$.

d) To a solution of 80 (0.8 mmol) in dioxane (5 mL) was added 1 M LiOH (5 mL). After stirring for 1 h at rt, the solution was diluted with ether (20 mL) and washed with 1 M HCl (3×10 mL). The organic layer was dried over MgSO$_4$ and the solvent was removed under reduced pressure to provide 0.238 g (90%, 2 steps) 81 which was used without further purification. ES (+) MS: m/e=314.9 (M−OH)$^+$.

e) The title compound was prepared according to the procedure of Example 1j,l except for using 81 instead of 12. ES (+) MS: m/e=602.1 (M+H)$^+$.

EXAMPLE 19

This example describes an exemplary synthesis of the compound below

An intermediate, compound 83, was synthesized as described in Scheme 21.

SCHEME 21 a) To a solution of chloride 4-(chloromethyl)-3,5-dimethylisoxazole (0.89 mL, 1.05 mmol) in dry DMF (7.0 mL) and CH$_2$Cl$_2$ (16.0 mL) was added di-t-butyl iminodicarboxylate potassium salt (1.88 g, 7.36 mmol) and a catalytic amount of tetrabutylammonium iodide. The resultant mixture was stirred at ambient temperature for 16 h, concentrated to dryness and partitioned between ether and H$_2$O. The organic layer was separated, washed with water, brine, dried and concentrated to give 82 as a colorless syrup which was used without further purification in the next step. ES (+) MS m/e=327 (M+H)$^+$.

b) The crude product 82 from the previous reaction was vigorously stirred in THF (20 mL) and 6.0 N HCl (20 mL) until no more starting material was detected by LC/MS. The reaction was concentrated to dryness to give a yellow solid which was triturated with dry ether to give 1.06 g (90%) of 83 as a light yellow crystalline powder. $^1$H NMR (DMSO-d$_6$) δ 8.47 (s, 3H), 3.84 (m, 2H), 2.47 (s, 3H), 2.33 (s, 3H).

An intermediate, compound 85, was synthesized as described in Scheme 22.

SCHEME 22

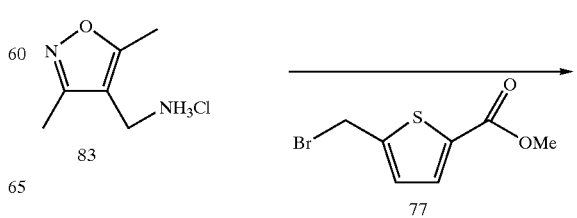

-continued

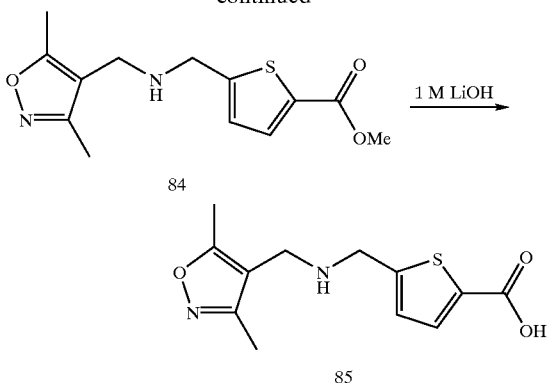

84

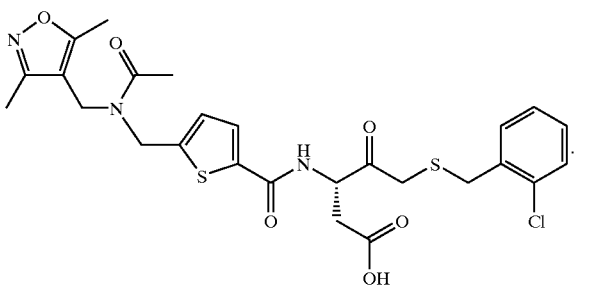

85 c) To a solution of 83 (0.152 g, 0.9 mmol) in DMF (3 mL) was dropwise added diisopropylethylamine (0.235 mL, 1.35 mmol) and a solution of 77 (0.200 g, 0.9 mmol) in DMF (1 mL). After stirring for 1 h at rt, the solution was diluted with ether (10 mL) and washed with saturated NaHCO$_3$. The organic layer was dried over MgSO$_4$ and the solvent was removed under reduced pressure to provide 0.164 g (65%) of 84 which was used without further purification. ES (+) MS: m/e=281.2 (M+H)$^+$.

d) To a solution of 84 (0.6 mmol) in dioxane (5 mL) was added 1 M LiOH (5 mL). After stirring for 1 h at rt, the solution was diluted with ether (20 mL) and washed with 1 M HCl (3×10 mL). The organic layer was dried over MgSO$_4$ and the solvent was removed under reduced pressure to provide 85 which was used without further purification.

e) The title compound was prepared according to the procedure of Example 1j,l except for using 85 as a reagent instead of 12. ES (+) MS: m/e=561.2 (M+H)$^+$.

EXAMPLE 20

This example describes an exemplary synthesis of the compound below

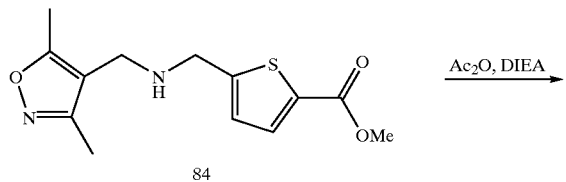

An intermediate, compound 87, was synthesized as described in Scheme 23.

SCHEME 23

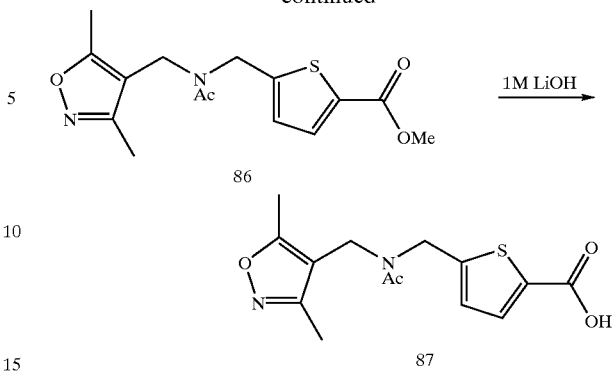

86

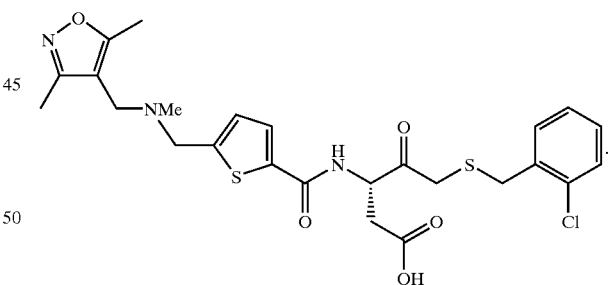

87 a) To a solution of 84 (0.160 g, 0.6 mmol) in CH$_2$Cl$_2$ (5 mL) was added acetic anhydride (0.113 mL, 1.2 mmol) and diisopropylethylamine (0.313 mL, 1.7 mmol). After stirring at rt for 1 h, the solution was diluted with CH$_2$Cl$_2$ (20 mL) and washed with 1 M HCl (3×10 mL). The organic layer was dried over MgSO$_4$ and the solvent was removed under reduced pressure to provide 86 which was used without further purification. ES (+) MS: m/e=323.2 (M+H)$^+$.

b) To a solution of 86 (0.6 mmol) in dioxane (5 mL) was added 1 M LiOH (5 mL). After stirring for 1 h at rt, the solution was diluted with ether (20 mL) and washed with 1 M HCl (3×10 mL). The organic layer was dried over MgSO$_4$ and the solvent was removed under reduced pressure to provide 87 which was used without further purification. ES (+) MS: m/e=309.2 (M+H)$^+$.

c) The title compound was prepared according to the procedure of Example 1j,l except for using 87 instead of 12. ES (+) MS: m/e=578.2 (M+H)$^+$.

EXAMPLE 21

This example describes an exemplary synthesis of the compound below

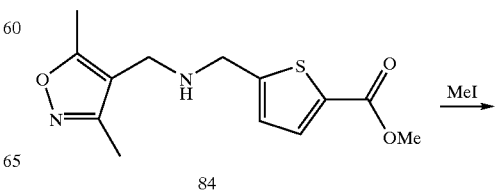

An intermediate, compound 89, was synthesized as described in Scheme 24.

SCHEME 24

84

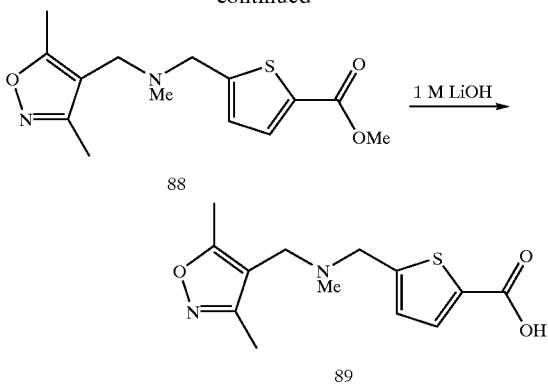

a) To a solution of 84 (0.180 g, 0.6 mmol) in CH$_2$Cl$_2$ (2 mL) was added iodomethane (0.108 mL, 0.7 mmol). After stirring at rt for 12 h, the solvent was removed under reduced pressure to provide 88 which was used without further purification. ES (+) MS: m/e=295.1 (M+H)$^+$.

b) To a solution of 88 (0.6 mmol) in dioxane (5 mL) was added 1 M LiOH (5 mL). After stirring for 1 h at rt, the solution was diluted with ether (20 mL) and washed with 1 M HCl (3×10 mL). The organic layer was dried over MgSO$_4$ and the solvent was removed under reduced pressure to provide 89 which was used without further purification. ES (+) MS: m/e=281.2 (M+H)$^+$.

c) The title compound was prepared according to the procedure of Example 1j,l except for using 89 instead of 12. ES (+) MS: m/e=550.1 (M+H)$^+$.

EXAMPLE 22

This example describes an exemplary synthesis of the compound below

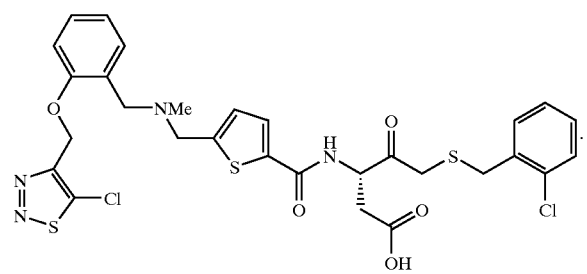

This compound was prepared according to the procedure of Example 14c–d except for using 5-chloro-4-(2-carboxyphenyloxymethyl)-1,2,3-thiadiazole as a reagent instead of instead of 5-formylsalicylic acid.

EXAMPLE 23

This example describes an exemplary synthesis of the compound below

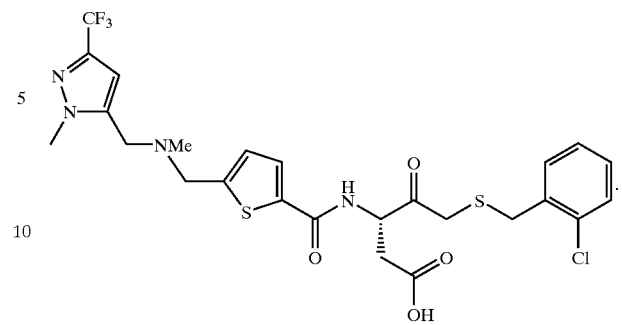

This compound was prepared according to the procedure of Example 14c–d except for using 5-[methyl-3-(trifluoromethyl)-1H-pyrazol-5-yl]thiophene-2-carbaldehyde as a reagent instead of 5-formylsalicylic acid.

EXAMPLE 24

This example describes an exemplary synthesis of the compound below

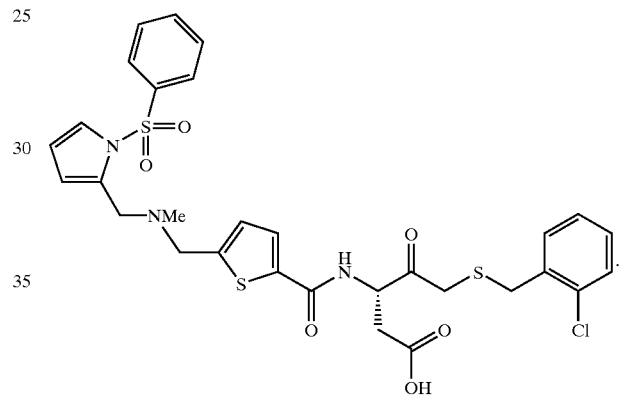

This compound was prepared according to the procedure of Example 14c–d except for using 1-(phenylsulfonyl)-2-pyrrolecarboxaldehyde as a reagent instead of 5-formylsalicylic acid.

EXAMPLE 25

This example describes an exemplary synthesis of the compound below

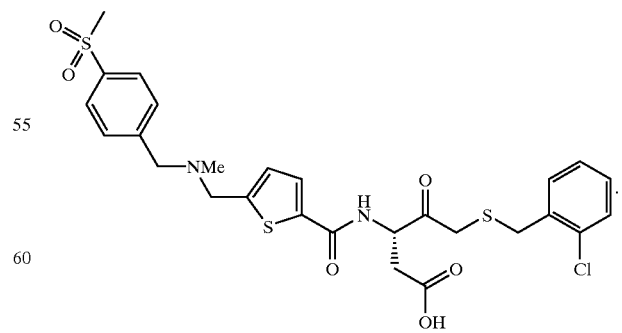

This compound was prepared according to the procedure of Example 14c–d except for using 4-methylsulphonyl benzaldehyde as a reagent instead of 5-formylsalicylic acid.

EXAMPLE 26

This example describes an exemplary synthesis of the compound below

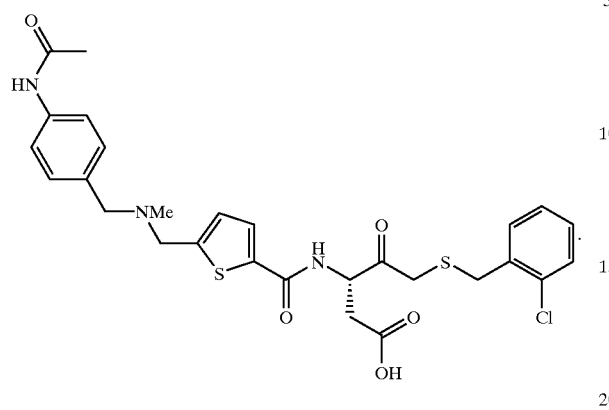

This compound was prepared according to the procedure of Example 14c-d except for using 4-acetamidobenzaldehyde as a reagent instead of 5-formylsalicylic acid.

EXAMPLE 27

This example describes an exemplary synthesis of the compound below

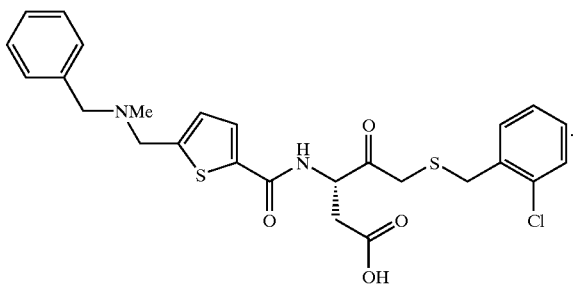

An intermediate, compound 91, was synthesized as described in Scheme 25.

SCHEME 25

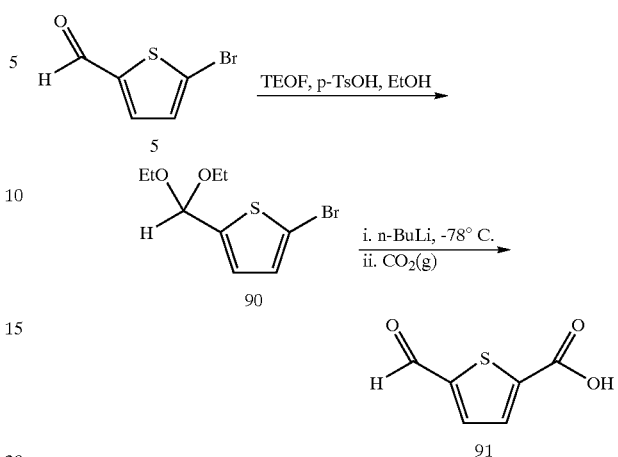

a) To a solution of 5-bromocarboxaldehyde 5 (10 g, 52.3 mmol) in anhydrous EtOH (86 mL) was added triethylorthoformate (43 mL, 262 mmol) and p-toluensulfonic acid (1.4 g, 7.3 mmol). After stirring for 12 h at rt, the solvent was removed under reduced pressure to half volume. The remaining solution was then diluted with ether (100 mL) and washed with saturated $NaHCO_3$. The solution was dried over $Na_2SO_4$ and the solvent was removed under reduced pressure. The crude residue was purified by silica gel chromatography (30:70 ethyl acetate/hexanes, first pre-eluted with triethylamine) to provide 13.9 g (100%) of 90.

b) To a solution of 90 (13.9 g, 52.3 mmol) in THF (188 mL) at −78° C. was dropwise added n-BuLi (57.5 mmol). After stirring for 30 min at −78° C., $CO_2$ (g) was bubbled into the solution for 15 min. After stirring for an additional 30 min, 1 M $NH_4Cl$ was added and the solution was allowed to warm to rt. The solution was diluted with ether (100 mL) and washed with 1 M HCl (3×50 mL). The solution was dried over $MgSO_4$ and the solvent was removed under reduced pressure. The crude residue was purified by silica gel chromatography (50:50 ethyl acetate/hexanes) to provide 8.8 g (100%) of 91.

Another intermediate, resin 95, was synthesized as described in Scheme 26.

SCHEME 26

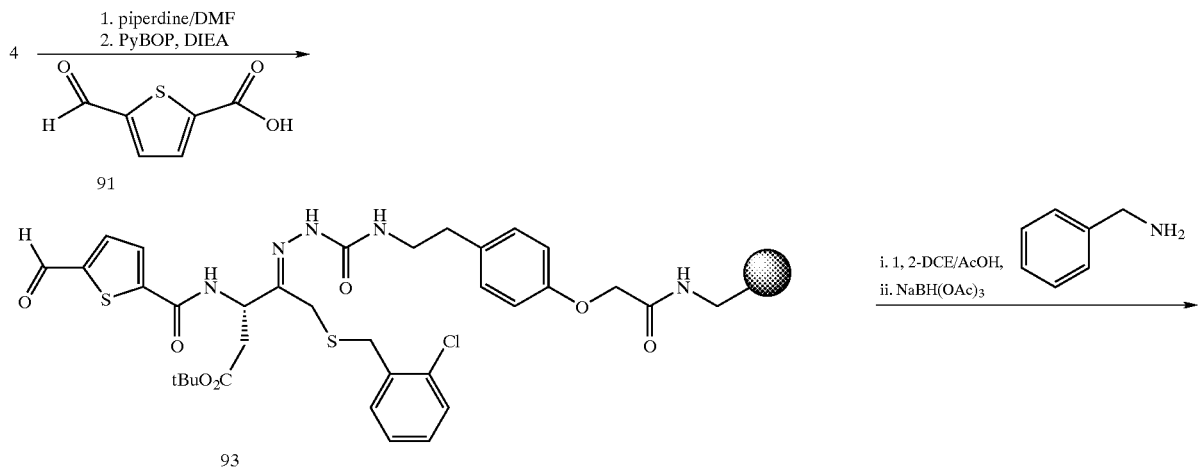

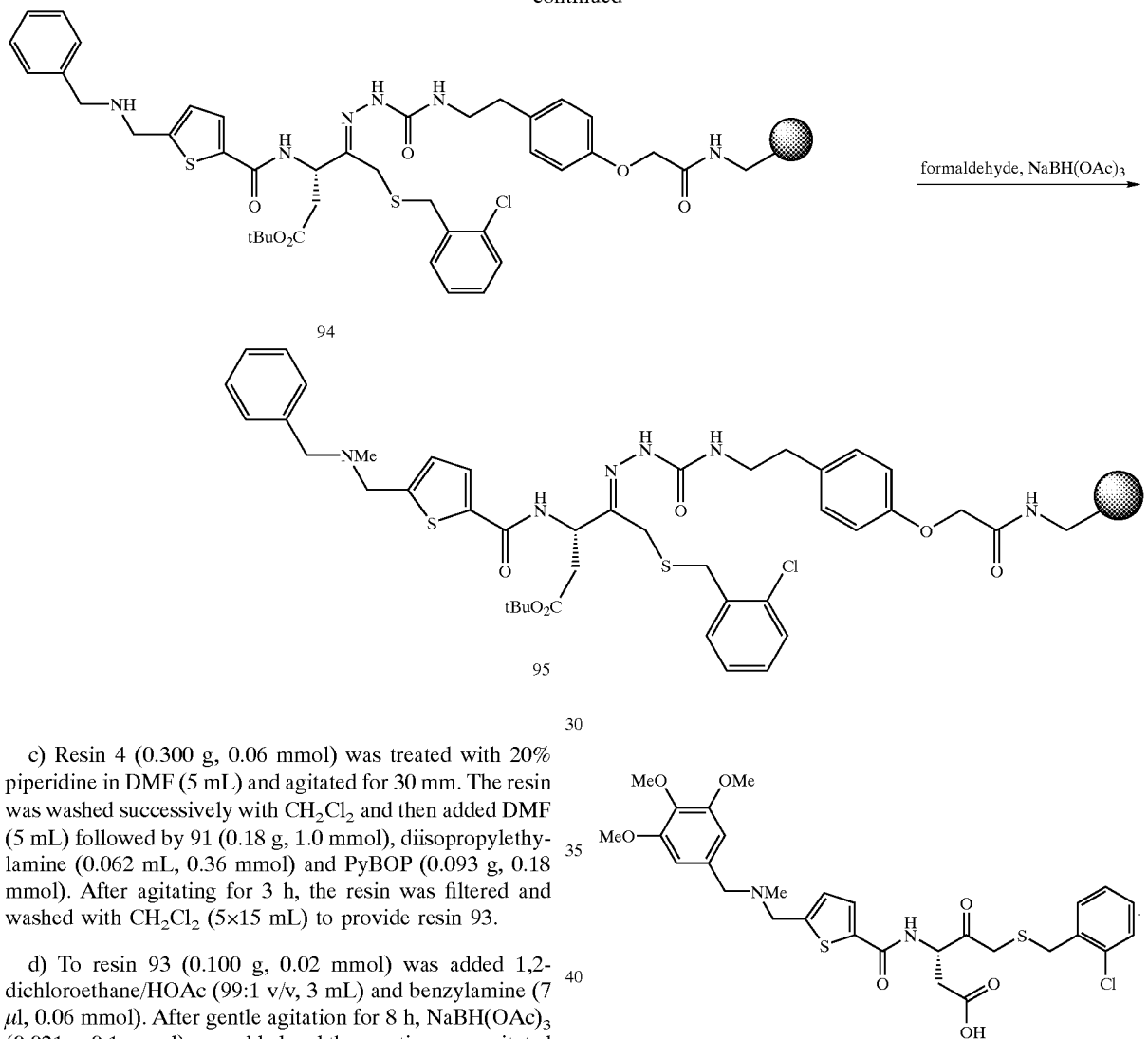

94

95 c) Resin 4 (0.300 g, 0.06 mmol) was treated with 20% piperidine in DMF (5 mL) and agitated for 30 mm. The resin was washed successively with $CH_2Cl_2$ and then added DMF (5 mL) followed by 91 (0.18 g, 1.0 mmol), diisopropylethylamine (0.062 mL, 0.36 mmol) and PyBOP (0.093 g, 0.18 mmol). After agitating for 3 h, the resin was filtered and washed with $CH_2Cl_2$ (5×15 mL) to provide resin 93.

d) To resin 93 (0.100 g, 0.02 mmol) was added 1,2-dichloroethane/HOAc (99:1 v/v, 3 mL) and benzylamine (7 µl, 0.06 mmol). After gentle agitation for 8 h, $NaBH(OAc)_3$ (0.021 g, 0.1 mmol) was added and the reaction was agitated for an additional 12 h to provide 94. The resin was washed with $CH_2Cl_2$ (3×10 mL), MeOH (2×10 mL) and $CH_2Cl_2$ (2×10 mL).

e) To resin 94 was added 1,2-dichloroethane/HOAc (99:1 v/v, 3 mL) and 37% formaldehyde (aq) (15 µl, 0.18 mmol). After gentle agitation for 1 h, $NaBH(OAc)_3$ (0.063 g, 0.3 mmol) was added and the reaction was agitated for an additional 12 h to provide 95. The resin was washed with $CH_2Cl_2$ (3×10 mL), MeOH (2×10 mL) and $CH_2Cl_2$ (2×10 mL)

f) Resin 95 was treated with $TFA/H_2O$ (9:1 v/v, 2 mL) and agitated for 15 min. The resin was filtered and washed with $CH_2Cl_2$ (2×4 mL). The combined filtrates were diluted with toluene (3 mL) and the solvent was removed under reduced pressure. The crude residue was purified by reverse-phase preparatory HPLC to afford the title compound.

EXAMPLE 28

This example describes an exemplary synthesis of the compound below

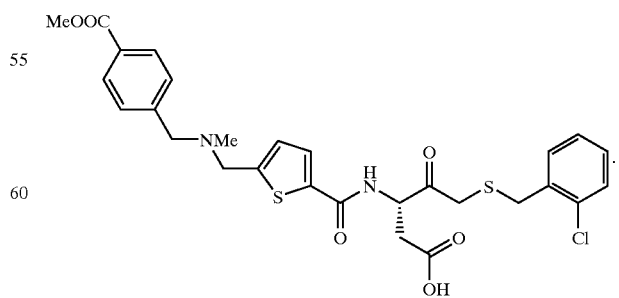

This compound was prepared according to the procedure of Example 27d–f except for using methyl-4-(aminomethyl) benzoate hydrochloride as a reagent instead of benzylamine. ES (+) MS: m/e=589.1 $(M+H)^+$.

EXAMPLE 29

This example describes an exemplary synthesis of the compound below

This compound was prepared according to the procedure of Example 27d–f except for using 3,4,5- trimethoxybenzylamine as a reagent instead of benzylamine. ES (+) MS: m/e=621.2 (M+H)⁺.

EXAMPLE 30

This example describes an exemplary synthesis of the compound below

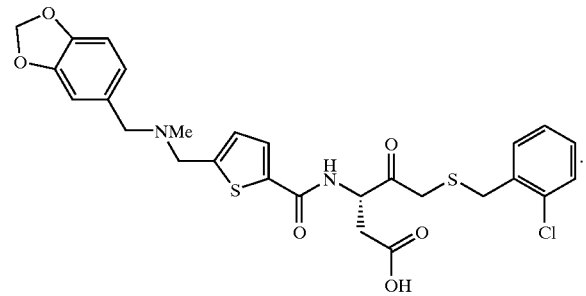

This compound was prepared according to the procedure of Example 27d–f except for using 3,4-methylenediocybenzylamine as a reagent instead of benzylamine. ES (+) MS: m/e=575.1 (M+H)⁺.

EXAMPLE 31

This example describes an exemplary synthesis of the compound below

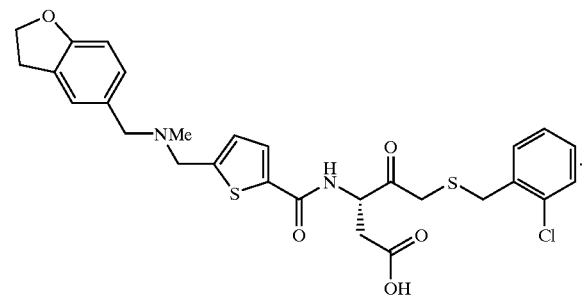

This compound was prepared according to the procedure of Example 27d–f except for using 5-aminomethyl-2,3-dihydrobenzo[B]furan as a reagent instead of benzylamine. ES (+) MS: m/e=573.2 (M+H)⁺.

EXAMPLE 32

This example describes an exemplary synthesis of the compound below

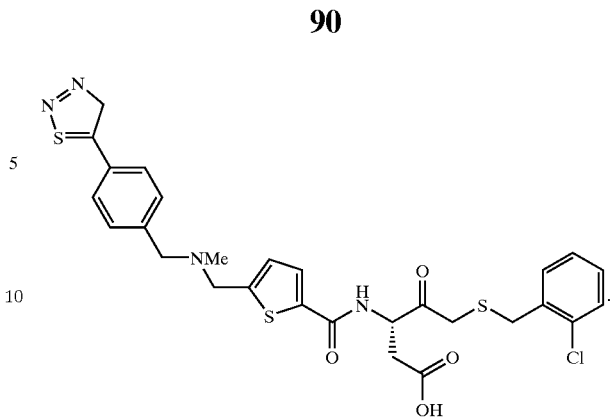

This compound was prepared according to the procedure of Example 27d–f except for using 4-(1,2,3-thiadiazol-4-yl)benzylamine as a reagent instead of benzylamine. ES (+) MS: m/e=615.1 (M+H)⁺.

EXAMPLE 33

This example describes an exemplary synthesis of the compound below

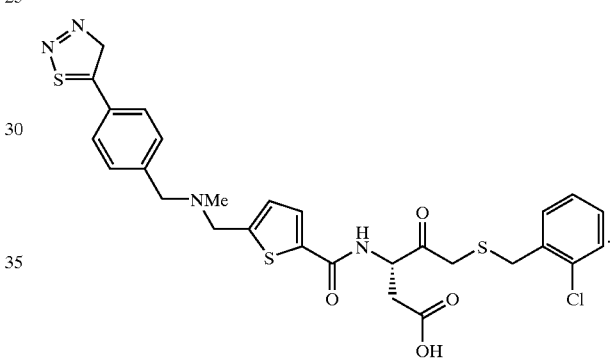

This compound was prepared according to the procedure of Example 27d–f except for using 4–91-H-pyrazol-1-yl)benzylamine as a reagent instead of benzylamine. ES (+) MS: m/e=597.2 (M+H)⁺.

EXAMPLE 34

This example describes an exemplary synthesis of the compound below

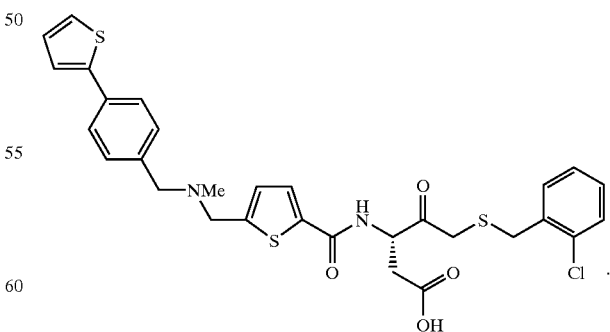

This compound was prepared according to the procedure of Example 27d–f except for using 4-(2-thienyl)benzylamine as a reagent instead of benzylamine. ES (+) MS: m/e=613.1 (M+H)⁺.

EXAMPLE 35

This example describes an exemplary synthesis of the compound below

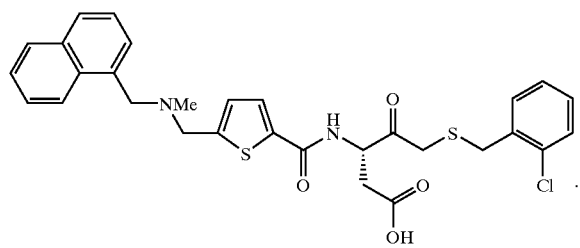

This compound was prepared according to the procedure of Example 27d–f except for using N-methyl-1-naphthalenemethylamine hydrochloride as a reagent instead of benzylamine.

EXAMPLE 36

This example describes an exemplary synthesis of the compound below

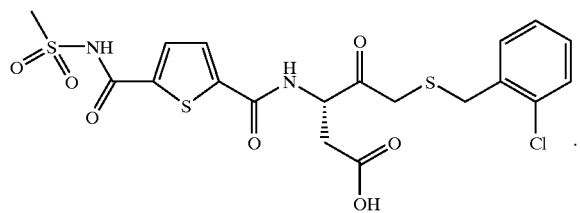

An intermediate, compound 98, was synthesized as described in Scheme 27.

SCHEME 27

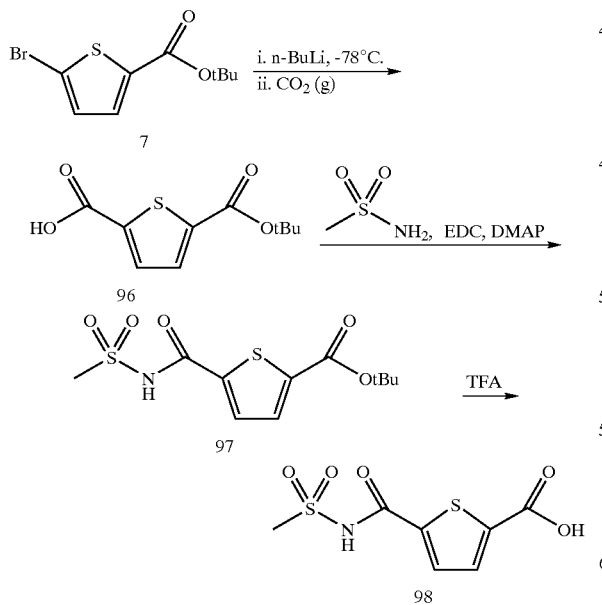

a) To a solution of 7 (4.78 g, 18.2 mmol) in THF (60 mL) at −78° C. was dropwise added 1.6 M n-BuLi (12.5 mL, 20 mmol). After stirring for 1 h, $CO_2$ (g) was bubbled into the solution for 15 min. After stirring for and addidional 40 min, the solution was added 1 M HCl (20 mL) and allowed to warm to rt. The solution was basified with 1 M NaOH (50 mL) and washed with ether (3×50 mL). The solution was then acidified with 1 M HCl (100 mL) and extracted with ether (3×50 mL). The solution was dried over $MgSO_4$ and the solvent was removed under reduced pressure to provide 96 which was used without further purification. ES (+) MS: m/e=173.1 (M−$^t$Bu)$^+$.

b) To a solution of 96 (1.76 g, 7.7 mmol) in $CH_2Cl_2$ (25 mL) was added EDC (1.91 g, 10 mmol), DMAP (1.2 g, 10 mmol) and methanesulfonamide (0.954 g, 10 mmol). After stirring for 12 h at rt, the solution was diluted with $CH_2Cl_2$ (50 mL) and washed with 1 M HCl (3×50 mL). The solution was dried over $MgSO_4$ and the solvent was removed under reduced pressure to provide 97 which was used without further purification. ES (+) MS: m/e=306.1 (M+H)$^+$.

c) A solution of 97 (7.7 mmol) in $TFA/CH_2Cl_2/H_2O$ (30:70:1 v/v/v, 20 mL) was stirred at rt for 5 h. The solvent was removed under reduced pressure to provide 98 which was used without further purification. ES (+) MS: m/e=328.2 (M+Na)$^+$.

d) The title compound was prepared according to the procedure of Example 1j,l except for using 98 instead of 12. ES (+) MS: m/e=519.1 (M+H)$^+$.

EXAMPLE 37

This example describes an exemplary synthesis of the compound below

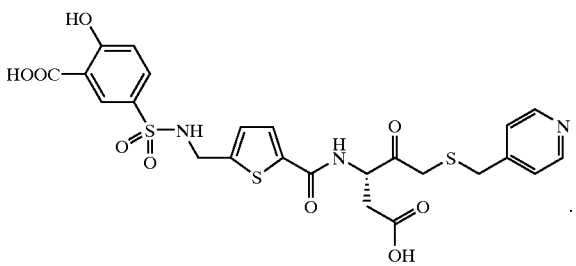

This compound was prepared using the same method as Example 1a,j–l except for using 3-picolyl mercaptan as a reagent instead of 2-chlorobenzenemethanethiol. ES (+) MS: m/e=533 (M+H)$^+$.

EXAMPLE 38

This example describes an exemplary synthesis of the compound below

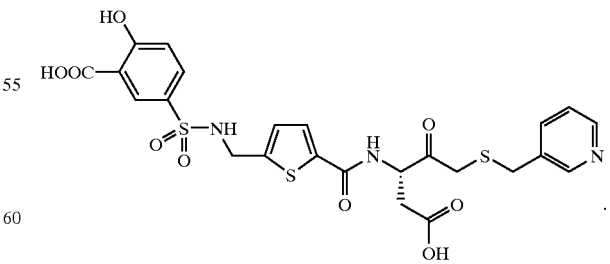

This compound was prepared using the same methods as Example 1a,j–l except for using 4-picolyl mercaptan as a reagent instead of 2-chlorobenzenemethanethiol. ES (+) MS: m/e=533 (M+H)$^+$.

EXAMPLE 39

This example describes an exemplary synthesis of the compound below

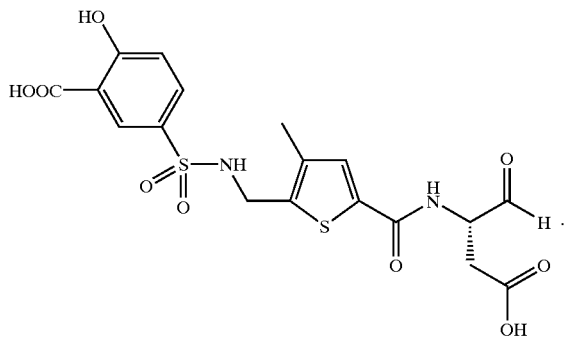

An intermediate, compound 107, was prepared as described in Scheme 28.

SCHEME 28

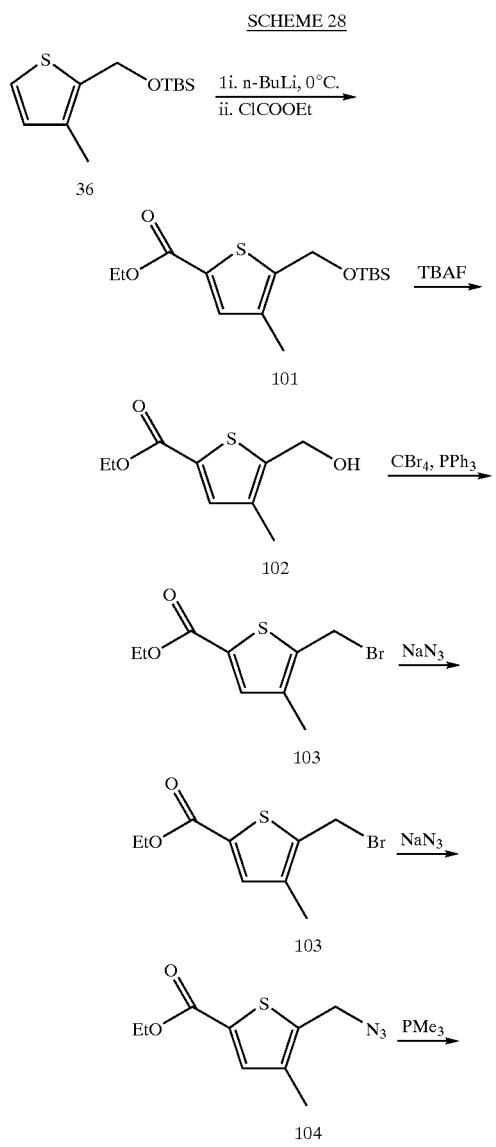

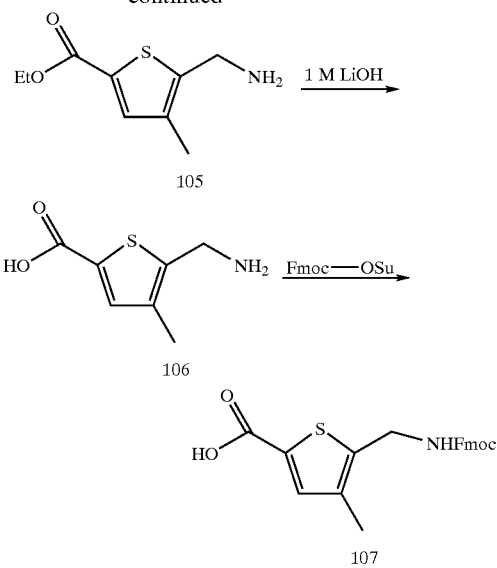

a) To a solution of 36 (13.7 g, 56.5 mmol) in ether (100 mL) at 0° C. was added dropwise a solution of 1.6 M n-BuLi (38.9 mL, 62.2 mmol). After stirring at 0° C. for 1 h, the reaction solution was warmed to rt for 30 min and then cooled to −78° C. This solution was added via cannula addition to a solution of ethyl chloroformate (6.0 mL, 62.2 mmol) in ether (50 mL) at −78° C. After stirring 1 h, the reaction was quenched with 1 M $NH_4Cl$ (20 mL) and warmed to rt. The organic layer was washed with 1 M $NH_4Cl$ (3×100 mL) and dried over $MgSO_4$. The solvent was removed under reduced pressure and the crude residue was purified by silica gel chromatography (5:95 ethyl acetate/hexanes) to provide 13.2g (78%) of 101.

b) To a solution of 101 (5 g, 15.9 mmol) in THF (30 mL) was added acetic acid (3.1 mL) and 1 M TBAF in THF (23.8 mL, 23.8 mmol). After stirring for 2 h, the solution was diluted with ether (50 mL) and washed with a solution of $NaHCO_3$ (3×50 mL). The organic layer was dried over $MgSO_4$ and the solvent was removed under reduced pressure. The crude residue was purified by silica gel chromatography (30:70 ethyl acetate/hexanes) to give 2.2 g (35%) of 102. ES (+) MS: m/e=186.2 $(M+H)^+$.

c) To a solution of 102 (1.8 g, 9.9 mmol) in THF (20 mL) was added $CBr_4$ (3.6 g, 10.9 mmol) and $PPh_3$ (2.8 g, 10.9 mmol). After stirring for 1 h, the suspension was filtered and the solvent was removed under reduced pressure. The crude residue was purified by silica gel chromatography (20:80 ethyl acetate/hexanes) to give 1.4 g (58%) of 103. ES (+) MS: m/e=265.1 $(M+H)^+$.

d) To a solution of 103 (1.4 g, 5.6 mmol) in DMF (15 mL) was added $NaN_3$ (0.402 g, 6.2 mmol). After stirring at 50° C. for 30 min, the solution was diluted with ether (30 mL) and washed with $H_2O$ (3×20 mL). The organic layer was dried over MgSO4 and the solvent was removed under reduced pressure to give 104 which was used without further purification. ES (+) MS: m/e=226.2 $(M-N_2)^+$.

e) To a solution of 104 (5.6 mmol) in THF (10 mL) was dropwise added 1 M $PMe_3$ in THF (6.1 mL, 6.1 mmol). After stirring at rt for 30 min, the mixture was diluted with ether (50 mL) and washed with a solution of saturated NaHCO$_3$. The organic layer was dried over MgSO$_4$ and the solvent was removed under reduced pressure to provide 105 which was used without further purification. ES (+) MS: m/e 183.1 (M−NH$_2$)$^+$.

f) To a solution of 105 (5.6 mmol) in dioxane (10 mL) was added 1 M LiOH (11 mL). After stirring for 1 h at rt, the solution was neutralized with 1 M HCl (10 mL) and the solvent was removed under reduced pressure to provide 106 which was used without further purification. ES (+) MS: m/e=155.1 (M−NH$_2$)$^+$.

g) To a solution of 106 (5.6 mmol) in H$_2$O/dioxane (1:1 v/v, 10 mL) was added NaHCO$_3$ (4.1 g, 49.3 mmol) and Fmoc-OSu (3.7 g, 10.9 mmol). After stirring for 3 h at rt, the solution was diluted with ether (30 mL) and washed with 1 M HCl (3×20 mL). The organic layer was dried over MgSO$_4$ and the solvent was removed under reduced pressure. The crude residue was purified by silica gel chromatography (95:5, ethyl acetate/MeOH) to provide 0.200 g (10%, 4 steps) of 107. ES (+) MS: m/e=416.1 (M+Na)$^+$.

Another intermediate, compound 111, was synthesized as described in Scheme 29.

SCHEME 29

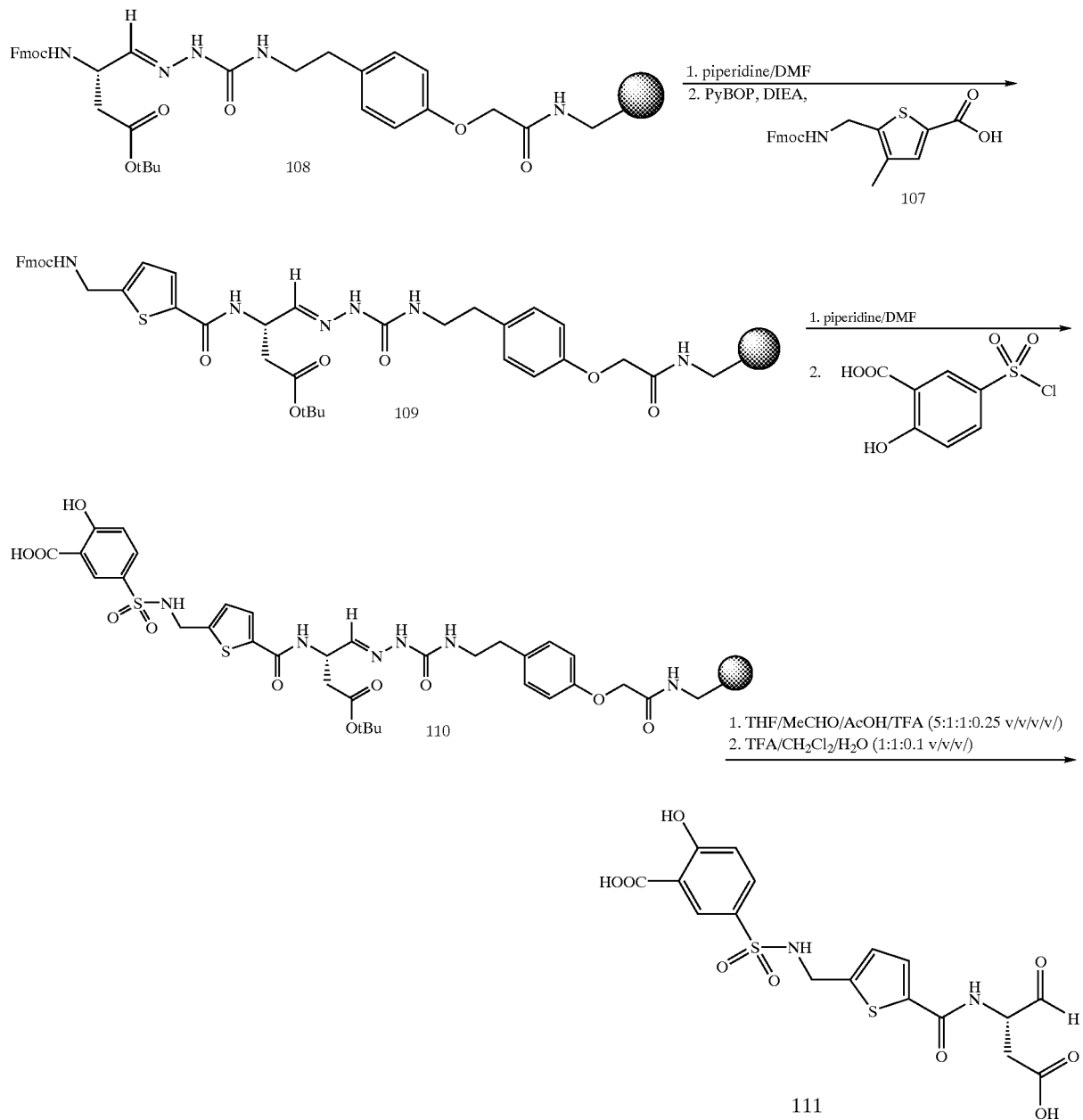

h) Resin 108, prepared according to the procedure of PCT international Publication No. WO 00/23421, pages 37–40, was treated with a solution of THF/HOAc/MeCHO/TFA (5:1:1:0.25 v/v/v/v, 5 mL) for 3 h to release Fmoc-Asp-CHO. Based on the mass balance of the cleaved material, the resin loading was calculated to be approximately 0.4 mmol/g. Resin 108 (0.300 g, 0.12 mmol) was treated with 20% piperidine in DMF (5 mL) for 30 min at rt. After washing the resin with $CH_2Cl_2$ (5×5 mL), the resin was suspended in DMF (20 mL) followed by addition of 107 (0.379 g, 1.0 mmol), diisopropylethylamine (0.525 mL, 3 mmol) and PyBOP (0.780 g, 1.5 mmol). After gently aggitation for 3 h, the resin was filtered and washed successively with $CH_2Cl_2$ (5×15 mL) and ether (3×15 mL) and dried in vacuo to provide resin 109.

i) Resin 109 (0.300 g, 0.06 mmol) was treated with 20% piperidine in DMF (5 mL) and agitated for 30 min. The resin was washed successively with $CH_2Cl_2$, resuspended in $CH_2Cl_2$ (5 mL), and treated with diisopropylethylamine (31 uL, 0.18 mmol) and 5-chlorosulfonyl-2-hydroxybenzoic acid (9 uL, 0.12 mmoL). After agitation for 3 h, the resin was filtered and washed with $CH_2Cl_2$ (5×5 mL) to yield resin 110.

j) Resin 110 was treated with THF/HOAc/MeCHO/TFA (5:1:1:0.25 v/v/v/v, 5 mL) and agitated for 3 h. The resin was filtered and washed with $CH_2Cl_2$ (2×4 mL). The combined filtrates were diluted with toluene (3 mL) and the solvent was removed under reduced pressure. The crude residue was then treated the $TFA/CH_2Cl_2/H_2O$ (50:50:1 v/v/v, 2 mL) for 1 h. The solvent was removed under reduced pressure to afford the crude product which was purified by reverse-phase preparatory HPLC to afford 111.

EXAMPLE 40

This example describes an exemplary synthesis of the compound below

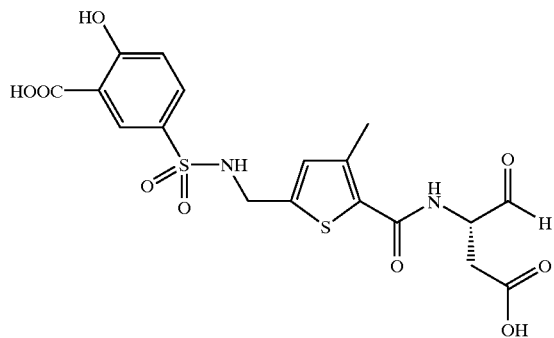

This compound was prepared according to the procedure of Example 39h–j except for using 43 (Example 9) instead of 107 (11.9 mg, 42%). $^1$H NMR (CD$_3$OD) δ 8.24 (s, 1H), 7.84 (dd, J=8.8, 1.0 Hz, 1H), 7.03 (d, J=8.8 Hz, 1H), 6.62 (s, 1H), 4.68 (dd, J=9.9, 4.1 Hz, 1H), 4.37 (m, 1H), 4.23 (s, 2H), 2.65–2.68 (m, 2H), 2.31 (s, 3H). ES (+) MS: m/e=471.0 (M+H)$^+$.

EXAMPLE 41

This example describes an exemplary synthesis of the compound below

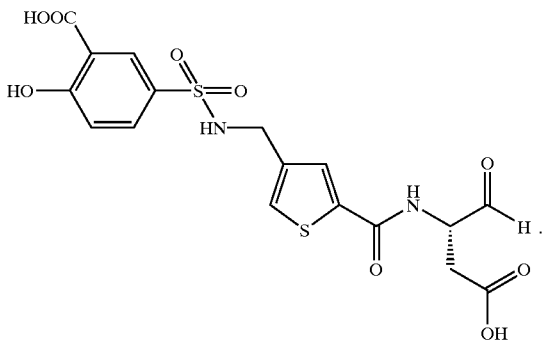

An intermediate, compound 112, was synthesized as described in Scheme 30.

SCHEME 30

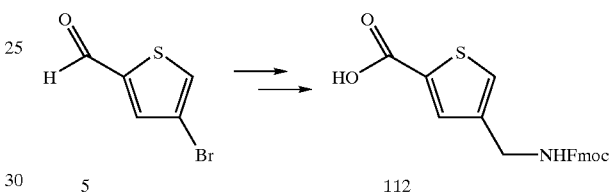

a) 112 was prepared through the same procedure as 12 (Example 1) except using 4-bromothiophene carboxaldehyde instead of 5-bromothiophene carboxaldehyde 5. ES (+) MS: m/e=402.2 (M+Na)$^+$.

b) The title compound was prepared according to the procedure of Example 39h–j except for using 112 instead of 107. (17.6 mg, 64%). $^1$H NMR (CD$_3$OD) δ 8.26 (s, 1H), 7.86 (d, J=8.8 Hz, 1H), 7.51 (d, J=7.0 Hz, 1H), 7.34 (s, 1H), 7.04 (dd, J=8.8, 2.6 Hz, 1H), 4.67 (dd, J=12.4 4.1 Hz, 1H), 4.43–4.44 (m, 1H), 4.06 (s, 2H), 2.64–2.72 (m, 2H). ES (+) MS: m/e=457.0 (M+H)$^+$.

EXAMPLE 42

This example describes an exemplary synthesis of the compound below

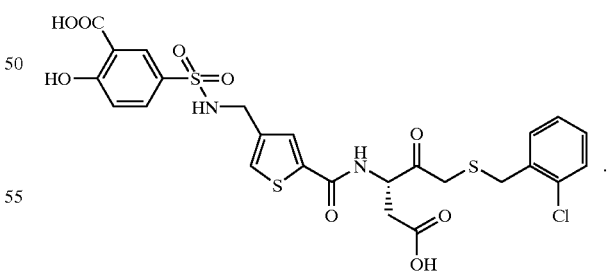

This compound was prepared according to the procedure of Example 1j–l except for using 112 instead of 12. (4.5 mg, 12%). $^1$H NMR (CD$_3$OD) δ 8.28 (d, J=2.3 Hz, 1H), 784 (dd, J=8.8 2.4 Hz, 1H), 7.47 (s, 1H), 7.34–7.38 (m, 2H), 7.20–7.23 (m, 2H), 6.99 (d, J=8.9 Hz 1H), 5.09 (t, J=6.3 Hz, 1H), 4.26 (s, 2H), 3.81 (s, 2H), 3.42–3.47 (m, 2H), 2.99 (dd, J=16.9, 6.4 Hz, 1H), 2.73 (dd, J=16.7, 6.5 Hz, 1H). ES (+) MS: m/e=707.0 (M+79)$^+$.

EXAMPLE 43

This example describes an exemplary synthesis of the compound below

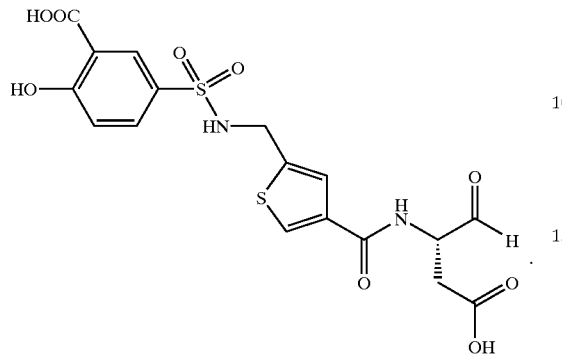

This compound was prepared according to the procedure of Example 39h–j except for using 43 (Example 9) instead of 107 (15.6 mg, 57%). $^1$H NMR (CD$_3$OD) δ 8.28 (d, J=2.3 Hz, 1H), 7.84–7.88 (m, 2H), 7.23 (d, J=5.1 Hz, 1H), 7.03 (dd, J=8.8, 2.4 Hz, 1H), 4.66 (dd, J=13.3, 4.0 Hz, 1H), 4.40–4.47 (m, 1H), 4.26 (s, 2H), 2.69–2.77 (m, 1H), 2.57–2.64 (m, 1H). ES (+) MS: m/e=457.0 (M+H)$^+$.

EXAMPLE 44

This example describes an exemplary synthesis of the compound below

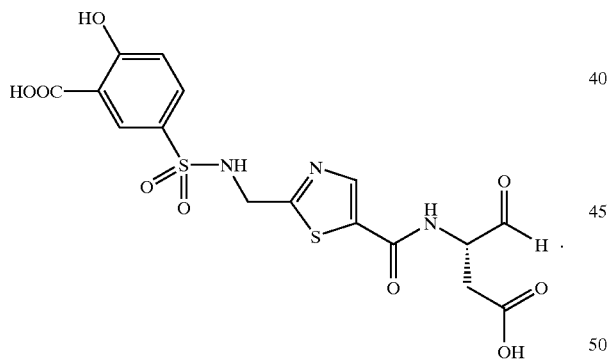

This compound was prepared according to the procedure of Example 39h–j except for using 52 (Example 10) instead of 107 (5.5 mg, 20%). $^1$H NMR (CD$_3$OD) δ 8.28 (d, J=2.6 Hz, 1H), 7.85–7.88 (m, 1H), 7.45 (dd, J=5.6, 3.9 Hz, 1H), 7.03 (dd, J=8.9, 3.2 Hz, 1H), 6.84 (d, J=2.6 Hz, 1H), 4.65 (dd, J=11.3, 4.1 Hz, 1H), 4.41 (m, 1H), 4.27 (d, J=1.3 Hz, 2H), 2.60–2.77 (m, 2H). ES (+) MS: m/e=457.0 (M+H)$^+$.

EXAMPLE 45

This example describes an exemplary synthesis of the compound below

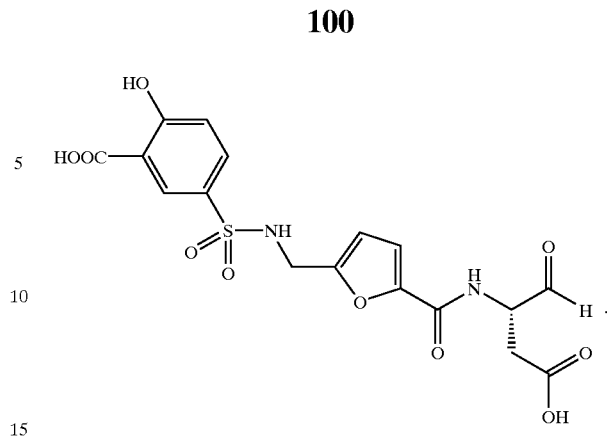

This compound was prepared according to the procedure of Example 39h–j except for using 56 (Example 11) instead of 107 (2.5 mg, 9%). $^1$H NMR (CD$_3$OD) δ 8.23 (s, 1H), 7.83 (d, J=9.1 Hz, 1H), 7.02 (d, J=8.8 Hz, 1H), 6.91 (s, 1H), 6.22 (s, 1H), 4.68–4.47 (m, 1H), 4.43–4.49 (m, 1H), 4.21 (s, 2H), 2.60–2.74 (m, 2H). ES (+) MS: m/e=441.0 (M+H)$^+$.

EXAMPLE 46

This example describes an exemplary synthesis of the compound below

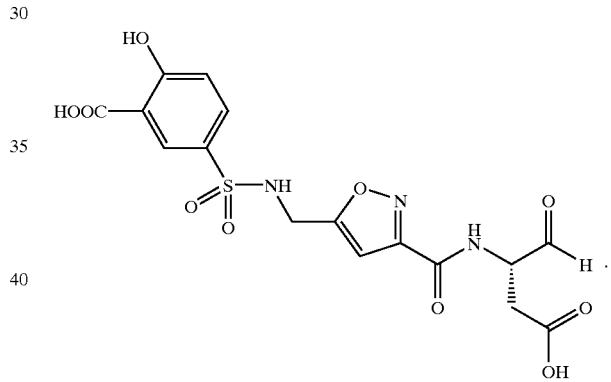

An intermediate, compound 116, was synthesized as described in Scheme 31.

SCHEME 31

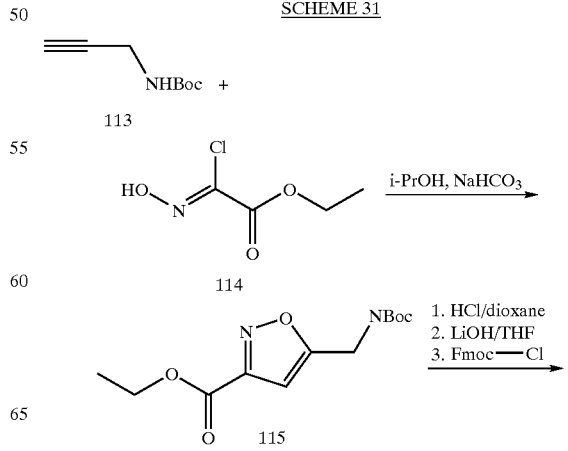

-continued

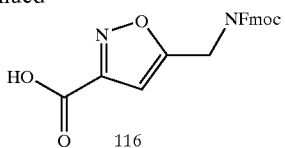

a) 113 was made according to the procedure of *J. Chem. Soc., Perkin Trans.* 1, 1999, 2713–2723. The crude crystals were used without further purification. $^1$H NMR (CDCl$_3$) δ 4.73 (s, 1H), 3.92 (s, 2H), 2.21 (s, 1H), 1.45 (s, 9H).

b) 114 was made according to the procedure of *J. Chem. Soc., Perkin Trans.* 1, 1999, 2713–2723. The crude product was used for next step without further purification. $^1$H NMR (CDCl$_3$) δ 1.41 (t, 3H), 4.42 (q, 2H), 9.63 (s, 1H).

c) To a solution of 113 (4.66 g, 30 mmol) in i-PrOH (150 mL) was added NaHCO$_3$ (2.52 g, 30 mmol). The reaction was stirred for 5 min at rt, then 114 (4.55 g, 30 mmol) was added. The resulting mixture was refluxed gently at 40° C. for 24 h. The solvent was removed under reduced pressure. The resulting residue was diluted with ethyl acetate and washed with H$_2$O and brine. The organic layer was dried over MgSO$_4$ and the solvent was removed under reduced pressure. The crude product was purified by silica gel chromatography (20:80 ethyl acetate/hexanes) to afford 1.05 g (74%) of 115 as a white solid. ES (+) MS: m/e=215 (M+H)$^+$. $^1$H NMR (CDCl$_3$) δ 6.58 (s, 1H), 5.05 (s, 1H), 4.45 (m, 4H), 1.43 (s, 9H), 1.39 (t, 3H).

d) A solution of 115 (0.271g, 1 mmol) in 4 M HCl in dioxane (5 mL) was stirred at rt for 2 h. The solvent was removed under reduced pressure. To a solution of the crude product in THF (2.5 mL) was added 1 M LiOH (2.5 mL). After stirring at rt for 2 h, the solvent was removed under reduced pressure and the resulting crude product was redissoved in dioxane/H$_2$O (1:1 v/v, 5 mL). To this solution was added NaHCO$_3$ (0.168 g, 2 mmol) and Fmoc-Cl (0.259 g, 1 mmol). The resulting reaction mixture was stirred at rt for 2 h. The solvent was removed under reduced pressure and the resulting residue was diluted with ethyl acetate and washed with H$_2$O and brine. The organic layer was dried over MgSO$_4$ and the solvent was removed under reduced pressure. The crude product was purified by silica gel chromatography (80:20:0.5 ethyl acetate/hexanes/acetic acid) to afford 0.286 g (78%) of 116 as a white solid. ES (+) MS: m/e=365.1 (M+H)$^+$.

e) The title compound was prepared according to the procedure of Example 39h–j except for using 116 as a reagent instead of 107.

EXAMPLE 47

This example describes an exemplary synthesis of the compound below

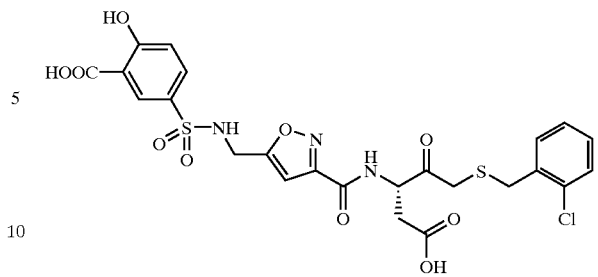

This compound was prepared according to the procedure of Example 1j–l except for using 116 as a reagent instead of 12. (8.5 mg, 23%). $^1$H NMR (CD$_3$OD) δ 8.25 (d, J=2.4 Hz, 1H), 7.85 (dd, J=8.8, 2.4 Hz, 1H), 7.30–7.40 (m, 2H), 7.15–7.25 (m, 2H), 7.00 (d, J=8.8 Hz, 1H), 6.51 (s, 1H), 5.15 (t, J=6.0 Hz, 1H), 4.30 (s, 2H), 3.79 (d, J=3.1 Hz, 2H), 3.40 (q, J=15.3 Hz, 1H), 2.70–3.05 (m, 2H). ES (+) MS: m/e= 612.0 (M+H)$^+$.

EXAMPLE 48

This example describes an exemplary synthesis of the compound below

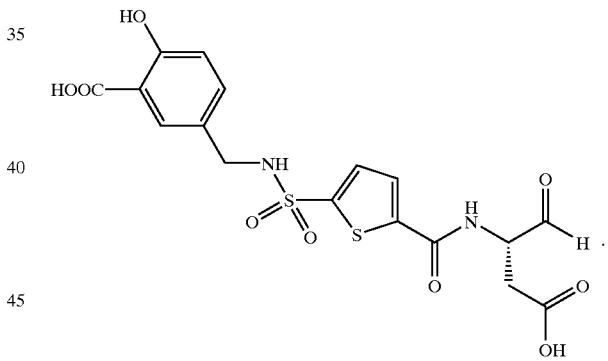

This compound was prepared according to the procedure of Example 39h–j except for using 116 as a reagent instead of 107. (3.1 mg, 12%). $^1$H NMR (CD$_3$OD) δ 8.28 (t, J=2.7 Hz, 1H), 7.85 (dt, J=8.2, 2.0 Hz, 1H), 7.02 (dd, J=8.8, 2.8 Hz, 1H), 6.48 (d, J=4.4 Hz, 1H), 4.65 (dd, J=7.6, 4.3 Hz, 1H), 4.39–4.48 (m, 1H), 4.30 (s, 2H), 2.55–2.76 (m, 2H). ES (+) MS: m/e=457.1 (M+H)$^+$.

EXAMPLE 49

This example describes an exemplary synthesis of the compound below

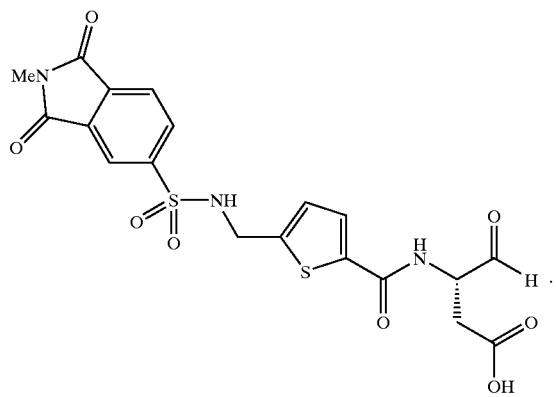

An intermediate, compound 117, was synthesized as described in Scheme 32.

SCHEME 32

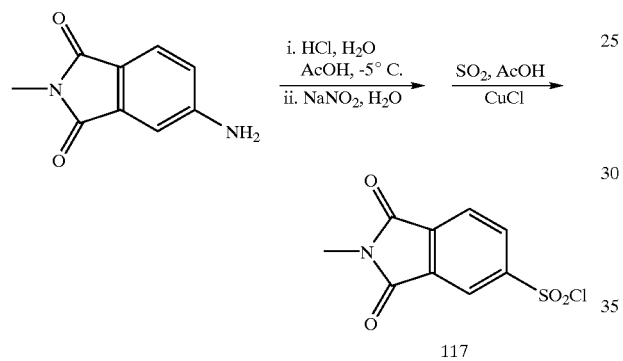

117 a) To a suspension of aniline (0.881 g, 5.0 mmol) in HCl/H$_2$O (1:1 v/v, 10 mL) at −5° C. was added acetic acid (10 mL). After stirring for 15 min, a solution of NaNO$_2$ (0.380 g, 5.5 mmol) in H$_2$O (3 mL) was added. To a second flask containing CuCl (0.124 g, 1.25 mmol) in AcOH (10 mL) was bubbled in SO$_2$ for approximately 30 min. The light blue solution with precipitate stirred for an additional 30 min. The diazonium salt solution was dropwise added via pipette to the saturated SO$_2$ solution resulting in a dark green cloudy solution. After stirring for 1 h, the solvent was removed under reduced pressure and the resulting residue was diluted with H$_2$O. The resulting precipitate was filtered and the light green solid was washed several times with water. The solid was dried in vacuo to give 117 as a white solid in 95% yield.

b) The title compound was prepared according to the procedure of Example 39i–j except for using 117 as a reagent instead of 5-chlorosulfonyl-2-hydroxybenzoic acid. ES (+) MS: m/e=457.1 (M+H)$^+$.

EXAMPLE 50

This example describes an exemplary synthesis of the compound below

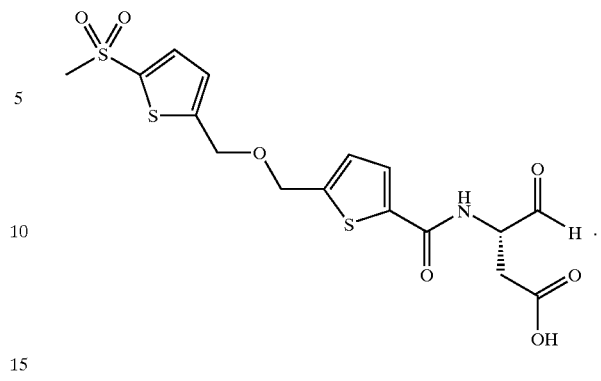

This compound was prepared according to the procedure of Example 39 h–j except for using 81 (Example 18) as a reagent instead of 107.

EXAMPLE 51

This example describes an exemplary synthesis of the compound below

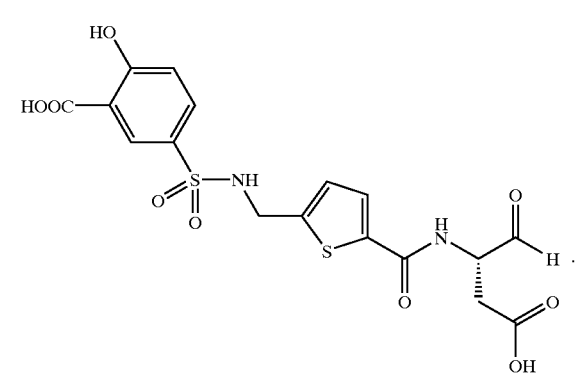

This compound was prepared according to the procedure of Example 39h–j except for using 12 (Example 1) instead of 107. (3.2 mg, 12%). $^1$H NMR (CD$_3$OD) δ 8.23 (s, 1H), 7.80 (d, J=8.8 Hz, 1H), 7.39 (t, J=3.9 Hz, 1H), 6.97 (dd, J=8.7, 2.6 Hz, 1H), 6.78 (d, J=3.6 Hz, 1H), 4.58 (dd, J=11.2, 4.1 Hz, 1H), 4.35–4.37 (m, 1H), 4.23 (s, 2H), 2.58–2.81 (m, 2H). ES (+) MS: m/e=457.0 (M+H)$^+$.

EXAMPLE 52

This example describes an exemplary synthesis o the compound below

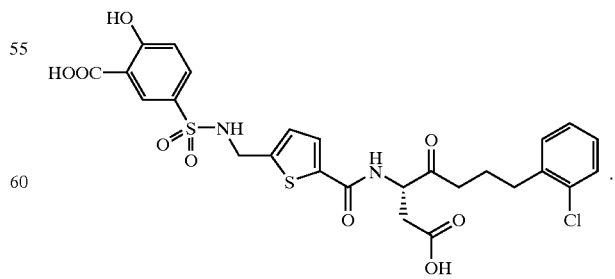

An intermediate, compound 120, was synthesized as described in Scheme 33.

SCHEME 33

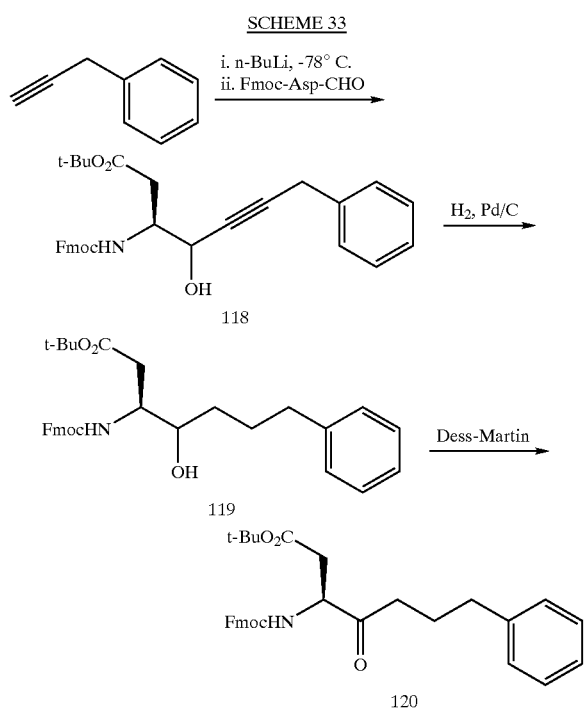

a) To a solution of 3-phenyl-1-propyne (1.8 mL, 14.5 mmol) in anhydrous THF (10 mL) at −78° C. was dropwise added 1.6 M n-BuLi (9.08 mL, 14.5 mmol) via addition funnel over 10 min. After stirring for 15 min, a solution of Fmoc-Asp-CHO (2.61 g, 6.6 mmol) in anhydrous THF (20 mL) was added dropwise via addition funnel over 15 min. The solution was stirred at −78° C. for an additional 40 min. The reaction mixture was quenched with water and warmed to rt. The resulting solution was diluted with ether and washed with 1 M HCl. The aqueous layer was back-extracted (2×) with ether and the combined organic layers dried over MgSO$_4$. The solution was concentrated and the residue purified by silica gel chromatography (30:70 to 40:60 ethyl acetate/hexanes) to give 0.890 g (27%) of 118 as a clear oil.

b) To a solution of 118 (0.890 g, 3.91 mmol) in EtOH (15 mL) was added a slurry of palladium on carbon (10% w/w, 0.125 g). The suspension was stirred at rt under a hydrogen balloon for 1 h. The suspension was filtered through Celite and washed with EtOH (2×10 mL). The combined filtrates were concentrated to give 119 in quantitative yield.

c) To a solution of 119 (0.700 g, 1.36 mmol) in CH$_2$Cl$_2$ (7 mL) was added Dess-Martin periodinane (0.865 g, 2.04 mmol) in one portion at rt. After stirring for 30 min, the solid was filtered off and washed with CH$_2$Cl$_2$ (2×5 mL). The combined filtrates were concentrated and purified by silica gel chromatography (25:75 ethyl acetate/hexanes) to give 0.325 g (47%) 120. $^1$H NMR (CDCl$_3$) δ 7.77 (d, J=7.6 Hz, 2H), 7.59 (d, J=7.1 Hz, 2), 7.41 (t, J=7.5 Hz, 2H), 7.31 (t, J=7.1 Hz, 2H), 7.26 (m, 2H), 7.17 (t, J=7.2Hz, 3H), 5.87 (d, J=7.8 Hz, 1H), 4.43 (m, 2H), 4.22 (t, J=7.0 Hz, 1H), 2.88 (m, 1H), 2.70 (dd, J=17.1, 4.7 Hz, 1H), 2.58 (m, 4H), 1.93 (m, 2H), 1.42 (s, 9H).

d) The title compound was prepared according to the procedure of Example 1 a, j–l except for using 120 as a reagent instead of 2-chlorobenzene-methanethiol. $^1$H NMR (CD$_3$OD) δ 8.27 (d, J=2.5 Hz, 1H), 7.85 (dd, J=8.8, 2.4 Hz, 1H), 7.44 (m, 1H), 7.20 (m, 2H), 7.13 (m, 3H), 7.02 (d, J=8.9 Hz, 1H), 6.88 (d, J=3.81 Hz, 1H), 4.80 (t, J=6.5 Hz, 1H), 4.31 (s, 2H), 2.96 (dd, J=16.8, 6.6 Hz, 1H), 2.67 (m, 1H), 2.58 (m, 4H), 1.89 (m, 2H).

EXAMPLE 53

This example describes an exemplary synthesis of the compound below

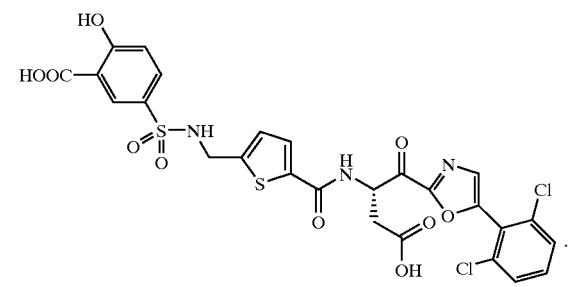

An intermediate, compound 123, was synthesized as described in Scheme 34.

SCHEME 34

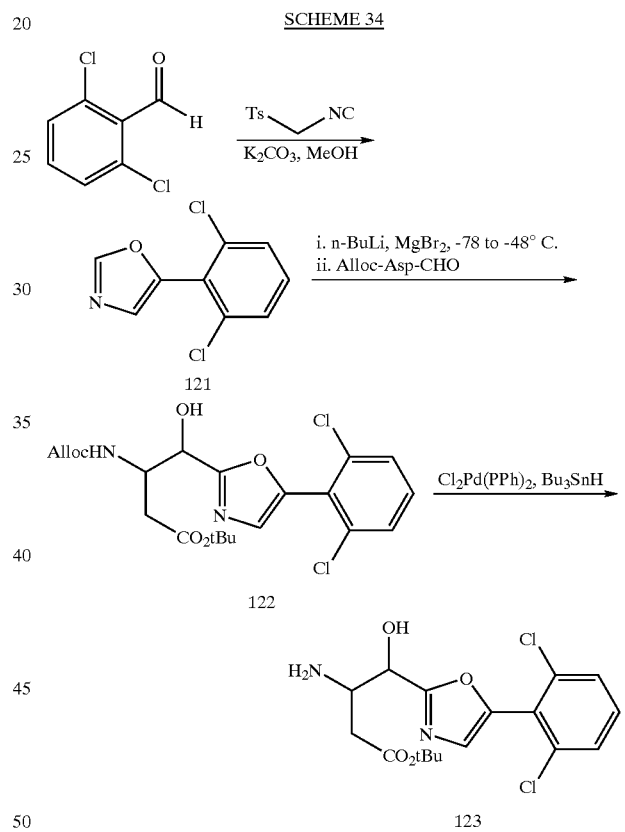

a) Into a 200 mL flask were weighed 2,6-dichlorobenzaldehyde (5.04 g, 28.8 mmol), tosylmethylisocyanate (5.75 g, 29.5 mmol), and potassium carbonate (4.71 g, 34.0 mmol). MeOH was added, and the flask became slightly warm. A condenser was added, and the mixture was heated to reflux under a nitrogen atmosphere for 4 h. The reaction was then cooled to rt, and diluted with water and CH$_2$Cl$_2$. The organic layer was removed, and the aqueous layer was extracted with CH$_2$Cl$_2$ (3×). The combined organic layers were dried MgSO$_4$, filtered, and concentrated to a yellow solid. Purification by silica gel chromatography (10:90 ethyl acetate/hexanes) provided 4.19 g (68%) of 121. $^1$H NMR (CDCl$_3$) δ 8.04 (s, 1H), 7.42 (d, J=7.9 Hz, 2H), 7.32 (t, J=7.9 Hz, 1H), 7.29 (s, 1H).

b) 122 was prepared from 121 and N-Alloc-Asp(OtBu)-CHO using the procedure of Bemis et. al. (U.S. Pat. No. 6,103,711) in 71% yield. ES (+) MS m/e=471 (M)$^+$.

c) 122 (0.705 g, 1.50 mmol) was transferred to a 100 mL Schlenk flask using THF (6 mL). A stir bar was added, followed by trans-dichloropalladium bis(triphenylphosphine) (61.3 mg, 0.087 mmol). The flask was cooled to 0° C., sealed with a septum, flushed with nitrogen and then left under a nitrogen atmosphere. Tributyltin hydride (3.4 mL, 12.6 mmol) was added, causing vigorous bubbling. After 15 min, TLC indicated that the starting material had been consumed. The reaction was then concentrated by rotary evaporation, and the resulting oil was purified by silica gel chromatography (95:5 $CH_2Cl_2$/2 N ammonia in MeOH) to provide 123. $^1$H NMR ($CDCl_3$) δ 7.41 (m, 2H), 7.26–7.34 (m, 1H), 7.23 (s, 1H), 4.82 (d, J=5.0 Hz, 0.4H), 4.70 (d, J=4.3 Hz, 0.6H), 3.69 (ddd, J=8.8, 4.3, 4.3 Hz, 0.6H), 3.61 (ddd, J=9.4, 5.1, 3.8 Hz, 0.4H), 2.56 (dd, J=16.1, 4.4 Hz, 0.6H), 2.50 (dd, J=16.2, 3.8 Hz, 0.4H), 2.40 (dd, J=16.1, 8.8 Hz, 0.4H), 2.28 (dd, J=16.2, 9.1 Hz, 0.4H), 1.45 (s, 9H). ES (+) MS: m/e=387 (M)$^+$.

Another intermediate, compound 128, was synthesized as described in Scheme 35.

SCHEME 35

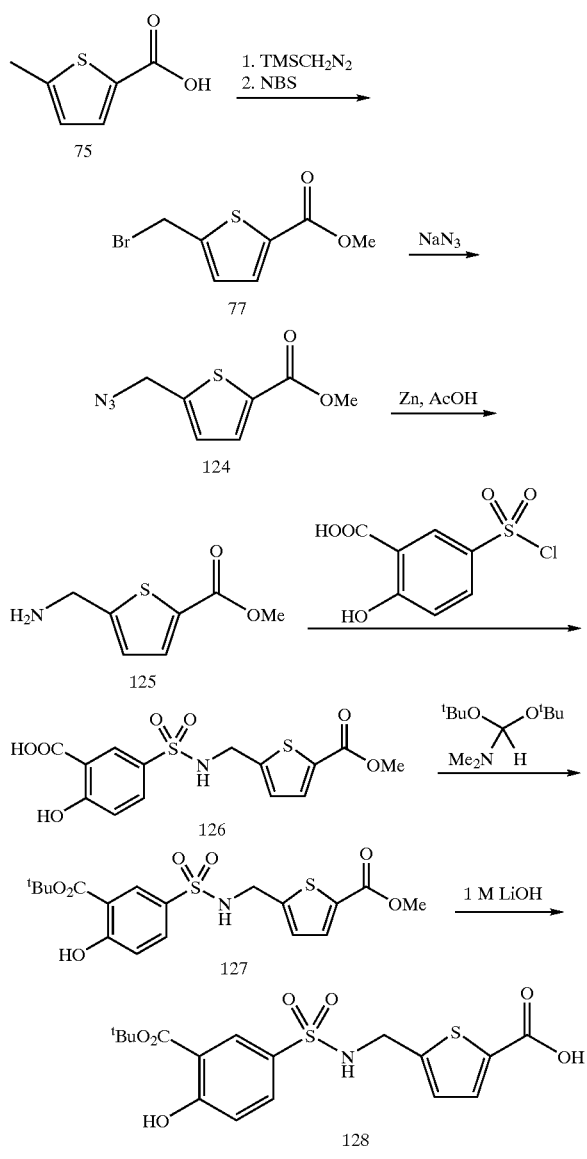

cc) To a solution of 5-methylthiophene-2-carboxylic acid 75 (20.0 g, 141 mmol) in benzene (120 mL) and methanol (14 mL) at 0° C. was dropwise added 2.0 M trimethylsilyldiazomethane in hexanes (80 mL, 160 mmol). The reaction was warmed to room temperature and the solvent concentrated in vacuo. Distillation under reduced pressure ($BP_{0.5}$= 88–93° C.) provided the methyl ester as a colorless oil (17.95 g, 82%). $^1$H NMR ($CDCl_3$) δ 7.61 (d, J=3.7 Hz, 1H), 6.76 (d, J=3.6 Hz, 1H), 3.85 (s, 3H), 2.52 (s, 3H). To a solution of the methyl ester (11.4 g, 72.9 mmol) in $CCl_4$ (200 mL) was added NBS (14.3 g, 80.3 mmol) and AIBN (91 mg, 0.55 mmol). The solution was heated to reflux for 2 h, at which point $^1$H NMR of a filtered aliquot indicated a 1:1 ratio of starting material to product. Another portion of AIBN (81 mg, 0.49 mmol) was added, and the solution was refluxed for another 2 h. The reaction was then cooled to room temperature, filtered and concentrated in vacuo to provide 77 as an orange oil (18.8 g, 110%) that contained ≅10% of the 5-dibromomethyl analogue. $^1$H NMR ($CDCl_3$) δ 7.63 (d, J=3.8 Hz, 1H), 7.09 (d, J=3.8Hz, 1H), 4.67 (s, 2H), 3.88 (s, 3H).

d) To a solution of 77 (18.76 g) in acetonitrile (41 mL) was added $NaN_3$ (9.39 g, 144.4 mmol), and the reaction was stirred at rt for 3 da, at which point, $^1$H NMR of an aliquot (diluted with $CH_2Cl_2$ and washed with $H_2O$) indicated consumption of starting material. The reaction was diluted with $CH_2Cl_2$, washed with water, dried over $MgSO_4$, filtered, and concentrated to provide 14.1 g (98%) of 124 which was used without further purification. ES (+) MS: m/e=198 (M+H)$^+$.

e) To a solution of 124 (7.48 g, 38 mmol) in acetic acid (75 mL) was added zinc dust (15.10 g, 232 mmol) in one portion. After stirring for 2 h, the reaction was filtered through Celite and the filtrate was concentrated under reduced pressure. The crude residue was azeotroped with toluene (2×30 mL) to remove excess acetic acid, providing 14.3 g of 125 which was used without further purification.

f) To a solution of 125 (14.35 g) in $CH_2Cl_2$ (70 mL) was added NMM (12.5 mL, 124 mmol) followed by 5-chlorosulfonyl-2-hydroxybenzoic acid (8.66 g, 36.7 mmol). After stirring at rt for 2 h, the solution was diluted with $CH_2Cl_2$ and washed with 1 N HCl. The organic solution was dried over $MgSO_4$, and the solvent was concentrated under reduced pressure to give 126 which was used without further purification.

g) 126 was suspended in toluene (60 mL) and heated to 90° C. A portion of dimethylformamide di-t-butyl acetal (21 mL, 87.6 mmol) was added to the hot solution, causing vigorous bubbling and separation of a brown oil. After 1 h, another portion of dimethylformamide di-t-butyl acetal (14 mL, 58.4 mmol) was added. The reaction was stirred and maintained at 90° C. for another 1.5 h, then diluted with $CH_2Cl_2$ and washed with 1 N HCl. The organic solution was dried over $MgSO_4$ and the solvent was removed under reduced pressure. The resulting crude residue was purified by silica gel chromatography (25:75 ethyl acetate/hexanes) to provide 4.19 g (26%) of 127 (4.19 g). $^1$H NMR indicated that the product comprised a 1:1 mixture of the t-butyl ester and the O-t-butyl phenol. ES (+) MS: m/e=450 (M+Na)$^+$.

h) To a solution of 127 (4.19 g, 9.84 mmol) in dioxane (40 mL) was added 1.0 M LiOH (40 mL, 41.3 mmol). The reaction was stirred at rt for 45 min, then diluted with ether and washed with 1 N HCl. The organic solution was dried over $MgSO_4$ and the solvent was removed under reduced pressure to provide 4.73 g (117%) of 128 which was used without further purification. $^1$H NMR ($CDCl_3$) δ 11.63 (s, 0.5H), 8.26 (d, J=2.4 Hz, 0.5H), 8.04 (d, J=2.4 Hz, 0.5H), 7.88 (dd, J=8.7, 2.4 Hz, 0.5H), 7.80 (dd, J=8.8, 2.5 Hz, 0.5H), 7.66 (d, J=3.8 Hz, 0.5H), 7.64 (d, J=3.8 Hz, 0.5H), 7.17 (d, J=8.8 Hz, 0.5H), 7.06 (d, J=8.8 Hz, 0.5H), 6.92 (d, J=4.7 Hz, 0.5H), 6.92 (d, J=4.2 Hz, 0.5H), 4.95 (t, J=6.4 Hz, 0.5H), 4.92 (t, J=6.3 Hz, 0.5H), 4.39 (d, J=6.3 Hz, 0.5H), 3.70 (s, 3H), 1.64 (s, 4.5H), 1.49 (s, 4.5H).

Another intermediate, compound 132, was synthesized as described in Scheme 36.
SCHEME 36
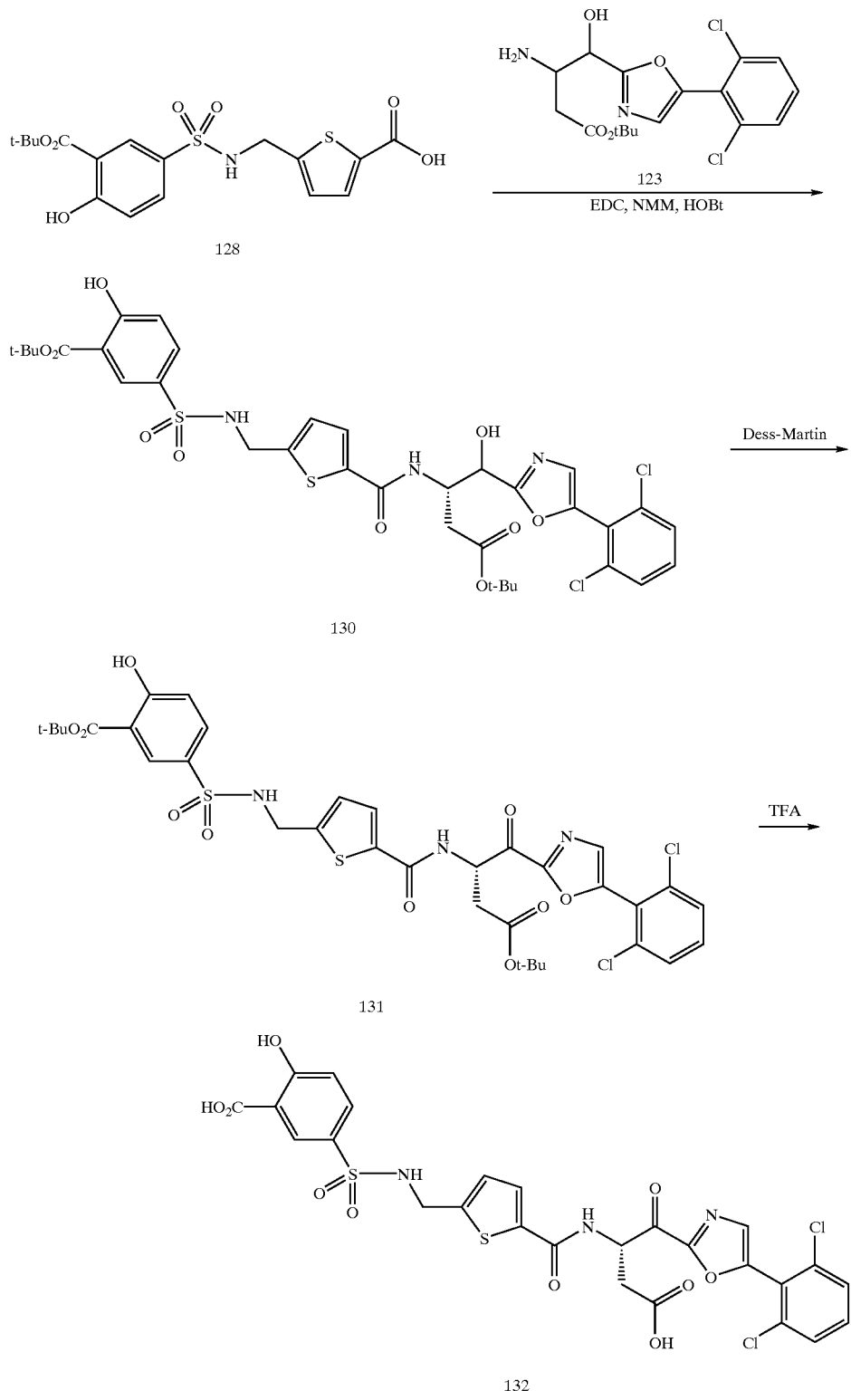

i) To a solution of 128 (56.8 mg, 0.138 mmol) and 123 (54.9 mg, 0.142 mmol) in DMF (1.4 mL) was added HOBt (20.3 mg, 0.150 mmol) and EDC (26.9 mg, 0.140 mmol). After stirring at rt for 1 h, the solution was diluted with ether and washed with water. The organic solution was dried over MgSO$_4$, filtered, and concentrated to a solid. Flash chromatography over silica gel (50:50 ethyl acetate/hexanes) provided 0.080 g (74%) of 130. ES (+) MS: m/e=782 (M)$^+$.

j) To a solution of 130 (80.3 mg, 0.103 mmol) in CH$_2$Cl$_2$ (1.5 mL) was added Dess-Martin periodinane (49.4 mg, 0.116 mmol). The reaction was stirred for 2 h, then washed with 1 N HCl. The organic solution was dried over MgSO$_4$, filtered, and concentrated to provide 0.106 g of 131 which was used without further purification. ES (+) m/e=669 (M−tBu)$^+$.

k) A solution of 131 (106 mg) in CH$_2$Cl$_2$/TFA (1:1 v/v, 2 mL) was stirred for 1.5 h at rt. The solvent was removed under reduced pressure and the crude residue was purified by reverse-phase HPLC to provide 0.030 g (30%, 2 steps) of 132. ES (+) MS: m/e=668 (M)$^+$.

EXAMPLE 54

This example describes an exemplary synthesis of the compound below

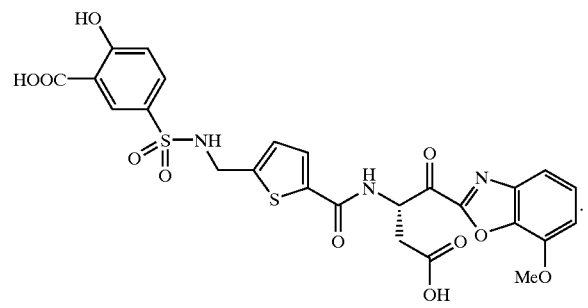

An intermediate, compound 136, was synthesized as described in Scheme 37.

SCHEME 37

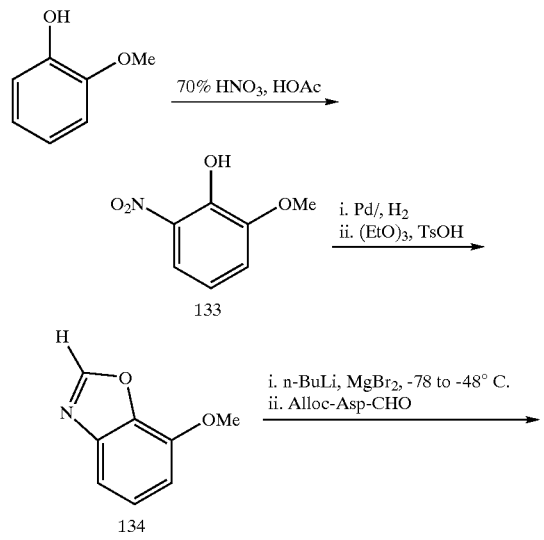

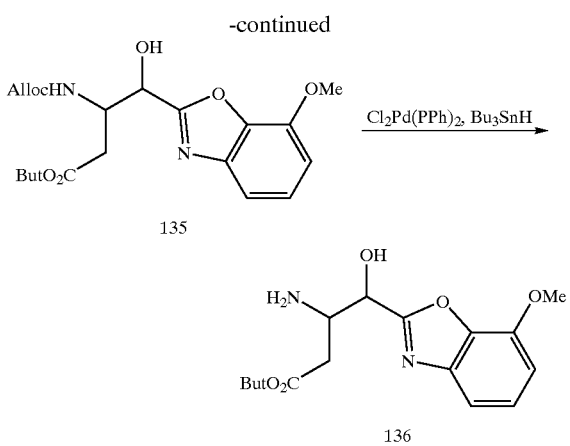

a) Giuacol (4.98 g, 40.1 mmol) was weighed into a 200 mL flask. Acetic acid (80 mL) was added, and the flask was placed in a rt water bath. 70% nitric acid (2.90 mL) was diluted with several mL acetic acid and added dropwise to the reaction over 2 min. After stirring for 21 h, the reaction was added to 600 mL of 10% sodium bisulfite. The aqueous solution was extracted with CH$_2$Cl$_2$, then with ether. The combined organic layers were dried over MgSO$_4$, filtered, and concentrated. Flash chromatography over silica gel (15:85 ethyl acetate/hexanes) provided 1.48 g (22%) of 133 as a pure isomer, as well as a comparable amount of the undesired para-nitration product. $^1$H NMR (CDCl$_3$) δ 10.77 (s, 1H), 7.70 (d, J=7.8 Hz, 1H), 7.14 (d, J=8.0 Hz, 1H), 6.92 (dd, J=8.0, 7.8 Hz, 1H), 3.95 (s, 3H).

b) 133 (1.48 g, 8.74 mmol) was transferred to a Parr flask and dissolved in 40 mL absolute EtOH. 10% palladium on carbon (300 mg) was added, and the flask was placed on a Parr shaker, evacuated and then back-filled with hydrogen. The reaction was shaken on the Parr shaker at 15 psi for 1.5 h, at which point TLC indicated consumption of the starting material. The mixture was then filtered through Celite and concentrated to a brown oil that rapidly darkened upon standing. The oil was redissolved in 10 mL absolute ethanol, and triethylorthoformate (4.30 mL, 25.9 mmol) and several small crystals of p-toluenesulfonic acid monohydrate were added. A condenser was installed, the apparatus was flushed with nitrogen, and heated to reflux for 1.25 h. The reaction was then cooled to room temperature and concentrated by rotary evaporation. Flash chromatography over silica gel provided 1.16 g (89%) of 134 as a white solid. ES (+) MS: m/e=150 (M+H)$^+$.

c) 135 was prepared from the 4-methoxybenzoxazole and N-Alloc-Asp(OtBu)-CHO using the procedure of Bemis et. al. (U.S. Pat. No. 6,103,711) in 83% yield. ES (+) MS: m/e=407 (M+H)$^+$.

d) 135 (526 mg, 1.29 mmol) was dissolved in THF (5 mL. trans-Dichloropalladium(bis)triphenylphosphine (43 mg, 0.061 mmol) was added, and the flask was sealed with a septum and flushed with nitrogen. Tributyltin hydride (1.40 mL, 5.20 mmol) was added dropwise, causing vigorous bubbling. After 20 min, TLC indicated consumption of the starting material. The reaction was concentrated to an oil, and applied directly to a silica column. Flash chromatography (95:5 CH$_2$Cl$_2$/5% 2 N ammonia/MeOH) provided 0.293 g (71%) of 136. $^1$H NMR (CDCl$_3$) δ 7.28 (d, J=7.5 Hz, 1H), 7.21 (dd, J=8.0, 7.5 Hz, 1H), 6.82 (d, J=8.0 Hz, 1H), 4.92 (d, J=5.0 Hz, 0.5H), 4.81 (d, J=4.0 Hz, 0.5H), 3.98 (s, 3H), 3.76 (m, 0.5H), 3.69 (m, 0.5H), 2.57 (dd, J=16.2, 4.5 Hz, 0.5H), 2.52 (dd, J=16.4, 3.7 Hz, 0.5H), 2.44 (dd, J=16.1, 8.8 Hz, 0.5H), 2.34 (dd, J=16.3, 9.4 Hz, 0.5H), 1.45 (s, 4.5H), 1.40 (s, 4.5H).

e) The title compound was prepared according to the procedure of Example 53i–k except for using 136 instead of 123. $^1$H NMR (acetone-d6) δ 8.35 (d, J=1.8 Hz, 1H), 8.06 (d, J=7.9 Hz, 1H), 7.96 (d, J=10.8 Hz, 1H), 7.88 (d, J=8.3 Hz, 1H), 7.20–7.60 (m, 3H), 7.20 (d, J=8.1 Hz, 1H), 7.11 (d, J=9.0 Hz, 1H), 6.94 (d, J=4.5 Hz, 1H), 5.86 (m, 1H), 4.38 (m, 3H), 4.05 (s, 3H), 3.30 (dd, J=17.6, 6.0 Hz, 1H), 3.14 (dd, J=17.6, 7.4 Hz, 1H). ES (+) MS: m/e=604 (M+H)$^+$.

EXAMPLE 55

This example describes an exemplary synthesis of the compound below

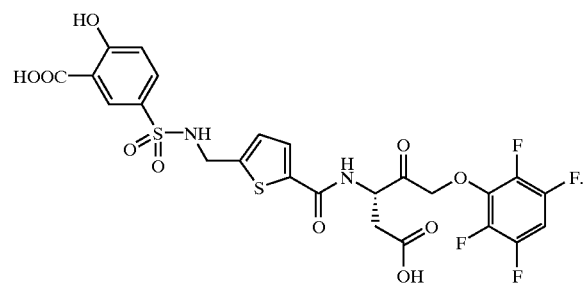

An intermediate, compound 139, was synthesized as described in Scheme 38.

SCHEME 38

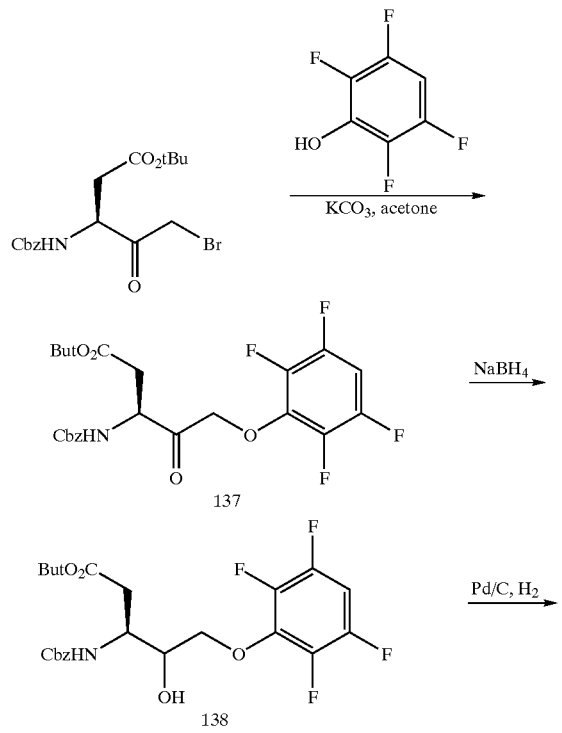

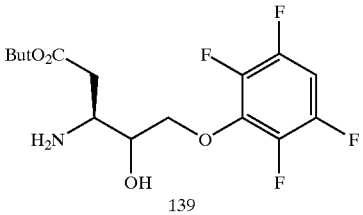

a) To a solution of 2,3,5,6-tetrafluorophenol (3.393 g, 20.43 mmol) in acetone (19 mL) was added K$_2$CO$_3$ (6.42 g, 46.43 mmol) in one portion at rt. After stirring for 10 min, a solution of Cbz-Asp(Ot-Bu)-CH$_2$Br (7.43 g, 18.57 mmol) in acetone (8.8 mL) was added dropwise to the phenoxide solution. The cloudy white solution stirred at rt for 30 min and was then diluted with ethyl acetate (60 mL). The solution was washed with 1 M HCl, saturated NaHCO$_3$ and brine. The organic layer was dried over MgSO$_4$ and the solvent removed under reduced pressure. The residue was purified by silica gel chromatography (20:80 to 25:75 ethyl acetate/hexanes) to give 7.7 g (86%) of phenoxymethyl ketone 137 as a clear oil.

b) 137 (7.7 g, 16.02 mmol) was dissolved in THF/MeOH (1:1 v/v, 300 mL) and cooled to 0° C. NaBH$_4$ (606 mg, 16.02 mmol) was added in one portion and the solution stirred for 30 min. The reaction mixture was diluted with ethyl acetate (200 mL) and carefully washed with 1 M HCl. The resulting mixture was partitioned and brine was added to remove emulsion. The layers were separated and the organic layer washed with brine. The organic layer was dried over MgSO$_4$ and purified by silica gel chromatography (25:75 to 30:70 ethyl acetate/hexanes) to give 3.49 g (45%) of 138.

c) 138 (3.38 g, 6.938 mmol) was dissolved in EtOH (40 mL). To this solution was added a slurry of palladium on carbon (10% w/w, 0.400 g). The solution was stirred under a balloon of hydrogen at rt for 12 h. The reaction mixture was filtered through Celite and washed with EtOH (2×20 mL). The combined filtrates were concentrated under reduced pressure to give 2.38 g (97%) of 139 as a clear oil.

d) The title compound was prepared according to the procedure of Example 53i–k except for using 139 instead of 123.

EXAMPLE 56

This example describes an exemplary synthesis of the compound below

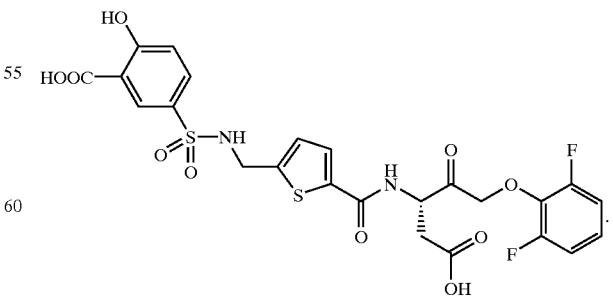

An intermediate, compound 140, was synthesized as described in Scheme 39.

SCHEME 39

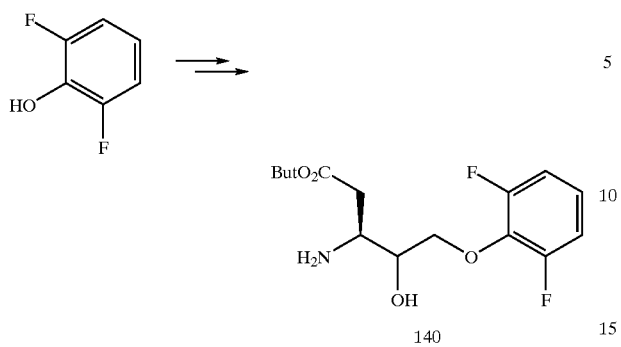

140 was prepared according to the procedure of Example 55 except for using 2,6-difluorophenol as a reagent instead of 2,3,5,6-tetrafluorophenol. The titled compound was prepared according to the procedure of Example 53i–k except for using 140 as a reagent instead of 123.

EXAMPLE 57

This example describes an exemplary synthesis of the compound below

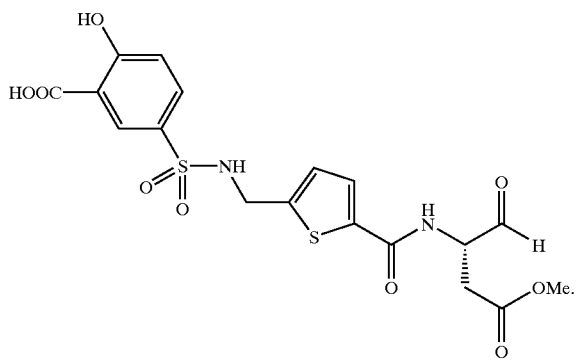

An intermediate, compound 142, was synthesized as described in Scheme 40.

SCHEME 40

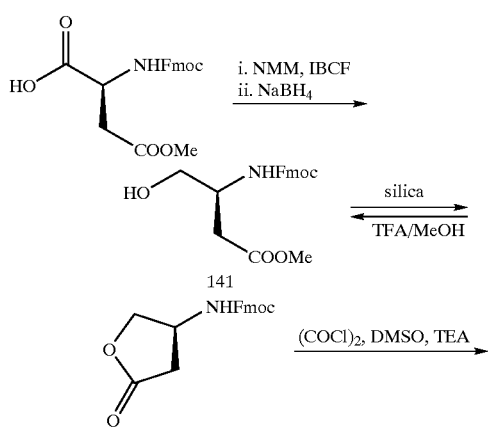

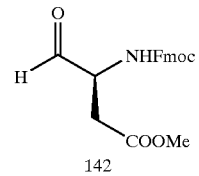

142 a) To a solution of Fmoc-Asp(OMe)-COOH (3.79 g, 10.3 mmol) in THF (20 mL) at 0° C. was dropwise added NMM (1.2 mL, 11.3 mmol) and IBCF (1.5 mL, 11.3 mmol). After stirring for 30 min, the solution was cooled to −78° C. and a slurry of NaBH$_4$ (0.798 g, 21 mmol) in THF/MeOH (3:1 v/v, 40 mL) was asdded. After stirring for 15 min, the suspension was warmed to rt and stirred for an additional 1 h. The solution was diluted with ether (100 mL) and washed with saturated NaHCO$_3$ (3×50 mL). The organic layer was dried over MgSO$_4$ and the solvent was removed under reduced pressure. The crude residue was purified by silica gel chromatography (40:60 ethyl acetate/hexanes) and resulted in lactonization of the desired product. The lactone was reesterified by dissolving the lactone in TFA/MeOH (10:90 v/v, 5 mL) and stirring at rt for 12 h. The solvent was removed under reduced pressure to provide 141 without further purification. ES (+) MS: m/e=378.2 (M+Na)$^+$.

b) To a solution of oxalyl chloride (0.824 mL, 9.5 mmol) at −78° C. was dropwise added DMSO (1.6 mL). After stirring for 10 min, a solution of triethylamine (4.8 mL) in CH$_2$Cl$_2$ (14 mL) was dropwise added. After stirring for 15 min, a solution of 141 (2.0 g, 5.6 mmol) in CH$_2$Cl$_2$ (7 mL) was dropwise added. After stirring for an additional 40 min, the solution was allowed to warm to rt. The solution was diluted with CH$_2$Cl$_2$ (50 mL) and washed with 1 M HCl (3×20 mL). The organic layer was dried over MgSO$_4$ and the solvent was removed under reduced pressure. The crude residue was purified by silica gel chromatography (40:60 ethyl acetate/hexanes) to provide 1.1 g (58%) of 142.

c) The title compound was prepared according to the procedure of Example 39h–j except for using 142 instead of Fmoc-Asp(OtBu)-CHO. ES (+) MS: m/e=471.1 (M+H)$^+$.

EXAMPLE 58

This example describes an exemplary synthesis of the compound below

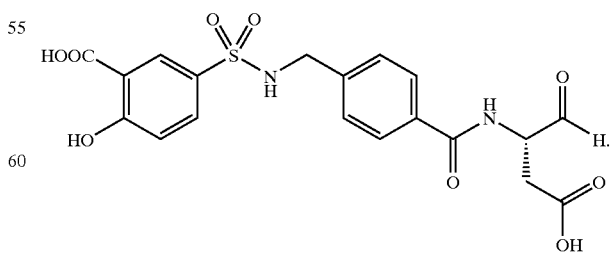

The method is described in Scheme 41.

SCHEME 41
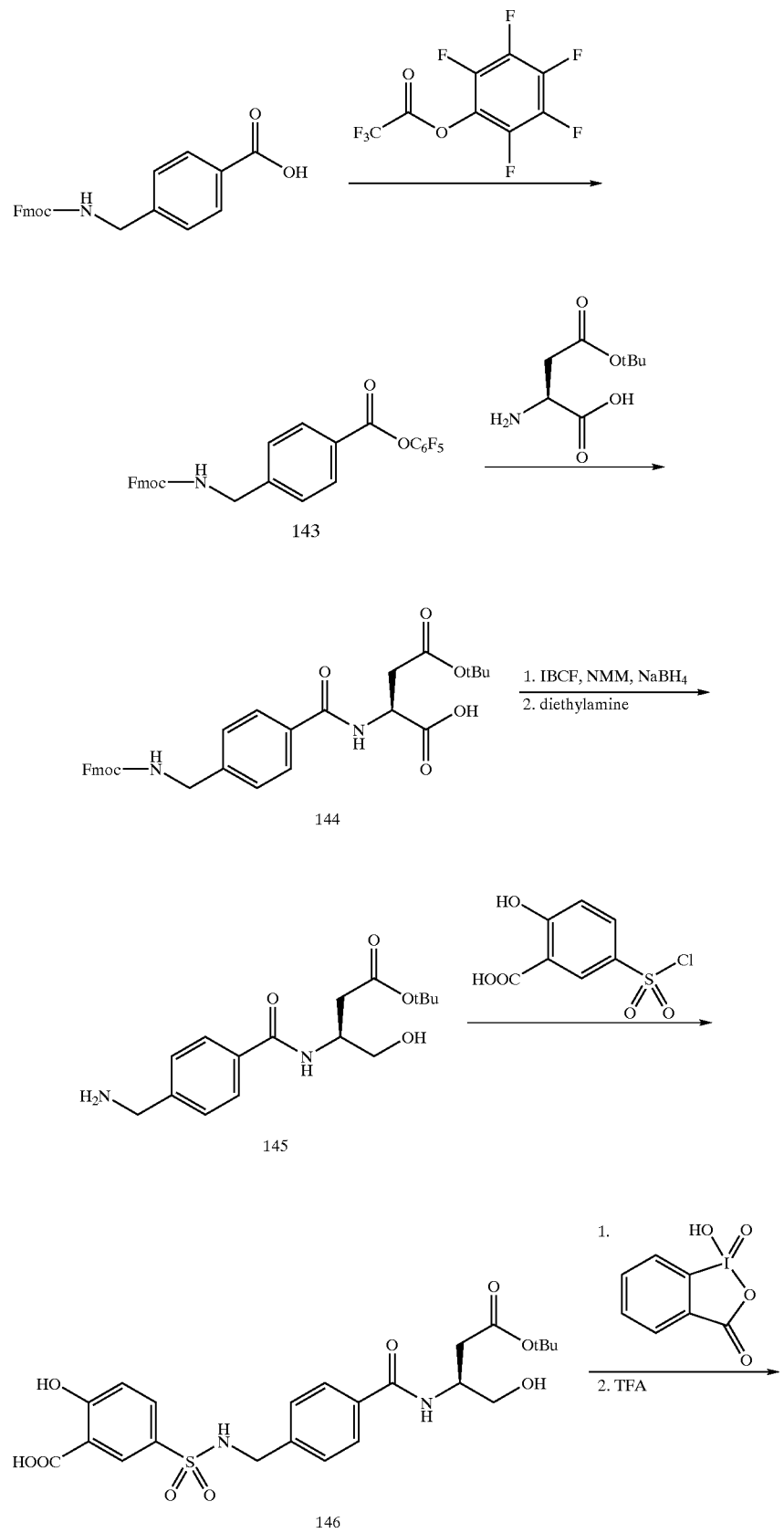

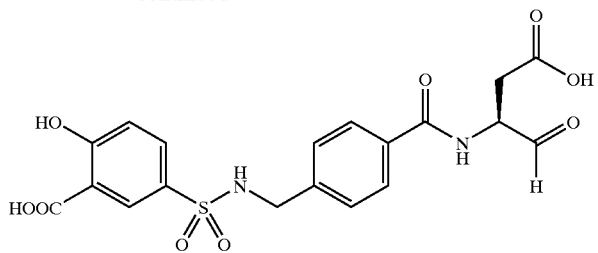

147 a) Fmoc-(4-aminomethyl)benzoic acid (2 g, 5.36 mmol) was dissolved in anhydrous DMF (20 mL). To this was added pyridine (0.47 mL, 5.81 mmol) and pentafluorophenyl trifluoroacetate (0.97 mL, 5.65 mmol). The reaction was stirred for 4.5 h and then flooded with ethyl acetate (100 mL), rinsed with 1 M $NaHSO_4$ (50 mL), saturated $NaHCO_3$ (50 mL), 1 M $NaHSO_4$ (50 mL), brine (50 mL), dried over $Na_2SO_4$, filtered, and the solvent removed under reduced pressure to yield 2.77 g (96%) of 143, which was used without further purification. ES (+) MS m/e=540 (M+H)$^+$.

b) 143 (2.77 g, 5.13 mmol) was mixed with $H_2N$-Asp (OtBu)-$CO_2H$ (0.98 g, 5.18 mmol) and suspended in anhydrous $CH_2Cl_2$ (40 mL). Then triethylamine (2.9 mL, 20.8 mmol) was added and the solution stirred for 4 h at which point it was flooded with ethyl acetate (100 mL), rinsed with 1 M $NaHSO_4$ (2×50 mL), brine (50 mL), dried over $Na_2SO_4$, filtered, and the solvent removed under reduced pressure to yield product which was purified using flash chromatography using 95:5:1 $CHCl_3$/methanol/acetic acid. This yielded 2.2 g (79%) of 144. ES (+) MS m/e=489 (M−tBu)$^+$.

c) 144 (2.195 g, 4.03 mmol) was dissolved in anhydrous THF (20 mL), chilled in an ice-water bath, and then N-methylmorpholine (1.0 mL, 9.1 mmol) and isobutyl chloroformate (1.1 mL, 8.48 mmol) were added. The reaction was stirred at 0° C. for 30 min, then $NaBH_4$ (0.76 g, 20.1 mmol) and methanol (5 mL) were added. After stirring at 0° C. for 3 h, the reaction was quenched with a few drops of acetic acid and flooded with ethyl acetate (100 mL). The organic layer was rinsed with 1 M $NaHSO_4$ (2×50 mL), saturated $NaHCO_3$ (50 mL), and brine (50 mL) and dried over $Na_2SO_4$. The solvent was removed under reduced pressure to yield a white solid which was dissolved in 1:1 anhydrous $CH_2Cl_2$/diethylamine (40 mL). The reaction was stirred at rt for 14 h, after which the solvent was removed under reduced pressure and the product purified via column chromatography using 19:2 $CHCl_3$/2 M ammonia in methanol to yield 0.626 g (50%) of 145. ES (+) MS m/e=309 (M+H)$^+$.

d) 145 (0.323 g, 1.0 mmol) was dissolved in 10 mL of anhydrous $CH_2Cl_2$, then 5-chlorosulfonyl-2-hydroxybenzoic acid (0.26 g, 1.1 mmol) and diisopropylethylamine (1 mL, 5.7 mmol) were added and the reaction was allowed to stir for three days at rt. Then the reaction was flooded with ethyl acetate (70 mL), rinsed with 1 M $NaHSO_4$ (3×50 mL), brine (50 mL) and dried over $Na_2SO_4$. The solvent was removed under reduced pressure to yield 0.5 16 g (100%) of 146, which was used without further purification. ES (+) MS m/e=453 (M−tBu)$^+$.

e) 146 (0.516 g, 1.0 mmol) was dissolved in anhydrous DMF (5 mL), then hydroxyiodinane oxide (IBX) (0.28 g, 1 mmol) was added and the reaction was stirred at rt for 18 h. The reaction was then flooded with ethyl acetate (100 mL), rinsed with 1 M $NaHSO_4$ (2×50 mL), brine (50 mL) and dried over $Na_2SO_4$. The solvent was removed under reduced pressure to yield a light yellow solid. This was redissolved in anhydrous $CH_2Cl_2$ (10 mL), chilled in an ice-water bath, and TFA (10 mL) was added. The reaction was removed from the ice-bath and allowed to stir for 40 min at rt. The solvent was removed under reduced pressure and the crude residue was purified using reverse-phase HPLC to yield 0.045 g (10%) of 147 as a slightly yellow solid. ES (+) MS m/e=451 (M+H)$^+$.

EXAMPLE 59

This example describes an exemplary synthesis of the compound below

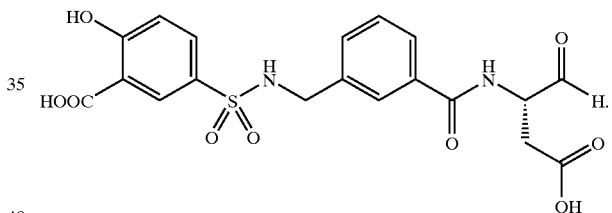

This compound was prepared according to the procedure of Example 58 a–e except for using Fmoc-(3-aminomethyl) benzoic acid (2.00 g, 5.36 mmol) as a reagent instead of Fmoc-(4-aminomethyl)benzoic acid. ES (+) MS m/e=451 (M+H)$^+$.

EXAMPLE 60

This example describes an exemplary synthesis of the compound below

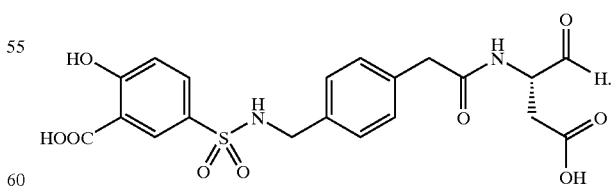

This compound was prepared according to the procedure of Example 58 a–e except for using Fmoc-(4-aminomethyl) phenylacetic acid (2 g, 5.16 mmol) as a reagent instead of Fmoc-(4-aminomethyl)benzoic acid. ES (+) MS m/e=465 (M+H)$^+$.

EXAMPLE 61

This example describes an exemplary synthesis of the compound below

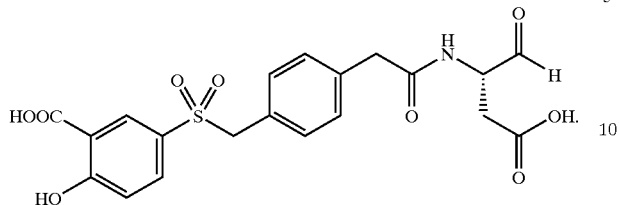

This compound was prepared according to the procedure of Example 58 a–e except for using Fmoc-(4-aminophenyl)acetic acid (1.00 g, 2.68 mmol) as a reagent instead of Fmoc-(4-aminomethyl)benzoic acid. ES (+) MS m/e=451 (M+H)$^+$.

EXAMPLE 62

This example describes an exemplary synthesis of the compound below

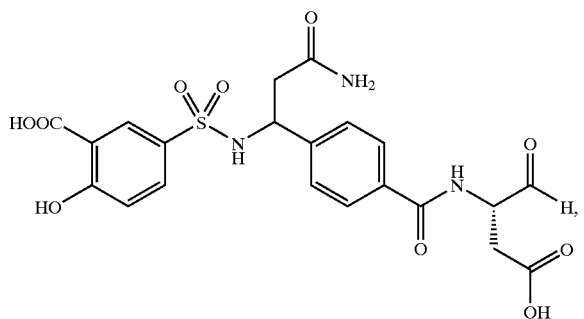

which was made according to Scheme 42.

SCHEME 42

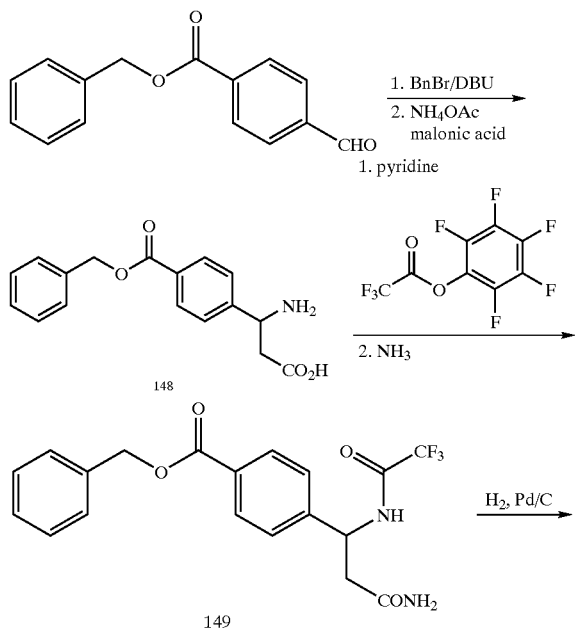

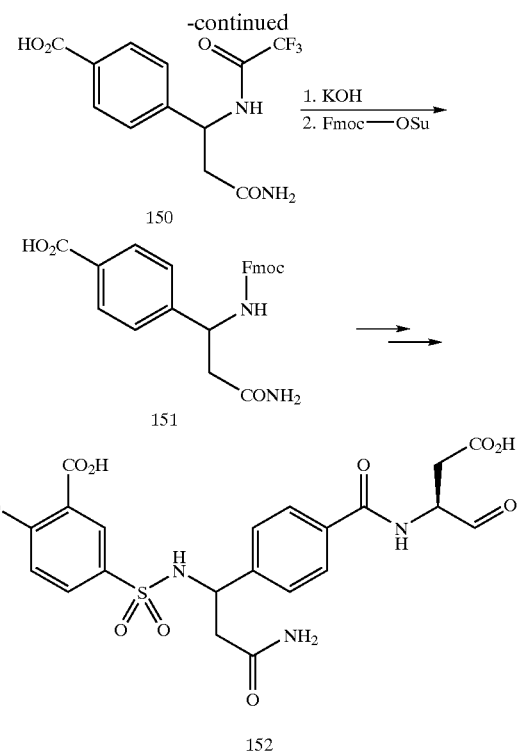

a) 4-Carboxybeuzaldehyde (6 g, 40 mmol) was dissolved in dry DMF (25 mL), then benzyl bromide (4.76 mL, 40 mmol) and 1,8-diazabicyclo[5.4.0]undec-7-ene (6.6 mL, 44 mmol) were added. The reaction was allowed to proceed for 45 min at rt, at which time it was flooded with ethyl acetate (100 mL), rinsed with 1 M HCl (50 mL), the aqueous layer was extracted with ethyl acetate (50 mL), and the combined organics were rinsed with 1 M HCl (50 mL), saturated NaHCO$_3$ (3×50 mL), brine (50 mL), dried over anhydrous Na$_2$SO$_4$, filtered, and the solvent removed under reduced pressure to yield a viscous yellow liquid (8.69 g, 90%) which was used without further purification. To a solution of the crude liquid in ethanol (50 mL) was added malonic acid (3.75 g, 36 mmol) and ammonium acetate (5.63 g, 72 mmol), followed by ethanol (150 mL). The solution was heated to reflux for 23 h, chilled in an ice-water bath, and filtered through a glass flit. The precipitate of 148 (6.08 g, 56%) was rinsed with ethanol and used without further purification. ES (+) MS m/e=300 (M+H)$^+$.

b) 148 (1.5 g, 5.01 mmol) was suspended in anhydrous DMF (20 mL), and then pyridine (0.86 mL) and pentafluorophenyl trifluoroacetate (1.81 mL, 10.5 mmol) were added. The reaction was allowed to stir at rt for 30 min, then 2 M ammonia in methanol (6 mL, 12 mmol) was added. After 2.5 h the reaction was flooded with ethyl acetate (100 mL), rinsed with 1 M NaHSO$_4$ (2×50 mL), saturated NaHCO$_3$ (2×50 mL), brine (50 mL), dried over Na$_2$SO$_4$, filtered, and the solvent removed under reduced pressure to yield 3.89 g (100%) 149 as a slightly viscous yellow oil which was used without further purification. ES (+) MS m/e=395(M+1)$^+$.

c) 149 (about 5 mmol) was dissolved in methanol (80 mL). The solution was placed under nitrogen, wet palladium on carbon (10% w/w, 1.06 g) was added, and the solution was stirred under a balloon filled with hydrogen for 50 min. The reaction was then filtered through Celite, and the solvent removed under reduced pressure to yield 2.3 g of crude 150, which was used without further purification. ES (+) MS m/e=305 (M+H)$^+$.

d) 150 was suspended in water (10 mL) and p-dioxane (10 mL), then KOH (2.81 g, 50 mmol) was added along with further water (10 mL) and p-dioxane (10 mL). The solution was stirred at rt for 2 h, at which point NaHCO$_3$ (4.62 g, 55 mmol) and Fmoc-OSu (1.7 g, 5.04 mmol) were added and the reaction allowed to proceed for 2 h. The solvent was removed under reduced pressure, resulting in a white residue which was resuspended in 1 N HCl (150 mL) and filtered through a glass frit. The precipitate of 151 was rinsed with 1 N HCl (50 mL), and used without further purification. ES (+) MS m/e=431 (M+H)$^+$.

e) 152 was prepared according to the method of Example 58a–e except for using 151 as a reagent instead of Fmoc-(4-aminomethyl)benzoic acid. ES (+) MS m/e=508 (M+H)$^+$.

EXAMPLE 63

This example describes an exemplary synthesis of the compound below

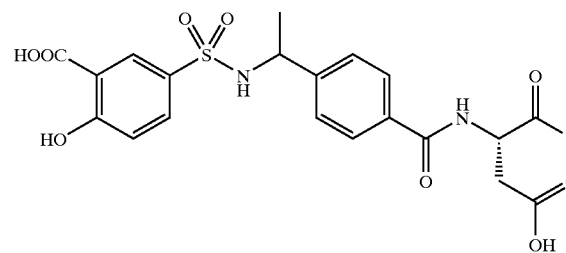

which was made according to Scheme 43.

SCHEME 43

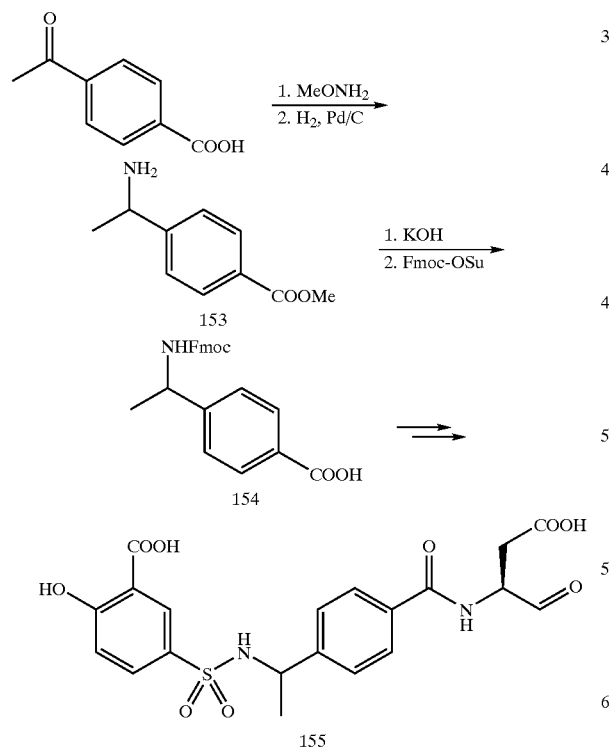

a) 4-Acetylbenzoic acid (3 g, 18.3 mmol) was mixed with methoxylamine hydrochloride (1.6 g, 19.2 mmol), suspended in MeOH (60 mL), and heated to 80° C. for 2 h. The reaction was then cooled to rt, purged with nitrogen; and then wet palladium on carbon (10% w/w, 1.94 g) was added and the reaction stirred under a hydrogen-containing balloon. After 5 h the reaction was filtered through Celite and the solvent removed under reduced pressure to yield 3.8 g (96%) of 153 as a colorless glass. ES (+) MS m/e=180 (M+H)$^+$.

b) 154 (2.6 g, 6.8 mmol, 38%) was prepared according to the procedure of Example 62d except for using 153 as a reagent instead of 150. ES (+) MS m/e=388 (M+H)$^+$.

c) 155 was prepared according to the method of Example 62a–e except for using 154 as a reagent instead of Fmoc-(4-aminomethyl)benzoic acid. ES (+) MS m/e=465 (M+H)$^+$.

EXAMPLE 64

This example describes an exemplary synthesis of the compound below

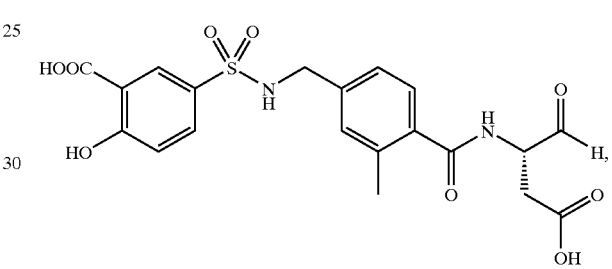

which was made according to Scheme 44.

SCHEME 44

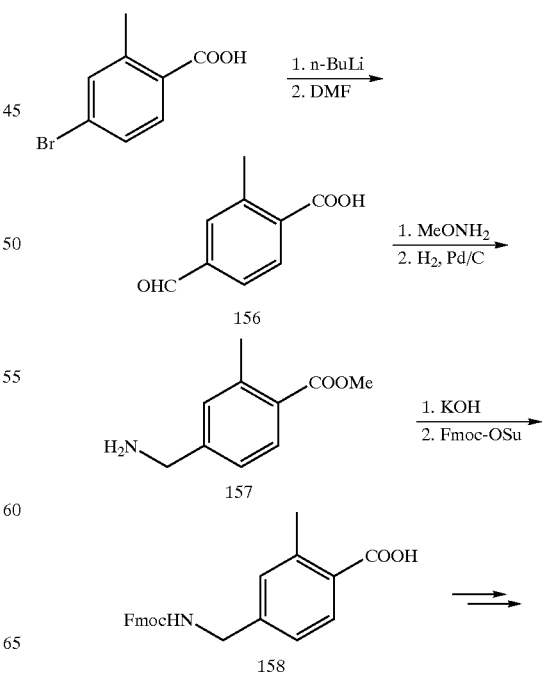

-continued

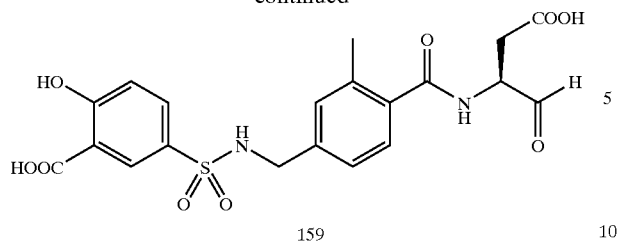

159 a) 4-Bromo-2-methylbenzoic acid (2.5 g, 11.6 mmol) was suspended in dry THF (100 mL), purged with nitrogen, and cooled to −78° C. To this was added n-butyllithium (15.3 mL of 1.6 M solution in hexane, 24.5 mmol) followed by dry DMF (2.00 mL, 25.8 mmol). The reaction was stirred at −78° C. for 1 h, then allowed to warm to rt for 1.5 h. The reaction was quenched with 1 M HCl (20 mL) and the solvent was removed under reduced pressure. The product was resuspended in ethyl acetate (100 mL) and washed with 1 N HCl (2×50 mL). The organic layer was then treated with 1 N NaOH (2×30 mL). The combined aqueous extracts were acidified with 1 M HCl (100 mL) and the aqueous layer was extracted with ethyl acetate (3×35 mL). The combined organic extracts were rinsed with 1 M HCl (50 mL) and brine (50 mL), dried over Na$_2$SO$_4$, filtered, and the solvent was removed under reduced pressure to yield 1.62 g (85%) of 156, which was used without further purification. ES(+) MS m/e=165 (M+H)$^+$.

b) 157 was prepared (1.1 g, 58%) according to the procedure of Example 63a except for using 156 as a reagent instead of 4-acetylbenzoic acid. ES (+) MS m/e=180 (M+H)$^+$.

c) 158 was prepared (1.5 g, 73%) according to the procedure of Example 62d except for using 157 as a reagent instead of 150. ES (+) MS m/e=388 (M+H)$^+$.

d) 159 was prepared according to the procedure of Example 58a–e except for using 158 as a reagent instead of Fmoc-(4-aminomethyl)benzoic acid. ES (+) MS m/e=465 (M+H)$^+$.

EXAMPLE 65

This example describes an exemplary synthesis of the compound below

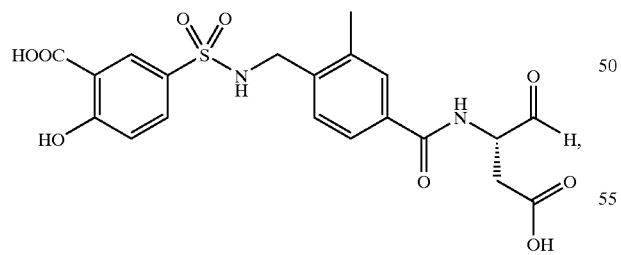

which was made according to Scheme 45.

SCHEME 45

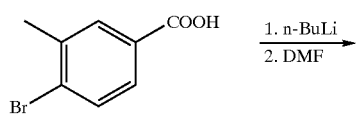

-continued

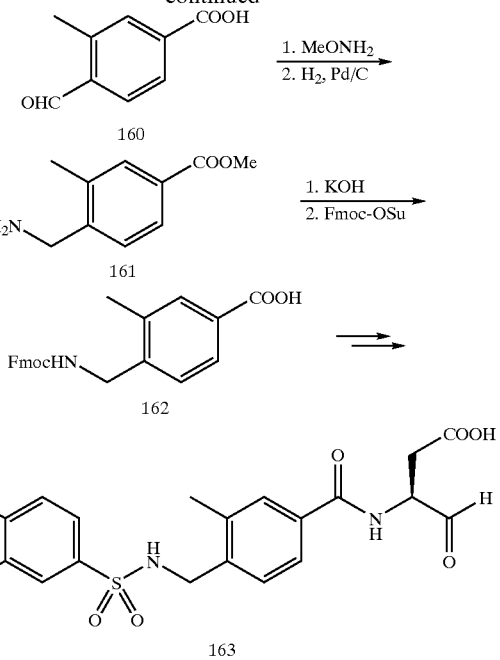

a) 160 was prepared according to the procedure of Example 64a except for using 4-bromo-3-methylbenzoic acid as a reagent material instead of 4-bromo-2-methylbenzoic acid. ES (+) MS m/e=165 (M+H)$^+$.

b) 161 was prepared (2.4 g, 67%) according to the procedure of Example 63a except for using 160 as a reagent instead of 4-acetylbenzoic acid. ES (+) MS m/e=179 (M)$^+$.

c) 162 was prepared (2.7 g, 58%) according to the procedure of Example 62d except for using 161 as a reagent instead of 150. ES (+) MS m/e=407 (M+20H)$^+$.

d) 163 was prepared according to the procedure of Example 58a–e except for using 162 as a reagent instead of Fmoc-(4-aminomethyl)benzoic acid. ES (+) MS m/e=465 (M+H)$^+$.

EXAMPLE 66

This example describes an exemplary synthesis of the compound below

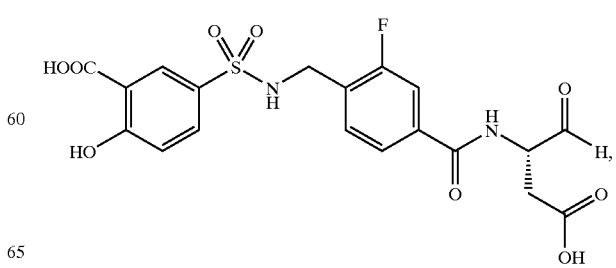

which was made according to Scheme 46.

SCHEME 46

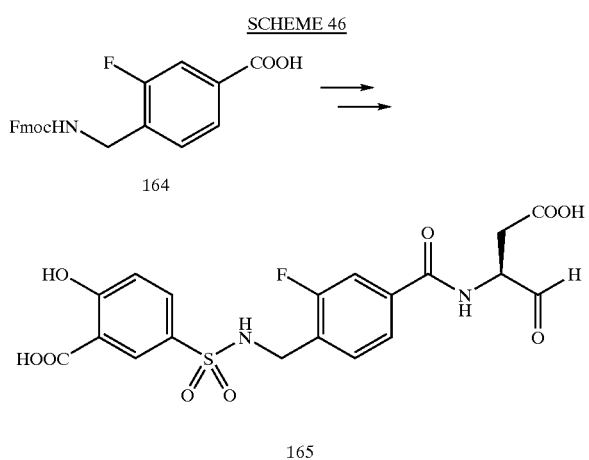

a) 164 was prepared according to the procedure of Example 64a–c except for using 4-bromo-3-fluorobenzoic acid as a reagent instead of 4-bromo-2-methylbenzoic acid. ES (+) MS m/e=169 (M+H)$^+$.

b) 165 was prepared according to the method of Example 58a–e except for using 164 as a reagent instead of Fmoc-(4-aminomethyl)benzoic acid. ES (+) MS m/e=558 (M+H)$^+$.

EXAMPLE 67

This example describes an exemplary synthesis of the compound below

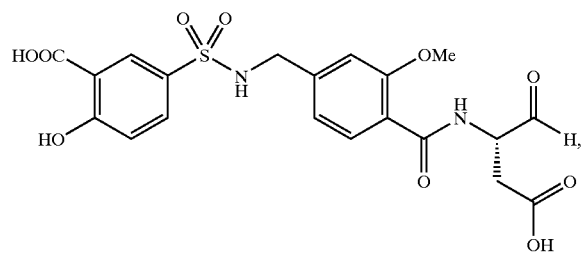

which was made according to Scheme 47.

SCHEME 47

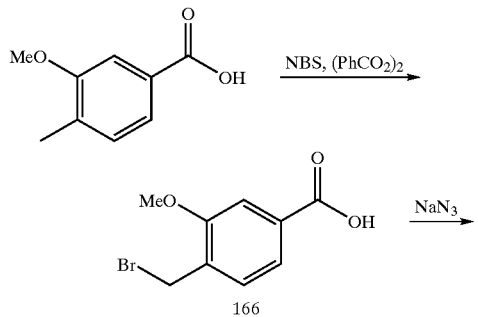

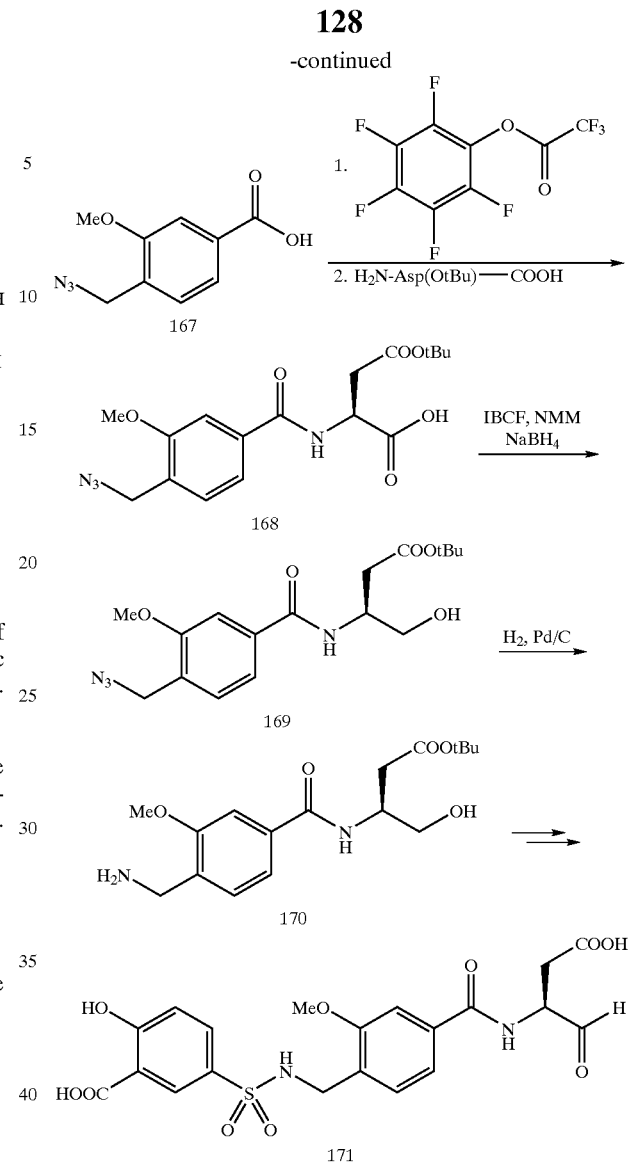

a) A solution of 3-methoxy-4-methylbenzoic acid (5.01 g, 30.2 mmol), N-bromosuccinimide (5.37 g, 30.15 mmol), and a few granules of benzoyl peroxide in benzene (50 mL) were heated to reflux for 4 h. After cooling to rt, the mixture was filtered and the benzene removed at reduced pressure. The residue was redissolved in ethyl acetate (50 mL) and washed with 1 M NaHSO$_4$ (2×30 mL), and brine (30 mL). The organic layer was dried over Na$_2$SO$_4$ and the solvent was removed to afford 166 in 97% yield. ES (+) MS m/e=245 (M+1)$^+$.

b) A solution of 166 (1.0 g, 4.08 mmol) and sodium azide (0.292 g, 4.49 mmol) in DMF (15 mL) was heated to 60° C. for 16 h. After removal of most of the DMF under reduced pressure, the reaction was flooded with ethyl acetate (50 mL). The organic layer was rinsed with water (20 mL) and dried over Na$_2$SO$_4$. The solvent was removed under reduced pressure to yield 167 in 93% yield. ES (+) MS m/e=208 (M+H)$^+$.

c) 168 was prepared according to the procedure of Example 58a–b except for using 167 as a reagent instead of Fmoc-(4-aminomethyl)benzoic acid. ES (+) MS m/e=379 (M+H)$^+$.

d) 168 (0.459 g, 1.21 mmol) was dissolved in THF, cooled to 0° C., and N-methylmorpholine (0.277 mL, 2.52 mmol)

was added followed by isobutyl chloroformate (0.318 mL, 2.45 mmol). The reaction was stirred at 0° C. for 30 min at which point NaBH$_4$ (0.229 g, 6.05 mmol) and methanol (4 mL) were added. After 2 h of stirring, the reaction was quenched with a few drops of acetic acid, flooded with ethyl acetate (100 mL), rinsed with 1 M NaHSO$_4$ (2×50 mL), saturated NaHCO$_3$ (50 mL), and brine (50 mL). The combined organic extracts were dried over Na$_2$SO$_4$ and the solvent was removed under reduced pressure to give 169 in quantitative yield. ES (+) MS m/e=365 (M+H)$^+$.

e) 169 (0.441 g, 1.21 mmol) and palladium on carbon (10% w/w, 0.129 g, 0.06 mmol) were suspended in methanol (15 mL) and placed under a hydrogen balloon for 2 h. The reaction was then filtered through Celite and the solvent was removed under reduced pressure. The product was purified by column chromatography using 9:1 CHCl$_3$/2 M ammonia in methanol to yield 170 in 29% yield. ES (+) MS m/e=339 (M+H)$^+$.

f) 171 was prepared according to the procedure of Example 58d–e except for using 70 as a reagent instead of 145. ES (+) MS m/e=539 (M+H)$^+$.

EXAMPLE 68

This example describes an exemplary synthesis of the compound below

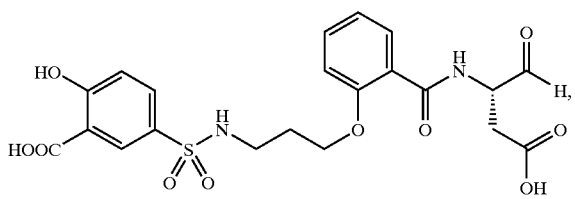

which was made according to Scheme 48.

SCHEME 48

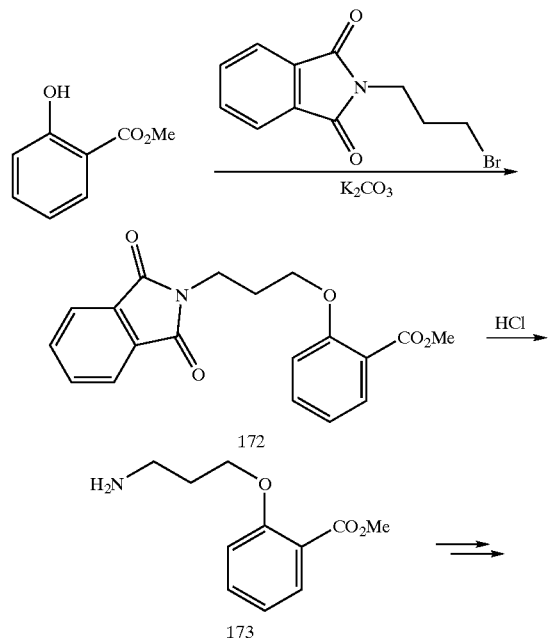

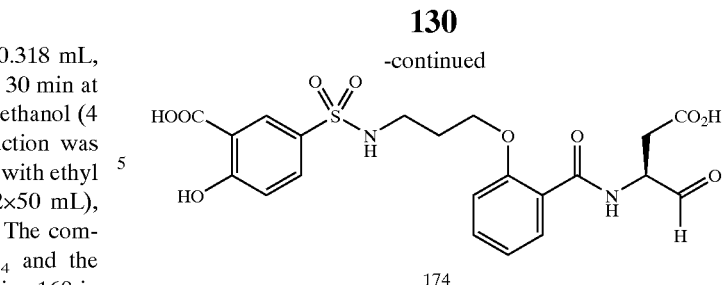

174 a) Methyl salicylate (3.41 mL, 26.29 mmol), N-(3-bromopropyl)phthalimide (7.40 g, 27.60 mmol), and K$_2$CO$_3$ (16.35 g, 118.3 mmol) were refluxed in acetone (100 mL) for 72 h. The acetone was removed under reduced pressure and the resulting residue was dissolved in CHCl$_3$ (50 mL) and filtered. The solvent was removed under reduced pressure and the product purified by column chromatography using 4:1 hexanes/ethyl acetate to yield 172 in 75% yield. ES (+) MS m/e=340 (M+1)$^+$.

b) 172 (2.0 g, 5.89 mmol) was dissolved in p-dioxane (10 mL) and concentrated aqueous HCl (10 mL) was added. The solution was refluxed for 42 h at which point the solvent was removed under reduced pressure. The residue was triturated with acetone to give 173 in 65% yield. ES (+) MS m/e=196 (M+H)$^+$.

c) 174 was prepared according to the procedures of Examples 62d and 58a–e except for using 173 as a reagent instead of 150. ES (+) MS m/e=495 (M+H)$^+$.

EXAMPLE 69

This example describes an exemplary synthesis of the compound below

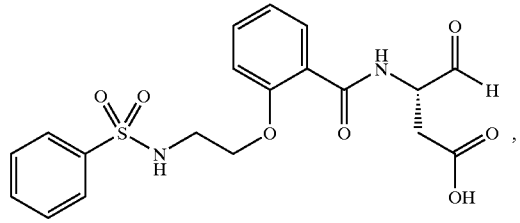

which was made according to Scheme 49.

SCHEME 49

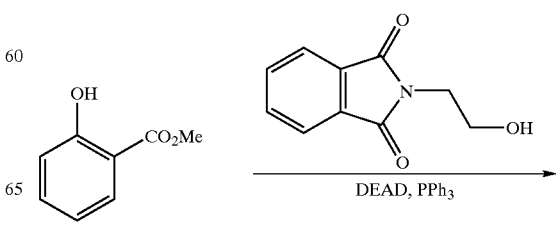

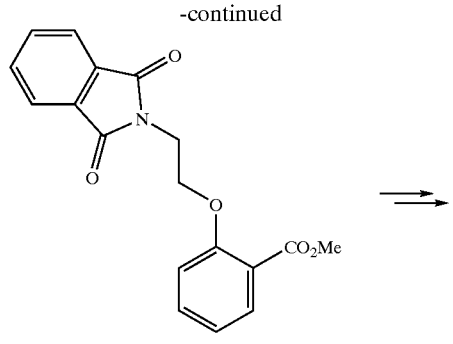

175

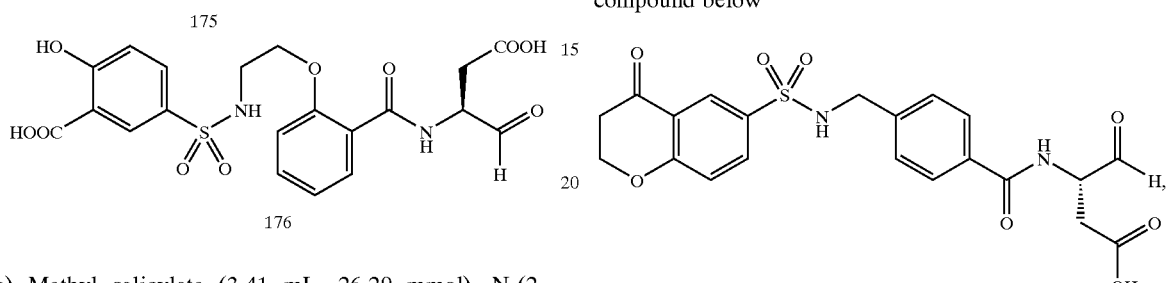

176 a) Methyl salicylate (3.41 mL, 26.29 mmol), N-(2-hydroxyethyl)phthalimide (5.03 g, 26.29 mmol), and triphenylphosphine (7.76 g, 29.58 mmol) were dissolved in THF and cooled to 0° C. Diethyl azodicarboxylate (4.66 mL, 29.58 mmol) was added dropwise at 0° C. and the reaction was stirred for 72 h and warmed to rt. The solvent was removed under reduced pressure and the residue was triturated with methanol to yield 175 in 39% yield. ES (+) MS m/e=325 (M+H)$^+$.

b) 176 was prepared according to the procedures of Example 68b–c except for using 175 as a reagent instead of 172. ES (+) MS m/e=481 (M+H)$^+$.

EXAMPLE 70

This example describes an exemplary synthesis of the compound below which was made according to Scheme 50.

SCHEME 50

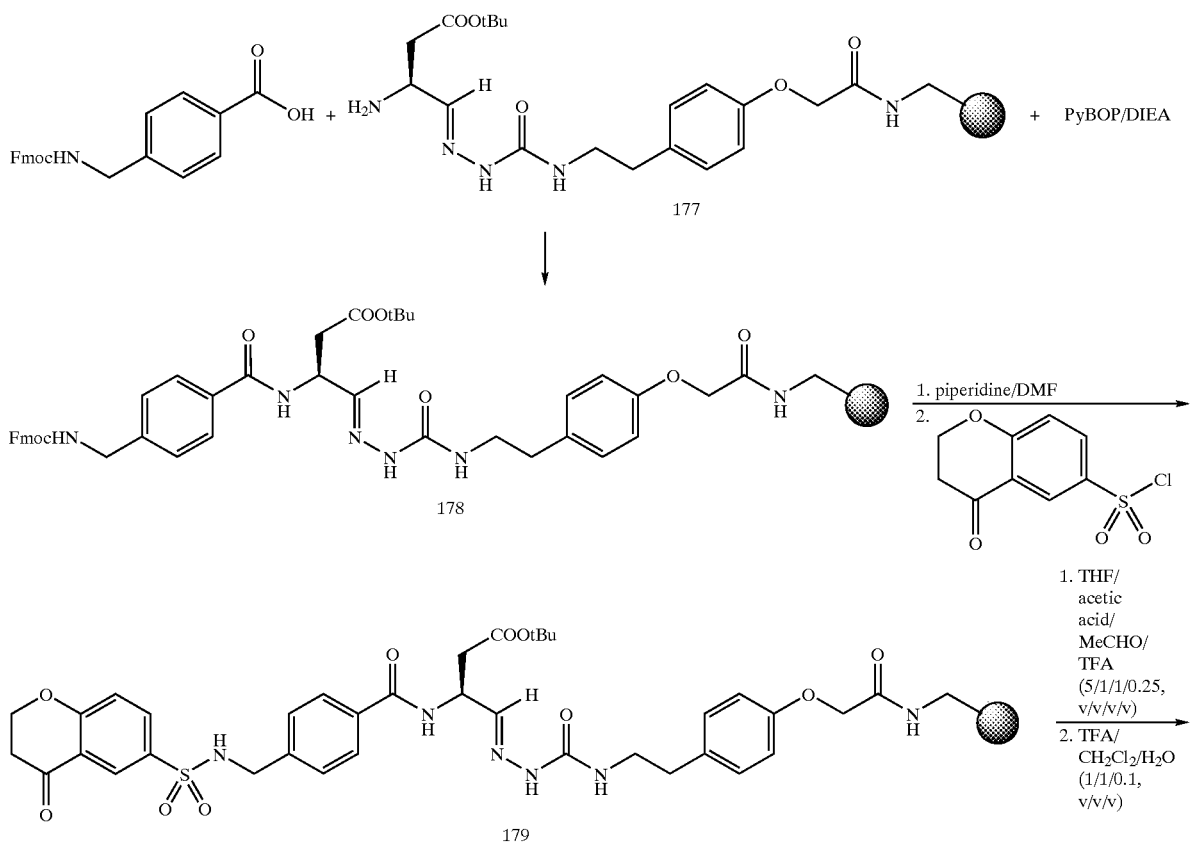

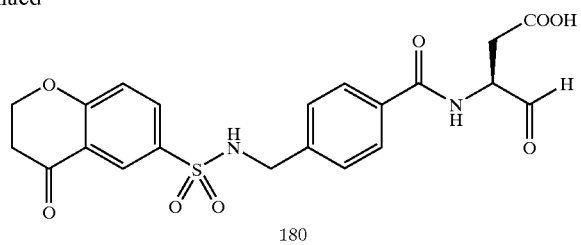

180

(3S)-3-(9-Fluorenylmethoxycarbonyl)amino-4-oxobutanoic acid tert-butyl ester semicarbazonyl-4-[2'-(4-ethylphenoxy acetic acid)], prepared according to the procedure of PCT International Publication No. WO 00/23421, pages 37–40, was coupled with a commercial amino-Merrifield resin in the presence of EDCI and HOBT in dichloromethane, and deprotected by treatment with a 20% piperidine in DMF solution (200 mL) and stirring for 30 min to afford resin 177, which was washed successively with DMF (3×300 mL) and CH$_2$Cl$_2$ (3×300 mL).

a) Resin 177 (11.7 g, 2.90 mmol) was suspended in DMF (110 mL) followed by addition of Fmoc7(4-aminomethyl)-benzoic acid (2.2 g, 5.8 mmol), diisopropylethylamine (3.0 mL, 17 mmol) and PyBOP (4.5 g, 8.7 mmol), and stirring at rt for 12 h to afford a suspension of resin 178, which was filtered through a sintered-glass funnel and washed successively with THF (3×200 mL), DMF (3×200 mL), CH$_2$Cl$_2$ (3×200 mL) and ether (2×200 mL). After drying the resin 178 in vacuo, an aliquot of the resin (0.300 g) was treated with a solution of THF/acetaldehyde/acetic acid/TFA (3 mL, 5:1:1:0.25 v/v/v/v) to release (3S)-3-Fmoc-amino-4-oxobutanoic acid tert-butyl ester. Based on the mass balance of the cleaved material, the resin loading was calculated to be approximately 0.5 mmol/g.

b) To a solution of 4-chromanone (0.59 g, 4.0 mmol) in CHCl$_3$ (10 mL) was added chlorosulfonic acid (1.0 mL, 15 mmol) and heated to 40° C. for 1 h. After cooling to rt, the solution was poured onto ice and extracted with CH$_2$Cl$_2$ (10 mL). The organic layer was washed with 1 M HCl (3×10 mL) and the combined organic extracts were dried over MgSO$_4$, filtered, and the solvent was removed under reduced pressure to afford 4-oxochroman-6-sulfonyl chloride as a grey solid in quantitative yield. $^1$H NMR (CD$_3$OD) δ 8.41 (s, 1H), 8.05 (d, 1H), 7.13 (d, 1H), 4.7 (t, 2H), 3.0 (t, 2H).

c) Resin 178 (0.3 g, 0.15 mmol) was treated with a 20% piperidine in DMF solution (5 mL) and stirred for 30 min. The resin was washed successively with DMF (3×5 mL) and CH$_2$Cl$_2$ (3×5 mL). The resin was suspended in CH$_2$Cl$_2$ (5 mL) and treated with diisopropylethylamine (0.218 g, 1.25 mmol) and 4-oxochroman-6-sulfonyl chloride (0.177 g, 0.750 mmol). After stirring for 4 h at rt, the resin suspension was filtered and washed with CH$_2$Cl$_2$ (3×5 mL) to yield Resin 179.

d) Resin 179 was treated with a solution of THF/acetaldehyde/acetic acid/TFA (3 mL, 5:1:1:0.25 v/v/v/v). After stirring for 3 h at rt, the supernatant was collected by suction and the resin was washed with CH$_2$Cl$_2$ (2×3 mL). The combined filtrates were diluted with toluene (10 mL) and the solvent was removed under reduced pressure. The residue was treated with a solution of CH$_2$Cl$_2$/TFA/water (2 mL, 1:1:0.1 v/v/v). After stirring for 1 h at rt, the solvent was removed under reduced pressure. The crude residue was purified by reverse-phase preparatory HPLC to afford 180 as a colorless oil. ES (+) MS: m/e=461.1 (M+H)$^+$.

EXAMPLE 71

This example describes an exemplary synthesis of the compound below

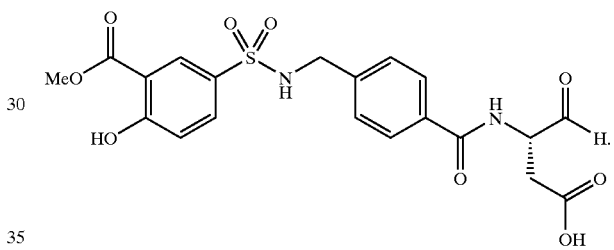

The title compound was prepared according to the procedure of Example 70b–d except for using methyl 3-hydroxybenzoate as a reagent instead of 4-chromanone. ES (+) MS: m/e=465.15 (M+H)$^+$.

EXAMPLE 72

This example describes an exemplary synthesis of the compound below

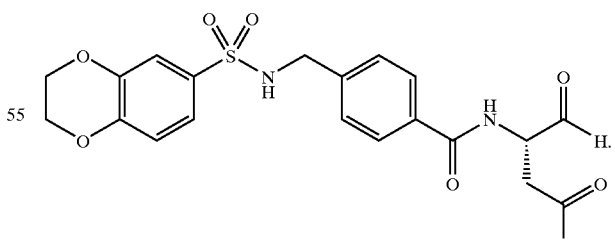

The title compound was prepared according to the procedure of Example 70b–d except for using 1,4-benzodioxan as a reagent instead of 4-chromanone. ES (+) MS: m/e=449.1 (M+H)$^+$.

EXAMPLE 73

This example describes an exemplary synthesis of the compound below

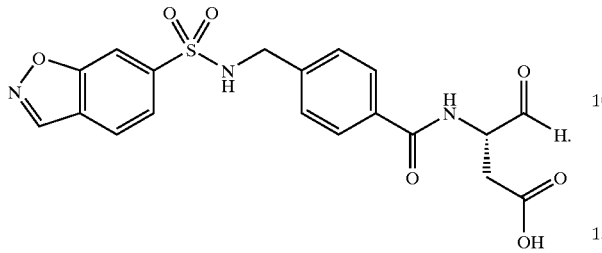

The title compound was prepared according to the procedure of Example 70b–d except for using 1,2-benzisoxazole as a reagent instead of 4-chromanone. ES (+) MS: m/e=432.1 (M+H)⁺.

EXAMPLE 74

This example describes an exemplary synthesis of the compound below

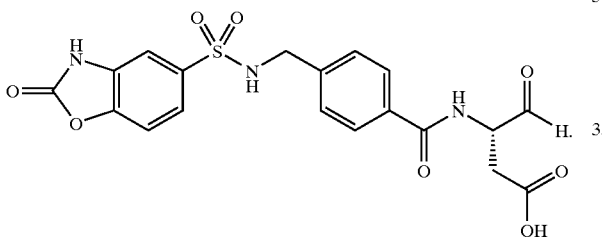

The title compound was prepared according to the procedure of Example 70b–d except for using 2-benzoxazolinone as a reagent instead of 4-chromanone.

EXAMPLE 75

This example describes an exemplary synthesis of the compound below

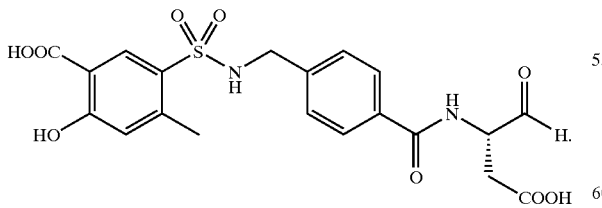

The title compound was prepared according to the procedure of Example 70b–d except for using 3-methylsalicylic acid as a reagent instead of 4-chromanone. ES (+) MS: m/e=465.1 (M+H)⁺.

EXAMPLE 76

This example describes an exemplary synthesis of the compound below

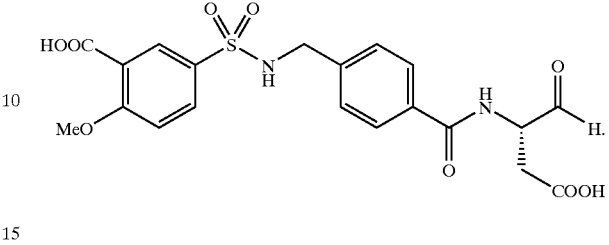

The title compound was prepared according to the procedure of Example 70b–d except for using 4-methylsalicylic acid as a reagent instead of 4-chromanone. ES (+) MS: m/e=465.0 (M+H)⁺.

EXAMPLE 77

This example describes an exemplary synthesis of the compound below

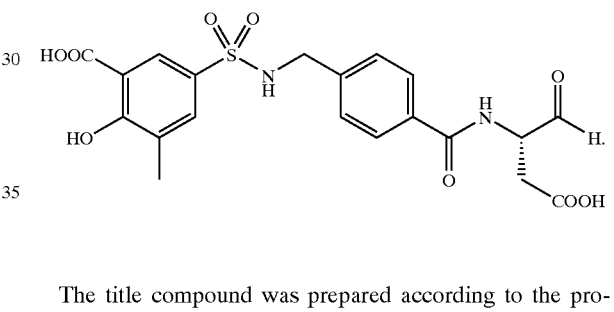

The title compound was prepared according to the procedure of Example 70b–d except for using 2-methoxybenzoic acid as a reagent instead of 4-chromanone. $^1$H NMR (CD$_3$OD) δ 8.73 (s, 1H), 7.87 (d, 1H), 7.68 (d, 2H), 7.28 (d, 2H), 7.18 (d, 1H), 4.71 (d, 1H), 4.66 (d, 1H), 4.48 (m, 1H), 4.12 (s, 2H), 3.99 (d, 1H), 3.94 (s, 3H), 2.69 (m. 2H).

EXAMPLE 78

This example describes an exemplary synthesis of the compound below

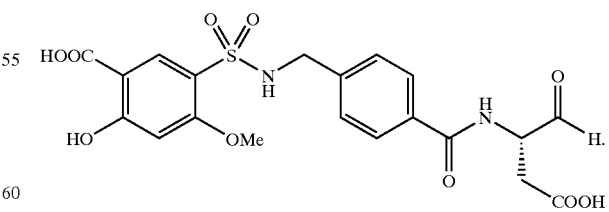

The title compound was prepared according to the procedure of Example 70b–d except for using 4-methoxysalicylic acid as a reagent instead of 4-chromanone. ES (+) MS: m/e=481.0 (M+H)⁺.

EXAMPLE 79

This example describes an exemplary synthesis of the compound below

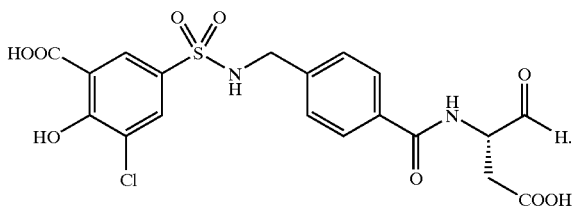

The title compound was prepared according to the procedure of Example 70b–d except for using 3-chlorosalicylic acid instead of 4-chromanone. ES (+) MS: m/e=485.0 (M+H)+.

EXAMPLE 80

This example describes an exemplary synthesis of the compound below

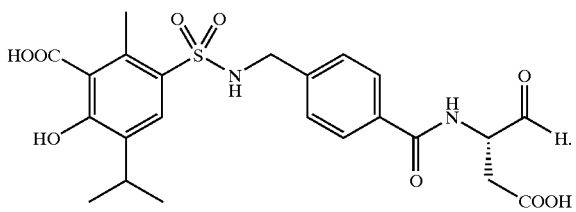

The title compound was prepared according to the procedure of Example 70b–d except for using 3-hydroxy-3-isopropyl-6-methylbenzoic acid as a reagent instead of 4-chromanone. $^1$H NMR (CD$_3$OD) δ 7.85 (s, 1H), 6.43 (d, 2H), 7.18 (d, 2H), 4.68 (dd, 1H), 4.42 (m, 1H), 4.09 (m, 2H), 2.70 (m, 2H), 2.68 (s, 3H), 2.54 (m, 1H), 1.15 (d, 6H).

EXAMPLE 81

This example describes an exemplary synthesis of the compound below

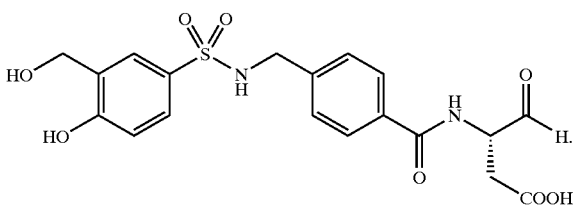

An intermediate, compound 183, was synthesized as described in Scheme 51.

SCHEME 51

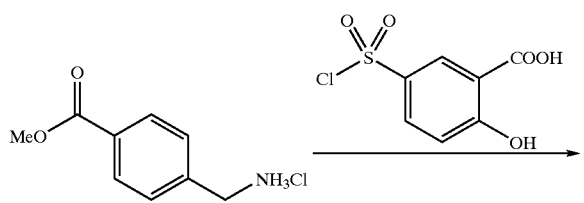

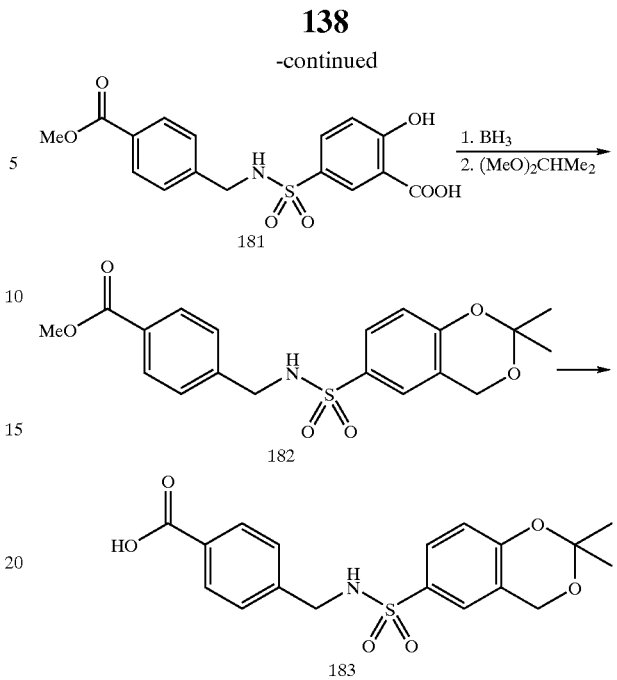

a) To a suspension of methyl-4-(aminomethyl)benzoate hydrochloride (0.20 g, 0.99 mmol) in CH$_2$Cl$_2$ (10 mL) was added diisopropylethylamine (0.5 mL, 2.9 mmol) followed by 5-chlorosulfonyl-2-hydroxybenzoic acid (0.234 g, 0.990 mmol). After stirring for 2 h at rt, the solution was diluted with ethyl acetate (20 mL) and washed with 1 M HCl (3×20 mL). The organic layer was dried over MgSO$_4$, filtered, and the solvent was removed under reduced pressure to afford 181 as a white solid in quantitative yield. ES (+) MS: m/e=388.0 (M+H)+.

b) A solution of 181 (0.50 g, 1.3 mmol) in THF (7 mL) was added 1 M BH$_3$ in THF (3 mL, 3 mmol) and heated to reflux for 1 h. After warming to rt, the solution was diluted with ethyl acetate (20 mL) and washed with 1 M HCl (3×20 mL). The organic layer was dried over MgSO$_4$, filtered, and the solvent was removed under reduced pressure to afford a white solid. The crude product was purified by column chromatography (70:30 to 90:10 ethyl acetate/hexanes) to afford the benzyl alcohol in 79% yield. The resulting alcohol (0.400 g, 1.1 mmol) was then dissolved in acetone (4 mL) and added Na$_2$SO$_4$ (0.241 g, 1.70 mmol) and dimethoxypropane (0.210 mL, 1.70 mmol). After heating for 2 h at 40° C., the solution was cooled to rt, diluted with ethyl acetate (20 mL) and washed with 0.3 M HCl (3×20 mL). The organic layer was dried over MgSO$_4$, filtered, and the solvent was removed under reduced pressure to afford 182 as a white solid. ES (+) MS: m/e=414.0 (M+Na)+.

c) To a solution of 182 (0.320 g, 0.8 mmol) in dioxane (3 mL) was added 1 M LiOH (aq) (2.3 mL, 2.3 mmol). After stirring for 1 h at rt, the solution was diluted with ethyl acetate (20 mL) and washed with 1 M HCl (3×20 mL). The organic layer was dried over MgSO$_4$, filtered, and the solvent was removed under reduced pressure to afford 183 as a white solid in quantitative yield. ES (+) MS: m/e=400.0 (M+Na)+.

d) The title compound was prepared according to the procedure of Example 70a,d except for using 183 as a reagent instead of Fmoc-(4-aminomethyl)-benzoic acid. ES (+) MS: m/e=437.1 (M+H)+.

EXAMPLE 82

This example describes an exemplary synthesis of the compound below

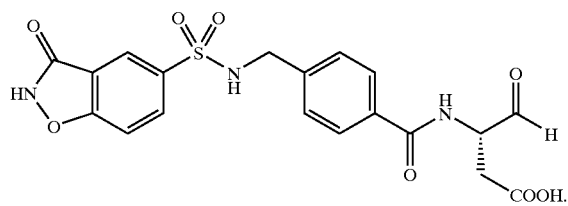

An intermediate, compound 185, was made as described in Scheme 52.

SCHEME 52

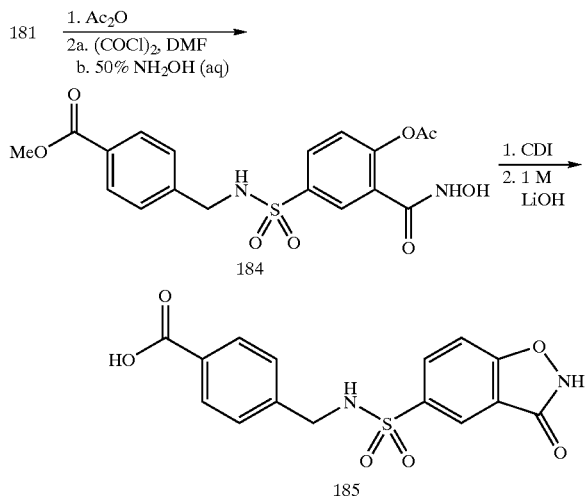

a) To a suspension of 181 (Example 82) (0.800 g, 2.18 mmol) in acetic anhydride (3.00 mL, 31.8 mmol) was added 2 drops of concentrated sulfuric acid. After stirring for 1 h at rt, the solvent was removed under reduced pressure to afford the crude product. Without further purification, this residue was dissolved in ethyl acetate (40 mL) and added oxalyl chloride (0.952 mL, 10.9 mmol) followed by 2 drops of DMF. After stirring for 1 h, the solvent was removed under reduced pressure to afford the crude acid chloride which was dissolved in THF (30 mL). To this solution was added 50% NH$_2$OH (aq) (0.681 mL, 10.9 mmol) dropwise. After stirring for 1 h, the solution was diluted with ethyl acetate (40 mL) and washed with 1 M HCl (3×40 mL). The organic layer was dried over MgSO$_4$, filtered, and the solvent was removed under reduced pressure to afford the crude hydroxamic acid product. The crude residue (0.760 g, 1.80 mmol) was then dissolved in methanol/water (16 mL, 1:1 v/v) and added potassium bicarbonate (0.302 g, 3.60 mmol). After stirring for 2 h at rt, the solution was diluted with ethyl acetate (40 mL) and washed with 1 M HCl (3×40 mL). The organic layer was dried over MgSO$_4$, filtered, and the solvent was removed under reduced pressure to afford 184 as a white solid which was used without further purification. ES (+) MS: m/e=385.0 (M+5H)$^+$.

b) To a solution of 184 (0.590 g, 1.60 mmol) in THF (16 mL) was added carbonyl diimidazole (0.778 g, 4.80 mmol). After heating at reflux for 3 h, the solution was diluted with ethyl acetate (40 mL) and washed with 1 M HCl (3×40 mL). The organic layer was dried over MgSO$_4$, filtered, and the solvent was removed under reduced pressure to afford the benzisoxazolinone as a white solid which was used crude without further purification. ES (+) MS: m/e=363.0 (M+H)$^+$.

c) To a solution of the benzisoxazolinone (0.600 g, 1.70 mmol) in dioxane (5 mL) was added 1 M LiOH (aq) (4 mL, 4 mmol). After stirring for 1 h at rt, the solution was diluted with ethyl acetate (20 mL) and washed with 1 M HCl (3×20 mL). The organic layer was dried over MgSO$_4$, filtered, and the solvent was removed under reduced pressure to afford 185 as a white solid which was used without further purification. ES (+) MS: m/e=371.1 (M+Na)$^+$.

d) The title compound was obtained according to the procedure of Example 70a,d except for using 185 as a reagent instead of Fmoc-(4-aminomethyl)-benzoic acid. ES (+) MS: m/e=448.1 (M+H)$^+$.

EXAMPLE 83

This example describes an exemplary synthesis of the compound below

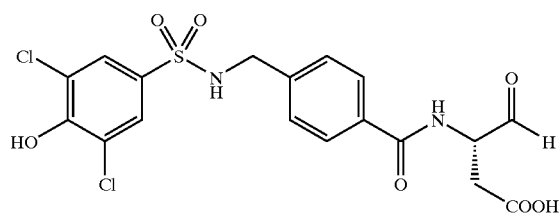

The title compound was prepared according to the procedure of Example 39h–j except for using 3,5-dichloro-4-hydroxybenzenesulfonyl chloride as a reagent instead of 4-oxochroman-6-sulfonyl chloride. ES (+) MS: m/e=476.0 (M+H)$^+$.

EXAMPLE 84

This example describes an exemplary synthesis of the compound below

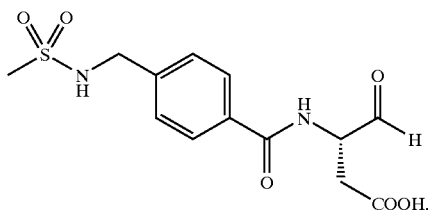

This compound was prepared according to the procedure of Example 70c–d except for using methanesulfonyl chloride as a reagent instead of 4-oxochroman-6-sulfonyl chloride. ES (+) MS: m/e=329.1 (M+H)$^+$.

EXAMPLE 85

This example describes an exemplary synthesis of the compound below

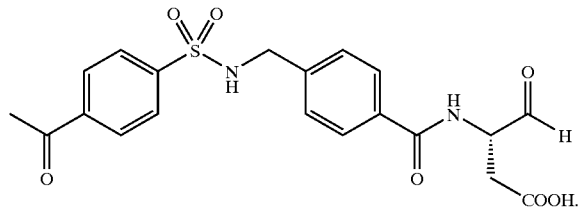

This compound was prepared according to the procedure of Example 70c–d except for using 4-acetylbenzenesulfonyl chloride as a reagent instead of 4-oxochroman-6-sulfonyl chloride. ES (+) MS: m/e=433.0 (M+H)$^+$.

EXAMPLE 86

This example describes an exemplary synthesis of the compound below

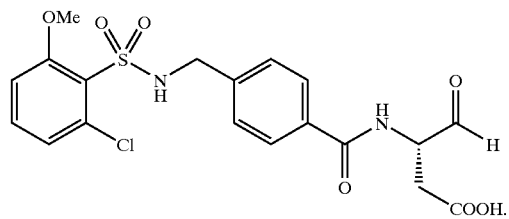

This compound was prepared according to the procedure of Example 70c–d except for using 4-chloro-2-methoxybenzenesulfonyl chloride as a reagent instead of 4-oxochroman-6-sulfonyl chloride. ES (+) MS: m/e=455.0 (M+H)$^+$.

EXAMPLE 87

This example desribes an exemplary synthesis of the compound below

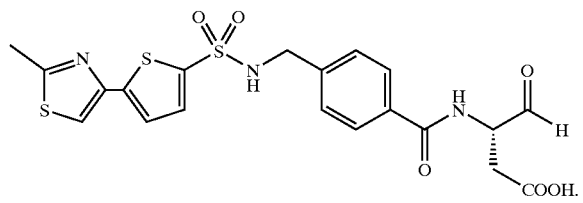

This compound was prepared according to the procedure of Example 70c–d except for using 5-(2-methylthiazol-4-yl)thiophene-2-sulfonyl chloride as a reagent instead of 4-oxochroman-6-sulfonyl chloride. ES (+) MS: m/e=494.1 (M+H)$^+$.

EXAMPLE 88

This example describes an exemplary synthesis of the compound below

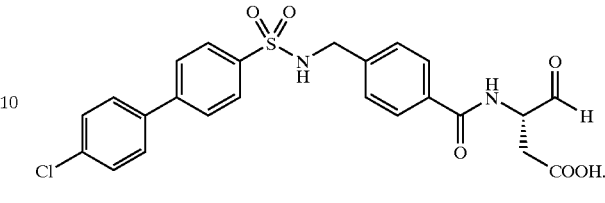

This compound was prepared according to the procedure of Example 70c–d except for using 4-(4-chlorophenyl)phenylsulfonyl chloride for 4-oxochroman-6-sulfonyl chloride. ES (+) MS: m/e=501.0 (M+H)$^+$.

EXAMPLE 89

This example describes an exemplary synthesis of the compound below

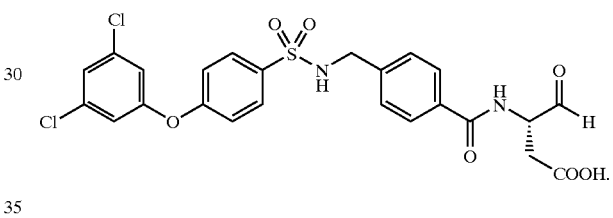

This compound was prepared according to the procedure of Example 70c–d except for using 4-(3,5-dichlorophenoxy)phenylsulfonyl chloride for 4-oxochroman-6-sulfonyl chloride. $^1$H NMR (CD$_3$OD) δ 7.83 (d, 2H), 7.72 (d, 2H), 7.35 (d, 2H), 7.30 (s, 1H), 7.15 (d, 2H), 7.03 (s, 2H), 4.64 (dd, 1H), 4.48 (m, 1H), 4.09 (s, 2H), 2.69 (m, 2H).

EXAMPLE 90

This example describes an exemplary synthesis of the compound below

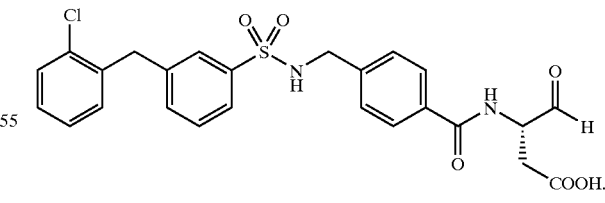

This compound was prepared according to the procedure of Example 70c–d except for using 3-(2-chlorophenoxy)phenylsulfonyl chloride as a reagent, instead of 4-oxochroman-6-sulfonyl chloride. $^1$H NMR (CD$_3$OD, 400 MHz) δ 7.69 (d, 2H), 7.53 (d, 2H), 7.45 (t, 2H), 7.39 (d, 2H), 7.31 (s, 1H), 7.21 (d, 2H), 7.18 (d, 1H), 7.92 (d, 2H), 4.69 (dd, 1H), 4.49 (m, 1H), 2.68 (m, 2H).

EXAMPLE 91

This example describes an exemplary synthesis of the compound below

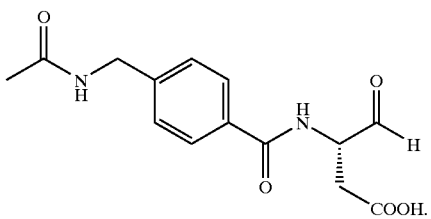

This compound was prepared according to the procedure of Example 70c–d except for using benzenesulfonyl chloride as a reagent instead of 4-oxochroman-6-sulfonyl chloride. ES (+) MS: m/e=391.3 (M+H)$^+$.

EXAMPLE 92

This example describes an exemplary synthesis of the compound below

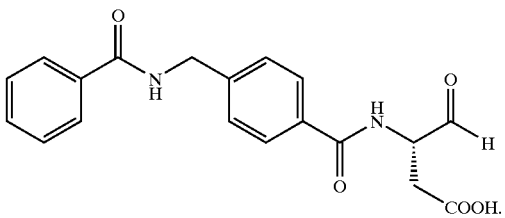

This compound was prepared according to the procedure of Example 70c–d except for using acetic anhydride as a reagent instead of 4-oxochroman-6-sulfonyl chloride. ES (+) MS: m/e=293.3 (M+H)$^+$.

EXAMPLE 93

This example describes an exemplary synthesis of the compound below

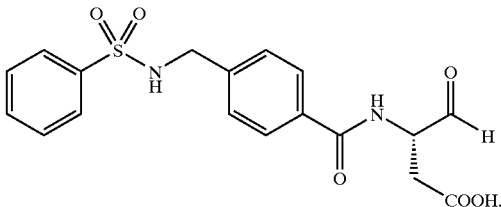

This compound was prepared according to the procedure of Example 70c–d except for using benzoic anhydride as a reagent instead of 4-oxochroman-6-sulfonyl chloride. ES (+) MS: m/e=355.3 (M+H)$^+$.

EXAMPLE 94

This example describes an exemplary synthesis of the compound below

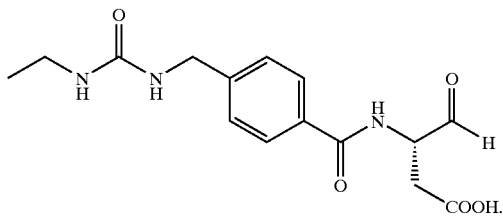

This compound was prepared according to the procedure of Example 70c–d except for using ethyl isocyanate as a reagent instead of 4-oxochroman-6-sulfonyl chloride. ES (+) MS: m/e=322.3 (M+H)$^+$.

EXAMPLE 95

This example describes an exemplary synthesis of the compound below

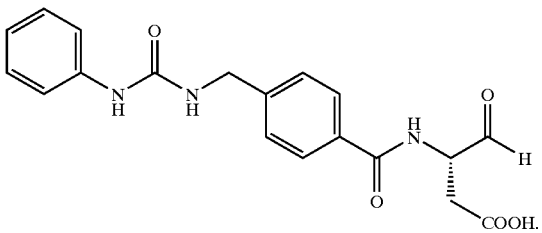

This compound was prepared according to the procedure of Example 70c–d except for using phenyl isocyanate as a reagent instead of 4-oxochroman-6-sulfonyl chloride. ES (+) MS: m/e=370.2 (M+H)$^+$.

EXAMPLE 96

This example describes an exemplary synthesis of the compound below

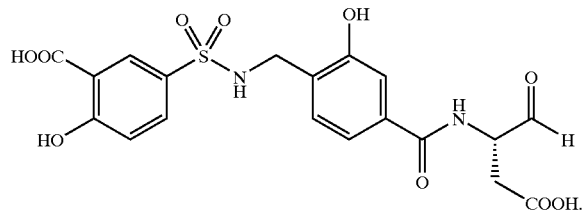

An intermediate, compound 189, was synthesized as described in Scheme 53.

SCHEME 53

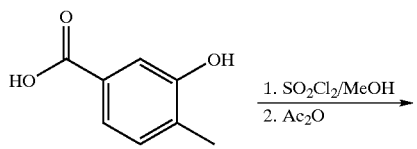

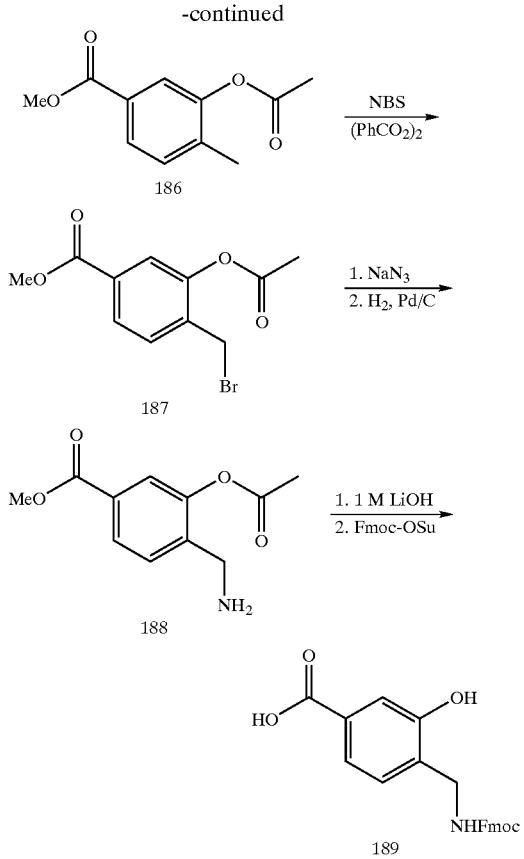

a) To a solution of 3-hydroxy-4-methylbenzoic acid (3.8 g, 19 mmol) in methanol (50 mL) was added thionyl chloride (2.8 mL, 38 mmol) dropwise. After stirring for 8 h at rt, the solvent was removed under reduced pressure. The crude methyl ester was then dissolved in $CH_2Cl_2$ (80 mL) and added diisopropylethyl amine (2.23 mL, 29.2 mmol) followed by acetic anhydride (2.75 mL, 29.2 mmol). After stirring for 12 h at rt, the solution was diluted with $CH_2Cl_2$ (150 mL) and washed with 1 M HCl (3×150 mL). The organic layer was dried over magnesium sulfate, filtered, and the solvent was removed under reduced pressure. The crude product was. purified by column chromatography (10:90 ethyl acetate/hexanes) to afford 186 as a white solid in 93% yield. ES (+) MS: m/e=209.1 (M+H)$^+$.

b) To a solution of 186 (4.7 g, 23 mmol) in benzene (75 mL) was added N-bromosuccinimide (3.6 g, 20 mmol) and benzoyl peroxide (0.545 g, 2.25 mmol). After heating at reflux for 6 h, the solution was diluted with ethyl acetate (150 mL) and washed with 1 M HCl (3×150 mL). The organic layer was dried over $MgSO_4$, filtered, and the solvent was removed under reduced pressure to afford 187 as a yellow oil in 68% yield, which was used without further purification. ES (+) MS: m/e=309.1 (M+Na)$^+$.

c) To a solution of 187 (4.69 g, 10.3 mmol) in DMF (54 mL) was added sodium azide (1.38 g, 21.2 mmol). After heating at 70° C. for 1 h, the solution was diluted with ethyl acetate (50 mL) and washed with 1 M HCl (3×50 mL). The organic layer was dried over $MgSO_4$, filtered, and the solvent was removed under reduced pressure to afford the crude product which was used without further purification. This crude material was then dissolved in ethanol (50 mL) and added palladium on carbon (10% w/w, 0.2 g). After shaking under 20 psi hydrogen for 20 min, the suspension was filtered over Celite and washed with $CH_2Cl_2$. The solvent was removed under reduced pressure to afford 188 as an orange oil which was used without further purification. ES (+) MS: m/e=224.1 (M+H)$^+$.

d) To a solution of 188 (10.3 mmol) in dioxane (50 mL) was added 1 M LiOH (aq) (50 mL, 50 mmol) and stirred for 1 h at rt. The solvent was removed under reduced pressure and the crude residue was purified by reverse-phase preparatory HPLC. The purified compound (0.165 g, 1.00 mmol) was then dissolved in dioxane/water (10 mL, 1:1 v/v) and added saturated $NaHCO_3$ (0.840 g, 5.00 mmol) and Fmoc-OSu (0.370 g, 1.10 mmol). After stirring for 30 min at rt, the solution was diluted with ethyl acetate (20 mL) and washed with 1 M HCl (aq) (3×20 mL). The organic layer was dried over $MgSO_4$, filtered, and the solvent was removed under reduced pressure. The crude product was purified by column chromatography (50:50 ethyl acetate/hexanes to 10:90 methanol/$CH_2Cl_2$) to afford 189 as a white solid in 91% yield. ES (+) MS: m/e=412.0 (M+Na)$^+$.

e) The title compound was prepared according to the procedure of Example 70a,c–d except for using 189 and 5-chlorosulfonyl-2-hydroxybenzoic acid as reagents instead of Fmoc-(4-aminomethyl)-benzoic acid and 4-oxochroman-6-sulfonyl chloride, respectively. ES (+) MS: m/e=466.0 (M+H)$^+$.

EXAMPLE 97

This example describes an exemplary synthesis of the compound below

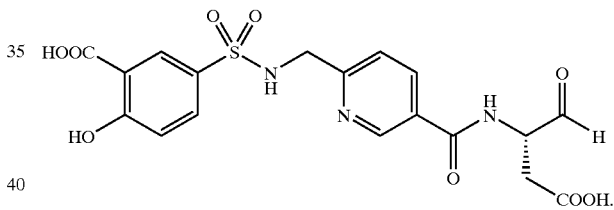

An intermediate, compound 192, was synthesized as described in Scheme 54.

SCHEME 54

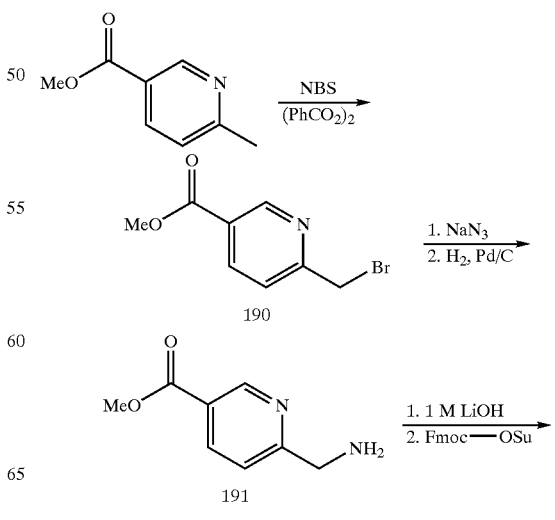

-continued

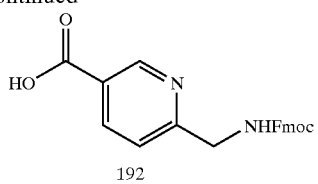

192 a) To a solution of methyl 6-methylnicotinate (5.0 g, 33 mmol) in benzene (110 mL) was added N-bromosuccinimde (5.3 g, 30 mmol), benzoyl peroxide (0.801 g, 3.31 mmol), and acetic acid (2 mL). After heating at reflux for 9 h, the solution was diluted with ethyl acetate (150 mL) and washed with 1 M HCl (aq) (3×150 mL). The organic layer was dried over MgSO$_4$, filtered, and the solvent was removed under reduced pressure. The crude product was purified by column chromatography (10:90 ethyl acetate/hexanes) to afford 190 in 38% yield. $^1$H NMR (CDCl$_3$) δ 9.17 (s, 1H), 8.31 (dd, J=8.1, 2.1 Hz, 1H), 7.53 (d, J=8.1 Hz, 1H), 4.60 (s, 2H), 3.96 (s, 3H). ES (+) MS: m/e=232.1 (M+H)$^+$.

b) To a solution of 190 (2.86 g, 12.8 mmol) in DMF (64 mL) was added sodium azide (1.09 g, 16.7 mmol). After heating at 70° C. for 30 min, the solution was diluted with ethyl acetate (100 mL) and washed with saturated NaHCO$_3$ (3×100 mL). The organic layer was dried over MgSO$_4$, filtered, and the solvent was removed under reduced pressure to afford 191 in 69% yield, which was used without further purification. ES (+) MS: m/e=193.1 (M+H)$^+$.

c) To a solution of 191 (1.66 g, 8.60 mmol) in ethanol (20 mL) was added Pd on carbon (10% w/w, 0.2 g) and stirred under 20 psi hydrogen for 20 min. The suspension was filtered over Celite, washed with CH$_2$Cl$_2$ and the solvent was removed under reduced pressure to afford 192 as an orange oil, which was used without further purification. ES (+) MS: m/e=167.1 (M+H)$^+$.

d) The title compound was prepared according to the procedure of Example 39h–j except for using 192 as a reagent instead of 107. $^1$H NMR (CD$_3$OD) δ 8.94 (s, 1H), 8.45 (d, J=8.3 Hz, 1H), 8.32 (s, 1H), 7.92 (d, J=8.7 Hz, 1H), 7.78 (d, J=2.4 Hz, 1H), 7.0 (m, 1H), 4.70–4.73 (m, 1H), 4.69 (m, 1H), 4.34 (s, 2H), 2.75–2.82 (m, 1H), 2.60–2.68 (m, 1H). ES (+) MS: m/e=452.1 (M+H)$^+$.

EXAMPLE 98

This example describes an exemplary synthesis of the compound below

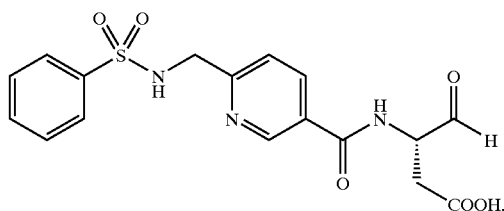

This compound was prepared according to the procedure of Example 39h–j except for using 192 (Example 97) and benzenesulfonyl chloride as reagents instead of 107 and 5-chlorosulfonyl-2-hydroxybenzoic acid, respectively (8.4 mg, 28%). $^1$H NMR (CD$_3$OD) δ 8.90 (s, 1H), 8.30 (dt, J=8.2, 2.1 Hz, 1H), 7.80–7.90 (m, 2H), 7.59–7.67 (m, 2H), 7.5–7.6 (m, 2H), 4.70 (d, J=11.1, 4.2 Hz, 1H), 4.47–4.56 (m, 1H), 4.31 (s, 2H), 2.74–2.84 (m, 1H) 2.60–2.70 (m, 1H).

EXAMPLE 99

This example describes an exemplary synthesis of the compound below

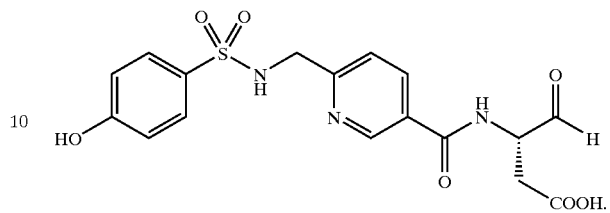

This compound was prepared according to the procedure of Example 39h,i,j except for using 192 (Example 97) and 17 (Example 4) as reagents instead of 107 and 5-chlorosulfonyl-2-hydroxybenzoic acid, respectively (9.3 mg, 30%). $^1$H NMR (CD$_3$OD) δ 8.90 (s, 1H), 8.30 (dt, J=8.3, 2.0 Hz, 1H), 7.67 (m, 2H), 7.60 (d, J=8.2 Hz, 1H), (m, 2H), 4.70 (dd, J=11.1, 4.1 Hz, 1H), 4.46–4.56 (m, 1H), 4.23 (s, 2H), 2.60–2.70 (m, 1H), 2.74–2.84 (m, 2H).

EXAMPLE 100

This example describes an exemplary synthesis of the compound below

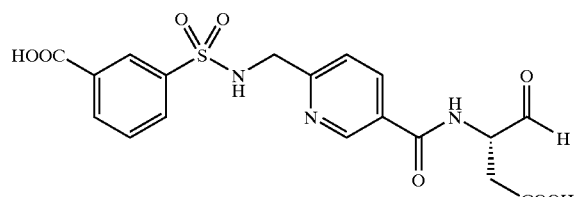

This compound was prepared according to the procedure of Example 39h–j except for using 192 (Example 97) and 3-carboxybenzenesulfonyl chloride as reagents instead of 107 and 5-chlorosulfonyl-2-hydroxybenzoic acid, respectively (3.6 mg, 11%). $^1$H NMR (CD$_3$OD) δ 8.84 (s, 1H), 8.44 (s, 1H), 8.15–8.24 (m, 2H), 8.05 (d, J=7.8 Hz, 1H), 7.65 (t, J=7.9 Hz, 1H), 7.58 (d, J=8.3 Hz, 1H), 4.70 (dd, J=11.3, 4.1 Hz, 1H), 4.47–4.56 (m, 1H), 4.34 (s, 2H), 2.74–2.84 (m, 1H), 2.60–2.70 (m, 1H).

EXAMPLE 101

This example describes an exemplary synthesis of the compound below

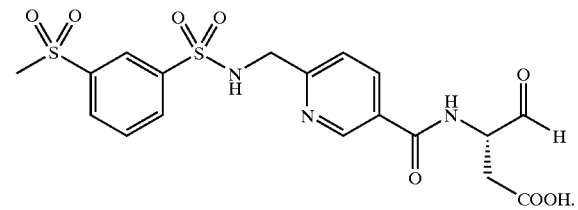

An intermediate, compound 193, was synthesized as described in Scheme 55.

SCHEME 55

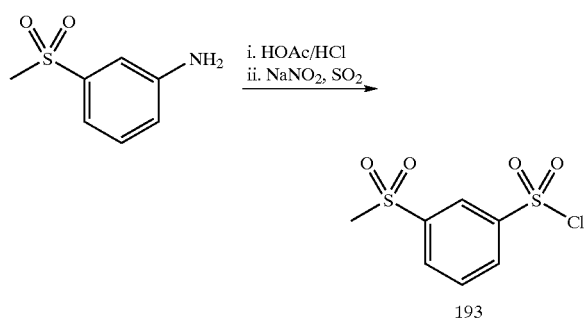

a) N-(3-Amino-phenyl)-methanesulfone (5.0 mmol) was dissolved in concentrated HCl (5 mL) and water (2 mL) followed by the addition of glacial acetic acid (5 mL) to give a yellow solution which was cooled to −10° C. A solution of NaNO$_2$ (6.0 mmol) in water (3 mL) was added dropwise while maintaining the temperature below −5° C. The resulting mixture was stirred at −5° C. for 15 min and added to a cooled (5° C.) solution of glacial acetic acid (10 mL) containing CuCl (1.25 mmol) that was previously saturated with SO$_2$ gas for 45 min. After vigorous gas evolution, the resulting green mixture was stirred for 1–2 h while allowing the reaction to warm to room temperature. Excess SO$_2$ and acetic acid were removed under reduced pressure and 193 was isolated by either precipitation from water or extraction with ethyl ether and washing with 1 N HCl, water, brine and drying.

b) The title compound was prepared according to the procedure of Example 39h–j except for using 192 and 193 as reagents instead of 107 and 5-chlorosulfonyl-2-hydroxybenzoic acid, respectively. (6.7 mg, 19%). $^1$H NMR (CD$_3$OD) δ 8.82 (s, 1H), 8.30 (s, 1H), 8.06–8.20 (m, 3H), 7.80 (t, J=7.9 Hz, 1H), 7.50 (d, J=8.1 Hz, 1H), 4.70 (dd, J=10.6, 4.1 Hz, 1H), 4.46–4.56 (m, 1H), 4.35 (s, 2H), 3.15 (s, 3H), 2.73–2.84 (m, 1H), 2.60–2.70 (m, 1H). ES (+) MS: m/e=470.0 (M+H)$^+$.

EXAMPLE 102

This example describes an exemplary synthesis of the compound below

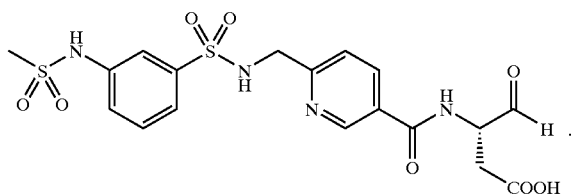

An intermediate, compound 194, was synthesized as described in Scheme 56.

SCHEME 56

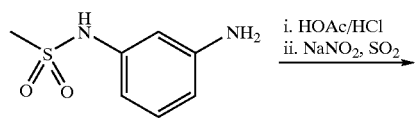

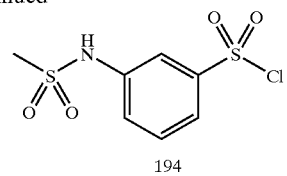

a) The sulfonylchloride 194 was prepared according to the procedure of Example 101a except using N-(3-aminophenyl)-methanesulfonamide as a reagent instead of N-(3-amino-phenyl)-methanesulfone (120 mg, 15%).

b) The title compound was prepared according to the procedure of Example 39h–j except for using 192 and 194 as reagents instead of 107 and 5-chlorosulfonyl-2-hydroxybenzoic acid, respectively. (10.7 mg, 30%). $^1$H NMR (CD$_3$OD) δ 8.86 (s, 2H), 8.20 (dt, J=8.3, 1.7 Hz, 1H), 7.90 (d, J=8.6 Hz, 2H), 7.60 (d, J=8.2 Hz, 1H), 7.30 (d, J=8.4 Hz, 2H), 4.70 (dd, J=11.4, 4.0 Hz, 1H), 4.46–4.56 (m, 1H), 4.30 (s, 2H), 3.00 (s, 3H), 2.74–2.83 (m, 1H), 2.59–2.70 (m, 1H).

EXAMPLE 103

This example describes an exemplary synthesis of the compound below

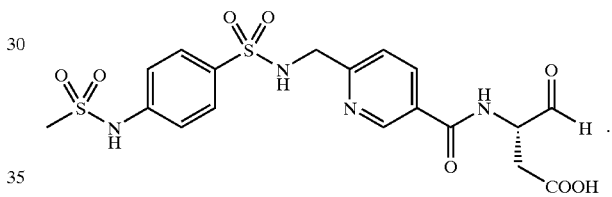

An intermediate, compound 195, was synthesized as described in Scheme 57.

SCHEME 57

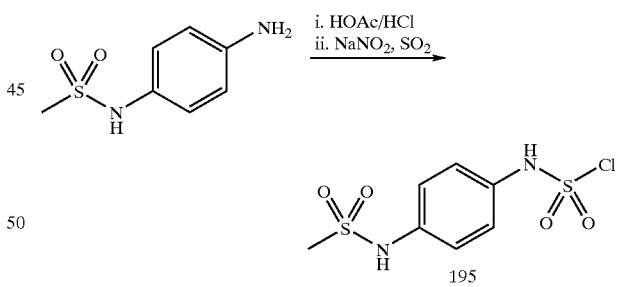

a) Sulfonylchloride 195 was prepared according to the procedure of Example 101a except using N-(4-aminophenyl)-methanesulfonamide as a reagent instead of N-(3-amino-phenyl)-methanesulfone (200 mg, 25%).

b) The title compound was prepared according to the procedure of Example 39h–j except for using 192 (Example 97) and 195 as reagents instead of 107 and 5-chlorosulfonyl-2-hydroxybenzoic acid, respectively. (5.8 mg, 16%). $^1$H NMR (CD$_3$OD) δ 8.89 (s, 1H), 8.30 (dt, J=8.3, 1.8 Hz, 1H), 7.70 (s, 1H), 7.65 (d, J=8.4 Hz, 1H), 7.57 (m, 1H), 7.50 (t, J=7.8 Hz, 1H), 7.41 (m, 1H), 4.70 (dd, J=11.4, 4.1 Hz, 1H), 4.47–4.57 (m, 1H), 4.35 (s, 2H), 2.96 (s, 3H), 2.73–2.83 (m, 1H), 2.59–2.69 (m, 1H).

EXAMPLE 104

This example describes an exemplary synthesis of the compound below

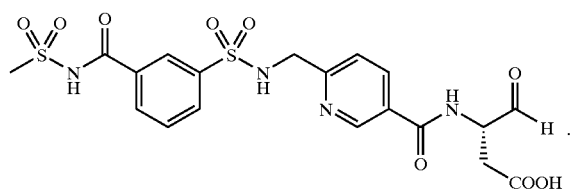

An intermediate, compound 196, was synthesized as described in Scheme 58.

SCHEME 58

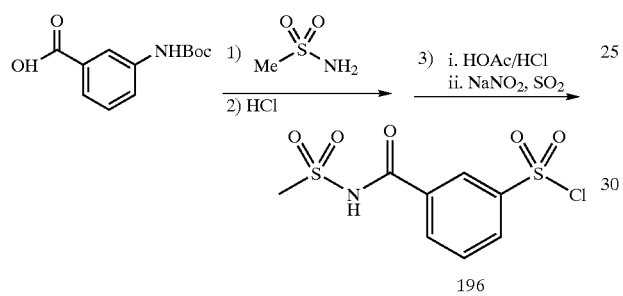

196 a) To a mixture of 3-tert-butoxycarbonylamino-benzoic acid (1.19 g, 5.0 mmol), methanesulfonamide (0.62 g, 6.50 mmol) and N,N-(dimethylamino)-pyridine (DMAP) (0.79 g, 6.50 mmol) in $CH_2Cl_2$ (17 mL), was added EDC (1.25 g, 6.50 mmol). The reaction mixture was stirred at room temperature for 24 h, concentrated in vacuo and purified by flash column chromatography (40% ethyl acetate in hexanes with 1% acetic acid) to afford the acylsulfonamide as a white solid (1.5 g, 95%). $^1$H NMR ($CDCl_3$) δ 7.94 (s, 1H), 7.54 (bd, 2H), 7.40 (m, 1H), 6.80 (bs, 1H), 3.42 (s, 3H), 1.53 (s, 9H). This material was treated with 4 N HCl in dioxane for 2 h at room temperature, concentrated in vacuo and subjected to previously described chlorosulfonylation conditions (Example 101a) to provide 196 as a white solid (376 mg, 63%). $^1$H NMR ($CDCl_3$) δ 8.51 (s, 1H), 8.22 (d, J=7.4 Hz, 1H), 8.16 (d, J=7.5 Hz, 1H), 7.69 (t, J=7.7 Hz, 1H), 3.30 (s, 3H).

b) The title compound was prepared according to the procedure of Example 39h–j except for using 192 (Example 97) and 196 as reagents instead of 107 and 5-chlorosulfonyl-2-hydroxybenzoic acid, respectively. (14.0 mg, 37%). $^1$H NMR ($CD_3OD$) δ 8.90 (s, 1H), 8.30 (m, 2H), 8.00–8.13 (m, 2H), 7.59–7.72 (m, 2H), 4.70 (dd, J=11.4, 4.1 Hz, 1H), 4.47–4.56 (m, 1H), 4.40 (s, 2H), 3.40 (s, 3H), 2.74–2.83 (m, 1H), 2.60–2.70 (m, 1H). ES (+) MS: m/e=513.0 (M+H)$^+$.

EXAMPLE 105

This example describes an exemplary synthesis of the compound below

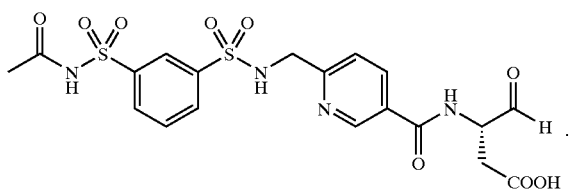

An intermediate, compound 197, was synthesized as described in Scheme 59.

SCHEME 59

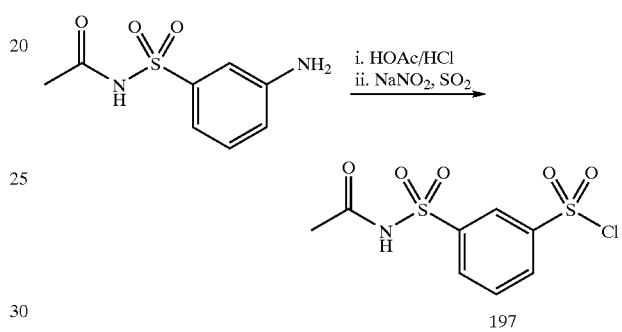

197 a) Sulfonylchloride 197 was prepared according to the procedure of Example 101a except using N-acetyl-3-amino-benzenesulfonamide as a reagent instead of N-(3-aminophenyl)-methanesulfone (458 mg, 51%). $^1$H NMR (DMSO-$d_6$) δ 12.12 (s, 1H), 8.09 (s, 1H), 7.85 (m, 2H), 7.58 (t, J=7.76 Hz, 1H), 1.92 (s, 3H). ES (+) MS: m/e=320.0 (M+Na)$^+$.

b) The title compound was prepared according to the procedure of Example 39h–j except for using 192 (Example 97) and 197 as reagents instead of 107 and 5-chlorosulfonyl-2-hydroxybenzoic acid, respectively. (10.0 mg, 27%). $^1$H NMR ($CD_3OD$) δ 8.80 (s, 1H), 8.40 (m, 1H), 8.25 (dt, J=8.2, 2.0 Hz, 1H), 8.17 (d, J=7.9 Hz, 1H), 8.05 (d, J=7.9 Hz, 1H), 7.72 (t, J=7.9 Hz, 1H), 7.58 (dd, J=8.2, 2.6 Hz, 1H), 4.70 (dd, J=10.1, 4.0 Hz, 1H), 4.47–4.56 (m, 1H), 4.38 (s, 2H), 2.73–2.83 (m, 1H), 2.59–2.69 (m, 1H), 2.0 (s, 3H). ES (+) MS: m/e=513.0 (M+H)$^+$.

EXAMPLE 106

This example describes an exemplary synthesis of the compound below

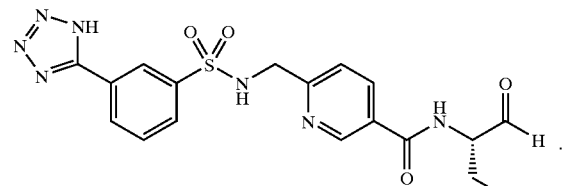

An intermediate, compound 198, was synthesized as described in Scheme 60.

SCHEME 60

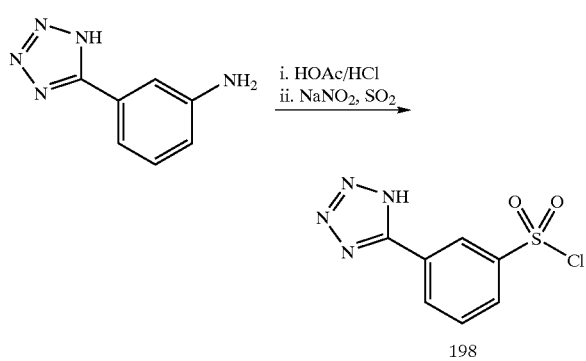

198 a) The sulfonylchloride 198 was prepared according to the procedure of Example 101a except using 3-(1H-tetrazol-5-1)-aniline as a reagent instead of N-(3-amino-phenyl)-methanesulfone (458 mg, 51%).

b) The title compound was prepared according to the procedure of Example 39h–j except for using 192 (Example 97) and 198 as reagents instead of 107 and 5-chlorosulfonyl-2-hydroxybenzoic acid, respectively (8.7 mg, 25%). $^1$H NMR (CD$_3$OD) δ 8.87 (s, 1H), 8.5 (s, 1H), 8.20–8.35 (m, 2H), 8.05 (d, J=7.8 Hz, 1H), 7.77 (t, J=7.8 Hz, 1H), 7.68 (d, J=8.1 Hz, 1H), 4.70 (dd, J=12.0, 4.1 Hz, 1H), 4.45–4.55 (m, 1H), 4.40 (s, 2H), 2.73–2.83 (m, 1H), 2.59–2.69 (m, 1H). ES (+) MS: m/e=460.0 (M+H)$^+$.

EXAMPLE 107

This example describes an exemplary synthesis of the compound below

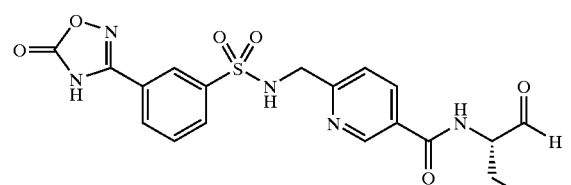

This compound was prepared according to the procedure of Example 39h–j except for using 192 (Example 97) and 23 (Example 7) as reagents instead of 107 and 5-chlorosulfonyl-2-hydroxybenzoic acid, respectively (11 mg, 31%). $^1$H NMR (CD$_3$OD) δ 8.87 (s, 1H), 8.18–8.30 (m, 2H), 7.95–8.10 (m, 2H), 7.73 (t d, J=7.9, 1.7 Hz, 1H), 7.61 (dd, J=8.2, 3.5 Hz, 1H), 4.70 (dd, J=11.4, 4.0 Hz, 1H), 4.47–4.57 (m, 1H), 4.37 (s, 2H), 2.74–2183 (m, 1H), 2.59–2.69 (m, 1H). ES (+) MS: m/e=476.0 (M+H)$^+$.

EXAMPLE 108

This example describes an exemplary synthesis of the compound below

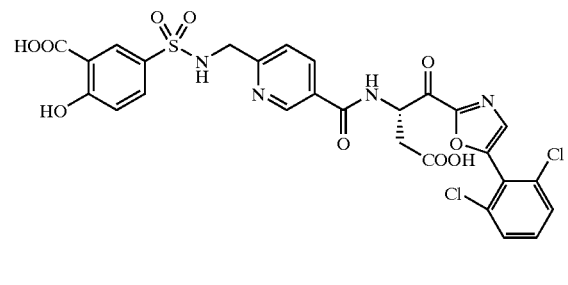

The title compound was prepared according to the procedure of Example 53cc,i,j,k except for using 6-methylnicotinic acid as a reagent instead of 75 (21 mg, 14%). $^1$H NMR (acetone-d6) δ 8.94 (s, 1H), 8.48 (d, J=7.4 Hz, 1H), 8.36 (d, J=2.4 Hz, 1H), 8.20 (d, J=8.0 Hz, 1H), 8.00 (dd, J=9.0, 2.5 Hz, 1H), 7.55–7.80 (m, 5H), 7.52 (d, J=7.5 Hz, 1H), 7.15 (m, 1H), 7.11 (d, J=8.6 Hz, 1H), 5.84 (m, 1H), 4.33 (m, 3H), 3.28 (dd, J=16.7, 5.5 Hz, 1H), 3.13 (dd, J=16.5, 7.3 Hz, 1H). ES (+) MS: m/e=663 (M+H)$^+$.

EXAMPLE 109

This example describes an exemplary synthesis of the compound below

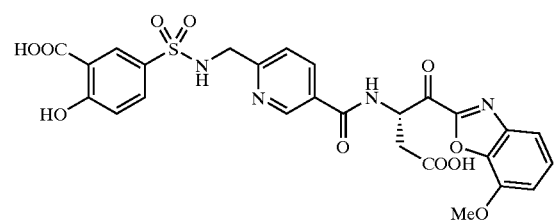

This compound was prepared according to the procedure of Example 53cc,i,j,k except for using 6-methylnicotinic acid and 136 (Example 54) as reagents instead of 75 and 123 respectively. ES (+) MS: m/e=599 (M+H)$^+$.

EXAMPLE 110

This example describes an exemplary synthesis of the compound below

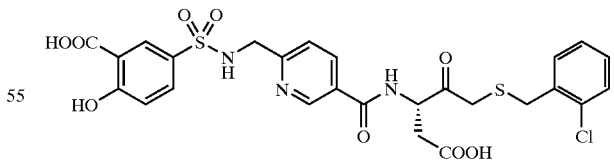

This compound was prepared according to the procedure of Example 1j–l except for using 192 (Example 98) as a reagent instead of 12. (14.4 mg, 33%). $^1$H NMR (CDCl$_3$) δ 8.86 (s, 1H), 8.27 (s, 1H), 8.20 (d, J=6.1 Hz, 1H), 7.88 (d, J=6.9 Hz, 1H), 7/56 (d, J=7.6 Hz, 1H), 7.22–7.40 (m, 4H), 7.03–7.05 (m, 1H), 5.18 (m, 1H), 4.29 (s, 2H), 3.83 (s, 2H), 3.44–3.48 (m, 2H), 2.81–3.02 (m, 2H). ES (+) MS: m/e= 622.0 (M+H)$^+$.

EXAMPLE 111

This example describes an exemplary synthesis of the compound below

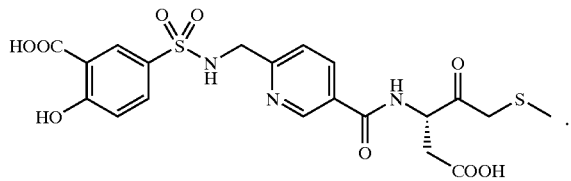

The title compound was prepared according to the procedure of Example 1 except for using methanethiol and 192 (Example 97) as reagents instead of 2-chlorobenzenemethanethiol and 12, respectively. (4.3 mg, 14%). $^1$H NMR (CD$_3$OD) δ 8.88 (d, J=1.7 Hz, 1H), 8.23–8.27 (m, 2H), 7.88 (dd, J=8.8, 2.4 Hz, 1H), 7.59 (d, J=8.2 Hz, 1H), 7.04 (J=8.8 Hz, 1H), 5.20 (t, J=6.4 Hz, 1H), 4.30 (s, 3H), 3.51 (d, J=14.7 Hz, 1H), 3.40 (d, J=14.7 Hz, 1H), 3.03 (dd, J=16.9, 6.2 Hz, 1H), 2.80 (dd, J=16.9, 6.9 Hz, 1H), 2.66 (s, 2H), ES (+) MS: m/e=512 (M+H)$^+$.

EXAMPLE 112

This example describes an exemplary synthesis of the compound below

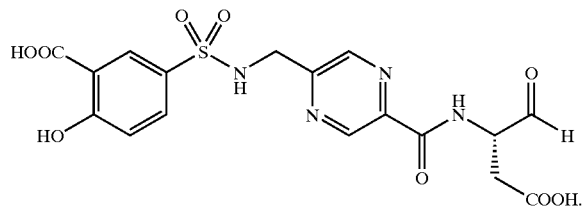

An intermediate, compound 199, was synthesized as described in Scheme 61.

SCHEME 61

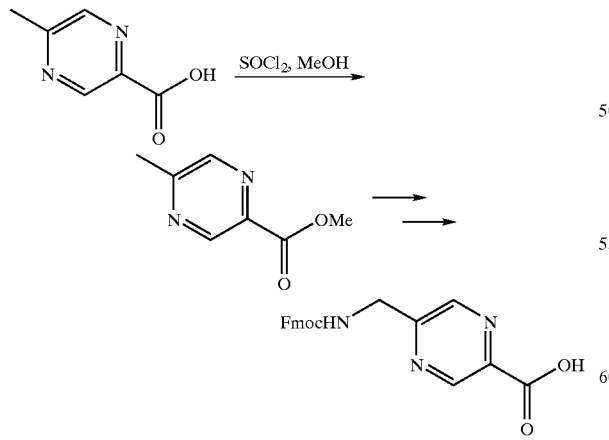

a) To a solution of 2-methylpyrazine-5-carboxylic acid (4.97 g, 35.3 mmol) in methanol (176 mL) was added thionyl chloride (7.7 mL, 106 mmol) dropwise. After stirring for 2 h at rt, the solvent was removed under reduced pressure and the crude 199 was used without further purification. ES (+) MS: m/e=153.1 (M+H)$^+$.

b) This compound was obtained according to the procedure of Example 39a–d except for using 199 as a reagent instead of 107. (3.2 mg, 12%). $^1$H NMR (CDCl$_3$) δ 9.04 (s, 1H), 8.58 (d, J=4.9 Hz, 1H), 8.24 (m, 1H), 7.87 (d, J=8.8 Hz, 1H), 7.02 (d, J=6.9 Hz, 1H), 4.72 (t, J=5.4 Hz, 1H), 4.50 (m, 1H), 4.35 (s, 2H), 2.65–2.74 (m, 2H). ES (+) MS: m/e=453.0 (M+H)$^+$.

EXAMPLE 113

This example describes an exemplary synthesis of the compound below

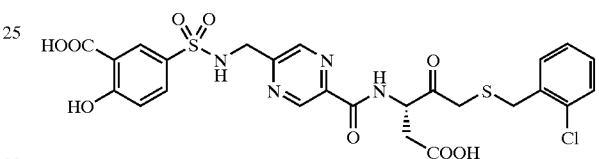

This compound was prepared according to the procedure of Example 1j–l except for using 192 (Example 97) as a reagent instead of 12. (0.8 mg, 2%). $^1$H NMR (CDCl$_3$) δ 7.45 (d, J=1.3 Hz, 1H), 6.99 (s, 1H), 6.63 (d, J=1H), 6.26 (dd, J=8.8, 2.4 Hz, 1H), 5.74–5.80 (m, 2H), 5.60–5.63 (m, 2H), 5.42 (d, J=8.8 Hz, 1H), 3.62–3.63 (m, 1H), 2.78 (s, 2H), 2.22 (s, 2H), 1.89 (d, J=15.4 Hz, 1H), 1.85 (d, J=15.1 Hz, 1H), 1.41 (dd, J=16.8, 5.6 Hz, 1H), 1.33 (dd, J=16.8, 5.5 Hz, 1H). ES (+) MS: m/e=623.0 (M+H)$^+$.

EXAMPLE 114

This example describes an exemplary synthesis of the compound below

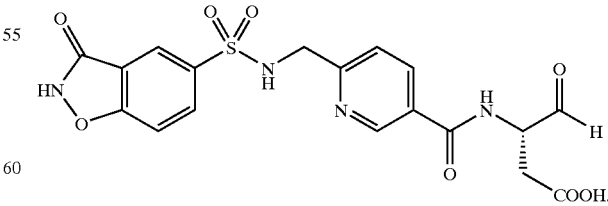

An intermediate, compound 204, was synthesized as described in Scheme 62.

SCHEME 62

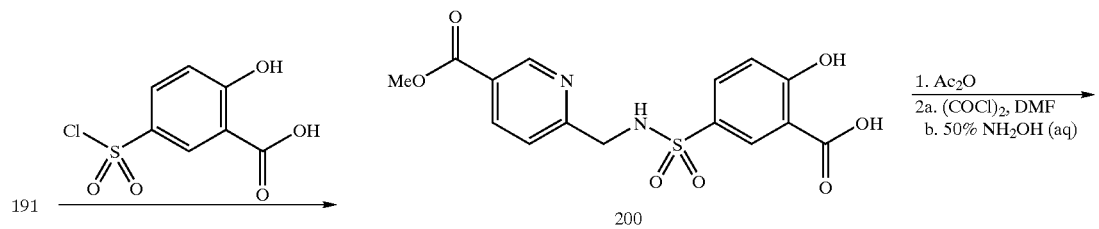

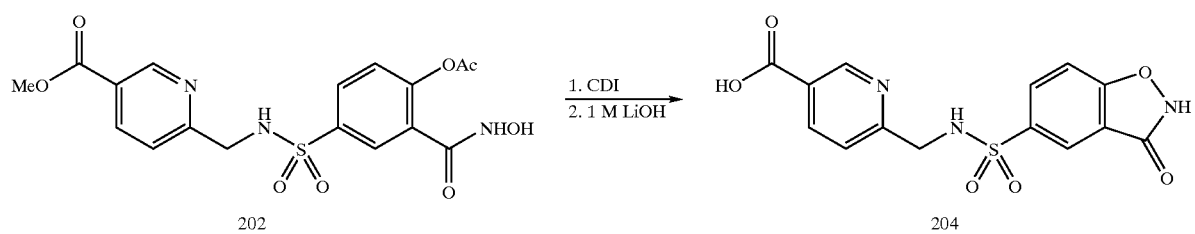

a) To a solution of 191 (1.2 g, 7.2 mmol) in CH$_2$Cl$_2$ (24 mL) was added diisopropylethylamine followed by 5-chlorosulfonyl-2-hydroxybenzoic acid (2.1 g, 7.9 mmol). After stirring for 1 h, the solvent was removed by reduced pressure and the crude 200 was used without further purification. ES (+) MS: m/e=367.1 (M+H)$^+$.

b) To a suspension of 200 (1.0 g, 2.4 mmol) in acetic anhydride (5 mL) was added 2 drops of concentrated sulfuric acid. After stirring for 1 h at rt, the solvent was removed under reduced pressure to afford 201, which was used without further purification. ES (+) MS: m/e=409.0 (M+H)$^+$.

c) To a solution of 201 (2.4 mmol) in ethyl acetate (20 mL) was slowly added oxalyl chloride (1.0 mL, 12 mmol) followed by 2 drops of DMF. After stirring for 1 h at rt, the solvent was removed under reduced pressure. The crude residue was dissolved in THF (20 mL). To this solution was added 50% NH$_2$OH (aq) (0.192 mL, 12.0 mmol) dropwise. After stirring for 1 h, the solvent was removed under reduced pressure and the crude residue was purified by reverse-phase preparatory HPLC to afford 202 as a white solid in 25% yield. ES (+) MS: m/e=382.0 (M+H)$^+$.

d) To a solution of 202 (0.260 g, 0.600 mmol) in THF (6 mL) was added carbonyl diimidazole (0.298 g, 1.80 mmol). After heating at reflux for 1 h, the solution was diluted with ethyl acetate (20 mL) and washed with a saturated NaHCO$_3$ solution (3×20 mL). The organic layer was dried over MgSO$_4$, filtered, and the solvent was removed under reduced pressure to afford 203 as a white solid which was used without further purification. ES (+) MS: m/e=365.1 (M+H)$^+$.

e) To a solution of 203 (0.109 g, 0.300 mmol) in dioxane (1 mL) was added 1 M LiOH (aq) (0.9 mL, 0.9 mmol). After stirring for 1 h at rt, the solution was neutralized with 1 M HCl and the solvent was removed under reduced pressure to afford 204 as a white solid which was used without further purification. ES (+) MS: m/e=351.1 (M+H)$^+$.

f) The title compound was prepared according to the procedure of Example 39h,j except for using 204 as a reagent instead of 107. ES (+) MS: m/e=450.0 (M+H$_2$O )$^+$.

EXAMPLE 115

This example describes an exemplary synthesis of the compound below

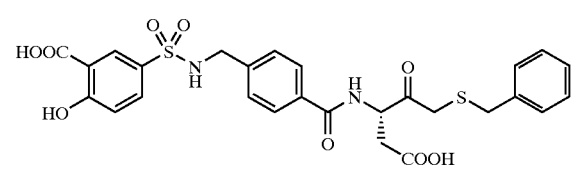

An intermediate, compound 208, was synthesized as described in Scheme 63.

SCHEME 63

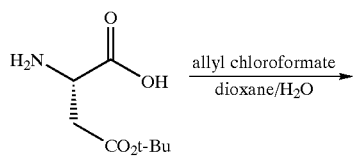

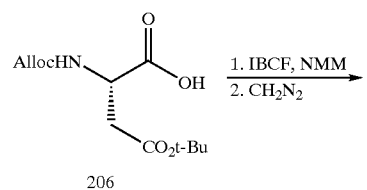

206

-continued

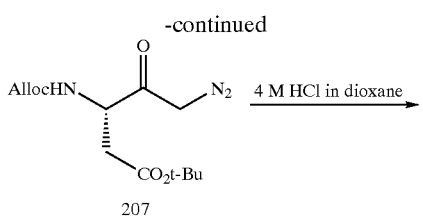

207

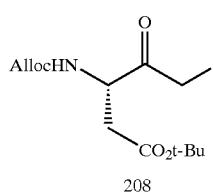

208 a) To a solution of H₂N-Asp(O-tBu)-OH (5.40 g, 28.5 mmol) in dioxane/water (1:2) (75 mL) was added Na₂CO₃ (3.324 g, 31.4 mmol). After the mixture was cooled to 0° C., allyl chloroformate (3.33 mL, 31.4 mmol) was added dropwise by syringe. The mixture was allowed to warm to rt and stirred overnight. The solution was diluted with ethyl acetate (200 mL) and washed with 1 M HCl. The organic layer was dried over MgSO₄ and the solvent was removed under reduced pressure. The resulting residue was azeotroped with toluene (2×) to give 7.31 g (94%) of 206 as a clear oil.

b) 206 (7.31 g, 26.75 mmol) was dissolved in THF (130 mL) and cooled to −20° C. To this solution was added isobutyl chloroformate (3.47 mL, 26.8 mmol) dropwise by syringe. To this solution was added N-methylmorpholine (2.94 mL, 26.8 mmol) dropwise by syringe over 30 min. The resulting suspension was stirred for 40 min and filtered, and the resulting solid was rinsed with THF (2×25 mL). The filtrate was poured into ethereal diazomethane solution in a 500 mL Erlenmeyer flask at 0° C. The deep yellow solution was allowed to stand for 16 h with warming to rt. Nitrogen was bubbled through the deep orange solution for 30 min. The solution was diluted with ether (200 mL) and washed with water (180 mL). The layers were separated and the organic layer washed with saturated NaHCO₃ and then brine. The resulting organic layer was dried over MgSO₄ and the solvent was removed under reduced pressure to give 6.82 g (85%) of 207 as a clear yellow liquid. ¹H NMR (CDCl₃) δ 5.89 (m, 1H), 5.80 (d, 1H), 5.31 (d, 1H), 5.23 (d, 1H), 4.59 (d, 2H), 4.51 (s, 1H), 3.0 (dd, 2H,), 1.43 (s, 9H).

c) 207 (15.16 g, 52.95 mmol) was dissolved in ether (500 mL) and cooled to 0° C. To this solution was added 4 M HCl (13.3 mL, 53 mmol). The solution was stirred for 1.5 h, allowed to warm to rt, then concentrated and purified by column chromatography (30:70 to 40:60 ethyl acetate/hexanes) to give 9.66 g (60%) of 208 as a yellow oil, which solidified after standing. ¹H NMR (CDCl₃) δ 5.89 (m, 1H), 5.80 (d, 1H), 5.31 (d, 1H), 5.26 (d, 1H), 4.65 (m, 1H), 4.63 (d, 2H), 4.41 (q, 2H), 3.0 (dd, 2H), 1.43 (s, 9H).

Another intermediate, compound 211, was synthesized as described in Scheme 64.

SCHEME 64

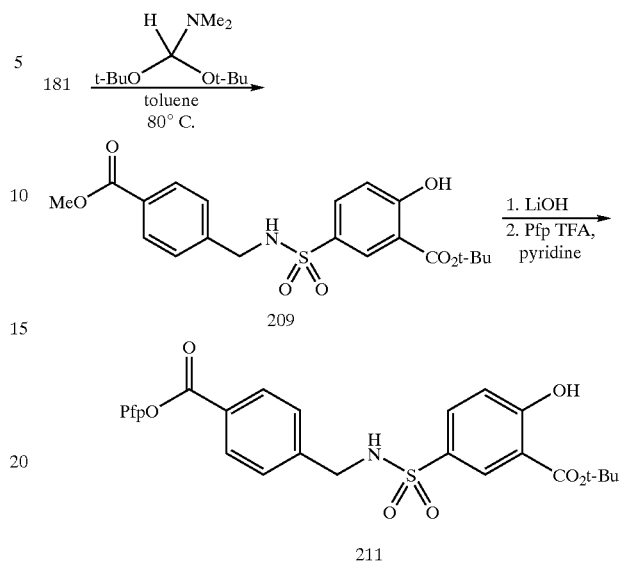

d) 181 (Example 82) (1.627 g, 4.458 mmol) was suspended in toluene (9 mL) and heated to 80° C. To this suspension was added N,N-dimethylformamide di-tert-butylacetal (2.14 mL, 1.81 mmol) dropwise by syringe. The solution was stirred at 80° C. for 30 min until a clear yellow solution resulted, then cooled to rt with stirring and diluted with ether (40 mL). The diluted solution was washed with water, saturated NaHCO₃, and brine. The organic layer was dried over MgSO₄ and concentrated to give 0.879 g (47%) of 209 as a white solid. ES (+) MS m/e=422 (M+H)⁺.

e) LiOH (970 mg, 40.4 mmol) was added to a solution of 209 (1.7 g, 4.04 mmol) in 1:1 THF/water (20 mL), and the reaction was stirred overnight at rt. The cloudy solution was diluted with ethyl acetate (100 mL) and acidified with 1 M HCl. The organic layer was dried over MgSO₄, and the solution was concentrated to give 210 in quantitative yield. ES (+) MS n/e=408(M+H)⁺.

f) 210 (1.164, 2.86 mmol) was dissolved in THF (14 mL). To this solution was added pyridine (254 μL, 3.15 mmol) followed by pentafluorophenyl trifluoroacetate (540 μL, 3.15 mmol). The solution was stirred for 3.5 h and then diluted with ethyl acetate (100 mL). The diluted solution was washed with 1 M HCl, saturated NaHCO₃ and brine. The organic layer was separated, dried over MgSO₄ and concentrated. The oily white solid was purified by column chromatography (40:60 ethyl acetate/hexanes) to give 1.18 g (73%) of 211 as a white solid. ES (+) MS m/c=574 (M+H)⁺.

The titled compound was synthesized as described in Scheme 65.

SCHEME 65

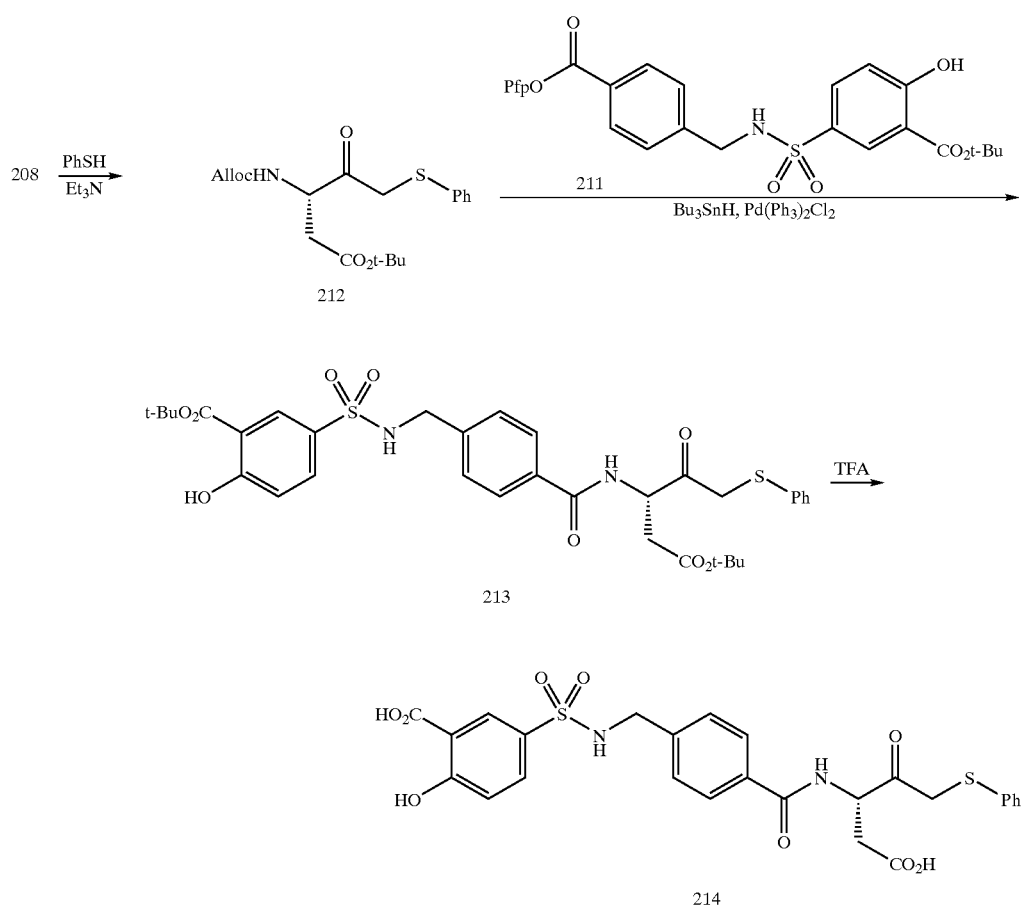

g) To 208 (0.076 g, 0.25 mmol) in 1.25 mL THF was added thiophenol (0.027 g, 0.25 mmol) followed by triethylamine (70 μL, 0.50 mmol). The solution was stirred for 2 h and then concentrated to give 212 as an off white solid. ES (+) MS m/e=380 (M+H)$^+$.

h) To a 0.2 M DMF (729 μL) solution of 212 (0.055 g, 0.146 mmol) was added 211 (0.084 g, 0.146 mmol). Pd(PPh$_3$)$_2$Cl$_2$ (0.019 g, 0.026 mmol) was added, and then Bu$_3$SnH (196 μL, 0.73 mmol) was added dropwise by syringe. Gas evolution was observed during the addition. The reaction mixture was stirred at rt overnight and then diluted with methanol (5 mL). The deep clear orange solution was partitioned with hexanes (5 mL) and the hexane layer decanted and discarded. This was repeated twice. The resulting methanol/DMF solution was removed under reduced pressure and the residue was purified by column chromatography (40:60 ethyl acetate/hexanes) to give 0.039 g (39%) of 213 as an orange residue.

i) 213 (0.0398 g, 0.058 mmol) was dissolved in 1:1 TFA/methylene chloride (1 mL) and stirred at rt for 45 min. The solvent was removed under reduced pressure and purified by reverse-phase HPLC to afford 214 as a white solid. ES (+) MS m/e=573 (M+H)$^+$.

EXAMPLE 116

This example describes an exemplary synthesis of the compound below

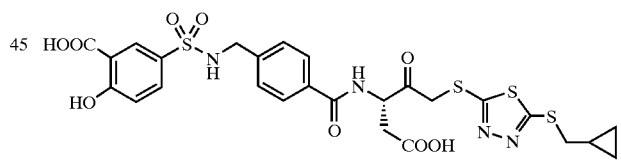

This compound was prepared according to the procedure of Example 115g–i except for using 5-(cyclopropylmethyl) thio-1,3,4-thiadiazole-2-thiol as a reagent instead of thiophenol. ES (+) MS m/e=667 (M+H)$^+$.

EXAMPLE 117

This example describes an exemplary synthesis of the compound below

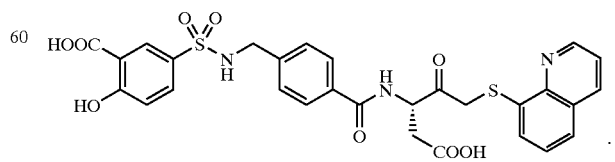

This compound was prepared according to the procedure of Example 115g–i except for using 8-mercaptoquinoline hydrochloride as a reagent instead of thiophenol. ES (+) MS m/e 624 (M+H)⁺.

EXAMPLE 118

This example describes an exemplary synthesis of the compound below

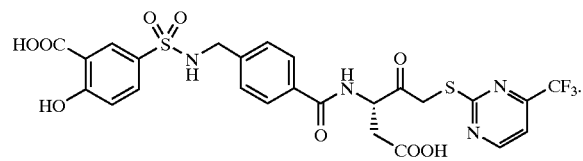

This compound was prepared according to the procedure of Example 115g–i except for using 4-(trifluoromethyl)pyrimidine-2-thiol as a reagent instead of thiophenol. ES (+) MS m/e=643 (M+H)⁺.

EXAMPLE 119

This example describes an exemplary synthesis of the compound below

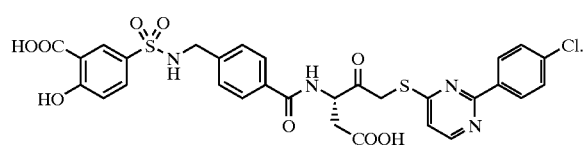

This compound was prepared according to the procedure of Example 115g–i except for using 4-(4-chlorophenyl)pyrimidine-2-thiol as a reagent instead of thiophenol. ES (+) MS m/e 685 (M+H)⁺.

EXAMPLE 120

This example describes an exemplary synthesis of the compound below

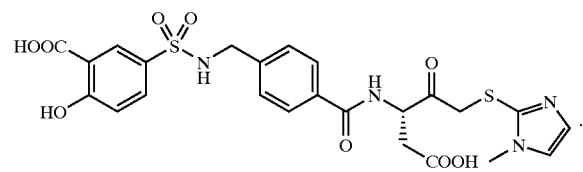

This compound was prepared according to the procedure of Example 115g–i except for using 2-mercapto-1-methylimidazole as a reagent instead of thiophenol. ES (+) MS m/e=577 (M+H)⁺.

EXAMPLE 121

This example describes an exemplary synthesis of the compound below

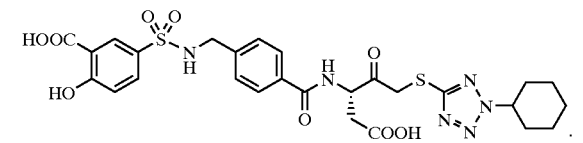

This compound was prepared according to the procedure of Example 115g–i except for using 1-cyclohexyl-5-mercapto-1H-tetrazole as a reagent instead of thiophenol. ES (+) MS m/e=647 (M+H)⁺.

EXAMPLE 122

This example describes an exemplary synthesis of the compound below

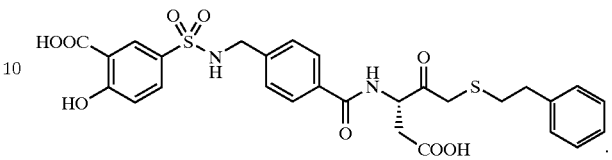

This compound was prepared according to the procedure of Example 115g–i except for using phenylethyl mercaptan as a reagent instead of thiophenol. ES (+) MS m/e=601 (M+H)⁺.

EXAMPLE 123

This example describes an exemplary synthesis of the compound below

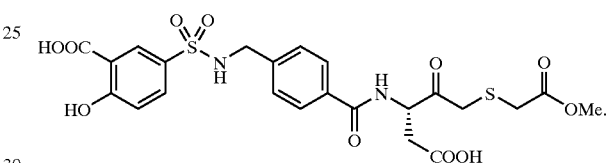

This compound was prepared according to the procedure of Example 115g–i except for using methyl thioglycolate as a reagent instead, of thiophenol. ES (+) MS m/e=569 (M+H)⁺.

EXAMPLE 124

This example describes an exemplary synthesis of the compound below

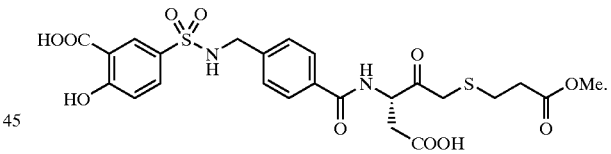

This compound was prepared according to the procedure of Example 115g–i except for using methyl 3-mercaptopropionate as a reagent instead of thiophenol. ES (+) MS m/e=583 (M+H)⁺.

EXAMPLE 125

This example describes an exemplary synthesis of the compound below

This compound was prepared according to the procedure of Example 115g–i except for using cyclohexanethiol as a reagent instead of thiophenol. ES (+) MS m/e=579 (M+1)⁺.

EXAMPLE 126

This example describes an exemplary synthesis of the compound below

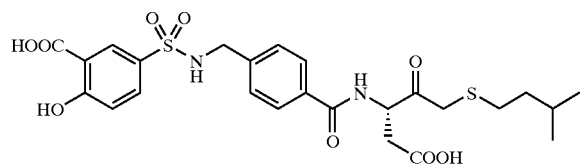

This compound was prepared according to the procedure of Example 115g–i except for using 3-methyl-1-butanethiol as a reagent instead of thiophenol. ES (+) MS m/e=567 (M+H)$^+$.

EXAMPLE 127

This example describes an exemplary synthesis of the compound below

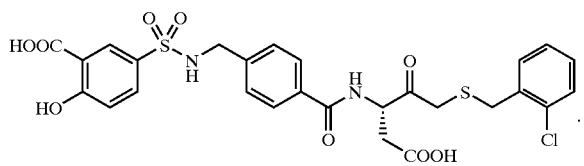

This compound was prepared according to the procedure of Example 115g–i except for using 3-chlorobenzyl mercaptan as a reagent instead of thiophenol. ES (+) MS m/e=621 (M+H)$^+$.

EXAMPLE 128

This example describes an exemplary synthesis of the compound below

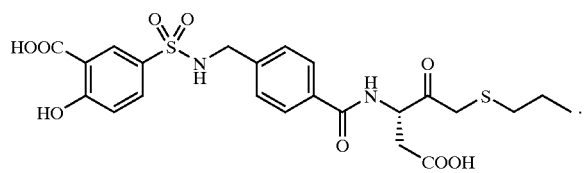

This compound was prepared according to the procedure of Example 115g–i except for using 1-propanethiol as a reagent instead of thiophenol. ES (+) MS m/e=539 (M+H)$^+$.

EXAMPLE 129

This example describes an exemplary synthesis of the compound below

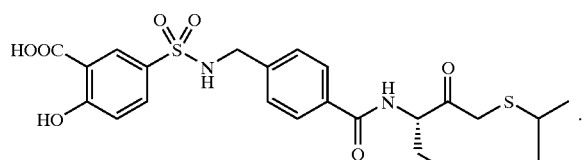

This compound was prepared according to the procedure of Example 115g–i except for using 2-propanethiol as a reagent instead of thiophenol. ES (+) MS m/e=539 (M+H)$^+$.

EXAMPLE 130

This example describes an exemplary synthesis of the compound below

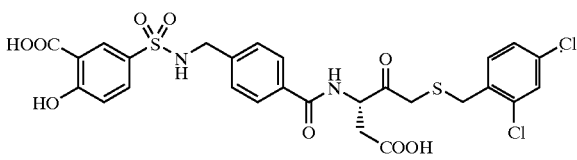

This compound was prepared according to the procedure of Example 115g–i except for using 2,4-dichlorobenzyl mercaptan as a reagent instead of thiophenol. ES (+) MS m/e=656 (M+H)$^+$.

EXAMPLE 131

This example describes an exemplary synthesis of the compound below

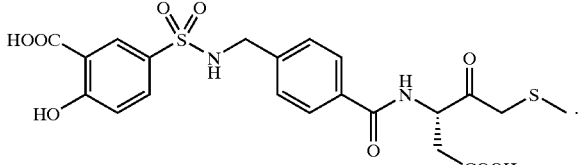

This compound was prepared according to the procedure of Example 115g–i except for using sodium methanethiolate as a reagent instead of thiophenol. ES (+) MS m/e=511 (M+H)$^+$.

EXAMPLE 132

This example describes an exemplary synthesis of the compound below

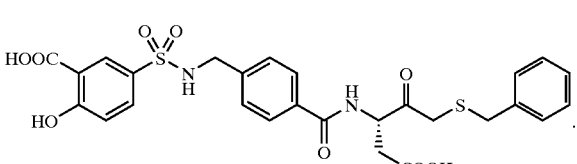

This compound was prepared according to the procedure of Example 115g–i except for using benzyl mercaptan as a reagent instead of thiophenol. ES (+) MS m/e=587 (M+H)$^+$.

EXAMPLE 133

This example describes an exemplary synthesis of the compound below

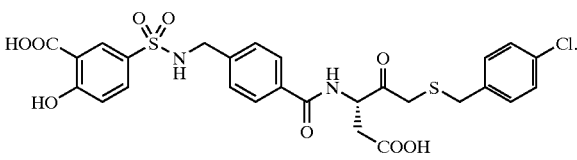

This compound was prepared according to the procedure of Example 115g–i except for using 4-chlorobenzyl mercaptan as a reagent instead of thiophenol. ES (+) MS m/e=621 (M+H)$^+$.

EXAMPLE 134

This example describes an exemplary synthesis of the compound below

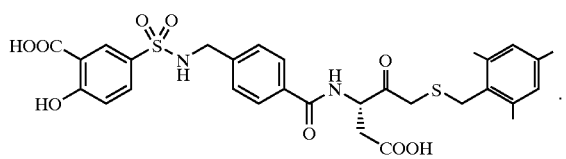

This compound was prepared according to the procedure of Example 115g–i except for using 2,4,6-trimethylbenzyl mercaptan as a reagent instead of thiophenol. ES (+) MS m/e=629 (M+H)$^+$.

EXAMPLE 135

This example describes an exemplary synthesis of the compound below

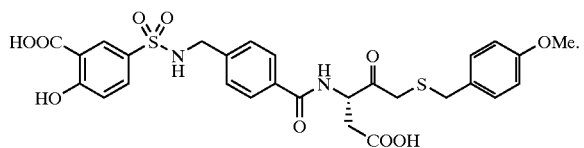

This compound was prepared according to the procedure of Example 115g–i except for using 4-methoxybenzyl mercaptan as a reagent instead of thiophenol. ES (+) MS m/e=617 (M+H)$^+$.

EXAMPLE 136

This example describes an exemplary synthesis of the compound below

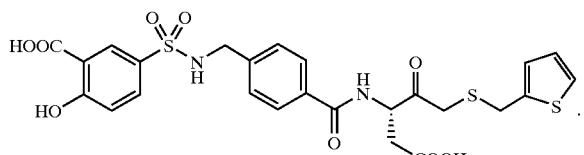

This compound was prepared according to the procedure of Example 115g–i except for using (2-thienyl)methyl mercaptan as a reagent instead of thiophenol. ES (+) MS m/e=593 (M+H)$^+$.

EXAMPLE 137

This example describes an exemplary synthesis of the compound below

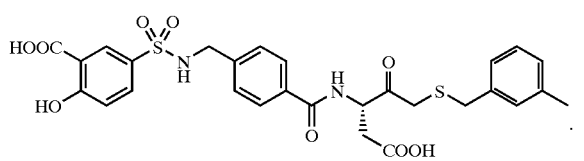

This compound was prepared according to the procedure of Example 115g–i except for using 3-methylbenzyl mercaptan as a reagent instead of thiophenol. ES (+) MS m/e=601 (M+H)$^+$.

EXAMPLE 138

This example describes an exemplary synthesis of the compound below

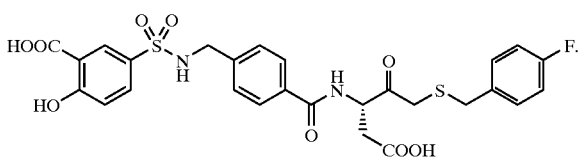

This compound was prepared according to the procedure of Example 115g–i except for using 4-fluorobenzyl mercaptan as a reagent instead of thiophenol. ES (+) MS m/e=605 (M+H)$^+$.

EXAMPLE 139

This example describes an exemplary synthesis of the compound below

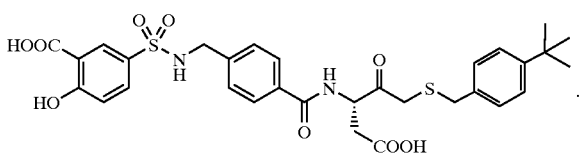

This compound was prepared according to the procedure of Example 115g–i except for using 4-(tert-butyl)benzyl mercaptan as a reagent instead of thiophenol. ES (+) MS m/e=643 (M+H)$^+$.

EXAMPLE 140

This example describes an exemplary synthesis of the compound below

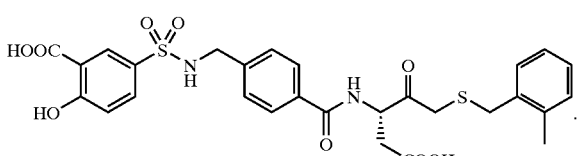

This compound was prepared according to the procedure of Example 115g–i except for using 2-methylbenzyl mercaptan as a reagent instead of thiophenol. ES (+) MS m/e=601 (M+H)$^+$.

EXAMPLE 141

This example describes an exemplary synthesis of the compound below

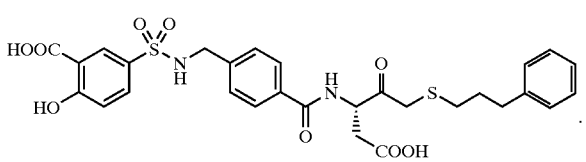

This compound was prepared according to the procedure of Example 115g–i except for using 3-phenyl-1-propanethiol as a reagent instead of thiophenol. ES (+) MS m/e=615 (M+H)$^+$.

EXAMPLE 142

This example describes an exemplary synthesis of the compound below

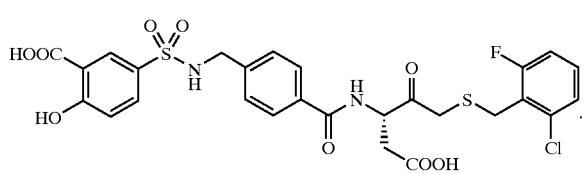

This compound was prepared according to the procedure of Example 115g–i except for using 2-chloro-6-fluorobenzyl mercaptan as a reagent instead of thiophenol. ES (+) MS m/e=640 (M+H)$^+$.

EXAMPLE 143

This example describes an exemplary synthesis of the compound below

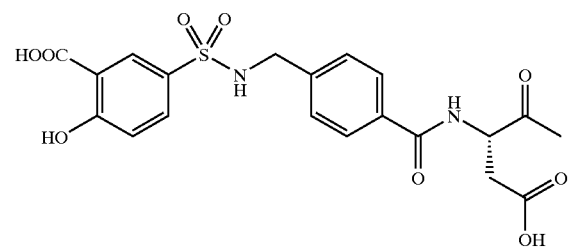

An intermediate, compound 215, was synthesized as described in Scheme 65.

SCHEME 66

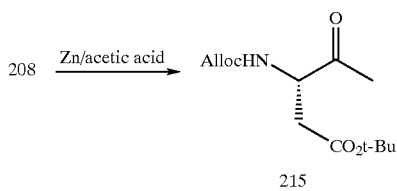

a) To 208 (Example 115) (0.153 g, 0.50 mmol) in acetic acid (6 mL) was added zinc dust (0.330 g, 5.0 mmol). The suspension was stirred overnight at rt. The mixture was filtered and concentrated to give 215.

b) The title compound was prepared according to the procedure of Example 115h–i except for using 215 as a reagent instead of 212. ES (+) MS m/e=(M+H)$^+$.

EXAMPLE 144

This example describes the synthesis of the compound below

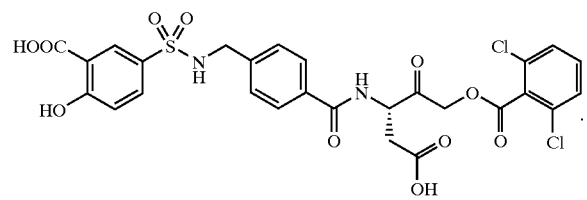

An intermediate, compound 216, was synthesized as described in Scheme 67.

SCHEME 67

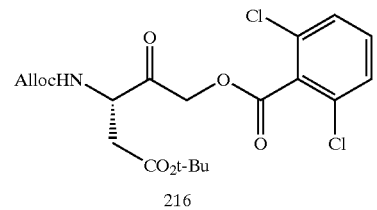

a) To 208 (Example 116) (0.306 g, 1.0 mmol) in DMF (5 mL) was added potassium fluoride (0.116 g, 2.0 mmol) followed by 2,6-dichlorobenzoic acid (0.191 g, 1.0 mmol). The mixture was heated to 60° C. and stirred for 16 h. The solvent was removed under reduced pressure to afford a crude residue which was diluted with ethyl acetate (10 mL). The solution was washed with 1 M HCl, saturated NaHCO$_3$, and brine. The organic layer was dried over MgSO$_4$, the solvent removed, and the residue purified by column chromatography (20:80 ethyl acetate/hexanes) to afford 216.

b) The title compound was prepared according to the procedure of Example 115h–i except for using 216 as a reagent instead of 212. ES (+) MS m/e=654 (M+H)$^+$.

EXAMPLE 145

This example describes the synthesis of the compound below

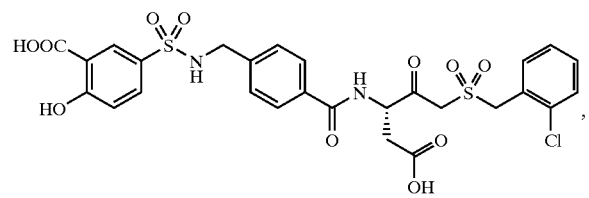

which was made according to Scheme 68.

SCHEME 68

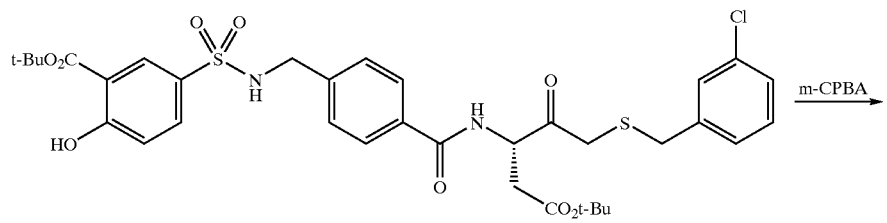

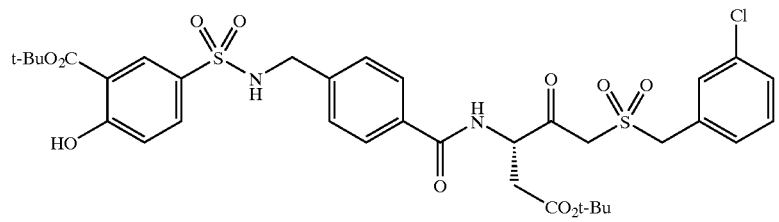
217

To the protected version of compound of Example 127 (0.100 g, 0.136 mmol) was added 3-chloroperoxybenzoic acid (94 mg, 0.544 mmol) in $CH_2Cl_2$ (1 mL) at 0° C. The reaction was stirred for 1 h, warming to rt. The mixture was diluted with ethyl acetate and washed with saturated $NaHCO_3$. The layers were separated and the organic layer dried over $MgSO_4$. The residue was treated with TFA/$CH_2Cl_2$ (1:1) for 30 min, then concentrated and purified by reverse-phase HPLC to afford 217 which was deprotected to yield the titled compound. ES (+) MS m/e=654 (M+H)$^+$.

EXAMPLE 146

This example describes an exemplary synthesis of the compound below

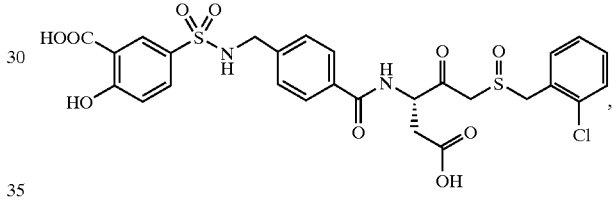

which was made according to Scheme 69.

SCHEME 69

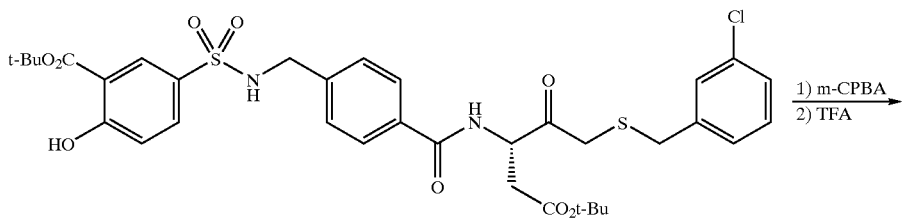

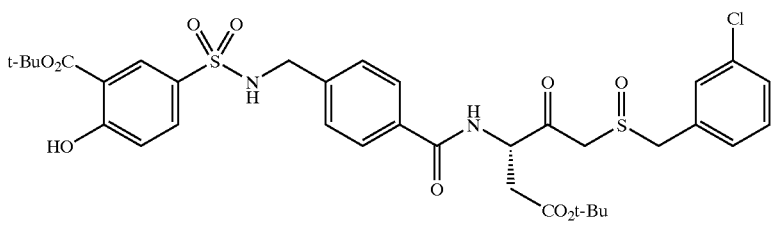
218

To the protected version of the compound of Example 127 (0.100 g, 0.136 mmol) was added 3-chloroperoxybenzoic acid (0.047 g, 0.272 mmol) in CH$_2$Cl$_2$ (1 mL) at 0° C. The reaction was stirred for 1 h and allowed to warm to rt. The mixture was diluted with ethyl acetate and washed with saturated NaHCO$_3$. The organic layer was dried over MgSO$_4$ and the solvent was removed under reduced pressure. The residue was then treated with TFA/CH$_2$Cl$_2$ (1:1) for 30 min, the solvent was removed under reduced pressure and the crude residue was purified by reverse-phase HPLC to afford 218 which was deprotected to yield the titled compound. ES (+) MS m/e=638 (M+H)$^+$.

EXAMPLE 147

This example describes an exemplary synthesis of the compound below

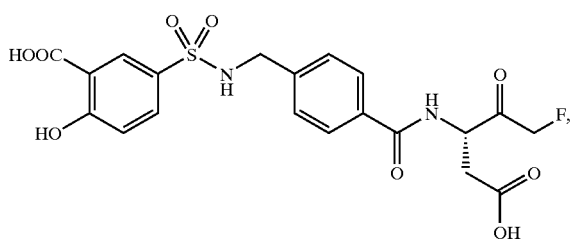

which was made according to Scheme 70.

219 was prepared according to published procedures (*Tetrahedron Lett.*, 1994, 9693). To 219 (0.313 g, 1.52 mmol) in DMF (8 mL) was added 209 (0.619 g, 1.52 mmol), followed by 1-hydroxybenzotriazole (0.243 g, 1.8 mmol) and 1-(3-dimethylaminopropyl)-3-ethylcarbodiimide hydrochloride (0.345 g, 1.8 mmol). The mixture was stirred overnight at rt. The solvent was removed under reduced pressure, and the residue diluted with ethyl acetate (12 mL). The resulting solution was washed with 1 M HCl (2×7 mL) and the organic layer separated and dried over MgSO$_4$. The dried solution was concentrated and the residue purified by column chromatography (40:60 ethyl acetate/hexanes to 5:95 methanol/CHCl$_3$) to give 220 as an off-white solid (0.143 g, 16%).

220 was treated with hydroxyiodinane oxide (IBX) (7 eq) in dimethylsulfoxide (2 mL) and stirred at rt for 3 days. The reaction mixture was purified by reverse-phase HPLC to yield the fluoromethyl ketone. This intermediate was treated with 1:1 TFA/CH$_2$Cl$_2$ for 30 min at rt and concentrated to give 221 as a white solid. ES (+) MS m/e=483 (M+H)$^+$.

EXAMPLE 148

This example describes an exemplary synthesis of the compound below

SCHEME 70

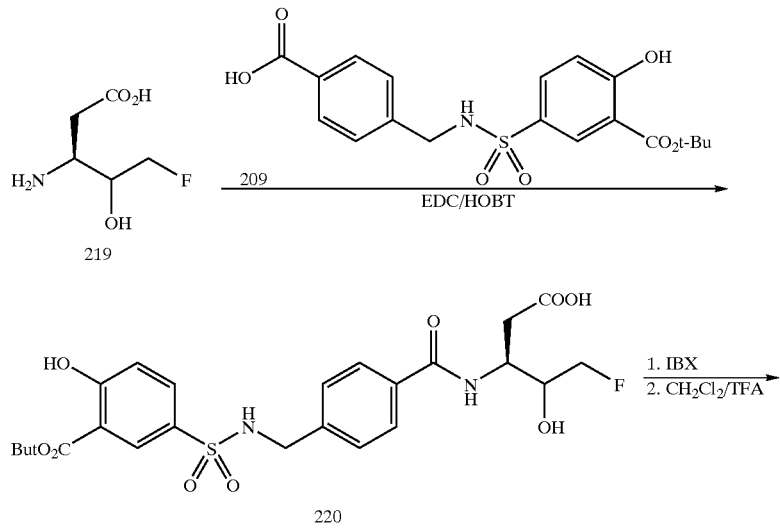

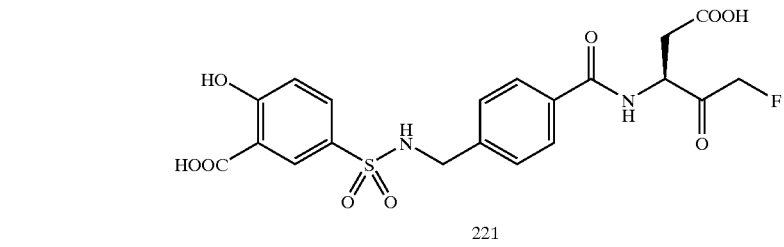

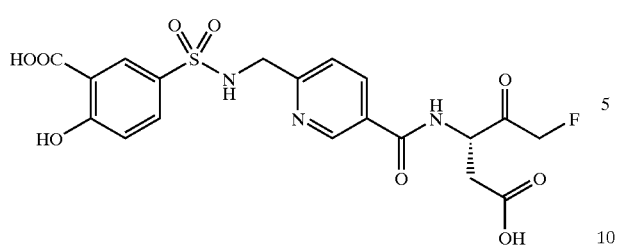

This compound was prepared according to the procedure of Example 147 except for using the 3-pyridyl analog of 209 (described in Example 115) as a reagent instead of 209. ES (+) MS m/e=484 (M+H)+.

EXAMPLE 149

This example describes an exemplary synthesis of the compound below

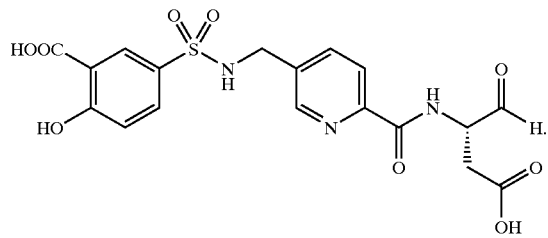

An intermediate, compound 224, was synthesized as described in Scheme 71.

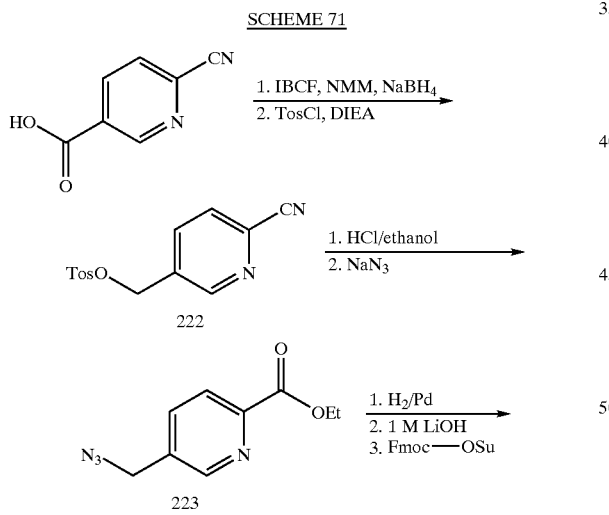

a) Commercially available 6-cyanonicotinic acid is treated with isobutyl chloroformate, N-methylmorpholine and sodium borohydride to provide the benzyl alcohol. Treatment with toluenesulfonyl chloride and diisopropylethylamine provides 222. Hydrolysis with HCl in ethanol followed by treatment with sodium azide gives 223. Hydrogenation, saponification with LiOH, and treatment with Fmoc-OSu affords 224.

b) The title compound is prepared according to the procedure of Example 39h–j except for using 224 as a reagent instead of 107.

EXAMPLE 150

This example describes an exemplary synthesis of the compound below

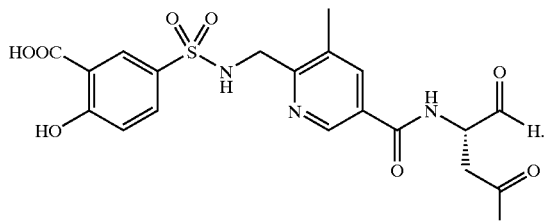

An intermediate, compound 230, was synthesized as described in Scheme 72.

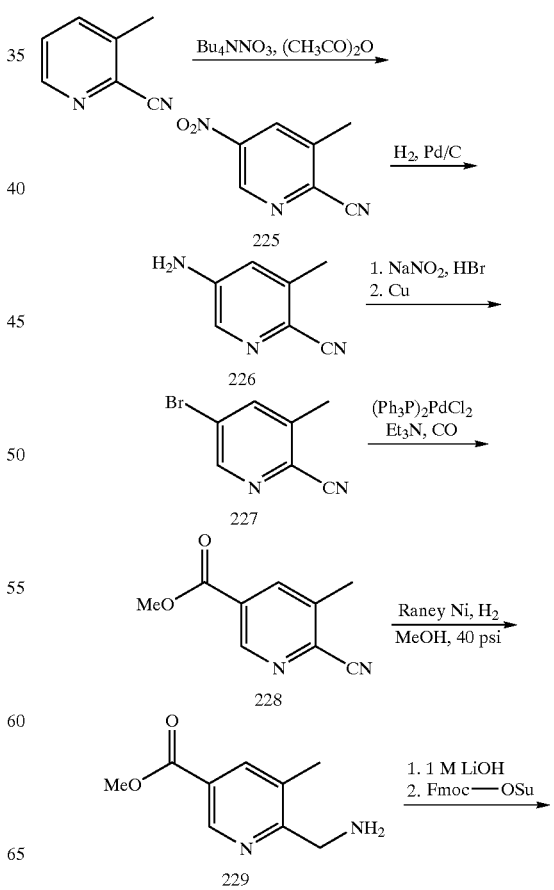

SCHEME 73

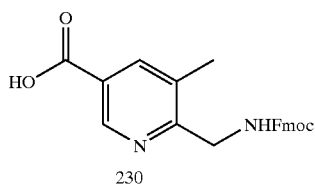
230

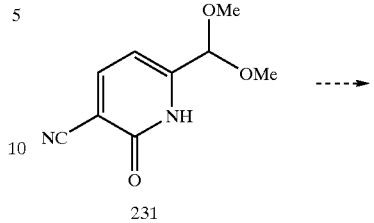
231 a) 225 was prepared according to a published procedure (Webber et al 1996, *J. Med. Chem.* 39:5072). To a solution of 225 (0.930 g, 5.700 mmol) in methanol/ethyl acetate (20:1, 20 mL) was added palladium on carbon (10% w/w) at rt. The reaction was treated with a hydrogen balloon and stirred for 4 h. The reaction mixture was filtered over Celite and the solvent was removed under reduced pressure. Purification by column chromatography (50:50 ethyl acetate/hexanes) afforded 0.630 g (83%) of 226. ES (+) MS m/e= 134 (M+H)$^+$.

b) 227 was synthesized according to a published procedure (Webber et al. 1996, *J. Med. Chem.* 39:5072). Purification by column chromatography (30:70 ethyl acetate/hexanes) afforded 227.

c) A mixture of 227 (0.562 g, 5.075 mmol) and bis(triphenylphosphine)palladium chloride(0.579 g, 0.825 mmol) in anhydrous DMF (6 mL), anhydrous methanol (12 mmol) and triethylamine (1.5 mL, 10.76 mmol) was heated at 60° C. for 20.5 h under a carbon monoxide atmosphere. The resulting solution was filtrated through Celite and the solvent removed under reduced pressure. Purification by column chromatography (30:70 ethyl acetate/hexanes) afforded 0.203 g (40%) of 228. ES (+) MS m/e=177 (M+H)$^+$.

d) Hydrogenation of 228 with Raney nickel and catalytic HCl affords 229. Hydrolysis followed by treatment with Fmoc-OSu provides 230 e) The title compound is prepared according to the procedure of Example 39h–j except for using 230 as a reagent instead of 109.

EXAMPLE 151

This example describes an exemplary synthesis of the compound below

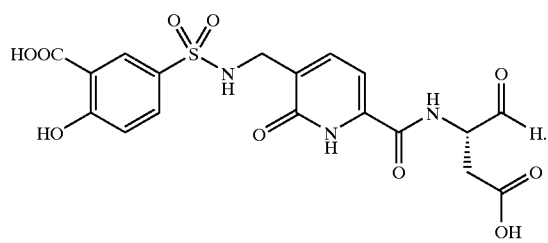

An intermediate, compound 235, was synthesized as described in Scheme 73.

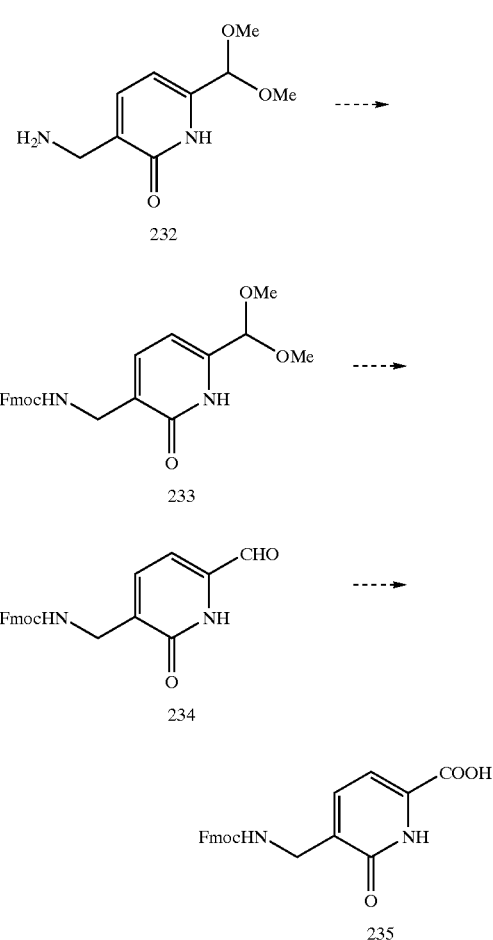

a) 231 (prepared by the procedure of Sanchez et al. 1994, *J. Heterocycl. Chem.* 31:297) is converted to 232 by catalytic hydrogenation over a PtO$_2$ catalyst (Fife et al. 2000, *J. Org. Chem.* 65:3579). Treatment with Fmoc-OSu followed by HCl/water provides 233, which is converted to 235 according to a published procedure for Jones oxidation.

b) The title compound is prepared according to the procedure of Example 39h–j except for using 235 as a reagent instead of 109.

EXAMPLE 152

This example describes an exemplary synthesis of the compound below

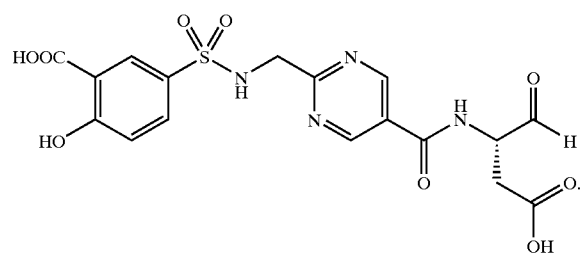

An intermediate, compound 238, was synthesized as described in Scheme 74.

SCHEME 74

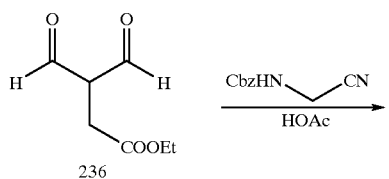

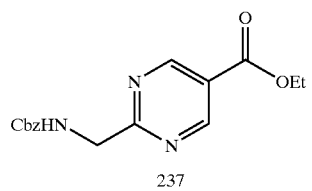

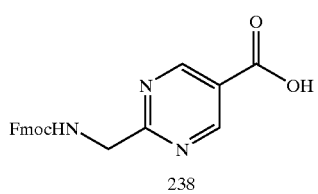

a) 238 was prepared according to literature procedure (Toru et al. *Synthesis* 1986, 400–402; Ueda et al. *Chem. Pharm. Bull.* 1968, 16, 2355–2361; Dyer et al. *J. Am. Chem. Soc.* 1934, 56, 222–225; Isoda et al. *Chem. Pharm. Bull.* 1980, 28, 1408).

b) The title compound is prepared according to the procedure of Example 39h–j except for using 238 as a reagent instead of 107. (1.1 mg, 4%). $^1$H NMR (CDCl$_3$) δ 8.95 (d, J=2.8 Hz, 2H), 8.25 (dd, J=6.3, 2.4 Hz, 1H), 7.84–7.88 (m, 1H), 6.99 (dd, J=8.8, 3.9 Hz, 1H), 4.68 (dd, J=9.1, 4.0 Hz, 1H), 4.47–4.51 (m, 1H), 4.40 (d, J=1.7 Hz, 2H), 2.62–2.77 (m, 2H). ES (+) MS m/e=453.0 (M+H)$^+$.

EXAMPLE 153

This example describes an exemplary synthesis of the compound below

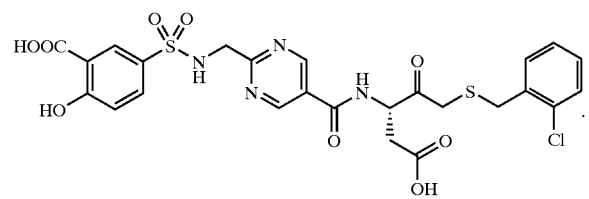

This compound is prepared according to the procedure of Example 1j–l except for using 238 as a reagent instead of 12. (6.4 mg, 17%). ES (+) MS m/e=623.0 (M+H)$^+$.

EXAMPLE 154

This example describes an exemplary synthesis of the compound below

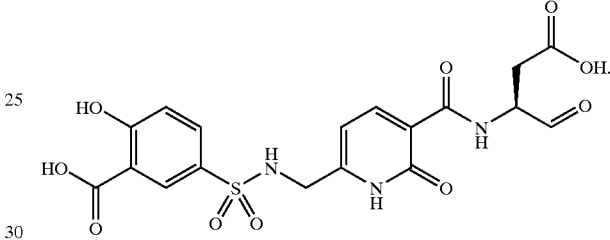

An intermediate, compound 238, was synthesized as described in Scheme 75.

SCHEME 75

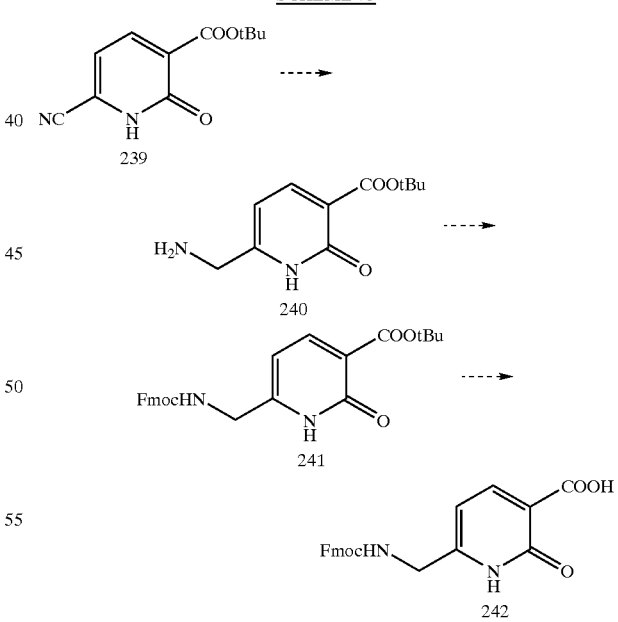

a) 239 (prepared by the procedure of Showalter et al. 1981, *J. Heterocycl. Chem.* 18:1609) is converted into 241 by the same method as described above for the preparation of 238 from 237. Treatment of 241 with TFA provides 242.

b) The title compound is prepared according to the procedure of Example 39h–j except for using 242 as a reagent instead of Fmoc-(4-aminomethyl)-benzoic acid.

EXAMPLE 155

This example describes a fluorescence intensity assay that were used to test compounds of this invention against the activity of human recombinant caspase-3 (Alexis Biochemicals 201-038-C005) and caspase-1 (BioMol PA SE-168). Caspase-3 was also expressed and purified (Rotunda et al. 1996, *Nature Struct. Biol.* 3(7):619–625 (1996); Garcia-Calvo et al. 1998, *J. Biol. Chem.* 273(49):32608–32613; Garcia-Calvo et al. 1999, *Cell Death and Differentiation* 6:362–369) for use in this and other assays. The coumarin-based fluorogenic substrates incorporated the optimal tetrapeptide recognition motifs for their respective enzymes, Ac-Asp-Glu-Val-Asp-AFC (Alexis Biochemicals 260-032-M005) for Caspase-3 and Ac-Trp-Glu-His-Asp-AFC (Enzyme Systems Products AFC-156) for Caspase-1. The enzyme (final concentrations used: caspase-3, 2.5 nM; caspase-1, 2.8 nM) was added to test compounds dissolved in DMSO and pre-incubated at room temperature for 30 minutes. The addition of the substrate (final concentrations used: Ac-Asp-Glu-Val-Asp-AFC, 15 µM; Ac-Trp-Glu-His-Asp-AFC, 4 µM) initiated the reaction and brought the final reaction volume to 50 µL. Assays were carried out in a 1× buffer solution of 25 mM Hepes, pH 7.4, 0.1% CHAPS, 50 mM KCl, and 5 mM β-mercaptoethanol in 96-well flat-bottom, black, polystyrene plates (Corning Costar 3915). Caspase activity was monitored through cleavage of AFC using a Molecular Devices' Microplate Spectrofluorometer Gemini XS with an excitation wavelength of 365 nm and an emission wavelength of 495 nm. Kinetic data was collected over a 20-minute assay run at room temperature. $IC_{50}$ values were calculated through direct fits of the data to a 4-parameter fit curve using the computer application SOFTmax PRO.

EXAMPLE 156

This example describes the cell-based assays that were used to test the compounds of the invention. Jurkat cells (Clone E6-1, ATCC) were grown in RPMI 1640 media (ATCC) supplemented with 10% fetal bovine serum, 10 mM Hepes, 1 mM sodium pyruvate, 4.5 g/L glucose, and 1.5 g/L sodium bicarbonate, at 37° C. with 5% $CO_2$. Apoptosis was initiated by the addition of SuperFas ligand (Alexis Biochemicals, 522-020-C005) to a final concentration of about 1–5 ng/mL. In some cases, staurosporine (Alexis Biochemicals, 380-014-M001) was also used to induce apoptosis at a final concentration of about 400 nM. The progression of apoptosis was followed using one or more of four different assays:

(1) PARP Cleavage

PARP cleavage was followed using a ELISA based assay. Assays were carried out in 24-well, flat bottomed plates (Becton Dickinson, Falcon 3047). 1 mL of cells (about 1.5×10⁶ cells) was added to each well, and incubated with a compound of this invention diluted in DMSO for various times before induction of apoptosis, which was allowed to proceed for about 3 hours. After centrifugation, the cell pellet was freeze-thawed, and lysed with 20 mM Hepes, 2 mM EDTA, 250 mM NaCl, and 0.1% NP-40, pH 7.5. The lysate was centrifuged at 14,000× g for 10 minutes to remove insoluble debris. Capture antibody (Purified Mouse Anti-Human PARP (Pharmingen, 66401A) was added to individual wells of a 96 well Nunc Immuno Plate (Maxisorb surface) at a concentration of 1 µg/mL in $Na_2CO_3$, pH 9.0 and nutated for 2 hours at room temperature or overnight at 4° C. After washing, the wells were blocked with 10 mM Tris-HCl, 150 mM $NaCl_2$, 0.05% Tween-20, pH 8.0 containing 5% dried milk for 30 minutes to 2 hours. Cell lysate, about 20 µg diluted in Superblock Blocking Buffer in PBS (Pierce, 37515) to a final volume of 100 µL, was added to each well and incubated for 30–60 minutes. After washing, detection antibody (Cleaved PARP (D214) Antibody (Human specific), Cell Signaling 9541L) diluted 1:1,000 in Superblock Blocking Buffer was added and incubated for about 30 minutes. Following washing, the final antibody (HRP-Goat Anti-Rabbit IgG (H+L), Zymed 62-6120) was diluted 1:2,000 in Superblock Blocking Buffer and incubated with the samples for 30 minutes. The plate was then washed, and the level of cleaved PARP was detected using the ImmunoPure TMB Substrate Kit (Pierce, 34021), followed by reading the plate in a Benchmark Biorad Microplate Reader at 450 nm.

(2) Annexin V Surface Expression

Cells were plated and treated as described above. Staining of cells was carried out using the Annexin V-FITZ Apoptosis Detection Kit (Pharmingen, 65874X), following the manufacturer's directions. Detection was carried out using a FACSCalibur System (Becton-Dickinson).

(3) DNA Fragmentation

Cells were plated and treated as described above. Cell analysis was carried out using the APO-BRDU Kit (Pharmingen, 6576KK), and detected using the FACSCalibur System (Becton-Dickinson).

(4) Cell Viability

Cells were plated at a density of about 2.5×10⁴ cells/mL in 96 well plates (Coming Costar 3595), preincubated with compounds of this invention diluted in DMSO for 1–2 hours before initiation of apoptosis. After about 16–24 hours, cell viability was assayed using the In Vitro Toxicology Assay Kit, MTT Based (Sigma, TOX01), following the recommended directions.

What is claimed is:

1. A compound having the structure (I):

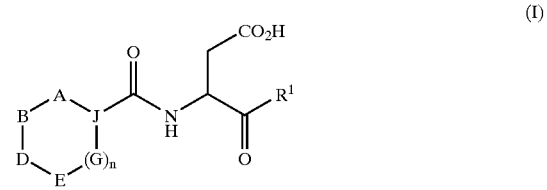

and pharmaceutically acceptable derivatives thereof, wherein $R^1$ is H, an aliphatic, heteroaliphatic, aryl, heteroaryl, alkylaryl, alkylheteroaryl, heteroalkylaryl, or heteroalkylheteroaryl moiety;

n is 0 or 1;

A is $CR^A$, $C(R^A)_2$, C=O, S, $NR^A$, $N(R^A)_2$, or O;

B is $CR^B$, $C(R^B)_2$, C=O, S, $NR^B$, $N(R^B)_2$, or O;

D is $CR^D$, $C(R^D)_2$, C=O, S, $NR^D$, $N(R^D)_2$, or O;

E is $CR^E$, $C(R^E)_2$, C=O, S, $NR^E$, $N(R^E)_2$, or O;

G is $CR^G$, $C(R^G)_2$, C=O, S, $NR^G$, $N(R^G)_2$, or O;

J is $CR^J$;

each of A—B, B—D, D—E, E—G, G—J and A—J are connected by a single or double bond as valency and stability permits;

each occurrence of $R^A$, $R^B$, $R^D$, $R^E$, $R^G$ and $R^J$ is independently hydrogen, halogen, $-OR^2$, $-N(R^2)_2$, $-SR^2$, $-CN$, $-COOR^2$, $-COR^2$, $-CON(R^2)_2$, $-SOR^2$, $-SO_2R^2$, $-SO_2N(R^2)_2$, $-NR^2SO_2R^2$, —O(C=O)N(R²)₂, —NR²(C=O)N(R²)₂, —NR² (C=S)N(R²)₂, —NR²SO₂N(R²)₂, or an aliphatic, heteroaliphatic, aryl, heteroaryl, alkylaryl, alkylheteroaryl, heteroalkylaryl, or heteroalkylheteroaryl moiety optionally independently substituted with one or more occurrences of R², wherein each occurrence of R² is independently hydrogen, halogen, —OR³, —N(R³)₂, —SR³, —CN, —COOR³, —COR³, —CON(R³)₂, —SOR³, —SO₂R³, —SO₂N(R³)₂, —NR³SO₂R³, —O(C=O)N(R³)₂, —NR³(C=O)N (R³)₂, —NR³(C=S)N(R³)₂, —NR³SO₂N(R³)₂, or an aliphatic, heteroaliphatic, aryl, heteroaryl, alkylaryl, alkylheteroaryl, heteroalkylaryl, or heteroalkylheteroaryl moiety;

wherein each occurrence of R³ is independently hydrogen, or an aliphatic, heteroaliphatic, aryl, heteroaryl, alkylaryl, alkylheteroaryl, heteroalkylaryl, or heteroalkylheteroaryl moiety, and wherein at least one of $R^B$ or $R^D$ comprises —SR², —SOR², —SO₂R², —SO₂N(R²)₂, —NR²SO₂R², —N(R²)₂, —(C=O)N(R²)₂, —NR²(C=O)R², —O(C=O)N(R²)₂, —NR²(C=O)N(R²)₂, —NR² (C=S)N(R²)₂, —NR²SO₂N(R²)₂, or is an alkyl or heteroalkyl group substituted with one or more occurrences of R², wherein R² is —SR³, —SOR³, —SO₂R³, —SO₂N(R³)₂, —NR³SO₂R³, —N(R³)₂, —(C=O)N (R³)₂, —NR³(C=O)R³, —O(C=O)N(R³)₂, —NR³ (C=O)N(R³)₂, —NR³(C=S)N(R³)₂, —NR³SO₂N (R³)₂, wherein R³ is an aliphatic, heteroaliphatic, aryl, heteroaryl, alkylaryl, alkylheteroaryl, heteroalkylaryl, or heteroalkylheteroaryl moiety, whereby each of the foregoing aliphatic, heteroaliphatic, alkyl and heteroalkyl moieties may be independently substituted or unsubstituted, cyclic or acyclic, linear or branched, and each of the foregoing aryl, heteroaryl, alkylaryl, alkylheteroaryl, heteroalkylaryl and heteroalkylheteroaryl moieties may be independently substituted or unsubstituted.

2. The compound of claim 1, having one or more of the following limitations:

a) R¹ is not CH₂X, if X is F or Cl;

b) if

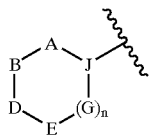

represents pyridyl, then $R^D$ is —SR², —SOR², —SO₂R², —SO₂N(R²)₂, —NR²SO₂R², —NR²SO₂N (R²)₂; or $R^D$ is an alkyl or heteroalkyl group substituted with one or more occurrences of R², wherein R² is —SR³, —SOR³, —SO₂R³, —SO₂N(R³)₂, —NR³SO₂R³, —N(R³)₂, —(C=O)N(R³)₂, —NR³ (C=O)R³, —O(C=O)N(R³)₂, —NR³(C=O)N(R³)₂, —NR³(C=S)N(R³)₂, —NR³SO₂N(R³)₂, wherein each occurrence of R³ is independently an aliphatic, heteroaliphatic, aryl, heteroaryl, alkylaryl, alkylheteroaryl, heteroalkylaryl, or heteroalkylheteroaryl moiety; or c) if

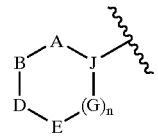

represents isoxazole, then $R^B$ or $R^D$ is not a group —CR^XR^YNHR³, wherein at least one of $R^X$ or $R^Y$ is a group other than hydrogen.

3. The compound of claim 1, wherein

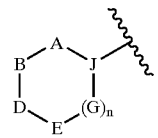

is an aryl or heteroaryl moiety.

4. The compound of claim 1, wherein

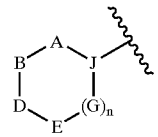

is an aryl or heteroaryl moiety having one of the structures:

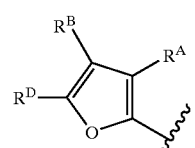 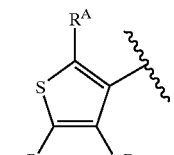

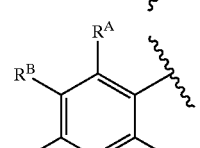 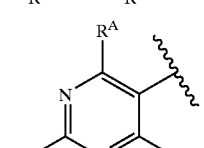

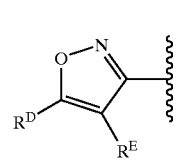 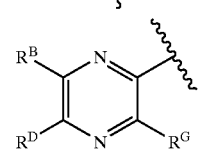

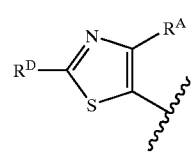

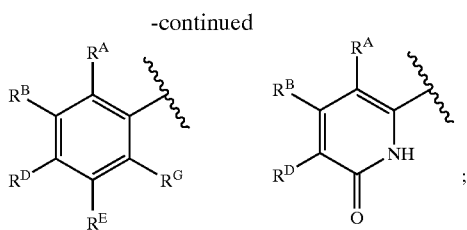

wherein $R^A$—$R^G$ are as defined in claim 1.

5. The compound of claim 1, wherein the compound has the structure:

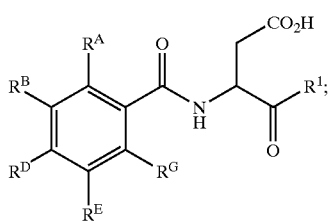

wherein $R^1$ and $R^A$—$R^G$ are as defined in claim 1.

6. The compound of claim 1, wherein the compound has the structure:

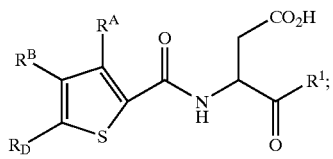

wherein $R^1$, $R^A$, $R^B$ and $R^D$ are as defined in claim 1.

7. The compound of any one of claims 4–6, wherein one of $R^B$ or $R^D$ is —($C_{0-3}$alkyl)$NR^3$—$SO_2$—($C_{0-3}$alkyl)$R^4$;
—($C_{0-3}$alkyl)$SO_2$—$NR^3$—($C_{0-3}$alkyl)$R^4$;
—($C_{0-3}$alkyl)$NR^3$($C_{0-3}$alkyl)$R^4$;
—($C_{0-3}$alkyl)$CONR^3$($C_{0-3}$alkyl)$R^4$;
—($C_{0-3}$alkyl)$OCONR^3$($C_{0-3}$alkyl)$R^4$;
—($C_{0-3}$alkyl)$NR^3CONR^3$($C_{0-3}$alkyl)$R^4$;
—($C_{0-3}$alkyl)$NR^3$(C=S)$NR^3$($C_{0-3}$alkyl)$R^4$;
—($C_{0-3}$alkyl)$NR^3SO_2NR^3$($C_{0-3}$alkyl)$R^4$, wherein each of the alkyl groups is independently substituted or unsubstituted, cyclic or acyclic, linear or branched, and wherein each occurrence of $R^3$ and $R^4$ is independently hydrogen or a substituted or unsubstituted alkyl, heteroalkyl, aryl, heteroaryl, alkylaryl, alkylheteroaryl, heteroalkylaryl, or heteroalkylheteroaryl moiety.

8. The compound of any one of claims 4–6, wherein one of $R^B$ or $R^D$ is

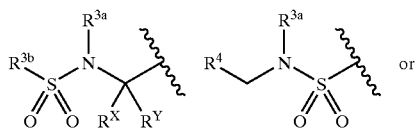 or

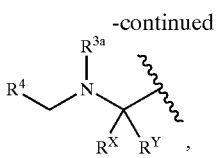

wherein each occurrence of $R^X$ and $R^Y$ is independently hydrogen or lower alkyl; each occurrence of $R^{3a}$ is independently hydrogen, lower alkyl or lower acyl; and each occurrence of $R^{3b}$ and $R^4$ is independently a substituted or unsubstituted aryl, heteroaryl, alkylaryl, alkylheteroaryl, heteroalkylaryl, or heteroalkylheteroaryl moiety.

9. The compound of any one of claims 4–6, wherein one of $R^B$ or $R^D$ is one of the structures:

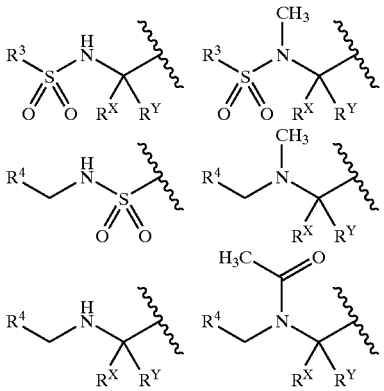

wherein each occurrence of $R^X$ and $R^Y$'s independently hydrogen or lower alkyl; and each occurrence of $R^3$ and $R^4$ is independently a substituted or unsubstituted aryl, heteroaryl, alkylaryl, alkylheteroaryl, heteroalkylaryl, or heteroalkylheteroaryl moiety.

10. The compound of any one of claims 4–6, wherein $R^1$ is hydrogen or a substituted or unsubstituted aryl, heteroaryl, alkylaryl, heteroalkylaryl, alkylheteroaryl, or heteroalkylheteroaryl moiety.

11. The compound of any one of claims 4–6, wherein $R^1$ is hydrogen or

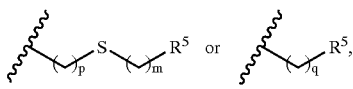

wherein $R^5$ is substituted or unsubstituted aryl, heteroaryl, alkyl or heteroalkyl; and m, p and q are each independently an integer from 0–6.

12. The compound of any one of claims 4–6, wherein $R^1$ is hydrogen or

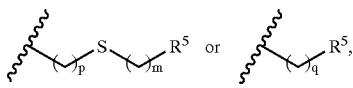

wherein $R^5$ is substituted or unsubstituted aryl, heteroaryl, alkyl or heteroalkyl; wherein the aryl, heteroaryl, alkyl or heteroalkyl group may be substituted with one or more occurrences of hydrogen, halogen, hydroxyl, lower alkoxy and/or lower alkyl; and m, p and q are each independently an integer from 0–6.

13. The compound of any one of claims 4–6, wherein $R^1$ is hydrogen or

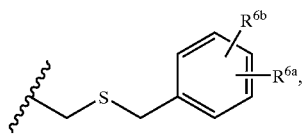

wherein $R^{6a}$ and $R^{6b}$ are each independently hydrogen, halogen, hydroxyl, lower alkoxy, or lower alkyl.

14. The compound of any one of claims 4–6, wherein $R^1$ is hydrogen or

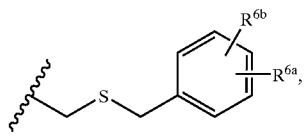

wherein $R^{6a}$ is hydrogen and $R^{6b}$ is halogen.

15. The compound of any one of claims 4–6, wherein $R^1$ is hydrogen or

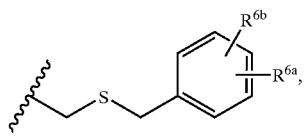

wherein $R^{6a}$ is hydrogen and $R^{6b}$ is Cl.

16. The compound of any one of claims 4–6, wherein each occurrence of $R^3$ and $R^4$ is independently a substituted or unsubstituted aryl, heteroaryl, alkylaryl, alkylheteroaryl, heteroalkylaryl, or heteroalkylheteroaryl moiety.

17. The compound of any one of claims 4–6, wherein each occurrence of $R^3$ and $R^4$ independently comprises an aryl, heteroaryl, alkylaryl, alkylheteroaryl, heteroalkylaryl, or heteroalkylheteroaryl moiety substituted with at least —COOH.

18. The compound of any one of claims 4–6, wherein each occurrence of $R^3$ and $R^4$ is independently phenyl or —(CH$_2$) phenyl substituted with —COOH (or an ester or bioisostere thereof) and optionally further substituted with one or more of hydroxyl, alkoxy, thio, thioalkyl, —COOH, —COO(alkyl), —CONH$_2$, —NH(CO)alkyl, —SO$_2$R$^{4a}$, lower alkyl, lower heteroalkyl, aryl, heteroaryl, alkylaryl, alkylheteroaryl, heteroalkylaryl, or heteroalkylheteroaryl, or wherein two adjacent groups taken together form an aryl, heteroaryl, cycloaliphatic, or heterocycloaliphatic group, wherein $R^{4a}$ is acyl, or substituted or unsubstituted alkyl or aryl.

19. The compound of any one of claims 4–6, wherein each occurrence of $R^3$ and $R^4$ is independently phenyl or —(CH$_2$) phenyl substituted with COOH or an ester or bioisostere of COOH.

20. The compound of any one of claims 4–6, wherein each occurrence of $R^3$ and $R^4$ is independently phenyl or —(CH$_2$) phenyl substituted with any one of COOH, acylsulfonamide, —CONH$_2$, tetrazole, or 5-oxo-1,2,4-oxadiazole.

21. The compound of any one of claims 4–6, wherein one of $R^B$ or $R^D$ is —(C$_{0-3}$alkyl)NR$^3$—SO$_2$—(C$_{0-3}$alkyl)R$^4$; —(C$_{0-3}$alkyl)SO$_2$—NR$^3$—(C$_{0-3}$alkyl)R$^4$; —(C$_{0-3}$alkyl)NR$^3$ (C$_{0-3}$alkyl)R$^4$; —(C$_{0-3}$alkyl)CONR$^3$(C$_{0-3}$alkyl)R$^4$; —(C$_{0-3}$alkyl)OCONR$^3$(C$_{0-3}$alkyl)R$^4$; —(C$_{0-3}$alkyl)NR$^3$CONR$^3$(C$_{0-3}$alkyl)R$^4$; —(C$_{0-3}$alkyl)NR$^3$(C=S)NR$^3$(C$_{0-3}$alkyl)R$^4$; —(C$_{0-3}$alkyl)NR$^3$SO$_2$NR$^3$(C$_{0-3}$alkyl)R$^4$; or subgroups defined generally above and herein, and the remaining groups $R^A$, $R^E$, $R^G$, and one of $R^B$ or $R^D$ are each independently hydrogen, alkyl, alkoxy, halogen, hydroxyl, thio or thioalkyl.

22. A compound having the structure:

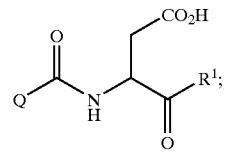

wherein Q is an aryl or heteroaryl moiety substituted with

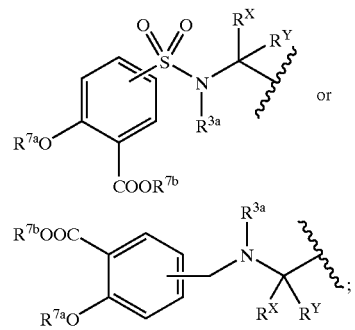

wherein $R^{3a}$ is hydrogen, a nitrogen protecting group, lower alkyl or lower acyl; $R^{7a}$ is hydrogen, a protecting group, lower alkyl or lower acyl; $R^{7b}$ is hydrogen, a protecting group or lower alkyl; $R^X$ and $R^Y$ are independently hydrogen or lower alkyl; and $R^1$ is hydrogen or

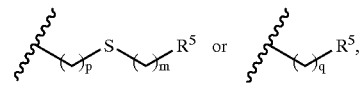

wherein $R^5$ is substituted or unsubstituted aryl, heteroaryl, alkyl or heteroalkyl; wherein the aryl, heteroaryl, alkyl or heteroalkyl group may be substituted with one or more occurrences of hydrogen, halogen, hydroxyl, lower alkoxy and/or lower alkyl; and m, p and q are each independently an integer from 0–6.

23. The compound of claim 22, wherein Q is an aryl or heteroaryl moiety having one of the structures:

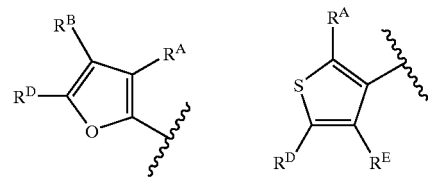

-continued

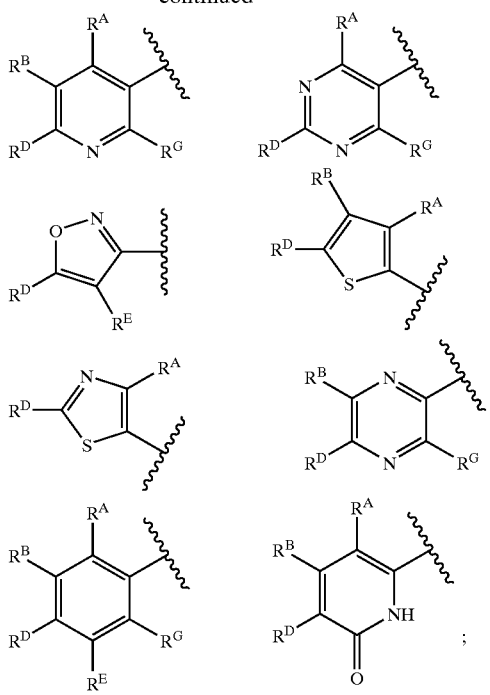

wherein $R^A$—$R^G$ are as defined in claim 1, and one of $R^A$—$R^G$ is

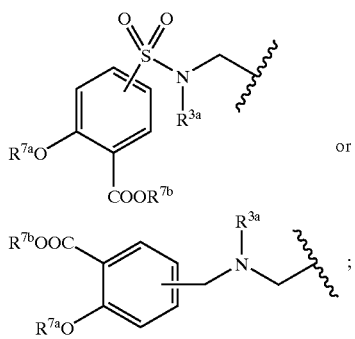

wherein $R^{3a}$ is hydrogen, a nitrogen protecting group, lower alkyl or lower acyl; $R^{7a}$ is hydrogen, a protecting group, lower alkyl or lower acyl; $R^{7b}$ is hydrogen, a protecting group or lower alkyl.

24. The compound of claim 22 having the structure:

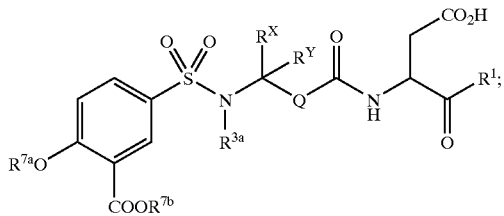

wherein Q is an aryl or heteroaryl moiety; $R^{3a}$ is hydrogen, a nitrogen protecting group, lower alkyl or lower acyl; $R^{7a}$ is hydrogen, a protecting group, lower alkyl or lower acyl; $R^{7b}$ is hydrogen, a protecting group or lower alkyl; $R^X$ and $R^Y$ are independently hydrogen or lower alkyl; and $R^1$ is hydrogen or

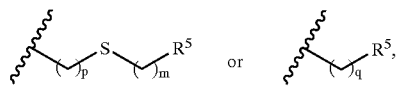

wherein $R^5$ is substituted or unsubstituted aryl, heteroaryl, alkyl or heteroalkyl; wherein the aryl, heteroaryl, alkyl or heteroalkyl group may be substituted with one or more occurrences of hydrogen, halogen, hydroxyl, lower alkoxy and/or lower alkyl; and m, p and q are each independently an integer from 0–6.

25. The compound of claim 24 having the structure:

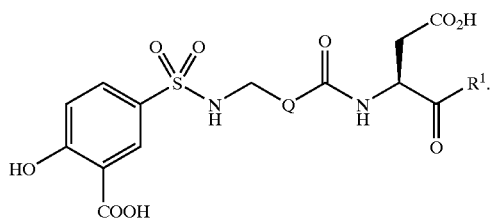

26. The compound of claim 22 having the structure:

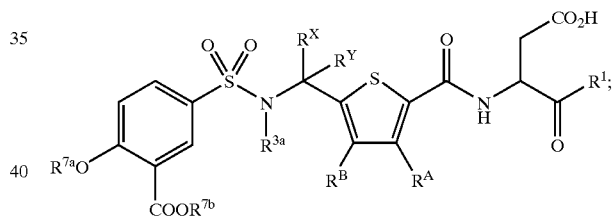

wherein $R^{3a}$ is hydrogen, a nitrogen protecting group, lower alkyl or lower acyl; and $R^{7a}$ is hydrogen, a protecting group, lower alkyl or lower acyl; $R^{7b}$ is hydrogen, a protecting group or lower alkyl; $R^A$ and $R^B$ are each independently hydrogen, lower alkyl, hydroxyl, lower alkoxy, or halogen; $R^X$ and $R^Y$ are independently hydrogen or lower alkyl; and $R^1$ is hydrogen or

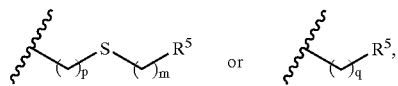

wherein $R^5$ is substituted or unsubstituted aryl, heteroaryl, alkyl or heteroalkyl; wherein the aryl, heteroaryl, alkyl or heteroalkyl group may be substituted with one or more occurrences of hydrogen, halogen, hydroxyl, lower alkoxy and/or lower alkyl; and m, p and q are each independently an integer from 0–6.

27. The compound of claim 26 having the structure:

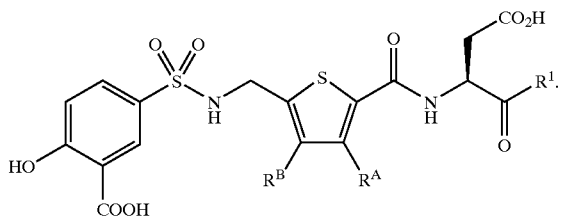

28. The compound of claim 22 having the structure:

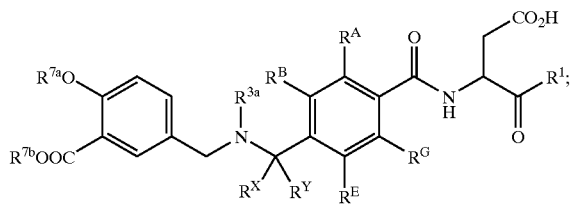

wherein $R^{3a}$ is hydrogen, a nitrogen protecting group, lower alkyl or lower acyl; and $R^{7a}$ is hydrogen, a protecting group, lower alkyl or lower acyl; $R^{7b}$ is hydrogen, a protecting group or lower alkyl; $R^A$, $R^B$, $R^E$ and $R^G$ are each independently hydrogen, lower alkyl, hydroxyl, lower alkoxy, or halogen; $R^X$ and $R^Y$ are independently hydrogen or lower alkyl; and $R^1$ is hydrogen or

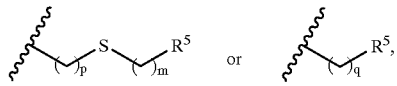

wherein $R^5$ is substituted or unsubstituted aryl, heteroaryl, alkyl or heteroalkyl; wherein the aryl, heteroaryl, alkyl or heteroalkyl group may be substituted with one or more occurrences of hydrogen, halogen, hydroxyl, lower alkoxy and/or lower alkyl; and m, p and q are each independently an integer from 0–6.

29. The compound of claim 28 having the structure:

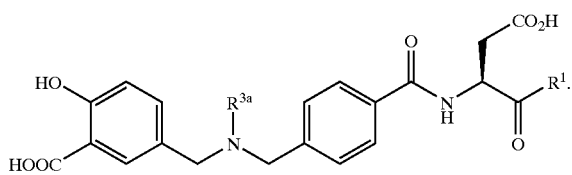

30. The compound of any one of claims 22–29 wherein $R^1$ is hydrogen or

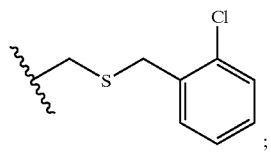

and $R^{3a}$ is hydrogen, Me or Ac.

31. A pharmaceutical composition comprising:
a compound of any one of claims 1–6, 22, 24, 26 or 28; and
a pharmaceutically acceptable carrier or diluent.

32. The pharmaceutical composition of claim 31, wherein the compound is present in an amount effective to inhibit a caspase.

33. The pharmaceutical composition of claim 32, wherein the caspase is caspase-3 or caspase-7.

34. The pharmaceutical composition of claim 31, optionally further comprising an additional therapeutic agent.

35. A method for treating a caspase-mediated disorder comprising:
administering to a subject in need thereof a therapeutically effective amount of a compound of any one of claims 1–6, 22, 24, 26 or 28.

36. The method of claim 35, optionally comprising further administering an additional therapeutic agent.

37. A method for treating a disorder caused by excessive apoptosis comprising:
administering to a subject in need thereof a therapeutically effective amount of a compound of any one of claims 1–6, 22, 24, 26 or 28.

38. The method of claim 37, optionally comprising further administering an additional therapeutic agent.

39. The method of claim 35, wherein the disorder is any one of: stroke, traumatic, brain injury, spinal cord injury, meningitis, Alzheimer's disease, Parkinson's disease, Huntington's disease, Kennedy's disease, prion disease, multiple sclerosis, spinal muscular atrophy, myocardial infarction, congestive heart failure and various other forms of acute and chronic heart disease, atherosclerosis, aging, bums, organ transplant rejection, graft versus host disease, hepatitis-B, -C, -G, various forms of liver disease including acute alcoholic hepatitis, yellow fever, dengue fever, Japanese encephalitis, glomerulonephritis, renal disease, *H pylori-*associated gastric and duodenal ulcer disease, HIV infection, tuberculosis, alopecia, diabetes, sepsis, Shigellosis, uveitis, inflammatory peritonitis, pancreatitis, erythematosus, scleroderma, chronic thyroiditis, Graves' disease, autoimmune gastritis, autoimmune hemolytic anemia, autoimmune neutropenia, thrombocytopenia, HIV-related encephalitis, myasthenia gravis, small bowel isehemia in disease or post-surgery, psoriasis, atopic dermatitis, myelodysplatic syndrome, acute and chronic myelogenous leukemia, metastatic melanoma, Kaposi's sarcoma, or Wiscott-Aldrich syndrome.

40. The method of claim 37, wherein the disorder is any one of: stroke, traumatic, brain injury, spinal cord injury, meningitis, Alzheimer's disease, Parkinson's disease, Huntington's disease, Kennedy's disease, prion disease, multiple sclerosis, spinal muscular atrophy, myocardial infarction, congestive heart failure and various other forms of acute and chronic hear disease, atherosclerosis, aging, bums, organ transplant rejection, graft versus host disease, hepatitis-B, -C, -G, various forms of liver disease including acute alcoholic hepatitis, yellow fever, dengue fever, Japanese encephalitis, glomerulonephritis, renal disease, *H. pylori-*associated gastric and duodenal ulcer disease, HIV infection, tuberculosis, alopecia, diabetes, sepsis, Shigellosis, uveitis, inflammatory peritonitis, pancreatitis, erythematosus, scleroderma, chronic thyroiditis, Graves' disease, autoimmune gastritis, autoimmune hemolytic anemia, autoimmune neutropenia, thrombocytopenia, HIV-related encephalitis, myasthenia gravis, small bowel isehemia in disease or post-surgery, psoriasis, atopic dermatitis, myelodysplatic syndrome acute and chronic myelogenous leukemia, metastatic melanoma, Kaposi's sarcoma, or Wiscott-Aldrich syndrome.

41. A method for inhibiting an apoptotic caspase comprising:

contacting cells with an effective amount of any one of any one of the compounds of claims 1–6, 22, 24, 26 or 28.

42. A method for inhibiting caspase-3 or caspase-7 comprising:

contacting cells with an effective amount of any one of the compounds of claims 1–6, 22, 24, 26 or 28.

43. The method of claim 42, wherein the method of inhibiting comprises inhibiting caspase-3.

* * * * *